United States Patent
Karlin et al.

(10) Patent No.: US 12,173,057 B2
(45) Date of Patent: Dec. 24, 2024

(54) ANTIBODIES AND THERAPEUTIC USES THEREOF

(71) Applicant: Ibex Biosciences, Inc., Cumberland, MD (US)

(72) Inventors: Michael Joseph Karlin, Bethesda, MD (US); Alberto Murat Croci, Washington, DC (US); Vidal Felix De La Cruz, Phoenixville, PA (US); Norman Zhennan Lai, N. Potomac, MD (US); Roy Feinson, Cumberland, MD (US)

(73) Assignee: Ibex Biosciences, Inc., Cumberland, MD (US)

( * ) Notice: Subject to any disclaimer, the term of this patent is extended or adjusted under 35 U.S.C. 154(b) by 870 days.

(21) Appl. No.: 17/283,434

(22) PCT Filed: Oct. 9, 2019

(86) PCT No.: PCT/US2019/055401
§ 371 (c)(1),
(2) Date: Apr. 7, 2021

(87) PCT Pub. No.: WO2020/076954
PCT Pub. Date: Apr. 16, 2020

(65) Prior Publication Data
US 2022/0025025 A1    Jan. 27, 2022

Related U.S. Application Data

(60) Provisional application No. 62/743,169, filed on Oct. 9, 2018.

(51) Int. Cl.
| | | |
|---|---|---|
| *C07K 16/18* | (2006.01) | |
| *A61P 35/00* | (2006.01) | |
| *G01N 33/574* | (2006.01) | |

(52) U.S. Cl.
CPC ............. *C07K 16/18* (2013.01); *A61P 35/00* (2018.01); *G01N 33/57415* (2013.01); *C07K 2317/24* (2013.01); *C07K 2317/33* (2013.01); *C07K 2317/622* (2013.01); *C07K 2317/73* (2013.01); *C07K 2317/80* (2013.01); *C07K 2317/92* (2013.01); *G01N 2333/4712* (2013.01)

(58) Field of Classification Search
CPC .......................... C07K 16/18; C07K 2317/24; C07K 2317/33; C07K 2317/622; C07K 2317/73; C07K 2317/80; C07K 2317/92; C07K 2317/70; C07K 16/30; C07K 16/2809; C07K 2317/565; A61P 35/00; G01N 33/57415; G01N 2333/4712; G01N 33/6854; A61K 2039/80; A61K 2039/812; A61K 2039/86; A61K 2039/884; A61K 47/62; A61K 51/10; A61K 51/1093; A61K 2039/505
See application file for complete search history.

(56) References Cited

U.S. PATENT DOCUMENTS

| | | | |
|---|---|---|---|
| 4,816,567 | A | 3/1989 | Cabilly et al. |
| 5,229,275 | A | 7/1993 | Goroff |
| 5,545,807 | A | 8/1996 | Surani et al. |
| 5,565,332 | A | 10/1996 | Hoogenboom et al. |
| 5,567,610 | A | 10/1996 | Borrebaeck et al. |
| 5,573,905 | A | 11/1996 | Lerner et al. |
| 5,589,369 | A | 12/1996 | Seidman et al. |
| 5,591,669 | A | 1/1997 | Krimpenfort et al. |
| 5,648,237 | A | 7/1997 | Carter |
| 5,851,829 | A | 12/1998 | Marasco et al. |
| 5,965,371 | A | 10/1999 | Marasco et al. |
| 8,680,243 | B2 | 3/2014 | Funahashi |
| 9,891,232 | B2 | 2/2018 | Shaw et al. |
| 2003/0157514 | A1 | 8/2003 | Finger et al. |
| 2004/0003418 | A1 | 1/2004 | Jakobovits et al. |
| 2006/0018923 | A1 | 1/2006 | Yuen et al. |
| 2008/0293162 | A1 | 11/2008 | Alper |
| 2010/0074906 | A1 | 3/2010 | Burioni et al. |
| 2010/0150902 | A1 | 6/2010 | Haeuw |
| 2014/0044721 | A1 | 2/2014 | Paris et al. |
| 2015/0373937 | A1 | 12/2015 | Reeves et al. |
| 2018/0171002 | A1 | 6/2018 | Wu et al. |
| 2018/0194809 | A1 | 7/2018 | Schief et al. |

FOREIGN PATENT DOCUMENTS

| | | |
|---|---|---|
| CN | 102027014 A | 4/2011 |
| CN | 107428821 A | 12/2017 |
| JP | 2018506045 A | 3/2018 |
| WO | WO 2002/088334 A1 | 11/2002 |
| WO | WO 2018/000324 A1 | 1/2018 |

(Continued)

OTHER PUBLICATIONS

Geiser, M., et al., "Antibody light chain variable region, partial [Mus musculus]," GenBank: CAA62406.1, GenPept, 1995, p. 1-2.
Alper, O., et al., "Novel anti-filamin-A antibody detects a secreted variant of filamin-A in plasma from patients with breast carcinoma and high-grade astrocytoma". Cancer Sci. (Sep. 2009); 100(9): 1748-1756.
Altschul, S.F., et al., "Basic local alignment search tool". Journal of Molecular Biology (Oct. 5, 1990); 215(3): 403-410.
Altschul, S.F., et al., "Gapped BLAST and PSI-BLAST: a new generation of protein database search programs". Nucleic Acids Research (Sep. 1, 1997); 25(17): 3389-3402.

(Continued)

*Primary Examiner* — Julie Wu
*Assistant Examiner* — Amber K Faust
(74) *Attorney, Agent, or Firm* — COOLEY LLP

(57) ABSTRACT

The disclosure teaches antibodies that are useful, inter alia, in methods for detecting and treating human cancer. In a particular aspect, the disclosure teaches novel antibodies that are useful for detecting and treating human breast cancer. In some embodiments, the disclosure teaches novel antibodies that bind to filamin A. In some embodiments, the antibodies are intrabodies.

44 Claims, 73 Drawing Sheets

Specification includes a Sequence Listing.

(56) References Cited

FOREIGN PATENT DOCUMENTS

| WO | WO 2018/027042 A1 | 2/2018 |
|---|---|---|
| WO | WO-2018085431 A1 | 5/2018 |
| WO | WO 2020/076954 A1 | 4/2020 |

OTHER PUBLICATIONS

Bachmann, A.S., et al., "Actin-binding protein filamin A is displayed on the surface of human neuroblastoma cells". Cancer Science (Dec. 2006); 97(12): 1359-1365.

Brüggemann, M., et al., "Designer mice: the production of human antibody repertoires in transgenic animals". Year Immunol. (1993); 7: 33-40.

Chothia, C., et al., "Domain association in immunoglobulin molecules: the packing of variable domains". Journal of Molecular Biology (Dec. 5, 1985); 186(3): 651-663.

Clackson, T, et al., Making antibody fragments using phage display libraries. Nature (Aug. 1991); 352(6336): 624-628.

GenBank Accession No. 075369 "RecName: Full=Filamin-B; Short=FLN-B; AltName: Full=ABP-278; AltName: Full=ABP-280 homolog; AltName: Full=Actin-binding-like protein; AltName: Full=Beta-filamin; AltName: Full=Filamin homolog 1; Short=Fh1; AltName: Full=Filamin-3; AltName: Full=Thyroid autoant.". Jun. 2, 2021, 24 pages.

GenBank Accession No. P21333 "RecName: Full=Filamin-A; Short=FLN-A; AltName: Full=Actin-binding protein 280; Short=ABP-280; AltName: Full=Alpha-filamin; AltName: Full=Endothelial actin-binding protein; AltName: Full=Filamin-1; AltName: Full=Non-muscle filamin". Jun. 2, 2021, 31 pages.

GenBank Accession No. Q14315 "RecName: Full=Filamin-C; Short=FLN-C; Short=FLNc; AltName: Full=ABP-280-like protein; AltName: Full=ABP-L; AltName: Full=Actin-binding-like protein; AltName: Full=Filamin-2; AltName: Full=Gamma-filamin". Jun. 2, 2021, 18 pages.

Gorlin, J.B., et al., "Human endothelial actin-binding protein (ABP-280, nonmuscle filamin): a molecular leaf spring". The Journal of Cell Biology (Sep. 1, 1990); 111(3): 1089-1105.

Griffiths, A.D., et al., "Human anti-self antibodies with high specificity from phage display libraries". The EMBO Journal (Feb. 1993); 12(2): 725-734.

Higgins, D.G., et al., "Using CLUSTAL for multiple sequence alignments". Methods Enzymol. (1996); 266: 383-402.

Invitation to Pay Additional Fees for International Application No. PCT/US2019/055401, mailed Dec. 26, 2019, 3 pages.

International Search Report and Written Opinion for International Application No. PCT/US2019/055401, mailed Mar. 3, 2020, 19 pages.

International Preliminary Report on Patentability for International Application No. PCT/US2019/055401, dated Apr. 8, 2021, 13 pages.

Jakobovits, A, et al., "Analysis of homozygous mutant chimeric mice: deletion of the immunoglobulin heavy-chain joining region blocks B-cell development and antibody production". Proceedings of the National Academy of Sciences (Mar. 15, 1993); 90(6): 2551-2555.

Jakobovits, A., et al., "Germ-line transmission and expression of a human-derived yeast artificial chromosome". Nature (Mar. 1993); 362(6417): 255-258.

Johnson and Chiswell, "Human antibody engineering". Current Opinion in Structural Biology (Aug. 1, 1993); 3(4): 564-571.

Jones, P.T., et al., "Replacing the complementarity-determining regions in a human antibody with those from a mouse". Nature (May 1986); 321(6069): 522-525.

Karlin, S., et al., "Applications and statistics for multiple high-scoring segments in molecular sequences". Proceedings of the National Academy of Sciences (Jun. 15, 1993); 90(12): 5873-5877.

Karlin, S., et al., "Methods for assessing the statistical significance of molecular sequence features by using general scoring schemes". Proceedings of the National Academy of Sciences (Mar. 1, 1990); 87(6): 2264-2268.

Köhler, G, et al., "Continuous cultures of fused cells secreting antibody of predefined specificity". Nature (Aug. 1975); 256(5517): 495-497.

Marks, J.D., et al., "By-passing immunization: human antibodies from V-gene libraries displayed on phage". Journal of Molecular Biology (Dec. 5, 1991); 222(3): 581-597.

McCafferty, J., et al., "Phage antibodies: filamentous phage displaying antibody variable domains". Nature (Dec. 6, 1990); 348(6301): 552-554.

Miller, S., "Protein-protein recognition and the association of immunoglobulin constant domains". Journal of Molecular Biology (Dec. 20, 1990); 216(4): 965-973.

Morrison, S.L., et al., "Chimeric human antibody molecules: mouse antigen-binding domains with human constant region domains". Proceedings of the National Academy of Sciences (Nov. 1, 1984); 81(21): 6851-6855.

Myers, E.W., et al., "Optimal alignments in linear space". Bioinformatics (Mar. 1, 1988); 4(1): 11-17.

Novotný, J., et al., "Structural invariants of antigen binding: comparison of immunoglobulin VL-VH and VL-VL domain dimers". Proceedings of the National Academy of Sciences (Jul. 1, 1985); 82(14): 4592-4596.

Padlan, E.A., et al., "Antibody Fab assembly: the interface residues between CH1 and CL". Molecular Immunology (Sep. 1, 1986); 23(9): 951-960.

Pearson, W.R., et al., Improved tools for biological sequence comparison. Proceedings of the National Academy of Sciences (Apr. 1, 1988); 85(8): 2444-2448.

Posey, Jr., A.D., et al., "Engineered CAR T cells targeting the cancer-associated Tn-glycoform of the membrane mucin MUC1 control adenocarcinoma". Immunity (Jun. 21, 2016); 44(6): 1444-1454.

Presta, L.G., "Antibody engineering". Current Opinion in Structural Biology (Aug. 1, 1992); 2(4): 593-596.

Reiser, J., et al., "Development of multigene and regulated lentivirus vectors". Journal of Virology (Nov. 15, 2000); 74(22): 10589-10599.

Riechmann, L., et al., "Reshaping human antibodies for therapy". Nature (Mar. 1988); 332(6162): 323-327.

Takafuta, T., et al., "Human β-filamin is a new protein that interacts with the cytoplasmic tail of glycoprotein Ibα". Journal of Biological Chemistry (Jul. 10, 1998); 273(28): 17531-17538.

Torelli, A., et al., "ADVANCE and ADAM: two algorithms for the analysis of global similarity between homologous informational sequences". Bioinformatics (Feb. 1, 1994); 10(1): 3-5.

Xie, Z.W., et al., "Molecular cloning of human ABPL, an actin-binding protein homologue". Biochemical and Biophysical Research Communications (Oct. 29, 1998); 251(3): 914-919.

Andrea LJ Marschall et al: "Specific in vivo knockdown of protein function by intrabodies", MABS, vol. 7, No. 6, Aug. 7, 2015 (Aug. 7, 2015), pp. 1010-1035, XP055572240.

Bu Zibin et al: "A Monoclonal Antibody SZ-117 That Recognizes Filamin A Derived from Tumor Cells", Hybridoma, vol. 31, No. 3, Jun. 1, 2012 (Jun. 1, 2012), pp. 214-218, XP055944099.

Extended European Search Report for European Application No. EP20190871405 dated Aug. 1, 2022, 13 Pages.

Gianpietro Dotti et al: "Design and development of therapies using chimeric antigen receptor-expressing T cells", Immunological Reviews, Wiley-Blackwell Publishing, Inc, US, vol. 257, No. 1, Dec. 13, 2013 (Dec. 13, 2013), pp. 107-126, XP071455751.

Ji Zhi-Min et al: "Silencing Filamin A Inhibits the Invasion and Migration of Breast Cancer Cells by Up-regulating 14-3-3 [sigma]", Current Medical Science, Huazhong University of Science and Technology, Wuhan, vol. 38, No. 3, Jun. 22, 2018 (Jun. 22, 2018), pp. 461-466, XP036617326.

Julia Stieglmaier et al: "Utilizing the BiTE (bispecific T-cell engager) platform for immunotherapy of cancer", Expert Opinion on Biological Therapy, vol. 15, No. 8, Aug. 3, 2015 (Aug. 3, 2015), pp. 1093-1099, XP055465777.

(56) References Cited

OTHER PUBLICATIONS

R. G. Bedolla et al: "Nuclear versus Cytoplasmic Localization of Filamin A in Prostate Cancer: Immunohistochemical Correlation with Metastases", Clinical Cancer Research, vol. 15, No. 3, Feb. 1, 2009 (Feb. 1, 2009), pp. 788-796, XP055083300.
Rajesh K Nallapalli et al: "Targeting filamin A reduces K-RAS-induced lung adenocarcinomas and endothelial response to tumor growth in", Molecular Cancer, Biomed Central, London, GB, vol. 11, No. 1, Aug. 2, 2012 (Aug. 2, 2012), p. 50, XP021115999.
Savoy Rosalinda M et al: "The dual role of filamin A in cancer: can't live with (too much of) it, can't live without it", Endocrine Related Cancer, vol. 20, No. 6, Oct. 9, 2013 (Oct. 9, 2013), pp. R341-R356, XP055943880.
Shobha Ravipaty et al: "Clinical 1-25 Validation of a Serum Protein Panel (FLNA, FLNB, and KRT19) for Diagnosis of Prostate Cancer", Journal of Molecular Biomarkers & Diagnosis, vol. 08, No. 02, Jan. 1, 2017 (Jan. 1, 2017), XP055489786.
Liu et al., "FLNa expression in the serum and tissue of patients with hepatocellular carcinoma," Chinese Journal of Tumor Prevention and Treatment, vol. 20, No. 13, 2013, pp. 1003-1006, with English abstract.

FIG. 1

| | TC | | | | Collagen | | | | Fibronectin | | | |
|---|---|---|---|---|---|---|---|---|---|---|---|---|
| -mAb (Control) | 154.86 | 162.40 | 9.09 | 66.09 | 238.72 | 236.46 | 30.23 | 19.21 | 208.03 | 260.82 | 15.59 | 10.33 |
| mAB: +1 mcg/mL | 194.94 | 46.76 | 29.88 | 43.39 | 244.33 | 280.53 | 56.21 | 47.27 | 155.36 | 227.31 | 54.87 | 29.74 |
| mAB: +20 mcg/mL | 348.04 | 189.51 | 414.30 | 624.39 | 254.35 | 247.21 | 34.06 | 69.53 | 258.54 | 223.61 | 86.31 | 16.22 |
| hAB: +1 mcg/mL | 158.68 | 152.98 | 18.09 | 11.31 | 210.26 | 203.33 | 80.82 | 126.81 | 102.42 | 110.09 | 34.13 | 28.65 |
| hAB: +20 mcg/mL | 242.68 | 149.45 | 109.89 | 22.13 | 246.92 | 244.61 | 58.73 | 24.45 | 195.80 | 253.24 | 80.69 | 13.75 |
| Apicidin | 198.31 | 140.98 | 139.78 | 35.48 | 335.30 | 206.11 | 40.81 | 223.05 | 196.07 | 175.05 | 56.36 | 71.98 |
| Cytochalasin B | 102.95 | 86.89 | 64.28 | 16.75 | 80.93 | 79.37 | 95.10 | 46.43 | 89.17 | 89.49 | 46.68 | 36.91 |
| Stopper not removed | 58.67 | 33.03 | 5.18 | 17.44 | 39.76 | 38.70 | 9.70 | 10.49 | 40.71 | 48.31 | 9.64 | 10.82 |

| | MDA-MB-231 | | HEK-293 | | MDA-MB-232 | | HEK-293 | | MDA-MB-233 | | HEK-293 | |
|---|---|---|---|---|---|---|---|---|---|---|---|---|
| | Avg | ±S.D. | Avg | ±S.D. | Avg | ±S.D. | Avg | ±S.D. | Avg | ±S.D. | Avg | ±S.D. |
| Control | 158.63 | 5.34 | 37.59 | 40.38 | 237.59 | 1.59 | 19.72 | 0.72 | 234.43 | 37.33 | 12.91 | 3.80 |
| mAB: +1 mcg/mL | 120.85 | 104.78 | 36.64 | 9.55 | 262.43 | 25.60 | 71.74 | 34.60 | 191.34 | 50.87 | 42.31 | 17.77 |
| mAB: +20 mcg/mL | 218.78 | 41.38 | 519.35 | 148.55 | 250.73 | 4.97 | 51.79 | 25.08 | 241.08 | 24.70 | 51.26 | 49.56 |
| hAB: +1 mcg/mL | 155.83 | 4.03 | 14.70 | 4.80 | 206.80 | 4.83 | 93.81 | 46.86 | 106.26 | 5.43 | 31.39 | 3.87 |
| hAB: +20 mcg/mL | 196.07 | 65.93 | 65.90 | 61.92 | 245.76 | 1.63 | 46.59 | 17.17 | 224.52 | 40.62 | 37.22 | 33.19 |
| Apicin (100 nM) | 159.64 | 40.54 | 82.63 | 80.83 | 220.70 | 30.54 | 131.93 | 128.86 | 185.56 | 14.87 | 64.17 | 11.05 |
| Cytochalasin B (30 μM) | 94.92 | 11.35 | 40.51 | 33.61 | 80.15 | 1.10 | 70.76 | 34.42 | 89.32 | 8.23 | 36.79 | 13.97 |
| Stopper | 45.85 | 18.14 | 11.31 | 8.62 | 39.23 | 0.75 | 18.10 | 0.56 | 44.51 | 5.37 | 9.83 | 0.27 |

Anti-Filamin A, clone 209#13 AHO1402 (Life Technologies)

Anti-Filamin A, mouse mAb

Anti-Filamin A, Chimeric mAb

Anti-Filamin A, clone 209#13 AHO1402 (Life Technologies)

Anti-Filamin A, clone 209#13 AHO1402 (Life Technologies)

FIG. 15
Anti-Filamin A, mouse mAb
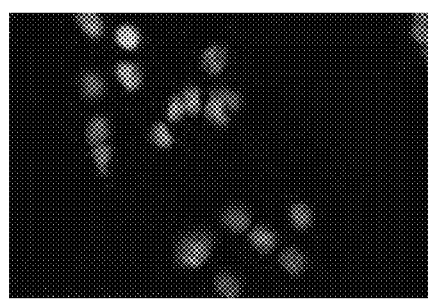
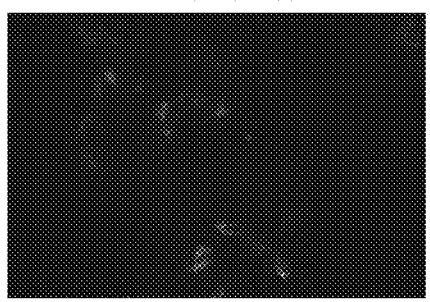
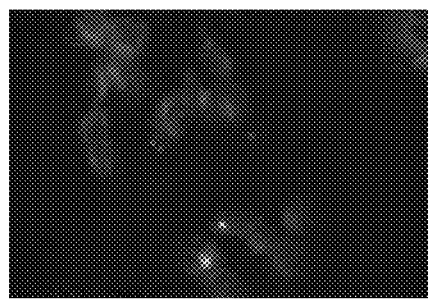
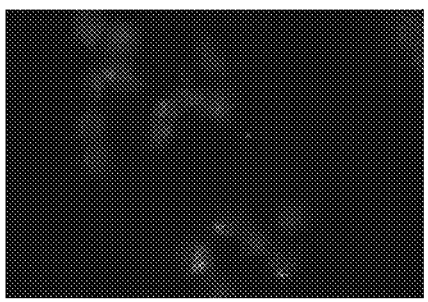

Anti-Filamin A, mouse mAb

Anti-Filamin A, Chimeric mAb

Anti-Filamin A, Chimeric mAb

Anti-Filamin A, clone 209#13 AHO1402 (Life Technologies)

Anti-Filamin A, clone 209#13 AHO1402 (Life Technologies)

Anti-Filamin A, mouse mAb

Anti-Filamin A, mouse mAb

Anti-Filamin A, Chimeric mAb

Anti-Filamin A, Chimeric mAb

FIG. 28

SEQ ID NO: 73

SEQ ID NO: 4

SEQ ID NO: 74

FIG. 31

SEQ ID NO: 24

FIG. 34A-B
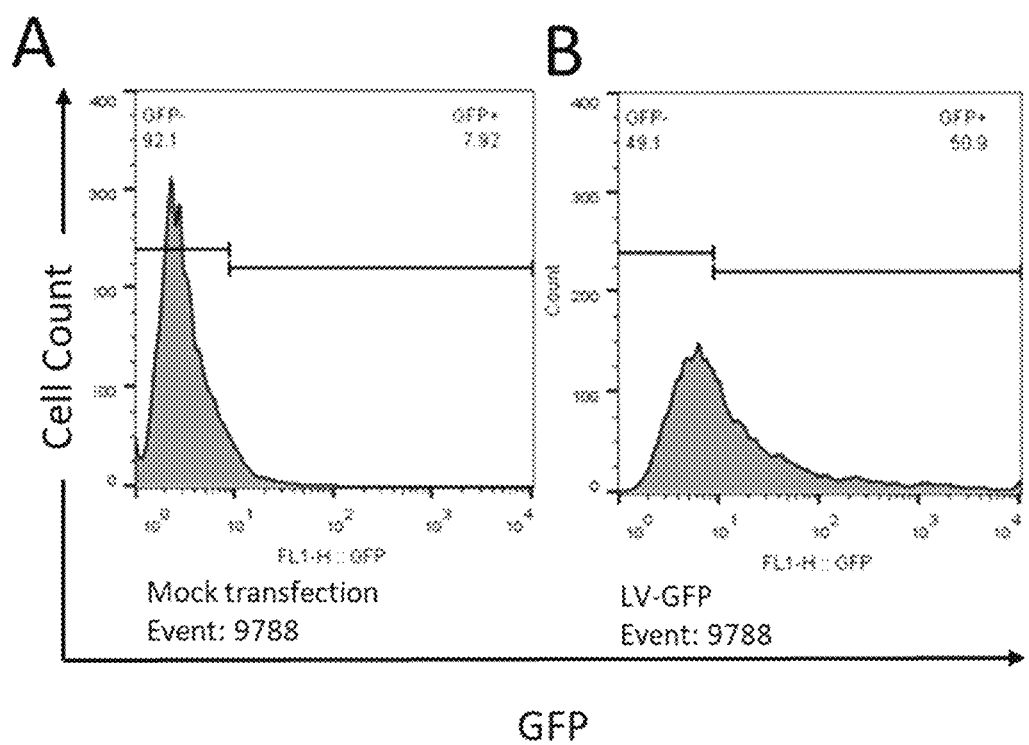

FIG. 34C-D
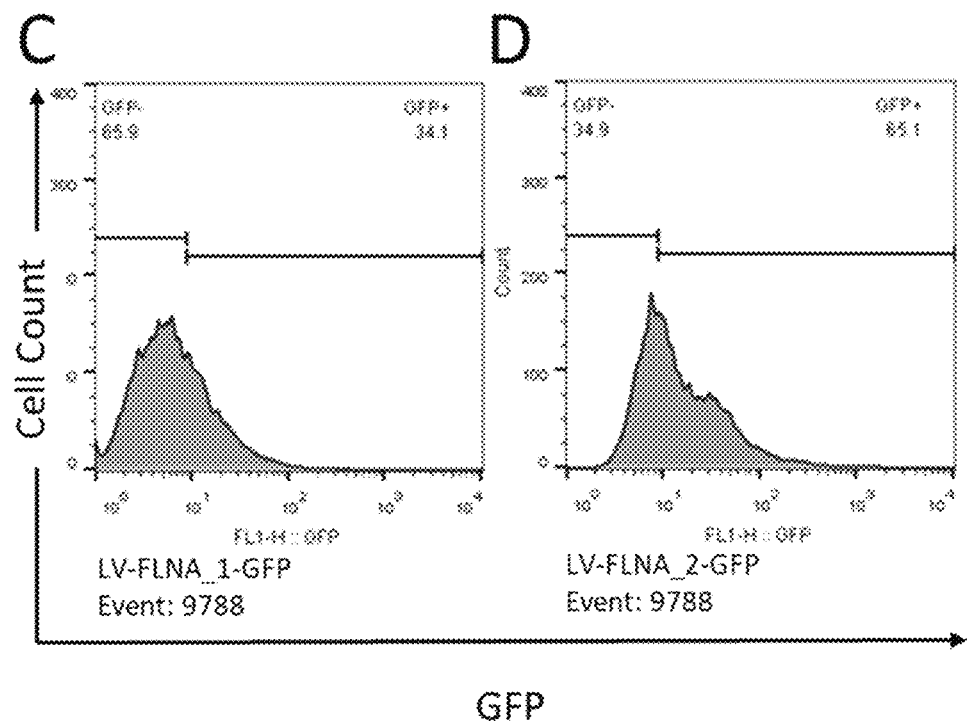

FIG. 35A-B
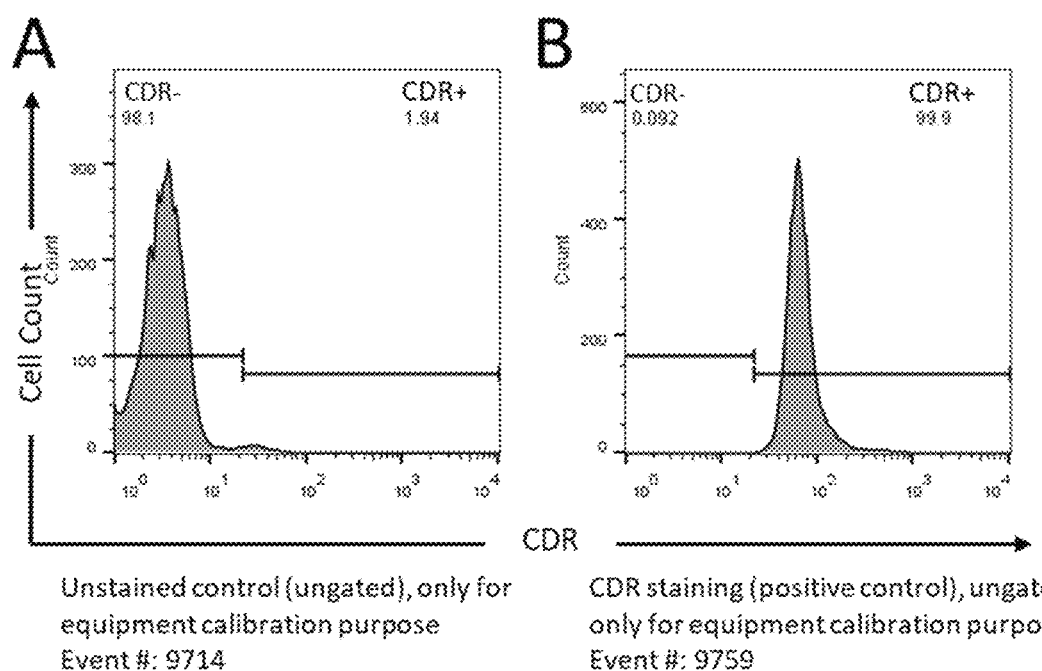

FIG. 35C- E
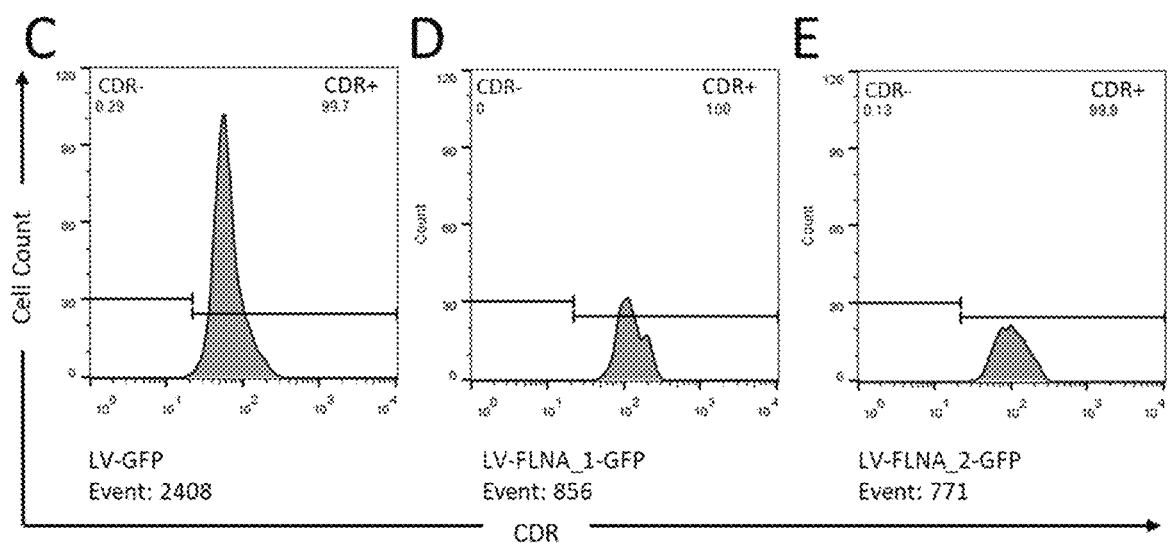

FIG. 37A-E
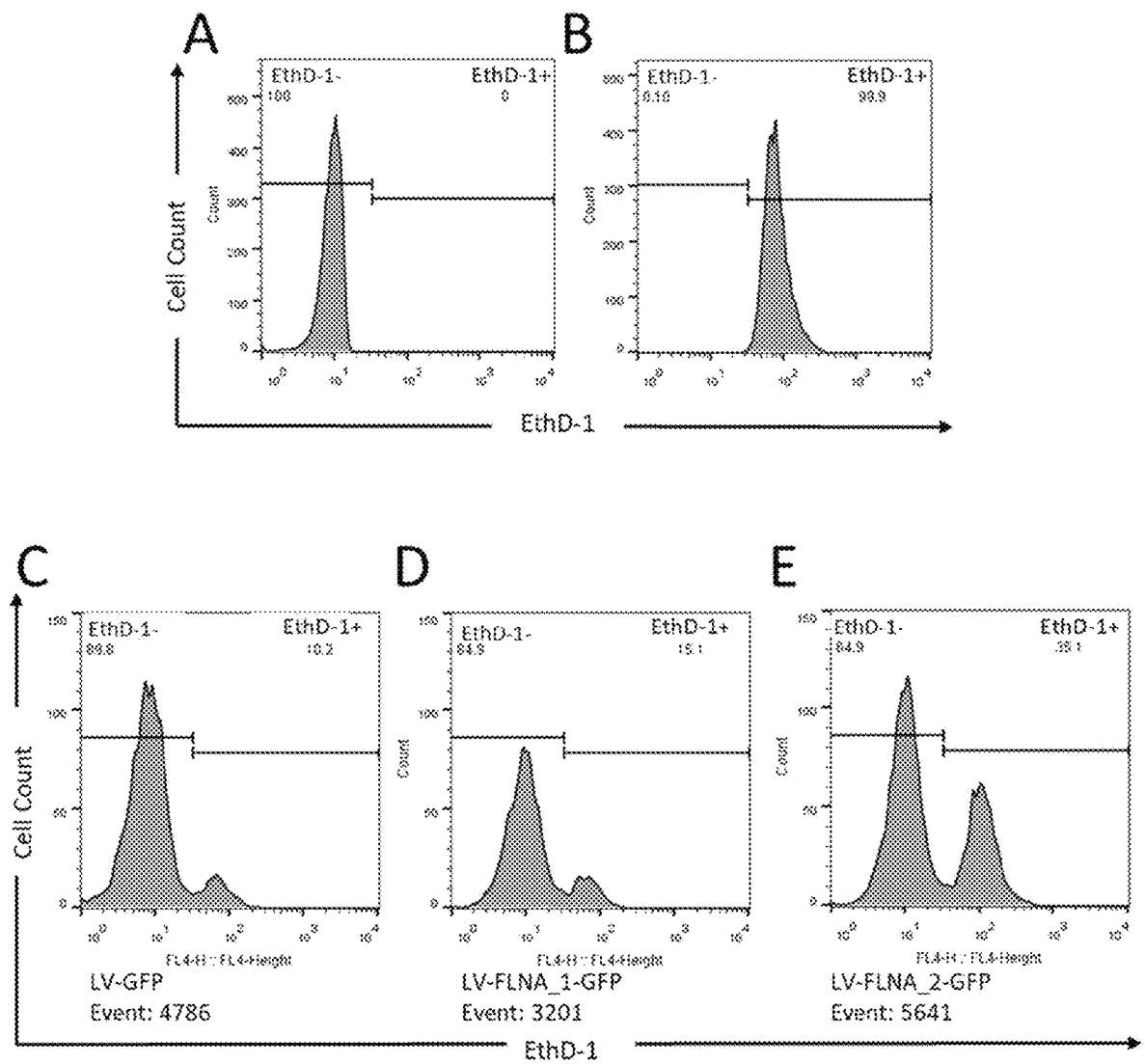

FIG. 61A-C ial Application PCT/US2019/055401, filed Oct. 9,
ANTIBODIES AND THERAPEUTIC USES THEREOF

CROSS-REFERENCE TO RELATED APPLICATIONS

This application is a 371 National Stage Entry of International Application PCT/US2019/055401, filed Oct. 9, 2019, which claims the benefit of priority to U.S. Provisional Application No. 62/743,169, filed Oct. 9, 2018, the entire contents of which are hereby incorporated by reference in their entireties.

DESCRIPTION OF THE TEXT FILE SUBMITTED ELECTRONICALLY

The contents of the text file submitted electronically herewith are incorporated herein by reference in their entireties: A computer readable format copy of the Sequence Listing (file name: IBEX_004_03US_SeqList_ST25.txt: date recorded: Apr. 7, 2021; file size: 4 kilobytes).

FIELD OF THE DISCLOSURE

The present disclosure relates to monoclonal antibodies (mAbs) and fragments thereof, new protein expression cell lines that secrete said antibodies or fragments thereof, and the use of the antibodies and antibody fragments to preferentially detect antigens and/or treat diseases. In some embodiments, the antibodies and fragments thereof provided herein modulate cellular metastasis. Particular embodiments of the disclosure teach human chimeric mAbs, intrabodies, and cellular immunotherapies that are useful for treating human cancer, such as, for example, breast cancer.

BACKGROUND OF THE DISCLOSURE

Cancer is a multifaceted disease characterized by an increase in the number of abnormal cells derived from a given normal tissue, with these cells typically invading adjacent tissues, or metastasizing, by spreading through the blood or lymphatic system to other regions of the body. Cancer typically progresses through a multistep process that begins with minor preneoplastic changes, which may progress to neoplasia. Neoplastic lesions may develop an increasing capacity for invasion, growth, metastasis, and heterogeneity.

There exists a tremendous variety of cancers, with examples including cancer of the lung, colon, breast, rectum, prostate, brain, and intestine. The incidence of cancer continues to climb as the population ages, as new cancers develop, and as susceptible populations grow. A considerable demand exists for new methods and compositions that can be used to treat patients having cancer.

Present methods of treating cancers are fairly non-selective. Surgery removes the diseased tissue, radiotherapy shrinks solid masses, and chemotherapy kills rapidly dividing cells. Radiation and chemotherapy are associated with a variety of undesirable side effects, such as the non-selective destruction of healthy cells along with cancerous cells.

Accordingly, there remains a need in the art for developing methods of treating cancer, which do not suffer from the drawbacks associated with current treatments. Specifically, there is a great need in the art for the development of highly selective therapeutics that preferentially target metastatic cells and do not destroy healthy cells.

The need for new highly selective cancer therapeutics and treatments are particularly acute with respect to breast cancer. Breast cancer is the most common cancer among American women, except for skin cancers. About 1 in 8 (12%) women in the US will develop invasive breast cancer during their lifetime. The American Cancer Society's estimates for breast cancer in the United States for 2015 are: about 231,840 new cases of invasive breast cancer will be diagnosed in women; about 60,290 new cases of carcinoma in situ (CIS) will be diagnosed (CIS is non-invasive and is the earliest form of breast cancer; and about 40,290 women will die from breast cancer. These are sobering statistics and underscore the great need in the art for the development of new therapeutics and methods for selectively targeting and preventing the spread of breast cancer.

SUMMARY OF THE DISCLOSURE

The present disclosure addresses the aforementioned need in the medical community, by providing, inter alia, novel antibodies and fragments thereof, including monoclonal antibodies (mAbs). In some embodiments, the mAbs selectively target and treat cancer (e.g., human breast cancer). In some embodiments, the antibodies provided herein are intrabodies.

In one aspect, the present disclosure provides antibodies, such as monoclonal antibodies (mAbs) that bind to a filamin-A antigen. The antibodies described herein are in some aspects human chimeric mAbs, which preferentially bind to a filamin-A antigen that is secreted by a mammalian cell, such as a human breast cancer cell. In other aspects, the human chimeric mAbs preferentially bind to a filamin-A antigen that is associated with the cell membrane of a mammalian cell, such as a human breast cancer cell. In some aspects, the antibodies or fragments provided herein are a part of a cell-based immunotherapy (e.g., a chimeric antigen receptor T cell (CAR-T), wherein the antibody or fragment binds to a filamin-A antigen that is associated with the cell membrane of a mammalian cell, such as a human breast cancer cell. In still further aspects, the antibodies taught herein are intrabodies. Thus, in some embodiments, the antibodies may bind to filamin-A antigen within a cell. In some embodiments, the antibodies taught herein may bind to filamin-A antigen within an intracellular vesicle. In further embodiments, the antibodies taught herein may bind to filamin-A antigen within an extracellular microvesicle or exosome.

The disclosure provides not only novel therapeutic mAbs capable of selectively targeting filamin-A antigen from cancer cells, but also teaches pharmaceutical compositions comprising said antibodies, and methods of treating patients with the antibodies. In some embodiments, the antibodies induce antibody-dependent cellular cytotoxicity (ADCC) and/or complement-dependent cytotoxicity (CDC). In some embodiments, the disclosure provides antibodies for delivery of targeted therapeutics to cancer cells that express filamin-A antigen. In further embodiments, the targeted therapeutics are selected from the group consisting of radionucleotides, active therapeutic agents, drugs, chemotherapeutic agents, other antibodies, nanoparticles, and gene therapy vectors. In some embodiments, the disclosure provide antibodies linked or conjugated to a therapeutic agent, wherein the antibody is endocytosed by cancer cells.

In some embodiments, the disclosure provides methods for expressing an intrabody specific for filamin-A antigen within a cell. In further embodiments, the cell is a cancer cell.

In some embodiments, the present disclosure provides an antibody that binds a filamin-A antigen, wherein the antibody comprises a heavy chain CDR3 region according to SEQ ID NO: 18, 19, 20, or 21. Such antibodies may be monoclonal antibodies, antibody fragments, isolated human chimeric antibodies, and/or intrabodies.

In an embodiment, the disclosure provides an antibody, e.g., an isolated human chimeric antibody, humanized antibody, antibody fragment, or intrabody, that binds a filamin-A antigen, comprising: a light chain variable domain comprising three complementarity determining regions (CDRs) CDR1, CDR2, and CDR3. In some embodiments, the light chain CDR1 comprises an amino acid sequence selected from SEQ ID NOs: 12 and 13. In some embodiments, the light chain CDR2 comprises an amino acid sequence of SEQ ID NO: 14. In some embodiments, the light chain CDR3 comprises an amino acid sequence of SEQ ID NO: 15. In some embodiments, the disclosure provides an isolated human chimeric antibody, antibody fragment, or intrabody that binds a filamin-A antigen, comprising: a heavy chain variable domain comprising three complementarity determining regions (CDRs) CDR1, CDR2, and CDR3. In some embodiments, the heavy chain CDR1 comprises an amino acid sequence of SEQ ID NO:16. In some embodiments, the heavy chain CDR2 comprises an amino acid sequence of SEQ ID NO: 17. In some embodiments, the heavy chain CDR3 comprises an amino acid sequence selected from SEQ ID NOs: 18, 19, 20, and 21.

In an embodiment of the disclosed antibodies (e.g., isolated human chimeric antibody, humanized antibody, antibody fragment, or intrabody), the light chain variable domain comprises SEQ ID NO: 1 or SEQ ID NO: 2. In an embodiment, the heavy chain variable domain comprises SEQ ID NO: 4, 5, 6, or 7. In an embodiment, the light chain variable domain comprises SEQ ID NO: 1 and the heavy chain variable region comprises SEQ ID NO: 4. In an embodiment, the light chain variable domain comprises SEQ ID NO: 1 and the heavy chain variable region comprises SEQ ID NO: 5. In an embodiment, the light chain variable domain comprises SEQ ID NO: 1 and the heavy chain variable region comprises SEQ ID NO: 6. In an embodiment, the light chain variable domain comprises SEQ ID NO: 1 and the heavy chain variable region comprises SEQ ID NO: 7. In an embodiment, the light chain variable domain comprises SEQ ID NO: 2 and the heavy chain variable region comprises SEQ ID NO: 4. In an embodiment, the light chain variable domain comprises SEQ ID NO: 2 and the heavy chain variable region comprises SEQ ID NO: 5. In an embodiment, the light chain variable domain comprises SEQ ID NO: 2 and the heavy chain variable region comprises SEQ ID NO: 6. In an embodiment, the light chain variable domain comprises SEQ ID NO: 2 and the heavy chain variable region comprises SEQ ID NO: 7.

In an embodiment of the disclosed antibodies (e.g., isolated human chimeric antibody, humanized antibody, antibody fragment, or intrabody), the light chain constant domain comprises SEQ ID NO:3; and the heavy chain constant domain comprises SEQ ID NO:11.

In some embodiments, the antibody is an scFv comprising a light chain variable domain comprising SEQ ID NO: 1 or 2 and a heavy chain variable domain comprising SEQ ID NO:4, 5, 6, or 7. In further embodiments, the antibody is an scFv comprising a light chain variable domain comprising SEQ ID NO: 2 and a heavy chain variable domain comprising SEQ ID NO: 7. In some embodiments, the scFv antibody is an intrabody.

In an embodiment of the disclosed antibodies (e.g., isolated human chimeric antibody, humanized antibody, antibody fragment or intrabody), the light chain variable domain comprises SEQ ID NO:1 or 2 and the light chain constant domain comprises SEQ ID NO:3 and the heavy chain variable domain comprises SEQ ID NO:4, 5, 6, or 7 and the heavy chain constant domain comprises SEQ ID NO:11. In some embodiments, the disclosed isolated human chimeric antibody comprises a light chain variable domain comprising SEQ ID NO: 2, a light chain constant domain comprising SEQ ID NO:3, a heavy chain variable domain comprising SEQ ID NO: 7, and a heavy chain constant domain comprising SEQ ID NO:11.

In some embodiments, the antibody or intrabody comprises light and heavy chain variable regions provided herein, wherein the variable regions are in a light-heavy orientation. Thus, in some embodiments, the light chain variable region is located amino terminal to the heavy chain variable region. In further embodiments, the antibody or intrabody comprises, from amino to carboxy terminus, a light chain variable region and a heavy chain variable region. In further embodiments, the antibody or intrabody comprise, from amino to carboxy terminus, a light chain variable region, a linker, and a heavy chain variable region.

In some embodiments, the antibody or intrabody comprises light and heavy chain variable regions provided herein, wherein the variable regions are in a heavy-light orientation. Thus, in some embodiments, the heavy chain variable region is located amino terminal to the light chain variable region. In further embodiments, the antibody or intrabody comprises, from amino to carboxy terminus, a heavy chain variable region and a light chain variable region. In further embodiments, the antibody or intrabody comprise, from amino to carboxy terminus, a heavy chain variable region, a linker, and a light chain variable region. In an aspect, the filamin-A antigen is a gene product encoded by the FLNA gene, or a homologue thereof. In some embodiments, the filamin-A antigen is intracellular. In some embodiments, the filamin-A antigen is secreted by a cell, such as a cancer cell. In some embodiments, the filamin-A antigen is associated with a cell surface, for example a cell membrane associated filamin-A antigen. In another aspect, the filamin-A antigen is attached to and/or associated with a cell associated structure such as a membrane or vesicle. Thus, in some embodiments, the antibodies provided herein may bind intracellular filamin-A antigen. In some embodiments, the filamin-A antigen is attached to and/or associated with a microvesicle. In some embodiments, the filamin-A antigen is attached to and/or associated with an exosome or other multicomponent complex. In some embodiments, the filamin-A antigen is a fragment. In an aspect, the filamin-A antigen is an approximately 280-kDa breast cancer cell secreted soluble filamin-A antigen.

In some embodiments, the antibody provided herein is capable of preferentially binding filamin-A antigen, or a fragment thereof, wherein said preferential binding is relative to a non-breast cancer filamin-A antigen. In some embodiments, the breast cancer cell filamin-A antigen is a soluble filamin-A antigen. In some embodiments, the breast cancer cell filamin-A antigen is associated with a cell surface. In some embodiments, the breast cancer cell filamin-A antigen is incorporated into a microvesicle, such an exosome or a multicomponent complex. In some embodiments, the breast cancer cell filamin-A antigen is found in secreted soluble form and in association with and/or attached to a cell surface and/or a vesicle.

In some embodiments, the antibody is capable of binding to filamin-A antigen with a specific affinity of between about $10^{-5}$ M and about $10^{-12}$ M. In further embodiments, the antibody is capable of binding to filamin-A antigen with a specific affinity of between about $10^{-7}$ M and about $10^{-11}$ M. In further embodiments, the antibody is capable of binding to filamin-A antigen with a specific affinity of between about $10^{-8}$ M and about $10^{-11}$ M.

Also taught herein are isolated polynucleotide DNA sequences encoding the antibodies provided herein. For example, the present disclosure provides isolated polynucleotide DNA sequences encoding human, chimeric, or humanized antibodies provided herein. Also provided herein are vectors comprising the polynucleotide DNA sequences encoding the antibodies provided herein. Also provided herein are host cells comprising said vectors. In some embodiments, the present disclosure provides an isolated nucleic acid encoding an intrabody provided herein. In some embodiments, the isolated nucleic acid is a polynucleotide DNA sequence. In some embodiment, the nucleic acid is an RNA sequence. In some embodiments, the present disclosure provides an RNA encoding an intrabody provided herein, wherein the intrabody encoded by the RNA is transiently expressed in transfected cells.

The disclosure provides methods of producing an isolated human chimeric antibody directed to filamin-A, comprising: culturing a host cell having a vector to express said antibody, expressing the antibody, and recovering the antibody expressed by the host cell.

The disclosure provides compositions and methods for producing an intrabody directed to filamin-A, compositions and methods for delivering an intrabody gene or protein to a target cell, and compositions and methods for delivering an intrabody gene or protein to a particular subcellular location within a cell. The disclosed methods include delivery via a recombinant virus, a non-viral gene delivery method (nanocarrier delivery system, such as a polymer or cationic lipid delivery system), or other plasmid or transposon system via a mechanical delivery technology, and delivery using a cell membrane-penetrating peptide or protein. Thus, the present disclosure provides compositions comprising a nanocarrier and an intrabody provided herein; and an intrabody fused or linked to a cell penetrating peptide or chemical moiety. In some embodiments, the non-viral vector is a transposable element, or transposon. In further embodiments, the non-viral vector comprises a sleeping beauty transposon, piggyBac transposon, or any other transposon known in the art. In some embodiments, the disclosed methods include delivery via a gene editing system. For example, in some embodiments, the disclosed methods include delivery via (i) clustered, regularly interspaced, palindromic repeats (CRISPR)-associated (Cas) system; (ii) a transcription activator-like effector nuclease (TALEN) system; or (iii) a zinc finger nuclease (ZFN) system.

In some embodiments, the disclosure provides a plasmid comprising a gene encoding an intrabody provided herein. In some embodiments, the plasmid is bacterial, or originated in bacteria, or is derived from non-bacterial sources such as, for example, fungi, algae, or plants. In some embodiments, the nucleic acid is a plasmid comprising a eukaryotic promotor to drive expression of the intrabody. In further embodiments, the plasmid comprises a CMV promoter.

In some embodiments, the methods include delivery of the intrabody with a sequence for targeting the intrabody to a subcellular structure. Subcellular structures to which the intrabody may be targeted include, for example, the nucleus, endoplasmic reticulum (ER), golgi apparatus, mitochondria, or lysosomes. In some embodiments, the nucleic acid may be stably or transiently expressed in the cell. In some embodiments, stable expression means that the nucleic acid has integrated into the cellular genome; in some embodiments, transient expression means that the transfected gene is expressed for a limited period of time. In some embodiments, RNA, siRNA, miRNA, or mRNA is used to effect transient expression of the intrabody in the cell.

In some aspects, the taught antibodies are immobilized on a solid phase. In some aspects, the taught antibodies are detectably labeled. In some aspects, the antibodies provided herein are conjugated to a drug, such as a cytotoxic drug. Thus, in some embodiments, the present disclosure provides antibody-drug conjugates. In some embodiments, the antibody-drug conjugates provided herein are internalized via endocytosis. In some aspects, the taught antibodies are conjugated to a radionuclide, or active therapeutic agent, or drug, or chemotherapeutic agent, or protein, or other antibody.

The disclosure also provides for pharmaceutical compositions, comprising: an antibody provided herein, (e.g., the isolated human chimeric antibody specific for filamin-A antigen); and a pharmaceutically acceptable carrier. In some embodiments, the disclosure provides a pharmaceutical composition comprising an intrabody provided herein (e.g., an intrabody specific for filamin-A antigen), or a delivery system comprising a gene or nucleic acid encoding an intrabody provided herein. For example, in some embodiments, the disclosure provides a pharmaceutical composition comprising a DNA or RNA encoding an intrabody provided herein. In some embodiments, the delivery system comprising a gene or nucleic acid encoding an intrabody provided herein is a non-viral or a viral delivery system. For example, in some embodiments, the viral delivery system is a lentiviral vector or an adenoviral vector. In some embodiments, the pharmaceutical composition further comprises a gene or protein for targeted delivery of an intrabody to a subcellular location. In some embodiments, the disclosure provides a pharmaceutical composition comprising a cell expressing a chimeric antigen receptor (CAR), wherein the CAR comprises a filamin-A binding domain provided herein.

The disclosure also teaches a kit for diagnosing human cancer, comprising: an antibody provided herein (e.g., the isolated human chimeric antibody specific for filamin-A antigen, and/or the intrabody specific for filamin-A antigen); and a secondary antibody that binds to the antibody, wherein the secondary antibody is conjugated to a detectable label. For example, in some embodiments, the disclosure provides a kit for diagnosing human breast cancer comprising an isolated human chimeric antibody specific for filamin-A antigen and a secondary antibody conjugated to a detectable label.

Also taught herein are methods for diagnosing cancer in a patient, comprising: obtaining a biological sample from a patient; contacting the biological sample with an antibody provided herein (e.g., the isolated human chimeric antibody specific for filamin-A antigen, and/or the intrabody specific for filamin-A antigen); and detecting whether the antibody binds to a cancer cell secreted soluble filamin-A antigen, and/or binds to a cancer cell membrane associated or bound filamin-A antigen and/or binds to an intracellular filamin-A antigen, wherein a positive binding interaction between said antibody and filamin-A antigen is indicative of cancer. In further embodiments, the cancer is human breast cancer.

The disclosure also provides for methods of treating cancer in a patient, comprising: administering an effective amount of an antibody provided herein. For example, the disclosure provides methods of treatment comprising administering the isolated human chimeric antibody specific for filamin-A antigen, and/or the intrabody specific for filamin-A antigen, and/or an immune cell comprising a CAR comprising a filamin-A antibody or fragment thereof (e.g., a filamin-A binding domain) provided herein to a patient in need thereof. In further embodiments, the cancer is human breast cancer. In some embodiments, the antibody provided herein binds to cancer cells and induces complement-dependent cytotoxicity (CDC) and/or antibody-dependent cellular cytotoxicity (ADCC).

Furthermore, the disclosure teaches a method for preventing or reducing the growth of cancer tumor cells, expressing filamin-A antigen, comprising: administering to a human patient in need thereof, an effective amount of an antibody provided herein. In some embodiments, the method comprises administering an antibody comprising a light chain CDR1 selected from SEQ ID NOs: 12 and 13; a light chain CDR2 of SEQ ID NO: 14; a light chain CDR3 of SEQ ID NO: 15; a heavy chain CDR1 of SEQ ID NO: 16; a heavy chain CDR2 of SEQ ID NO: 17; and/or a heavy chain CDR3 selected from SEQ ID NOs: 18, 19, 20, and 21. In certain embodiments, said antibody comprises a light chain CDR1, CDR2, and CDR3 according to SEQ ID NOs: 13, 14, and 15, respectively; and a heavy chain CDR1, CDR2, and CDR3 according to SEQ ID NOs: 16, 17, and 21, respectively. In some embodiments, said antibody comprises a light chain variable region comprising SEQ ID NO: 2 and a heavy chain variable region comprising SEQ ID NO: 7.

In some embodiments, the antibody preferentially binds a mammalian cancer cell (such as a breast cancer cell) secreted soluble filamin-A antigen, relative to a non-cancer cell secreted soluble filamin-A antigen. In some embodiments, the antibody preferentially binds a filamin-A antigen that is intracellular and/or located in a vesicle, such as an exosome.

In some embodiments, the antibody is a monoclonal antibody. In some embodiments, antibody is a human chimeric antibody. In some embodiments, the antibody is a humanized antibody. In some embodiments, the antibody is a fully human antibody. In some embodiments, the antibody is an intrabody.

In some embodiments, the antibody is a bispecific antibody or a multispecific antibody. In some embodiments, the bispecific or multispecific antibody comprises a first antibody provided herein that binds to filamin-A antigen, and a second antibody that binds to an antigen on an immune cell. The immune cell, in some embodiments, is selected from a T cell, B cell, NK cell, macrophage, monocyte, or dendritic cell. In some embodiments, the antigen is a T cell antigen. In some embodiments, the T cell antigen is selected from the group consisting of CD3, CD2, CD4, CD5, CD6, CD8, CD25, CD28, CD30, CD40, CD40L, CD44, CD45, CD69, and CD90. In some embodiments, the antibody is a bispecific antibody that binds to filamin-A antigen and CD3.

In further embodiments, the isolated human chimeric antibody exhibits reduced immunogenicity, as compared to a murine antibody directed to filamin-A, and does not lead to a negative immune response from a patient administered the antibody. In other embodiments, the disclosed antibodies are humanized to further reduce the immunogenicity of said antibodies. In other aspects, the antibodies have their immunogenicity decreased by other methods besides humanizing, for example by "deimmunizing" the antibodies.

BRIEF DESCRIPTION OF THE DRAWINGS

FIG. 1: Results of motility assays, as reported in RFU. The results are presented as the motility of MDA-MB-231 and HEK-293 cells in the presence of a number of experimental treatments and controls displayed along the left side of the figure.

FIG. 15: Immunofluorescence micrograph of MDA-MB-231 cancer cells stained with DAPI DNA stain, mouse filamin-A antibody with DYLIGHT 488 stain, and beta actin rabbit antibody with rhodamine stain.

Figure 28:
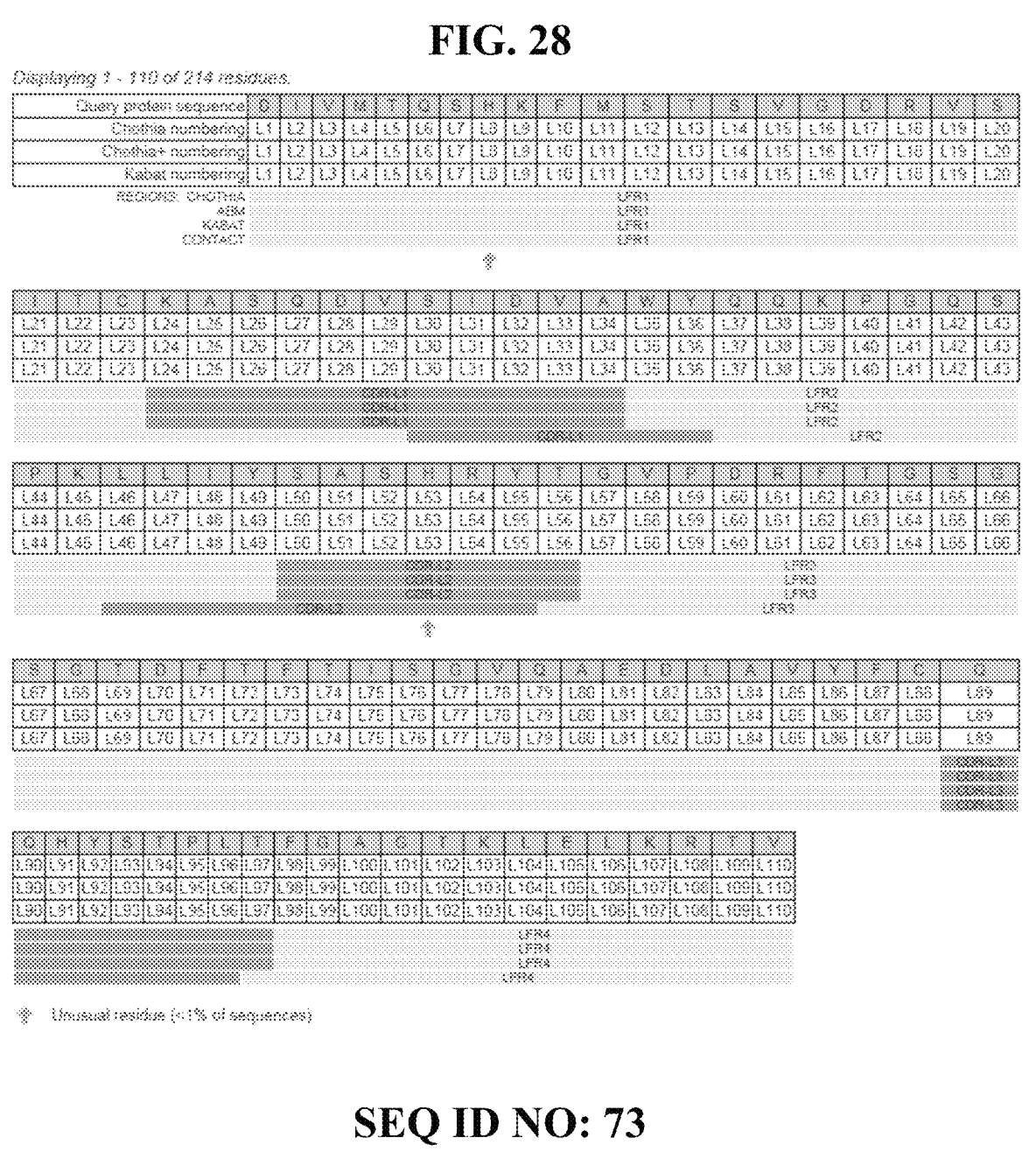

FIG. 28: SEQ ID NO: 73 with depiction of residue alignments amongst CDR regions as predicted by Chothia, ABM, Kabat, and Contact systems utilizing the Abysis database; predicted CDR regions for human chimeric light chain variable CDR binding domain regions.

FIG. 31: SEQ ID NO: 24 with depiction of residue alignments amongst CDR regions as predicted by Chothia, ABM, Kabat, and Contact systems utilizing the Abysis database; predicted CDR regions for murine heavy chain variable CDR binding domain regions.

FIG. 34: Histograms of GFP expression in A549 cells at 72 hr post-infection. FIG. 34A shows mock transfected cells. FIGS. 34B, 34C, and 34D show LV-GFP, LV-FLNA_1-GFP, and LV-FLNA 2-GFP transfected cells, respectively.

FIG. 35: Histograms of CDR (Calcein Deep Red) in transfected A549 cells 72 hours after transfection (live cell analysis of GFP gated cells). FIG. 35A is unstained control. FIG. 35B is positive control FIGS. 35C, 35D, and 35E are LV-GFP, LV-FLNA 1-GFP, and LV-FLNA 2-GFP transfected cells, respectively.

FIG. 37: Histograms of EthD-1 in transfected A549 cells 72 hours after transfection (dead cell analysis of GFP gated cells). FIG. 37A is unstained control. FIG. 37B is positive control.

FIGS. 37C, 37D, and 37E are LV-GFP LV-FLNA_1-GFP, and LV-FLNA_2-GFP transfected, respectively.

FIG. 39A is unstained control; FIGS. 39B, 39C, and 39D are LV-GFP, LV-FLNA 1-GFP, and LV-FLNA_2-GFP transfected, respectively. FIG. 39E is a statistical analysis of FIG. 39A-D (n=3; student's t-test, two-tail unpaired). Total acquisition events (cell #) for each group: 10,000.

FIG. 40A (top panel, A1): LV-GFP, FIG. 40A (bottom panel, A2): Bright field of A1. FIG. 40B (top panel, B1): LV-FLNA_2-GFP; FIG. 40B (bottom panel, B2): Bright field of B1. FIG. 40C (top panel, C1: LV-FLNA_1-GFP; FIG. 40C (bottom panel, C2): Bright field of C1. FIG. 40D (top and middle panels, D1 and D2): Selected views (white rectangle) zoomed-in from C1 or C2. FIG. 40D (bottom panel, D3): A merged view of D1 and D2. The white arrows suggests co-expression of FLNA with GFP in the A549 cells.

Merge of both histograms. Arrows pointing to left-most peak indicate peak of EthD-1 positive cells (dead cells); arrows pointing to right-most peak indicate the absence of Calcein AM positive (live cells) after treatment by FLNA_1/2 as compared to LV-GFP; arrows pointing to middle peak indicate cells with intermediate signals of Calcein AM in FLNA-treated cells. Total acquisition on event (cell #) for each group: 50,000.

Figure 42:
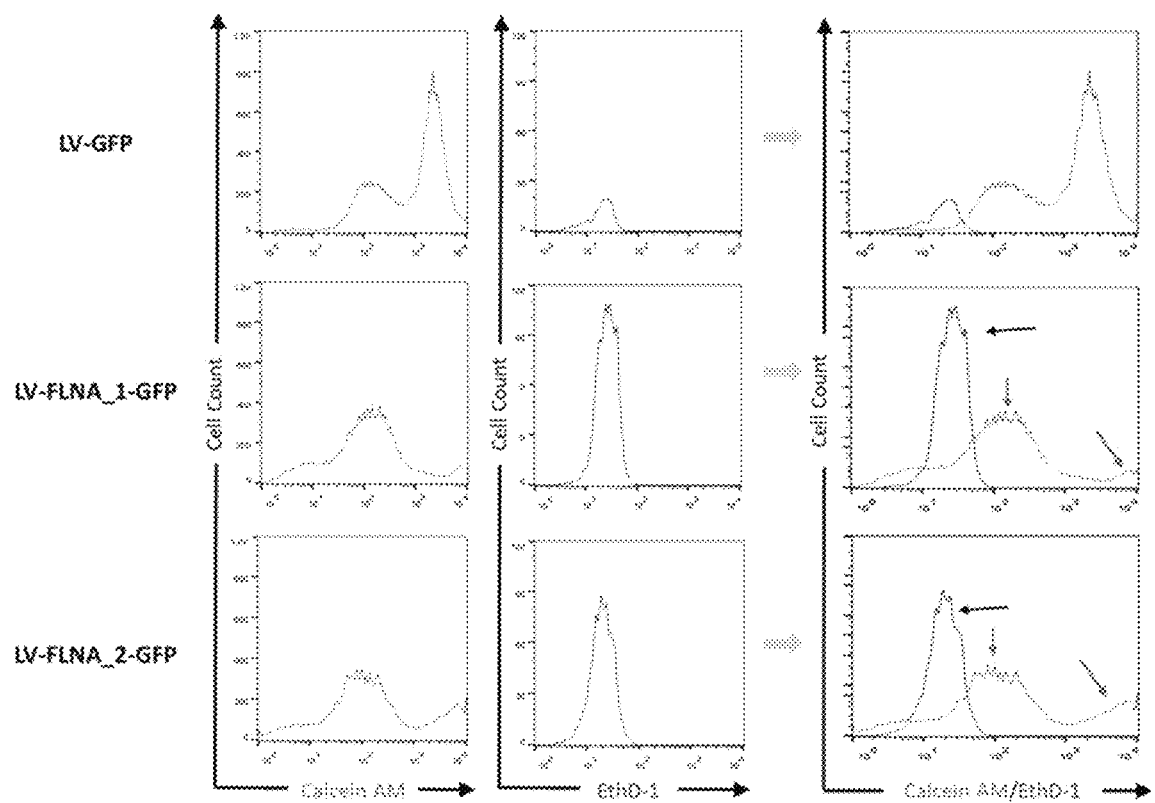
FIG. 42: Cell viability assays on U87MG cells treated by Filamin A (FLNA) intrabody: Calcein AM (live cells) and EthD-1 (dead cells) analysis. Expression of FLNA intrabody in U87MG cells results in decreased cell viability. Left panel: Histogram of Calcein AM staining (green); Middle panel: Histogram of EthD-1 staining (red); Right panel.
Figure 43:
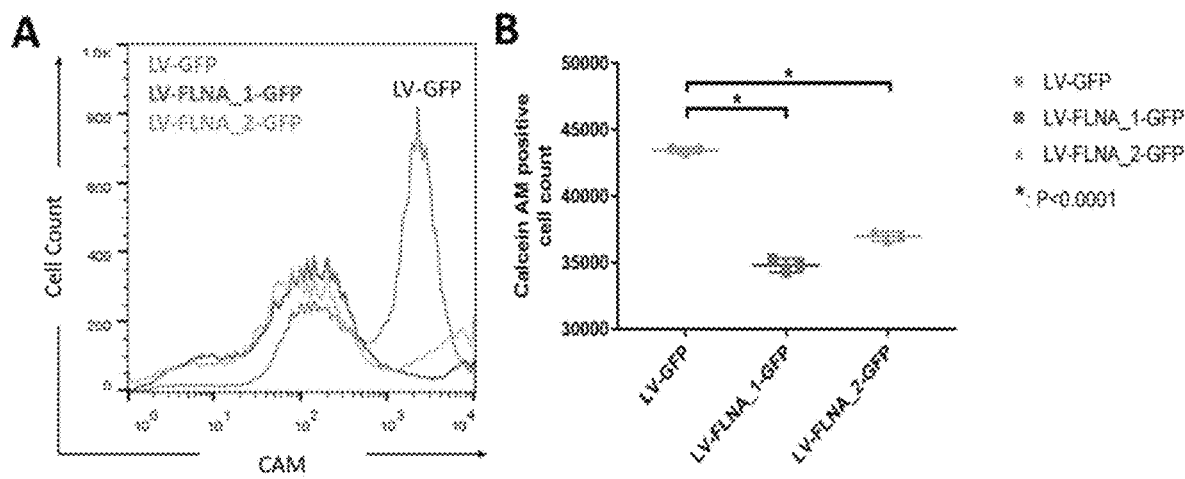

FIG. 43: Cell viability assays on U87MG cells treated by Filamin A (FLNA) intrabody: summary of live cell analysis. FIG. 43A: Merged histograms of Calcein AM (live cells) from FIG. 42 (left panel); FIG. 43B: Statistical analysis of A (n=3; student's t-test, two-tail unpaired). Total acquisition events (cell #) for each group: 50,000.

Figure 44:
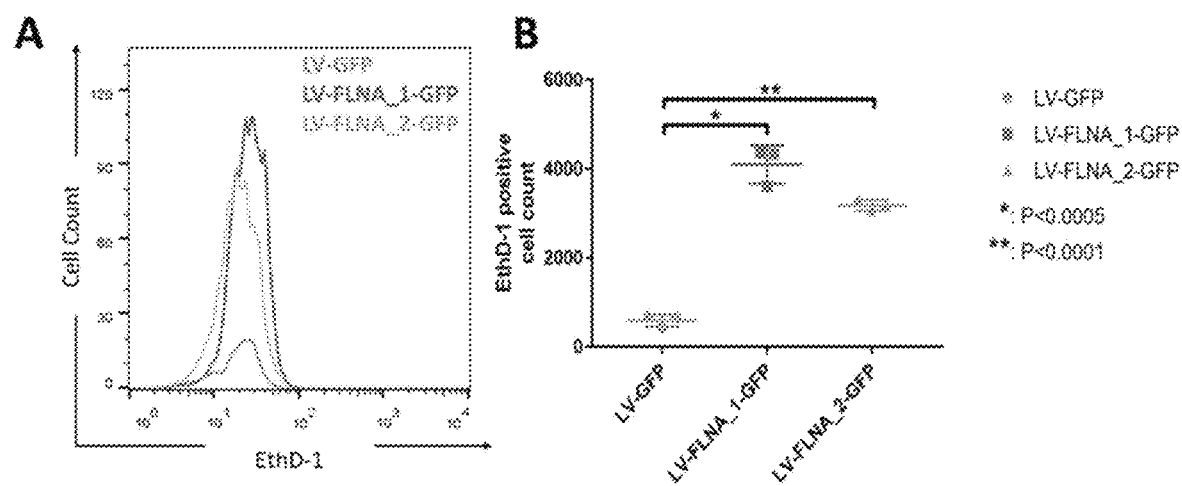

FIG. 44: Cell viability assays on U87MG cells treated by Filamin A (FLNA) intrabody: summary of dead cell analysis. FIG. 44A: Merged histograms of EthD-1 (dead cells) from FIG. 42 (middle panel); FIG. 44B: Statistical analysis of A (n=3; student's t-test, two-tail unpaired). Total acquisition events (cell #) for each group: 50,000.

Figure 45:
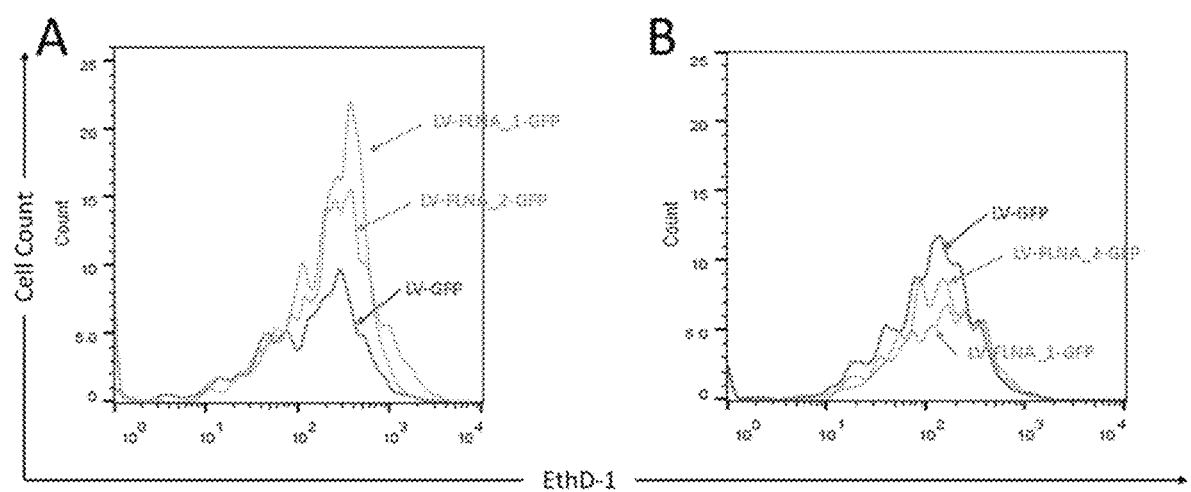

FIG. 45: FLNA intrabody treatment results in cell death in LN229 cells but not HBEC-5i cortical epithelial cells 72 hours post-transfection. FIG. 45A: Histogram of EthD-1 staining (GFP gated) in LN229 cells transfected with the indicated constructs. FIG. 45B: Histogram of EthD-1 staining (GFP gated) in HEBC-5i transfected with the indicated constructs. There are no significant differences among of treated groups compared with control groups in panel B. (Total acquisition time: 30 seconds for each group).

Figure 46:
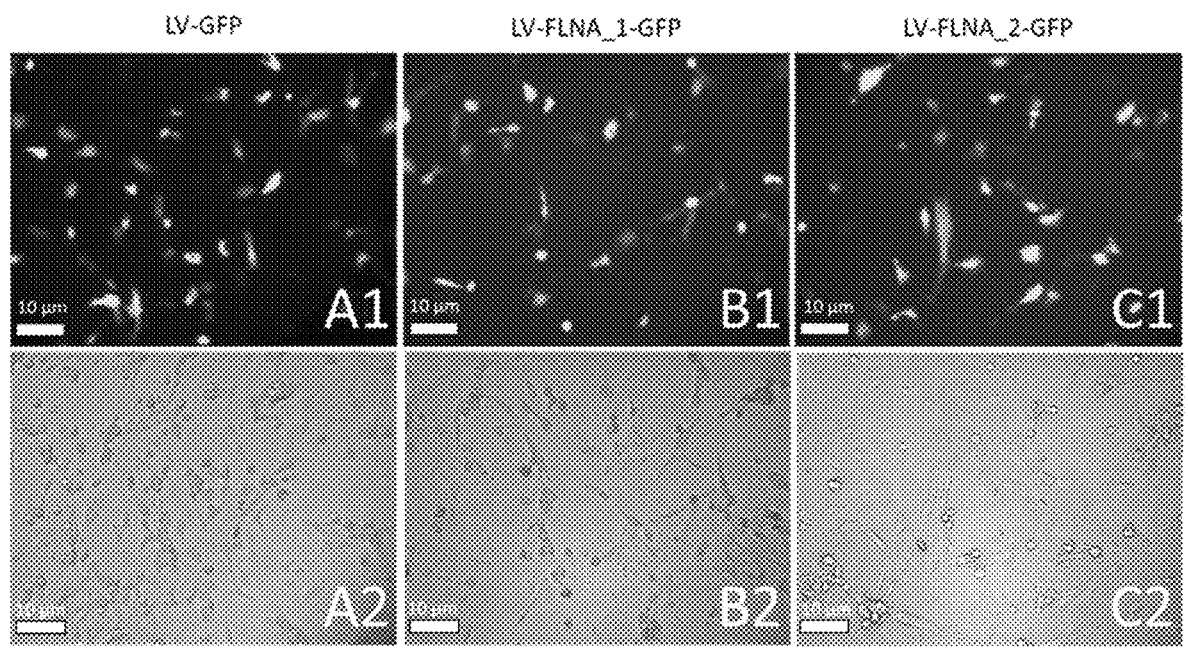

FIG. 46: Microscopy studies on U87MG cells after treatment with FLNA intrabody; observations at 24 hours post-transfection. FIG. 46A top panel (A1): LV-GFP, FIG. 46A bottom panel (A2): bright-field of A1, FIG. 46 top panel (B1): LV-FLNA_1-GFP, FIG. 46 bottom panel (B2): bright-field of B1, FIG. 46C top panel (C1): LV-FLNA_2-GFP FIG. 46C bottom panel (A2): bright-field of C1.

Figure 47:
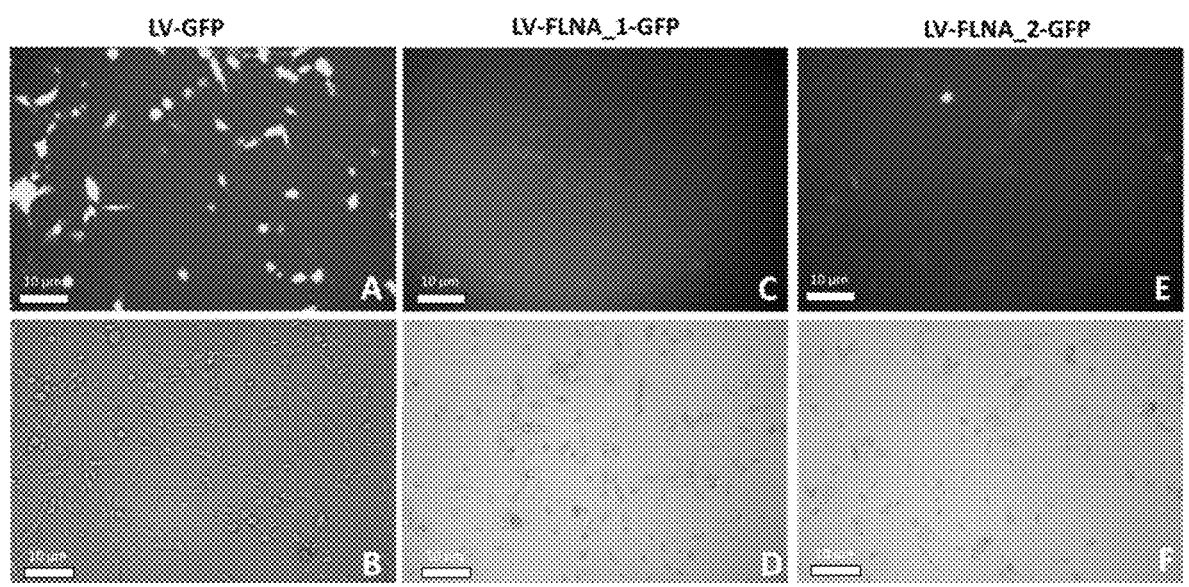

FIG. 47: Microscopy studies on U87MG cells after treatment with FLNA intrabody; observations at 72 hours post-transfection. FIG. 47A: LV-GFP, FIG. 47B: bright-field of 47A, FIG. 47C: LV-FLNA 1-GFP, FIG. 47D: bright-field of 47C, FIG. 47E: LV-FLNA 2-GFP, FIG. 47E: bright-field of 47E.

Figure 48:
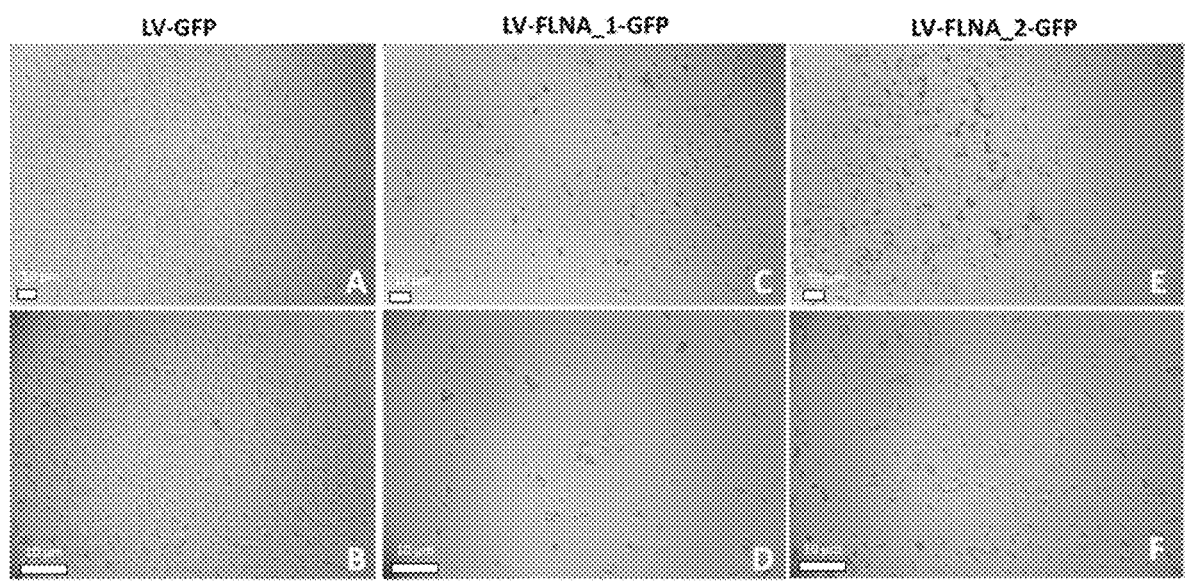

FIG. 48: Microscopy studies on U87MG cells after treatment with FLNA intrabody; observations at 72 hours post-transfection. Bright field images of U87MG cells transfected with the indicated constructs. FIGS. 48A,B: LV-GFP; FIGS. 48C,D: LV-FLNA_1-GFP; FIGS. 48E,F: LV-FLNA 2-GFP. 48A, 48C, 48E were taken at 4× magnification while 48B, 48D, 48F were taken at 10× magnification.

Figure 49:
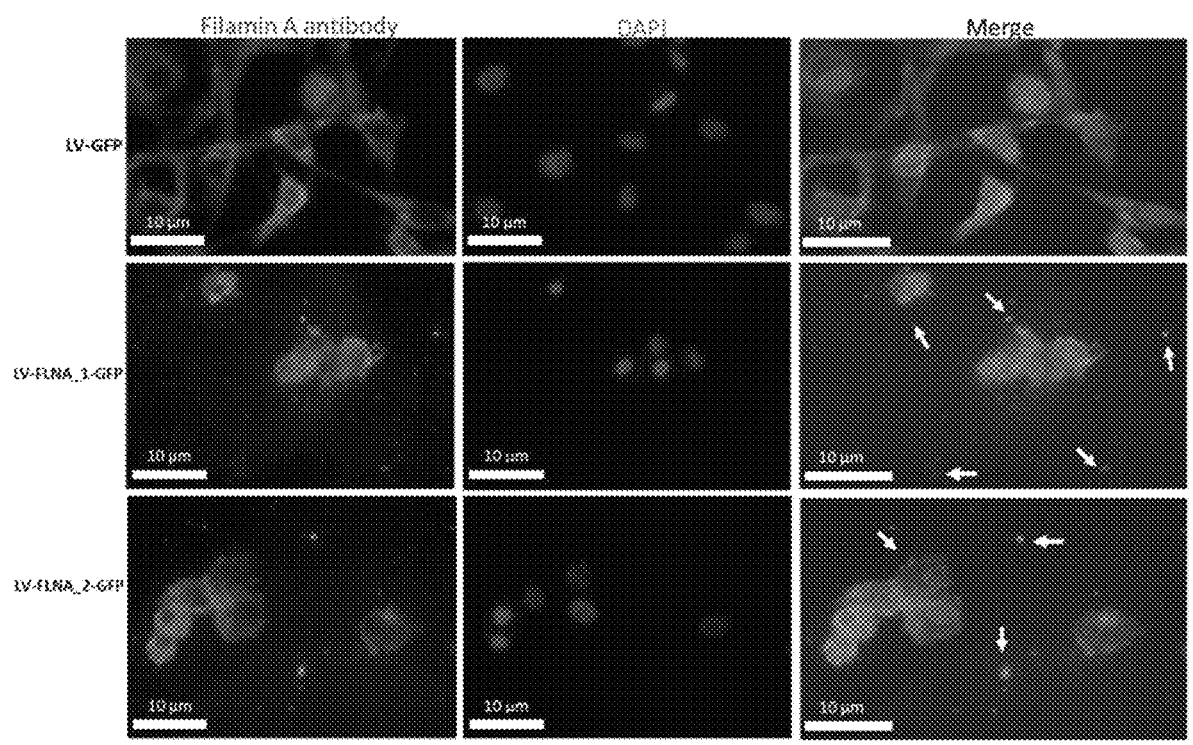

FIG. 49: Analysis of FLNA in U87MG cells treated with FLNA intrabodies by immunocytochemistry (ICC). U87MG cells treated with FLNA intrabody 72 hours after transfection show disruption in FLNA protein by ICC analysis. Left column of panels: FLNA staining in U87MG cells treated with LV-GFP (top row), FLNA_1 (middle row), and FLNA_2 (bottom row). Middle column of panels: DAPI nuclear staining. Right column of panels: Merged images; arrows indicate extracellular FLNA debris.

Figure 50:
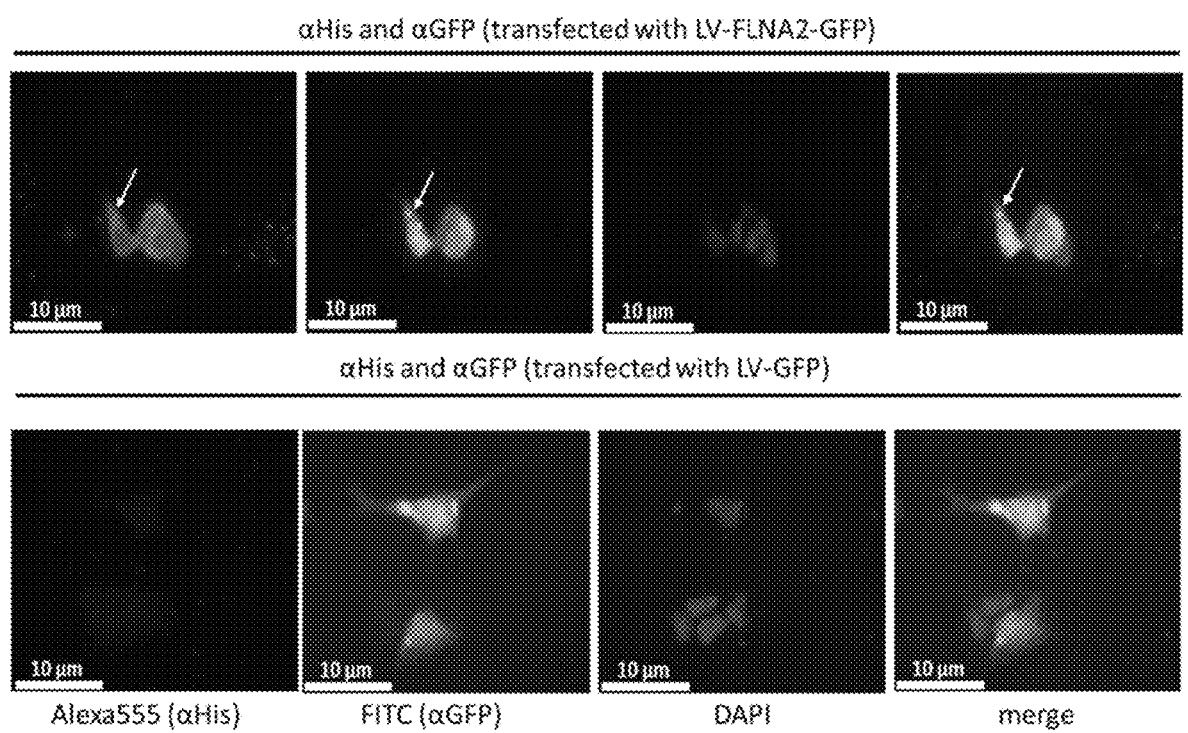

FIG. 50: Analysis of FLNA scFv in U87MG cells transfected with FLNA intrabody. U87MG cells were treated with LV-FLNA_2-GFP intrabody (top row of panels) and LV-GFP (lower row of panels). At 48 hours post-transfection, FLNA intrabody was detected by anti-His-tag antibody (R&D Systems) with anti-mouse IgG secondary antibody conjugated to Alexa555 (1:200, ThermoFisher) (first panel). The expression of GFP was confirmed by anti-GFP antibody (R&D Systems) (second panel). DAPI staining is shown in the third panel, and the fourth panel is a merged image. All images were taken with the same microscope settings. The white arrows indicate co-expression of FLNA intrabody and GFP.

Figure 51:
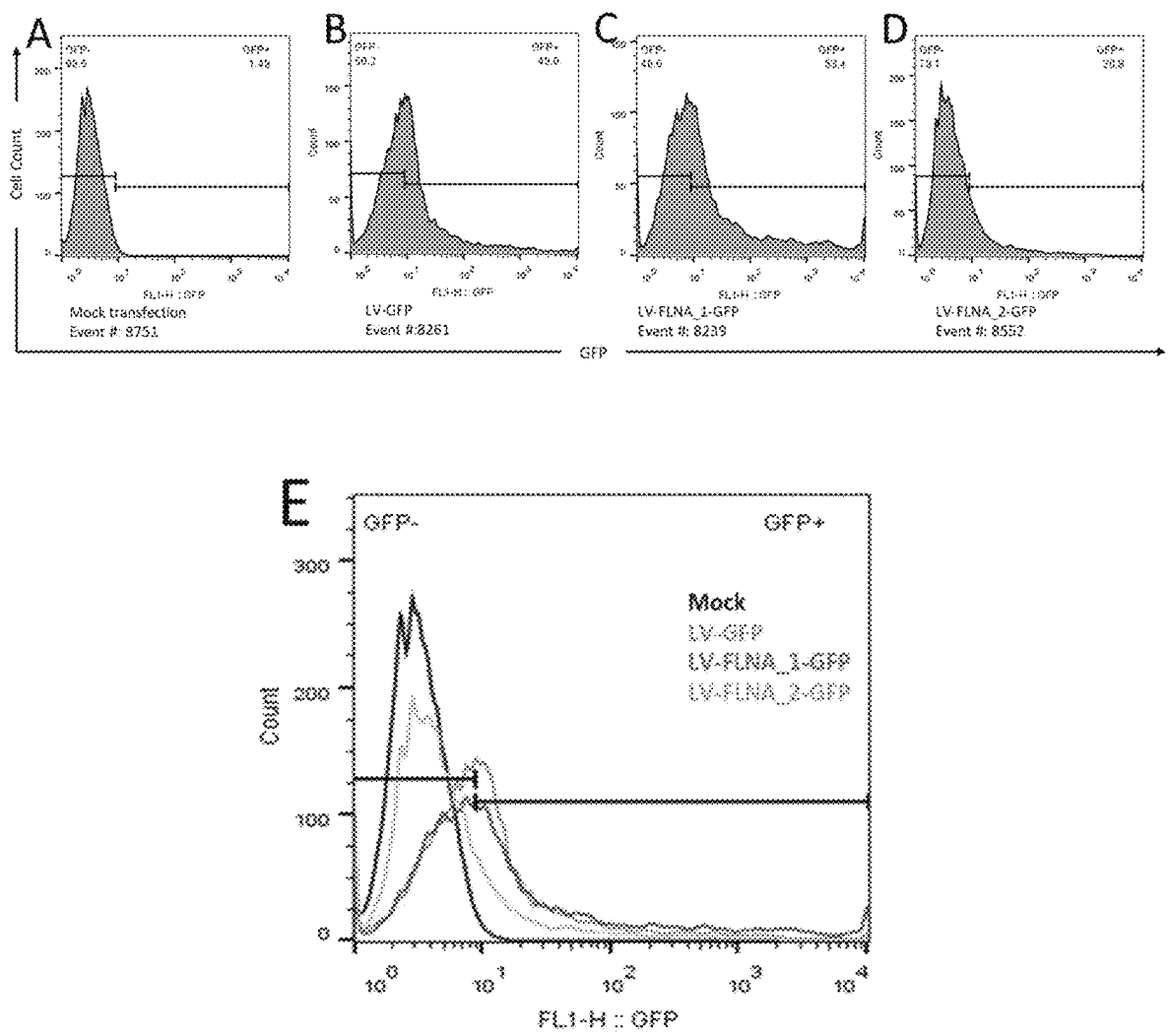

FIG. 51: Cell viability assays on DU145 cells treated with Filamin A intrabody: GFP expression at 72 hours post-transfection. FIG. 51A, mock transfection. FIG. 51B, LV-GFP transfection. FIG. 51C, LV-FLNA_1-GFP transfection. FIG. 51D, LV-FLNA_2-GFP transfection. FIG. 51E, merge of 51A-D. Total ungated acquisition events (cell #) for each group: 10,000.

Figure 52:
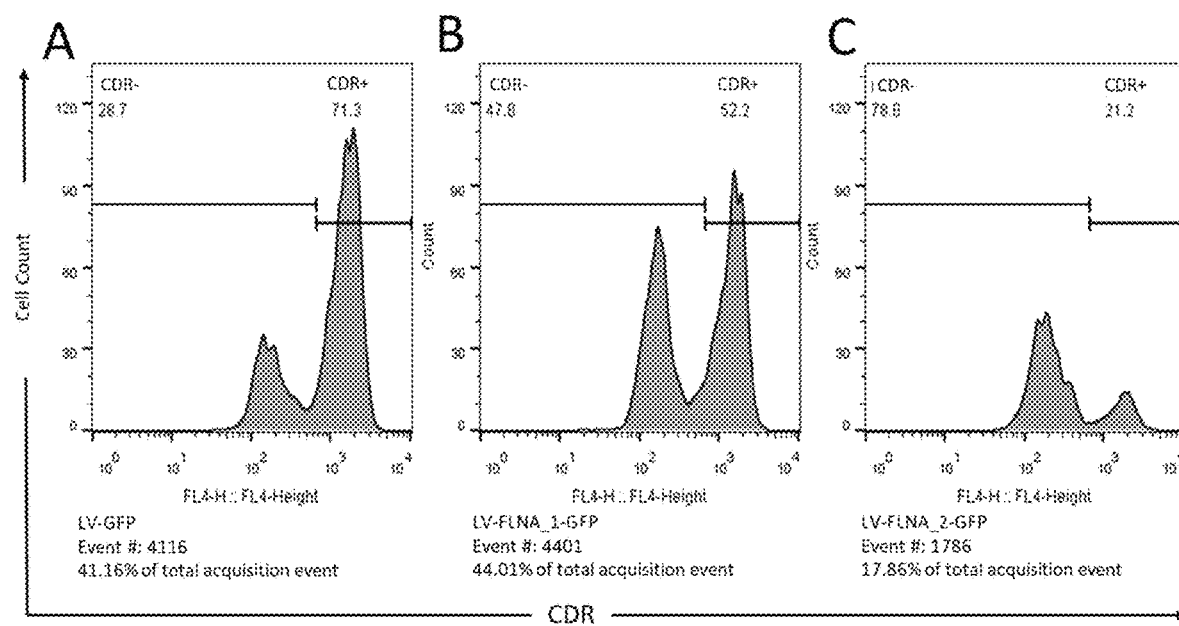

FIG. 52: Cell viability assays on DU145 cells treated by Filamin A (FLNA) intrabody: live cell analysis by Calcein Deep Red (CDR) (GFP gated cells). FIG. 52A: LV-GFP transfected. FIG. 52B: LV-FLNA_1-GFP transfected; FIG. 52C: LV-FLNA_2-GFP transfected. Total ungated acquisition events (cell #) for each group: 10,000.

Figure 53:
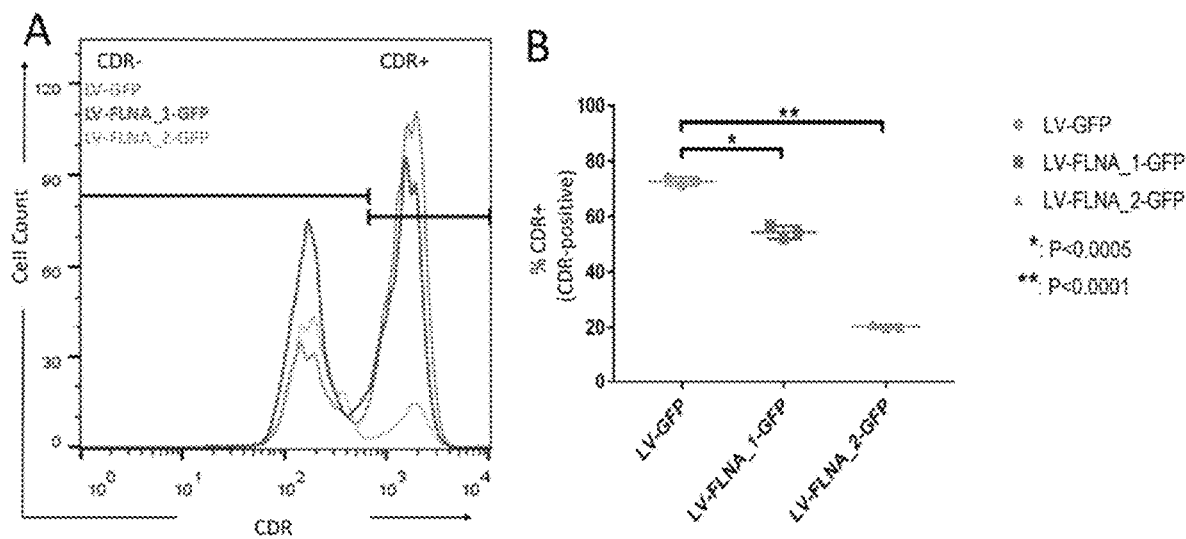

FIG. 53: Cell viability assays on DU145 cells treated by Filamin A (FLNA) intrabody: summary of live cell analysis. FIG. 53A: Merged histograms of Calcein AM (live cells) from FIG. 52A-C. FIG. 53B: Statistical analysis of FIG. 53A (n=3; student's t-test, two-tail unpaired). Total acquisition events (cell #) for each group: 50,000.

Figure 54:
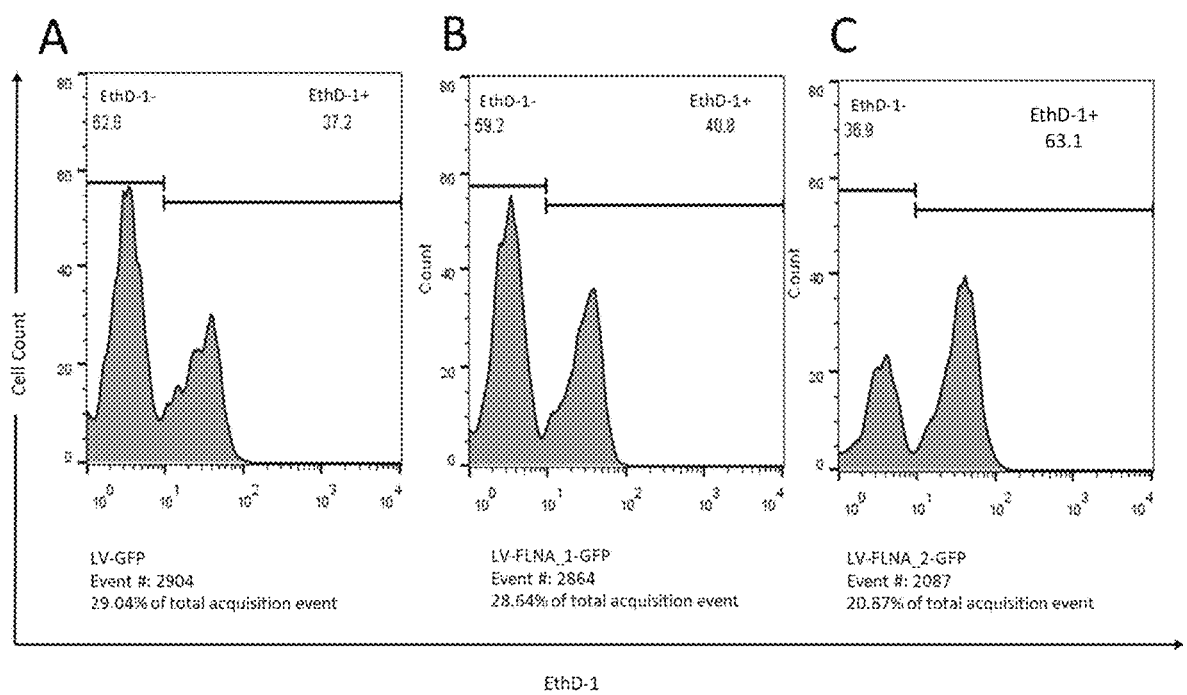

FIG. 54: Cell viability assays on DU145 cells treated by Filamin A (FLNA) intrabody: dead cell analysis by EthD-1 staining (GFP gated cells). FIG. 54A: LV-GFP transfected. FIG. 54B: LV-FLNA_1-GFP transfected; FIG. 54C: LV-FLNA_2-GFP transfected. Total ungated acquisition events (cell #) for each group: 10,000.

Figure 55:
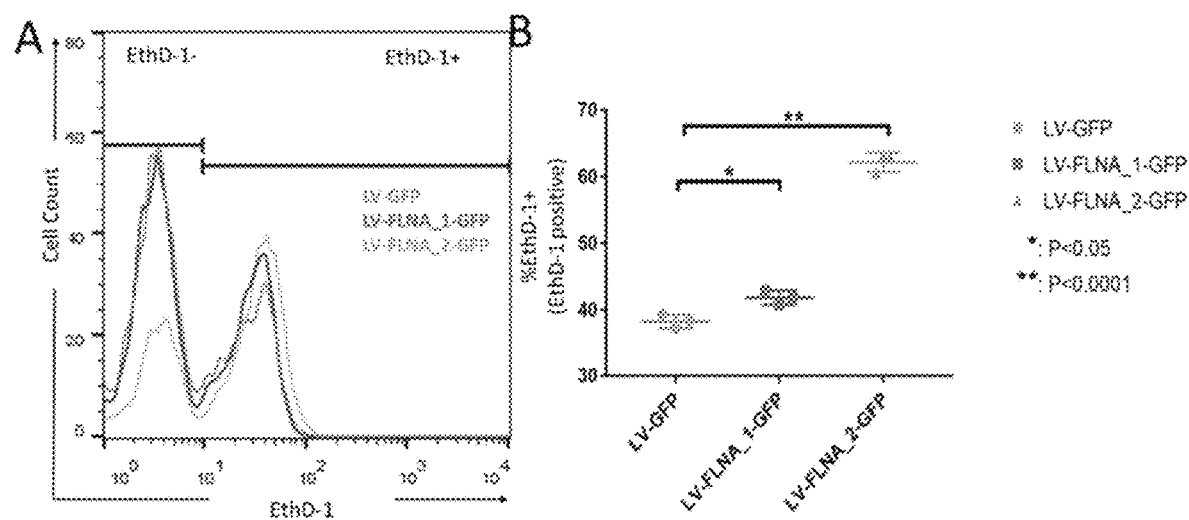

FIG. 55: Cell viability assays on DU145 cells treated by Filamin A (FLNA) intrabody: summary of dead cell analysis. FIG. 55A: Merged histograms of EthD-1 (dead cells) from FIG. 54A-C; FIG. 55B: Statistical analysis of 55A (n=3; student's t-test, two-tail unpaired). Total acquisition events (cell #) for each group: 50,000.

Figure 56:
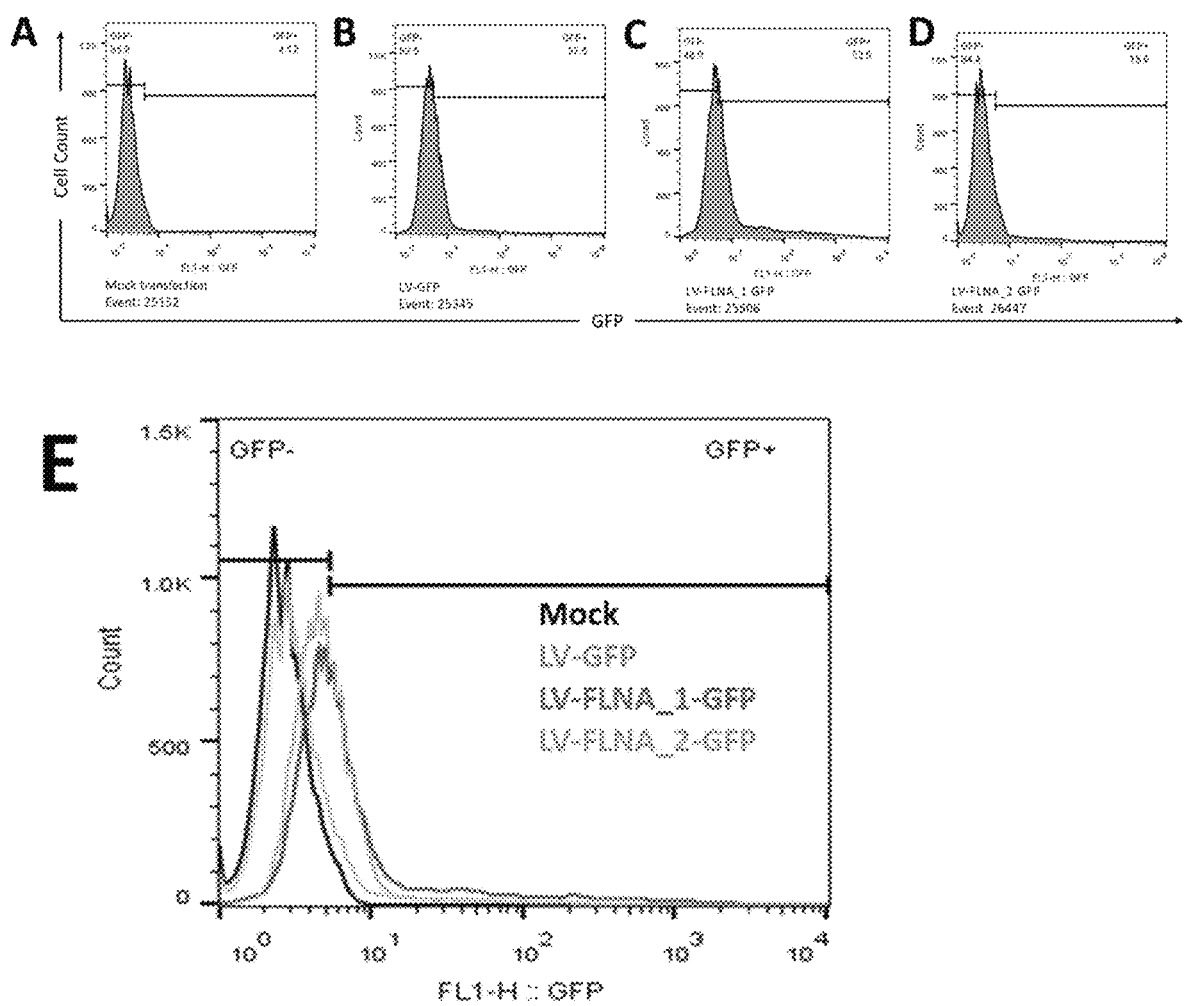

FIG. 56: Cell proliferation assay (EdU) on MDA-MB-234 cells treated with FLNA intrabody: GFP expression at 72 hours post transfection. FIG. 56A, mock transfection. FIG. 56B, LV-GFP transfection. FIG. 56C, LV-FLNA_1-GFP transfection. FIG. 56D, LV-FLNA 2-GFP transfection. FIG. 56E, merge of 56A-D. Total ungated acquisition events (cell #) for each group: 30,000.

Figure 57:
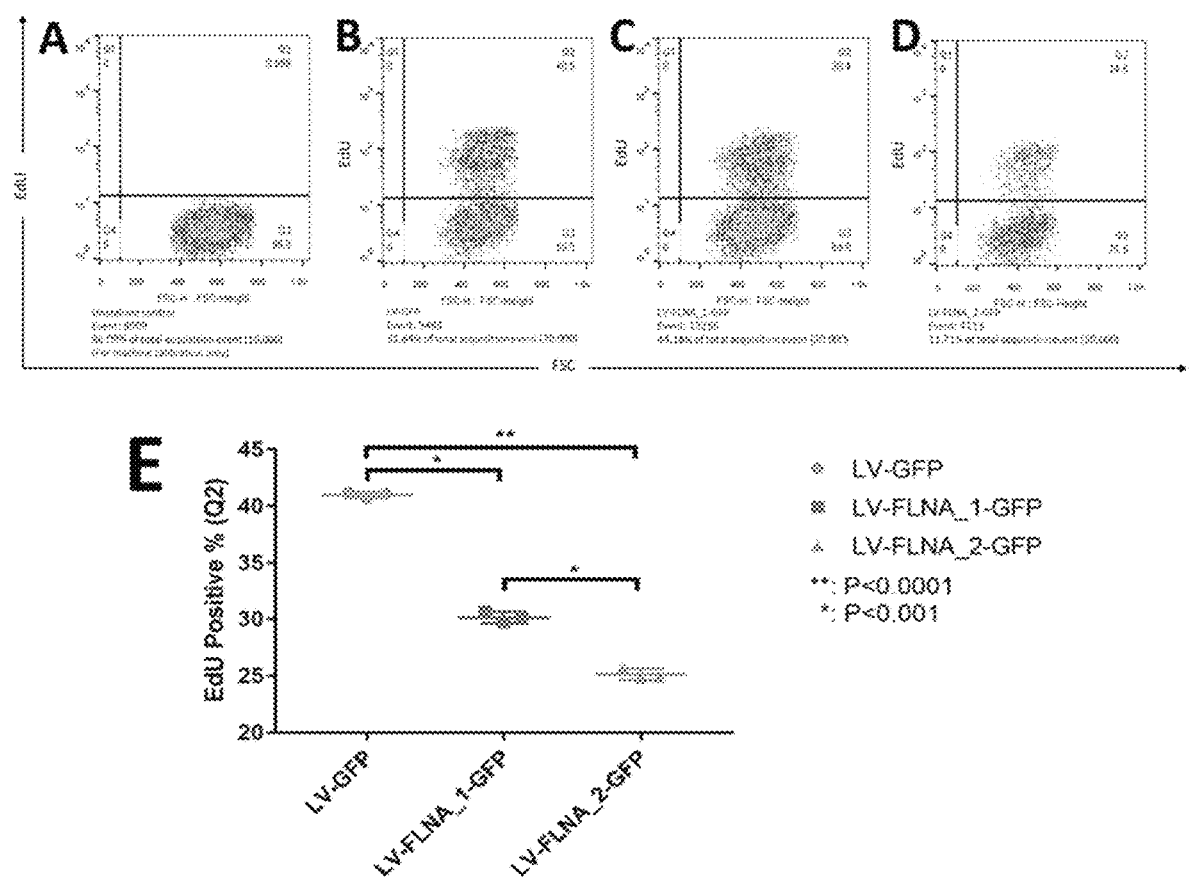

FIG. 57: Cell proliferation assay (EdU) on MDA-MB-234 cells treated with FLNA intrabody: MDA-MB-231 cells expressing FLNA intrabody show reduced cell proliferation (GFP gated and stained by EdU). FIG. 57A: Unstained control; FIG. 57B: LV-GFP; FIG. 57C: LV-FLNA_1-GFP; FIG. 57D: LV-FLNA_2-GFP. FIG. 57E: Statistical analysis of FIG. 57A-D (n=3; student's t-test, two-tail unpaired). Total acquisition events (# cells) for each group: 30,000.

Figure 58:
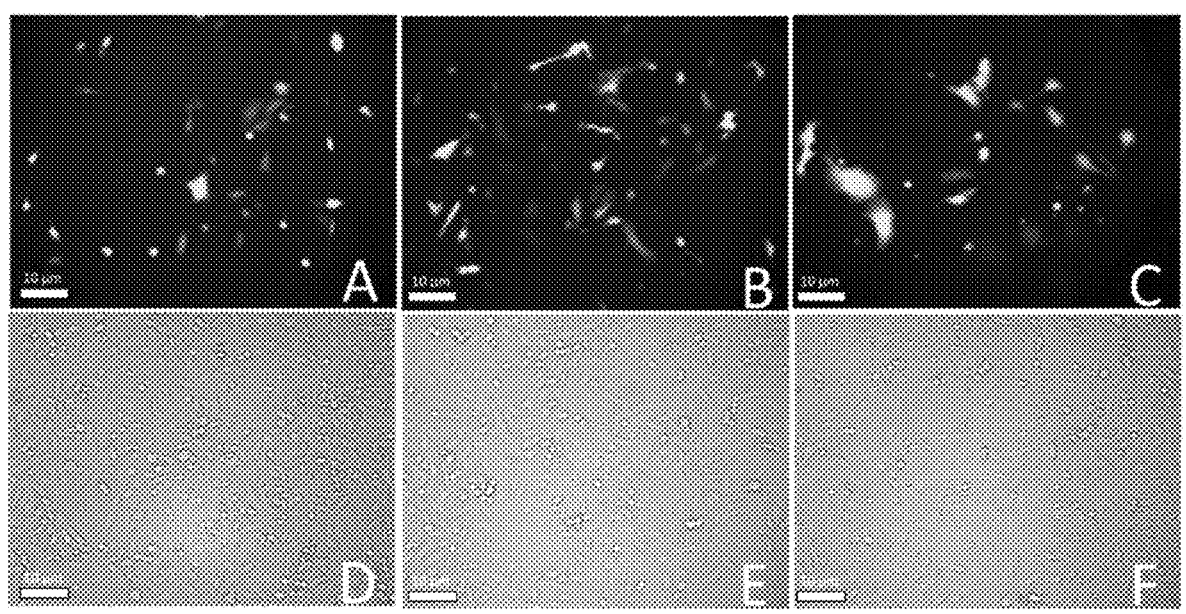

FIG. 58: Microscopy studies on MDA-MB-231 cells after treatment with FLNA intrabody: observation of GFP expression 24 hours post-transfection. FIGS. 58A,D: LV-GFP; FIGS. 58B,E: LV-FLNA_1-GFP; FIGS. 58C,F: LV-FLNA_2-GFP. FIGS. 58A, 58B, 58C show GFP expression while FIGS. 58D, 58E, 58F are the respective bright field images.

Figure 59:
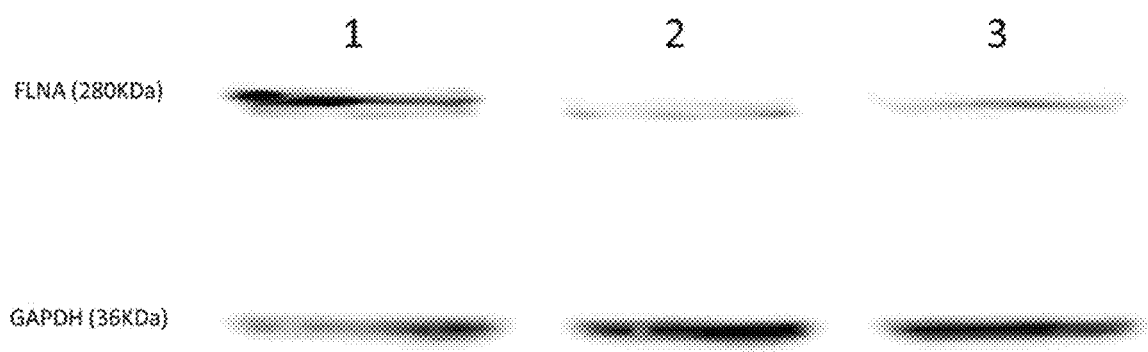

FIG. 59: FLNA protein levels post-intrabody treatment by western blot analysis. Lane 1: LV-GFP; lane 2: LV-FLNA_1-GFP; lane 3: LV-FLNA_1-GFP (GAPDH was used as the loading control).

Figure 60:
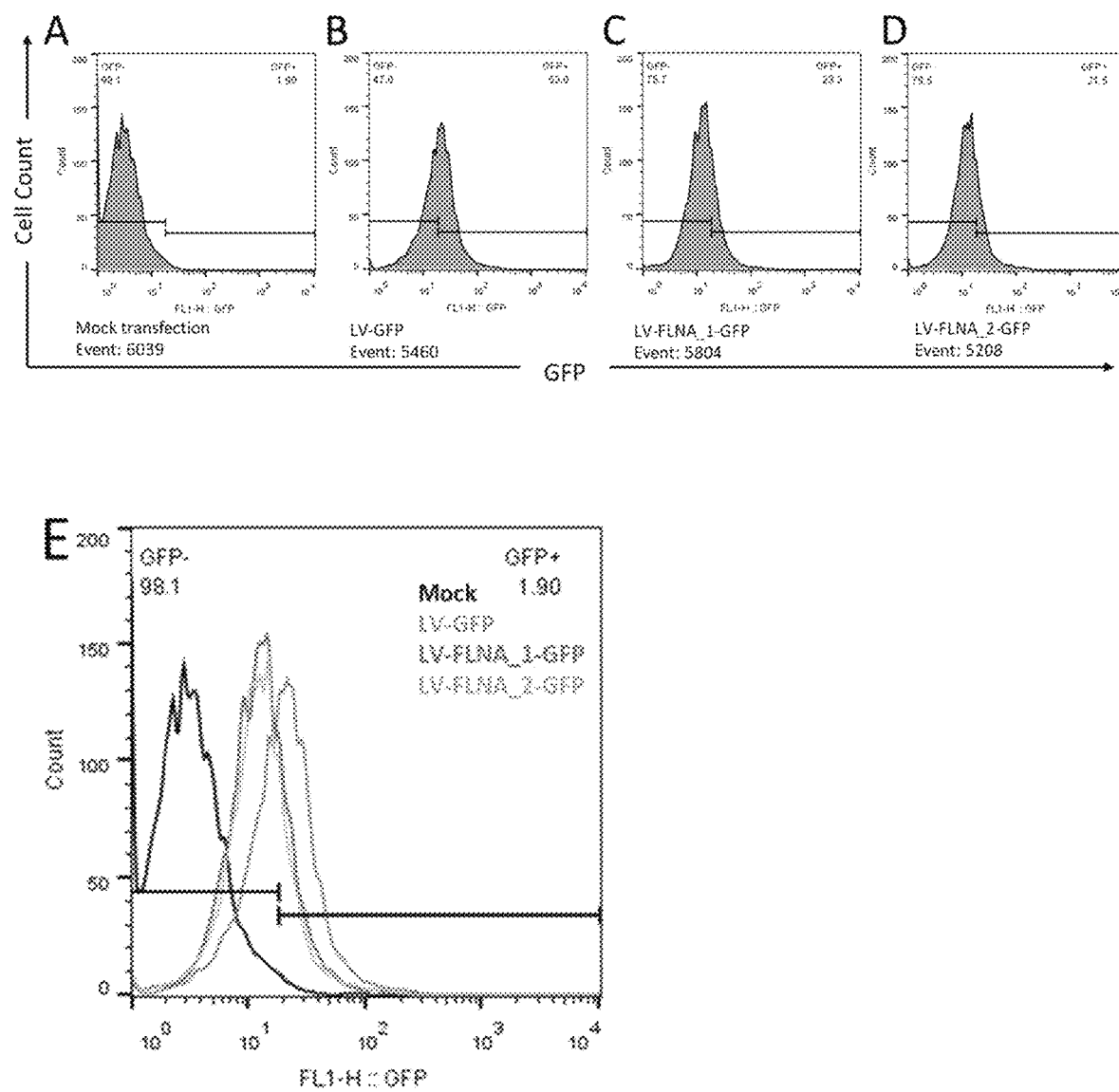

FIG. 60: Histograms of GFP expression in normal human astrocyte cells at 24 hr post-transfection. 60A: Mock transfection; 60B: LV-GFP; 60C: LV-FLNA_1-GFP; 60D: LV-FLNA 2-GFP; 60E: Merge of 60A-D.

Figure 61:
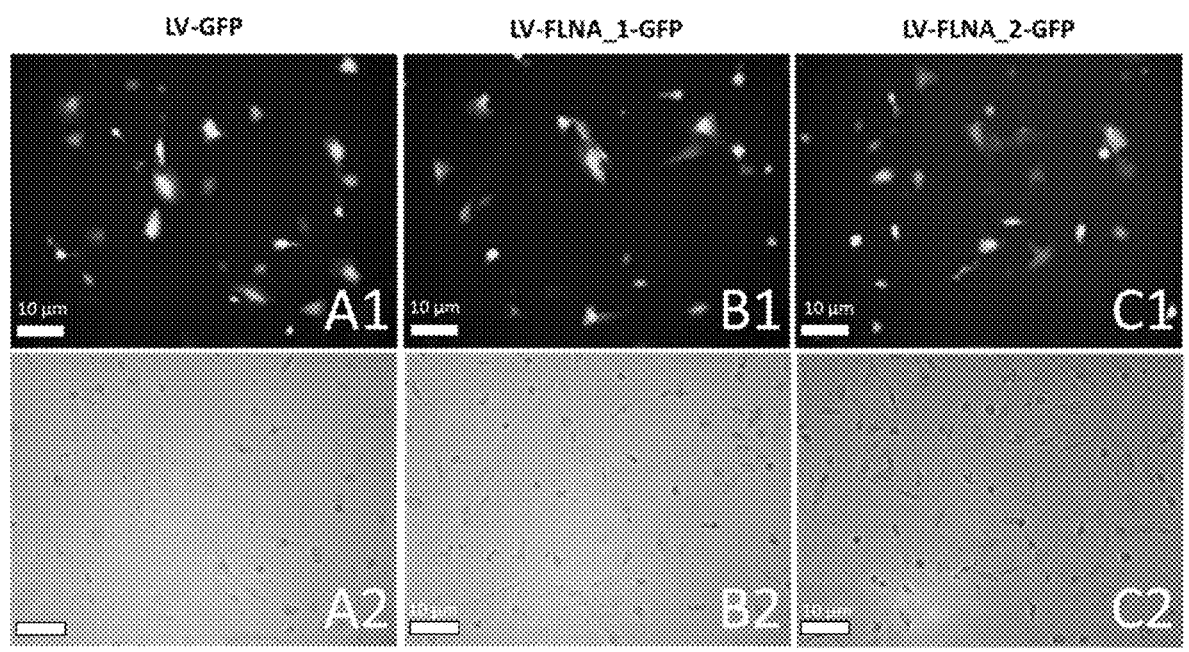

FIG. 61: Microscopy studies on normal human astrocyte cells after treatment with FLNA intrabody. GFP expression in normal human astrocyte cells transfected with the indicated constructs. 61A1: LV-GFP (bottom panel, A2: bright-field of top panel, A1); 61B1: LV-FLNA_1-GFP (bottom panel, B2: bright-field of top panel, B1); 61C1: LV-FLNA_2-GFP (61C2 bottom panel, C2: bright-field of top panel, C1).

Figure 62:
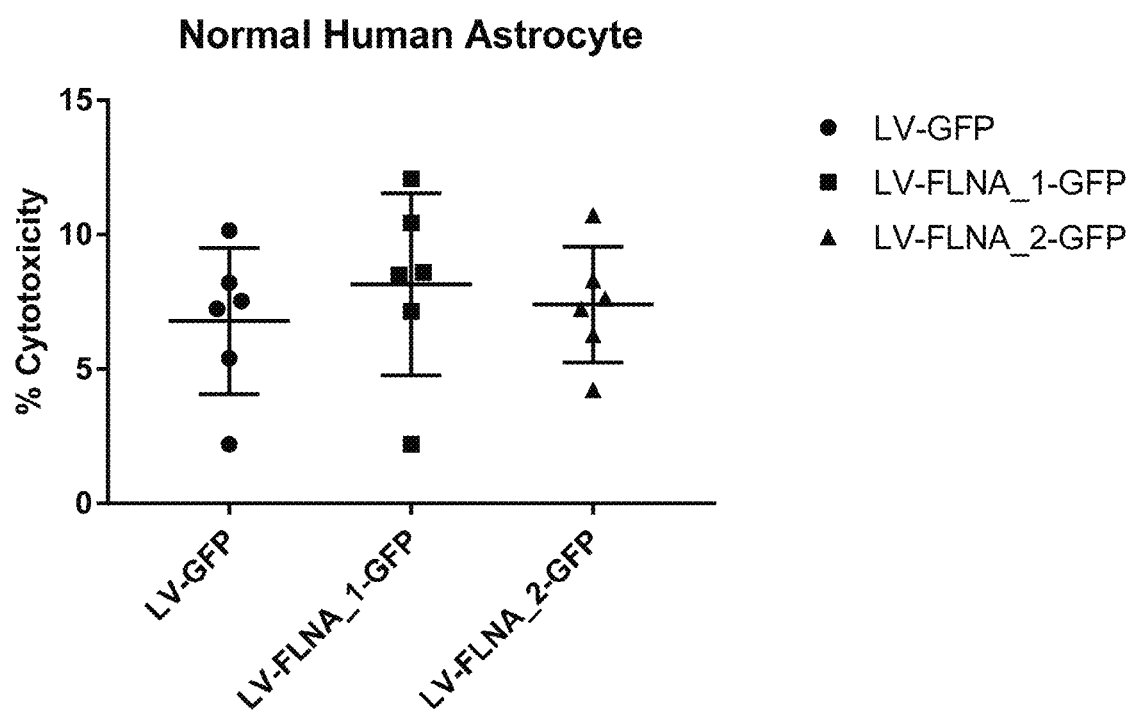

FIG. 62: Percent Cytotoxicity in normal human astrocyte cells 72 hrs post-transfection. LDH cytotoxicity was calculated using the calculation in the kit protocol: % cytotoxicity=((compound-treated LDH activity-spontaneous LDH activity)×100)/(maximum LDH activity-spontaneous LDH activity)). The compound-treated wells were the LDH release recorded from the indicated treatment group (LV-GFP, LV-FLNA_1-GFP, LV-FLNA_2-GFP). Spontaneous release was the LDH release recorded from the mock transfection group (to be subtracted as background caused by transfection reagent). Maximum LDH was LDH release recorded from total cell lysis. There was no significant difference in % cytotoxicity among the three treatment groups.

Figure 63:
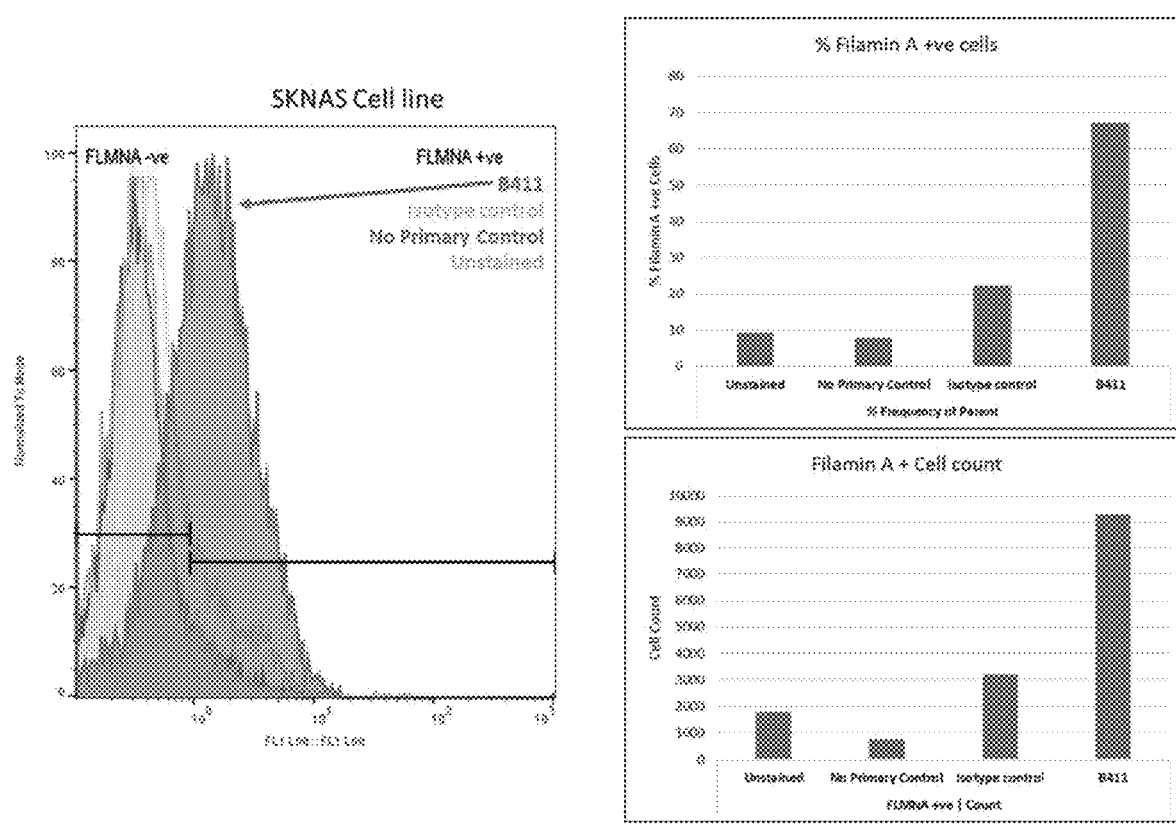
Figure 64:
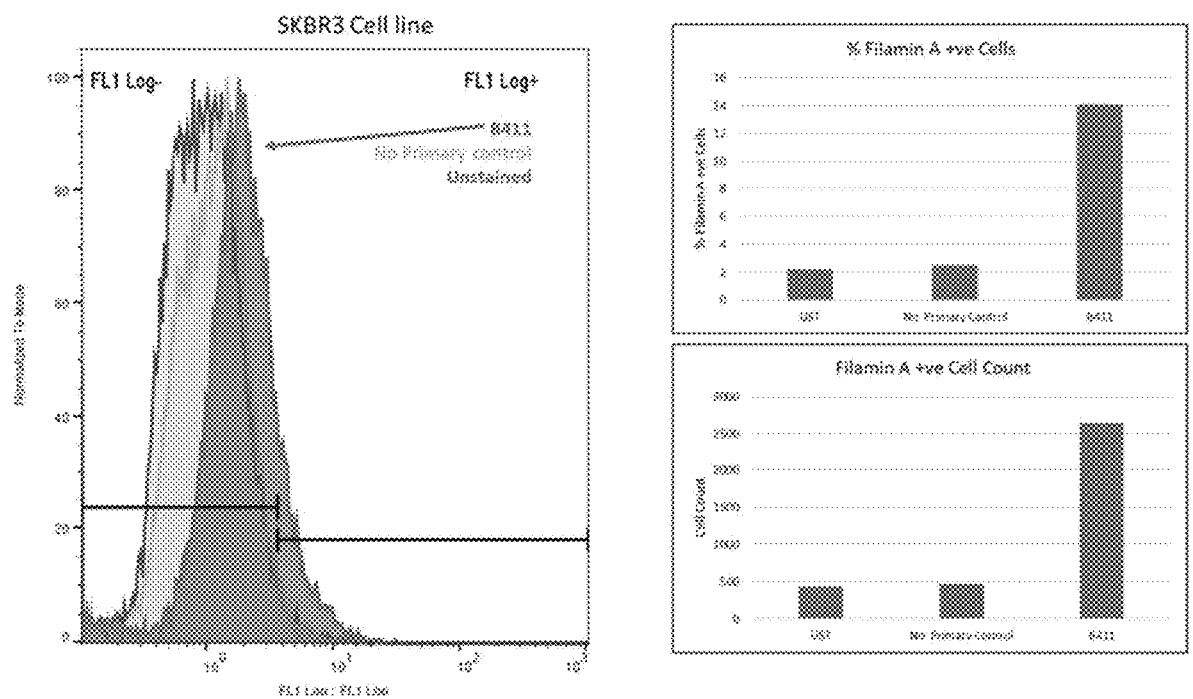
Figure 66:
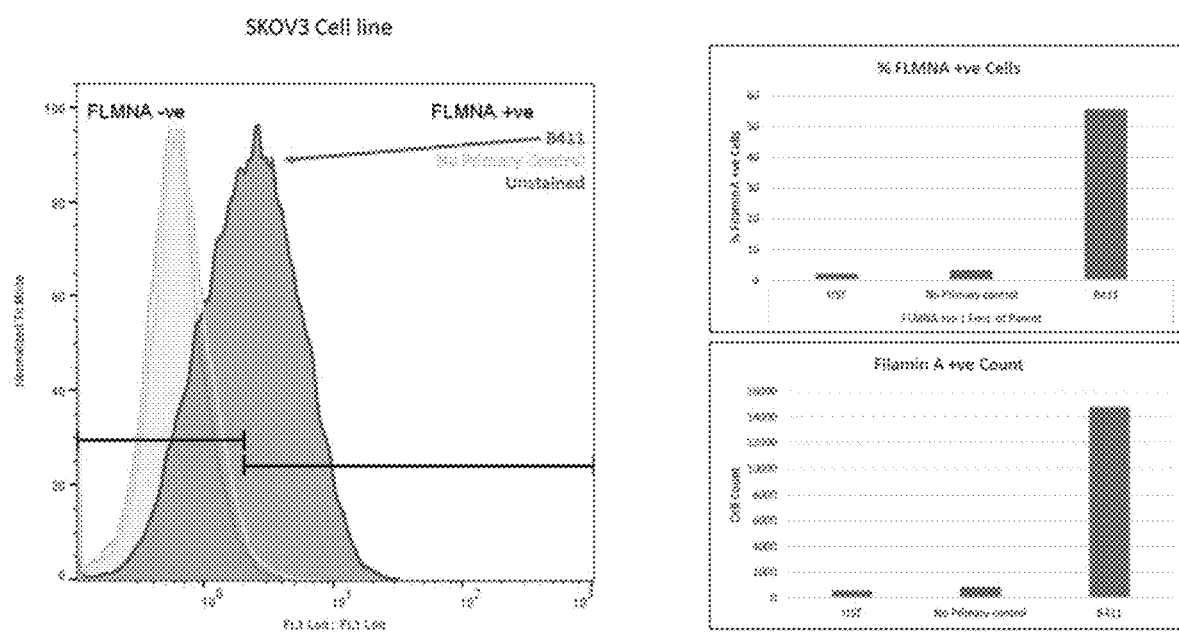
Figure 67:
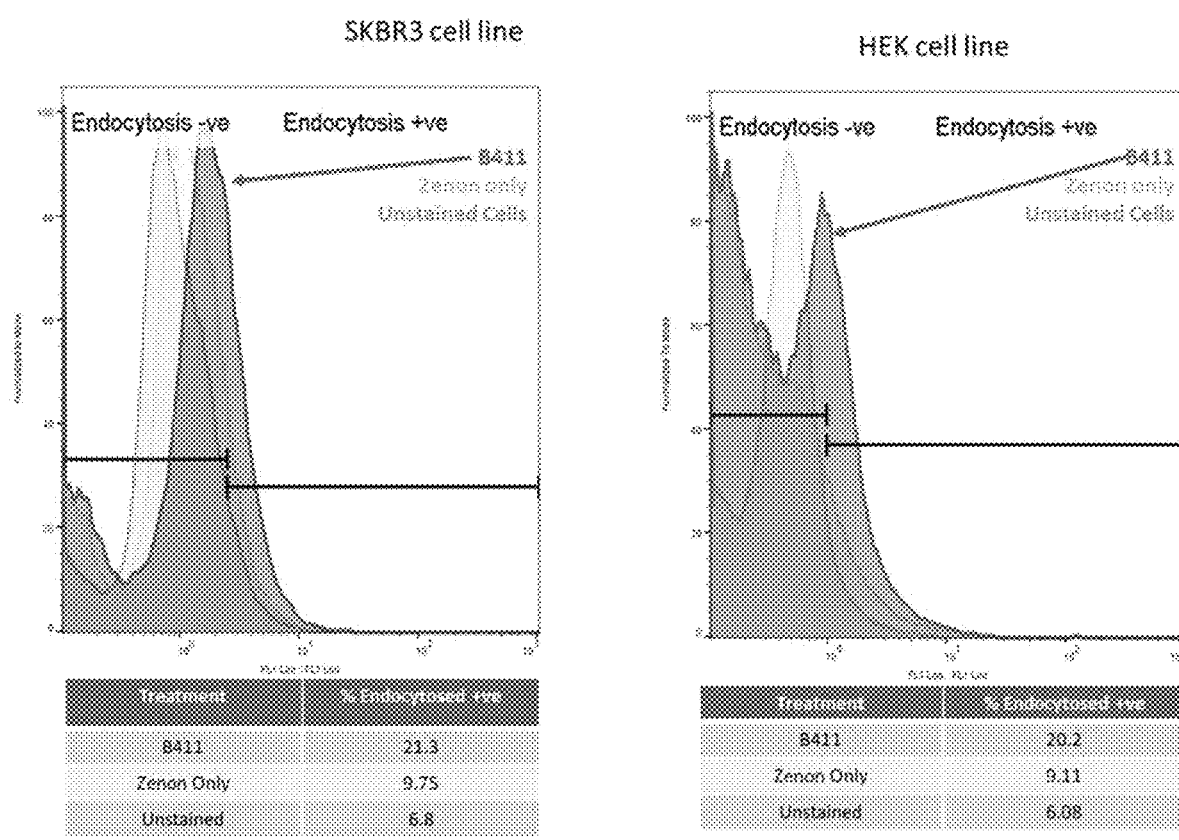
Figure 68:
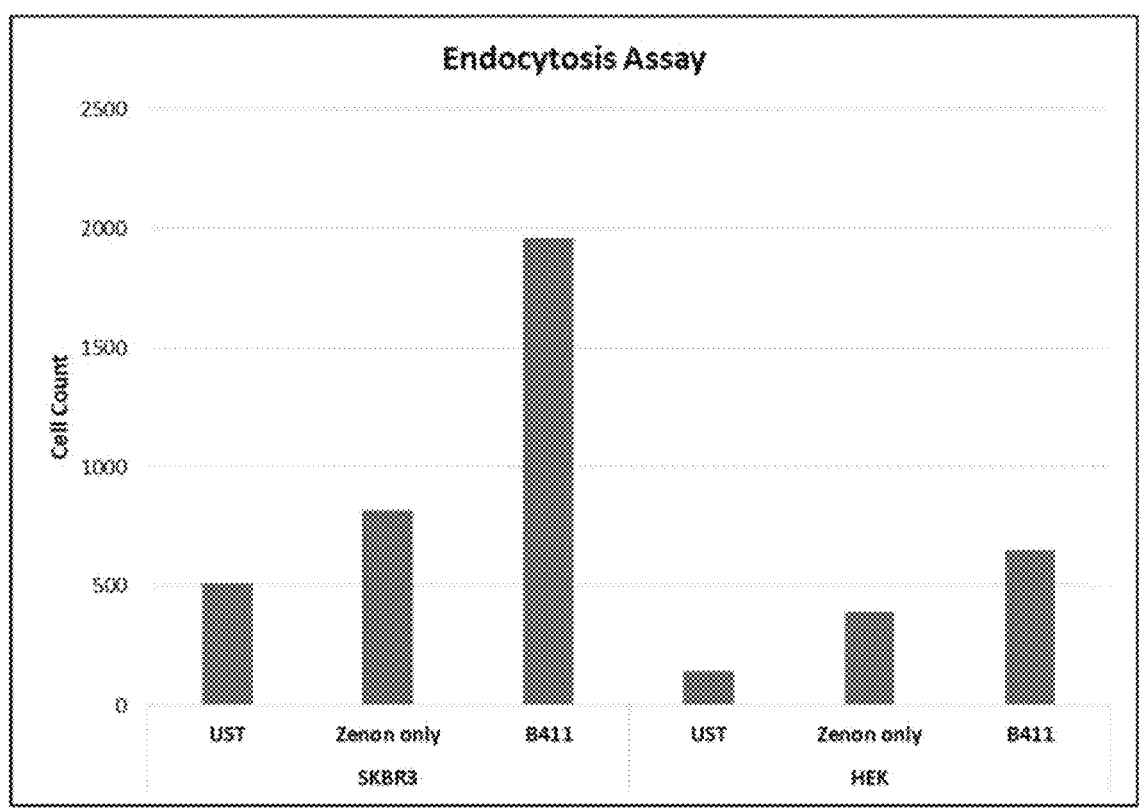

FIG. 63: Surface staining of B411 on SKNAS cells.
FIG. 64: Surface staining of B411 on SKBR3 cells
FIG. 65: Surface staining of B411 on Hela cells.
FIG. 66: Surface staining of B411 on SKOV cells.
FIG. 67: Histograms showing the percent B411 endocytosis positive SKBR3 cells (left panel) or HEK cells (right panel).
FIG. 68: Bar graph showing the total cell count of B411 endocytosis positive SKBR3 and HEK cells, compared to the negative controls (Zenon label only, or unstained (UST).

DETAILED DESCRIPTION OF THE DISCLOSURE

Definitions

"About" means plus or minus a percent (e.g., +5%) of the number, parameter, or characteristic so qualified, which would be understood as appropriate by a skilled artisan to the scientific context in which the term is utilized. Furthermore, since all numbers, values, and expressions referring to quantities used herein, are subject to the various uncertainties of measurement encountered in the art, then unless otherwise indicated, all presented values may be understood as modified by the term "about."

As used herein, the articles "a," "an," and "the" may include plural referents unless otherwise expressly limited to one-referent, or if it would be obvious to a skilled artisan from the context of the sentence that the article referred to a singular referent.

Where a numerical range is disclosed herein, then such a range is continuous, inclusive of both the minimum and maximum values of the range, as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include any and all subranges between the minimum value of 1 and the maximum value of 10. Exemplary subranges of the range "1 to 10" include, but are not limited to, 1 to 6.1, 3.5 to 7.8, and 5.5 to 10.

The terms "filamin," "human actin binding protein," or "human ABP" refers to a family of proteins that crosslink actin filaments into orthogonal networks in cortical cytoplasm and participate in the anchoring of membrane proteins for the actin cytoskeleton. Filamins include three functional domains: an N-terminal filamentous actin-binding domain, a C-terminal self-association domain, and a membrane glycoprotein-binding domain. The family of filamin proteins includes the following three proteins: filamin-A, filamin B, and filamin C.

The terms "filamin-A," "human filamin-A," "alpha-filamin", "filamin 1", "ABP-280" "endothelial actin-binding protein" and "nonmuscle filamin" refer to an approximately 280-kD filamin protein encoded by the FLNA gene, which is a widely expressed protein that regulates reorganization of the actin cytoskeleton by interacting with integrins, transmembrane receptor complexes, and second messengers. Filamin A (or a portion thereof) is also displayed on the surface of human neuroblastoma cells (e.g., NMB-7). It is also present in the integral membrane fraction of NMB-7 cells, as well as the hydrophilic protein fraction containing cytoplasmic and peripheral membrane proteins. It may therefore be found throughout the cell, including the extracellular surface. FLNa has also been shown to be present on the cell surface of human cell lines HeLa (cervical cancer), SKOV3 (ovarian cancer) and HEK293 (human embryonic kidney). See Bachmann et al., *Cancer Sci.* 97 (12), 2006, incorporated herein by reference in its entirety for all purposes. The polypeptide sequence of filamin-A is available at GenBank Accession No. P21333 (Gorlin, et al., 1990, J. Cell Biol. 111 (3): 1089-1105). As used herein, "filamin-A" includes variants thereof, mutants thereof, recombinant versions thereof, and fragments thereof.

The terms "filamin B," "human filamin B," "beta-filamin," "ABP-278," "endothelial actin-binding protein," and "nonmuscle filamin" refer to an approximately 278-kD encoded by the FLNB gene that binds actin filaments. The polypeptide sequence of filamin B is available at Gen Bank Accession No. 075369 (Takafuta et al., 1998, J. Biol. Chem. 273 (28), 17531-17538).

The terms "filamin C," "human filamin C," "filamin 2," "gamma filamin," "ABP-280, Autosomal Form" refer to an approximately 280-kD protein encoded by the FLNC gene that binds actin filaments. The polypeptide sequence of filamin C is available at GenBank Accession No. Q14315 (Xie et al., 1998, Biochem. Biophys. Res. Commun. 251 (3), 914-919).

The term "antibody" as used herein refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., filamin-A), or (b) conservatively substituted derivatives of such immunoglobulin polypeptides or fragments that immunospecifically bind to the antigen (e.g., filamin-A). Antibodies are generally described in, for example, Harlow & Lane, *Antibodies: A Laboratory Manual* (Cold Spring Harbor Laboratory Press, 1988). The term "antibody" as used herein encompasses antibody fragments. Thus, in some embodiments, the antibody is a single domain antibody (sdAb), such as a VhH antibody or domain antibody, or a single chain variable fragment (scFv) or other antibody fragment (e.g., Fab, Fab', F(ab')$_2$, or Fv fragment).

The term "intrabody" as used herein refers to an antibody or fragment thereof (e.g., a single chain variable fragment (scFv) or other single chain or single domain antibody) that binds to intracellular proteins and has an effect within a cell.

In some embodiments, an intrabody is expressed within the target cell, e.g. via gene therapy. For example, a DNA or RNA encoding an intrabody is delivered to a cell using a plasmid, viral delivery system, or non-viral delivery system. Viral delivery systems include, for example, lentiviral or retroviral vectors. Non-viral delivery systems include plasmid or DNA fragments, or RNA, delivered to the cell using, for example, cationic lipids, lipid emulsions, nanoparticles, peptide vectors (e.g., cationic peptides), polymers (e.g., cationic polymers such as synthetic polyethylene mine (PEI), chitosan, poly (DL-lactide) (PLA) or poly (DL-lactide-co-glycoside (PLGA) particles), dendrimers or mechanical delivery techniques. In some embodiments, an intrabody may be delivered intracellularly via a cell membrane penetrating peptide, or cellular internalization peptide. Optionally, the intrabodies provided herein may include a nuclear localization signal, or signal that targets the intrabody to a different subcellular structure such as, for example, the endoplasmic reticulum (ER), golgi apparatus, mitochondria, lysosomes, or other locations. Thus, intrabodies once expressed within the cell may remain in the cytoplasm, or may localize to a particular subcellular structure. Intrabodies may include additional modifications to increase resistance to intracellular microenvironments or enhance stability.

In the context of immunoglobulin polypeptides or fragments thereof as defined above, "conservative substitution" means one or more amino acid substitutions that do not substantially reduce specific binding (e.g., as measured by the $K_D$) of the immunoglobulin polypeptide or fragment thereof to an antigen (i.e., substitutions that increase binding, that do not significantly alter binding, or that reduce binding by no more than about 40%, typically no more than about 30%, more typically no more than about 20%, even more typically no more than about 10%, or most typically no more than about 5%, as determined by standard binding assays such as, e.g., ELISA).

An "antibody derivative" as used herein means an antibody, as defined above, which is modified by covalent attachment of a heterologous molecule such as, e.g., by attachment of a heterologous polypeptide, or by glycosylation, acetylation or phosphorylation not normally associated with the antibody, and the like. For instance, a chemotherapeutic agent, or fluorescent label, or radiochemical, or active drug, may be attached, among others.

Naturally occurring antibodies (immunoglobulins) comprise two heavy chains linked together by disulfide bonds and two light chains, each light chain being linked to one of the heavy chains by disulfide bonds. Each chain has an N-terminal variable domain (VH or VL) and a constant domain (CH or CL) at its C-terminus; the constant domain of the light chain is aligned with and disulfide bonded to the first constant domain of the heavy chain, and the light chain variable domain is aligned with the variable domain of the heavy chain. The heavy chain constant region includes (in the N- to C-terminal direction) the CH 1 and hinge regions. The light chain also contains a hinge domain. Particular amino acid residues are believed to form an interface between and disulfide bond the light and heavy chain variable domains, see e.g. Chothia et al., J. Mol. Biol. 186:651-663 (1985); Novotny and Haber, Proc. Natl. Acad. Sci. USA 82:4592-4596 (1985); Padlar et al., Mol. immunol., 23 (9): 951-960 (1986); and S. Miller, J. Mol. Biol., 216:965-973 (1990).

The constant domains are not involved directly in binding the antibody to an antigen, but are involved in various effector functions, such as participation of the antibody in antibody-dependent cellular cytotoxicity and complement dependent cytotoxicity. The variable domains of each pair of light and heavy chains are involved directly in binding the antibody to the antigen. The domains of natural light and heavy chains have the same general structure, the so-called immunoglobulin fold, and each domain comprises four framework (FR) regions, whose sequences are somewhat conserved, connected by three hyper-variable or complementarity determining regions (CDRs) (see Kabat, E. A. et al, Sequences of Proteins of Immunological Interest, National Institutes of Health, Bethesda, Md., (1987)). The four framework regions largely adopt a β-sheet conformation and the CDRs form loops connecting, and in some cases forming part of, the β-sheet structure. The CDRs in each chain are held in close proximity by the framework regions and, with the CDRs from the other chain, contribute to the formation of the antigen binding site.

Antibodies can be divided into a variety of antigen-binding fragments. The Fv fragment is a heterodimer containing only the variable domains of the heavy chain and the light chain. The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group.

Also taught herein are "Antibody fragments" that includes the aforementioned Fab, Fab', F(ab')$_2$, ScFvs, and Fv fragments, as well as any portion of an antibody of the present disclosure having specificity toward a desired target epitope or epitopes. In one aspect, an antibody of the present disclosure is anti-Filamin-A antibody. Expression of antibody fragments is taught in, for example, U.S. Pat. No. 5,648,237, which is herein incorporated by reference in its entirety. In particular embodiments, the antibodies provided herein are intrabodies comprising an scFv or other antibody fragment.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature, 352:624-628 (1991) and Marks et al, J. Mol. Biol, 222:581-597 (1991), for example. Specific examples of monoclonal antibodies herein include chimeric antibodies, humanized antibodies, and human antibodies.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, so long as they exhibit the desired biological activity (U.S. Pat. No. 4,816,567; Morrison et al, Proc. Natl. Acad. Sci. USA, 81:6851-6855 (1984)).

"Humanized" forms of non-human (e.g., murine) antibodies are chimeric antibodies that contain minimal sequences derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., Nature 321:522-525 (1986); Riechmann et al, Nature 332:323-329 (1988); and Presta, Curr. Op. Struct. Biol. 2:593-596.

A "human antibody" herein is one comprising an amino acid sequence structure that corresponds with the amino acid sequence structure of an antibody obtainable from a human B-cell. Such antibodies can be identified or made by a variety of techniques, including, but not limited to: production by transgenic animals (e.g., mice) that are capable, upon immunization, of producing human antibodies in the absence of endogenous immunoglobulin production (see, e.g., Jakobovits et al, Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807)); selection from phage display libraries expressing human antibodies (see, for example, McCafferty et al., Nature 348:552-553 (1990); Johnson et al., Current Opinion in Structural Biology 3:564-571 (1993); Clackson et al., Nature, 352:624-628 (1991); Marks et al., J. Mol. Biol. 222:581-597 (1991); Griffith et al., EMBO J. 12:725-734 (1993); U.S. Pat. Nos. 5,565,332 and 5,573,905); generation via in vitro activated B cells (see U.S. Pat. Nos. 5,567,610 and 5,229,275); and isolation from human antibody producing hybridomas.

A "multispecific antibody" herein is an antibody having binding specificities for two or more different epitopes. In some embodiments, the multispecific antibody is trispecific or quadraspecific. In some embodiments, the multispecific antibody may be bivalent, trivalent, or quadravalent.

A "bispecific antibody" is an antibody with binding specificities for two different epitopes. In some embodiments, the bispecific antibody is monovalent or bivalent.

Antibody Conjugates, Fusion Proteins, and Bispecific Antibodies: These refer to monoclonal antibodies conjugated by chemical methods with radionuclides, drugs, macromolecules, or other agents.

Antigen: This refers to one or more molecules or one or more portions of a molecule capable of being bound by an antibody, which is additionally capable of inducing an animal to produce an antibody capable of binding to an epitope of that antigen. An antigen can have one or more than one epitope. The specific reaction referred to above is meant to indicate that the antigen will react, in a highly preferential manner, with its corresponding antibody and not with the multitude of other antibodies which can be evoked by other antigens.

Epitope: This refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest, in some aspects, for the present disclosure are epitopes of a moiety of filamin-A. An epitope of filamin-A can be identified with a cross-clocking assay such as described in Antibodies, A Laboratory Manual, Cold Spring Harbor Laboratory, Ed Harlow and David Lane (1988), herein incorporated by reference in its entirety.

Complementarity Determining Region or CDR: This refers to amino acid sequences which together define the binding affinity and specificity of the natural Fv region of a native immunoglobulin binding site. The light and heavy chains of an immunoglobulin each have three CDRs. The CDRs can be located and described using the numbering convention delineated by Kabat et al., (1991) Sequences of Proteins of Immunological Interest, 5th Edition, Department of Health and Human Services, Public Health Service, National Institutes of Health, Bethesda (NIH Publication No. 91-3242), herein incorporated by reference in its entirety.

Framework Region or FWR: This refers to amino acid sequences interposed between CDRs. These portions of the antibody serve to hold the CDRs in an appropriate orientation for antigen binding.

Specificity Determining Residue or SDR: This refers to amino acid residues unique to antibodies of the present disclosure when compared to other IgGs. In one aspect, the SDR is the part of an immunoglobulin that is directly involved in antigen contact.

Constant Region: This refers to the portion of an antibody molecule which confers effector functions. A heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. A light chain constant region can be of the kappa or lambda type.

Immunogenicity: A measure of the ability of a targeting protein or therapeutic moiety to elicit an immune response (humoral or cellular) when administered to a recipient.

Immunoreactivity: A measure of the ability of an immunoglobulin to recognize and bind to a specific antigen.

Filamin-A Antibodies or FilA mAbs: These terms are used herein interchangeably with the terms "filamin-A specific antibodies" and "filamin-A antigen specific antibodies" and "filamin-A antigen binding antibodies" and the like. These terms refer to antibodies capable of preferentially binding to expression products of the filamin-A gene and homologues of the filamin-A gene, and can include antibodies specific to modified forms of the expression product that are produced by cancer cells. The antibodies include variants, such as chimeric, humanized, and other variants known to those skilled in the art. Filamin-A antibodies are said to be specific for the filamin-A antigen or epitope of the present disclosure if they exhibit preferential binding to a filamin-A antigen or epitope with a binding affinity at least 5 fold, at least 10 fold, at least 50 fold, at least 100 fold, or at least 500 fold higher relative to another protein. In one aspect, filamin-A antibodies are said to be specific for the filamin-A antigen or epitope of the present disclosure if they bind with greater than 1000 fold higher affinity relative to any other protein. A naked filamin-A antibody is a filamin-A antibody of the present disclosure that is not conjugated or otherwise bound to a heterologous molecule, such as biotin or radiolabel.

Filamin-A Antigens: This refers to expression products generated by a filamin-A gene, wherein the expression products can be used as antigens, target molecules, biomarkers, or any combination thereof. A filamin-A antigen can be produced by the filamin-A gene and homologues of the filamin-A gene, and can include various modifications. Modifications may include amino acid mutations and/or post-translational mutations. For example, the filamin-A antigen may include modifications introduced by the cells expressing a filamin-A antigen, such as cancer cells. In some embodiments, the filamin-A antigens are recombinant proteins made using the FLNa gene, or modifications thereof.

Substantially Similar Binding Properties: This refers to the ability of a chimeric antibody, such as a humanized antibody or fragments thereof, to retain the ability to preferentially bind an antigen recognized by the parent antibody used to produce the chimeric antibody. In one aspect, the affinity of a chimeric antibody that has "substantially similar binding properties" to a parent antibody is one in which the binding affinity is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% specific to the antigen targeted by the parent antibody.

In another aspect, the affinity of a chimeric antibody, humanized antibody, or antibody fragment is between: about 10% and about 95%, about 10% and about 50%, about 50% and about 95%, about 10% and about 25%, about 25% and about 50%, about 50% and about 95%, about 10% and about 20%, about 20% and about 30%, about 30% and about 40%, about 40% and about 50%, about 50% and about 60%, about 60% and about 70%, about 70% and about 80%, or about 80% and about 90% of the affinity of the parent antibody.

Methods for assaying antigen-binding affinity are known in the art and include half-maximal binding assays, competition assays, and Scatchard analysis. In one aspect, antigen-binding affinity is assayed using a competition assay.

Substantially Homologous: May refer to immunoglobulin sequences that exhibit at least about 85%, 86%, 87%, 88%, 89%, 90%, 91%, 92%, 93%, 94%, 95%, 96%, 97%, 98%, or 99% sequence identity with a reference immunoglobulin sequence, where percent identity is determined by comparing the number of identical amino acid residues between the two immunoglobulins, where the positions of the amino acid residues are indicated, such as by using the Kabat numbering scheme.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In certain embodiments, the two sequences are the same length.

The term "substantially identical," in the context of two nucleic acids or polypeptides, refers to two or more sequences or subsequences that have at least 50%, at least 55%, at least 60%, at least 65%, at least 70%, at least 75%, at least 80%, at least 85%, at least 90%, at least 95%, or at least 96%, 97%, 98%, or 99% identity (as determined using one of the methods set forth infra).

"Similarity" or "percent similarity" in the context of two or more polypeptide sequences, refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or even 95% or more identical, or conservatively substituted, to the second amino acid sequence when compared to an equal number of amino acids as the number contained in the first sequence, or when compared to an alignment of polypeptides that has been aligned by a computer similarity program known in the art (see infra).

The determination of percent identity or percent similarity between two sequences can be accomplished using a mathematical algorithm. A non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul, et al., 1990, J. Mol. Biol. 215:403-410. BLAST nucleotide searches can be performed with the NBLAST program, score=100, wordlength=12 to obtain nucleotide sequences homologous to a nucleic acid encoding a protein of interest. BLAST protein searches can be performed with the XBLAST program, score=50, wordlength=3 to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. (See, e.g., Internet web site address: ncbi.nlm.nih.gov.) Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. Ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

Substantially pure: For the purpose of the present disclosure, substantially pure refers to a homogeneous preparation. In one aspect, the homogenous preparation is of a filamin-A antibody or antibody fragment, or other chemical or biological agents. Substantially pure immunoglobulins of at least about 85%, 86%, 87%, 88%, 89%, 90%, 91%, 92%, 93%, 94%, 95%, 96%, 97%, 98%, or 99% homogeneity are envisioned.

Filamin-A antigen expression: includes measurement of presence or abundance of filamin-A antigen in a particular tissue specimen, blood, serum, or plasma, in one aspect, a tissue specimen from a patient suffering from a disease characterized by the expression of gene products of filamin-A, homologues thereof, variants thereof, mutants thereof, recombinant versions thereof, and/or fragments thereof. Such diseases include breast cancer, stomach cancer, and colon cancer.

An "affinity reagent" of the subject disclosure has an analyte binding domain, moiety or component that has a high binding affinity for a target analyte. By high binding affinity is meant a binding affinity of at least about $10^{-4}$ M, usually at least about $10^{-6}$ M or higher, e.g., $10^{-9}$ M or higher. In aspects, the binding affinity of the antibodies taught herein may be at least $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or higher, or any combination or range of the aforementioned. The affinity reagent may be any of a variety of different types of molecules, so long as it exhibits the requisite binding affinity for the target protein when present as tagged affinity ligand. As such, the affinity reagent may be a small molecule or large molecule ligand.

Also of interest to the disclosure are recombinantly produced antibodies and antibody fragments, such as single chain antibodies or scFvs, where such recombinantly produced antibody fragments retain the binding characteristics of the above antibodies. Such recombinantly produced antibody fragments generally include at least the VH and VL domains of the subject antibodies, so as to retain the binding characteristics of the subject antibodies. These recombinantly produced antibody fragments or mimetics of the subject disclosure may be readily prepared using any convenient methodology, such as the methodology disclosed in U.S. Pat. Nos. 5,851,829 and 5,965,371; the disclosures of which are herein incorporated by reference.

The above described antibodies, fragments, and mimetics thereof may be obtained from commercial sources and/or prepared using any convenient technology, where methods of producing polyclonal antibodies, monoclonal antibodies, fragments and mimetics thereof, including recombinant derivatives thereof, are known to those of skill in the art.

Sequences and CDR Regions of a First Embodiment

Table 1A provides exemplary variable and constant regions of the antibodies provided herein.

TABLE IA

Exemplary variable and constant regions

| SEQUENCE INFORMATION | SEQUENCE (where applicable, CDRs are bolded and underlined) |
|---|---|
| SEQ ID NO: 1 is the VL domain of mAbs B185, B405, B406, and B407 | DIVMTQSHKFMSTSVGDRVSITCKASQDVSIDVAWYQQKPGQ SPKLLIYSASHRYTGVPDRFTGSGSGTDFTFTISGVQAEDLAVY FCQQHYSTPLTFGAGTKLELK (SEQ ID NO: 1) |
| SEQ ID NO: 2 is the human chimeric mAb VL domain of mAbs B408, B409, B410, and B411 | DIVMTQSHKFMSTSVGDRVSITCKASQDVSLDVAWYQQKPGQ SPKLLIYSASHRYTGVPDRFTGSGSGTDFTFTISGVQAEDLAVY FCQQHYSTPLTFGAGTKLELK (SEQ ID NO: 2) |
| SEQ ID NO: 3 is the CL domain (Km3 allotype, kappa) of human chimeric filamin-A antibodies provided herein | RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC (SEQ ID NO: 3) |
| SEQ ID NO: 4 is the VH domain of mAbs B185 and B408 | EVKLVESGGGLVQPGGSLKLSCAASGFTFSSYTMSWVRQTPE KRLEWVAYISNGGGSTYYPDTVKGRFTISRDNAKNTLYLQMS SLKSEDTAMYYCASDGLLRPFAYWGQGTLVTVSA (SEQ ID NO: 4) |
| SEQ ID NO: 5 is the VH domain of mAbs B406 and B410 | EVKLVESGGGLVQPGGSLKLSCAASGFTFSSYTMSWVRQTPE KRLEWVAYISNGGGSTYYPDTVKGRFTISRDNAKNTLYLQMS SLKSEDTAMYYCASDGLIRPFAYWGQGTLVTVSA (SEQ ID NO: 5) |

TABLE IA-continued

Exemplary variable and constant regions

| SEQUENCE INFORMATION | SEQUENCE (where applicable, CDRs are bolded and underlined) |
|---|---|
| SEQ ID NO: 6 is the VH domain of mAbs B405 and B409 | EVKLVESGGGLVQPGGSLKLSCAASGFTFSSYTMSWVRQTPE KRLEWVAYISNGGGSTYYPDTVKGRFTISRDNAKNTLYLQMS SLKSEDTAMYYCASDGILRPFAYWGQGTLVTVSA (SEQ ID NO: 6) |
| SEQ ID NO: 7 is the VH domain of mAbs B407 and B411 | EVKLVESGGGLVQPGGSLKLSCAASGFTFSSYTMSWVRQTPE KRLEWVAYISNGGGSTYYPDTVKGRFTISRDNAKNTLYLQMS SLKSEDTAMYYCASDGIIRPFAYWGQGTLVTVSA (SEQ ID NO: 7) |
| SEQ ID NO: 8 is CH1 for the human chimeric mAb | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKKVEPKSCDKTHTCPPCP (SEQ ID NO: 8) |
| SEQ ID NO: 9 is CH2 for the human chimeric mAb | APELLGGPSVFLFPPKPKDTLMISRTPEVTCVVVDVSHEDPEVK FNWYVDGVEVHNAKTKPREEQYNSTYRVVSVLTVLHQDWLN GKEYKCKVSNKALPAPIEKTISKAK (SEQ ID NO: 9) |
| SEQ ID NO: 10 is CH3 for the human chimeric mAb | GQPREPQVYTLPPSRDELTKNQVSLTCLVKGFYPSDIAVEWES NGQPENNYKTTPPVLDSDGSFFLYSKLTVDKSRWQQGNVFSCS VMHEALHNHYTQKSLSLSPGK (SEQ ID NO: 10) |
| SEQ ID NO: 11 is the constant domain (G1m17 allotype) of human chimeric filamin-A antibodies provided herein | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKKVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPI EKTISKAKGQPREPQVYTLPPSRDELTKNQVSLTCLVKGFYPSD IAVEWESNGQPENNYKTTPPVLDSDGSFFLYSKLTVDKSRWQQ GNVFSCSVMHEALHNHYTQKSLSLSPGK (SEQ ID NO: 11) |
| SEQ ID NO: 12 is the VL CDR1 of the mouse mAb VL domain and of mAbs B185, B405, B406, and B407 | QDVSID (SEQ ID NO: 12) |
| SEQ ID NO: 13 is the VL CDR1 of mAbs B408, B409, B410, and B411 | QDVSLD (SEQ ID NO: 13) |
| SEQ ID NO: 14 is the VL CDR2 of the mouse mAb VL domain and of mAbs B185, B405, B406, B407, B408, B409, B410, and B 411 | SASH (SEQ ID NO: 14) |
| SEQ ID NO: 15 is the VL CDR3 of the mouse mAb VL domain and of mAbs B185, B405, B406, B407, B408, B409, B410, and B 411 | CQQHYSTPL (SEQ ID NO: 15) |
| SEQ ID NO: 16 is the VH CDR1 of the mouse mAb VH domain and of mAbs B185, B405, B406, B407, B408, B409, B410, and B 411 | GFTFSSYT (SEQ ID NO: 16) |
| SEQ ID NO: 17 is the VH CDR2 of the mouse mAb VH domain and of mAbs B185, B405, B406, B407, B408, B409. B410, and B 411 | ISNGGGST (SEQ ID NO: 17) |
| SEQ ID NO: 18 is the VH CDR3 of the mouse mAb VH domain and of mAbs B185 and B408 | ASDGLLRPFA (SEQ ID NO: 18) |
| SEQ ID NO: 19 is the VH CDR3 of mAbs B406 and B410 | ASDGLIRPFA (SEQ ID NO: 19) |
| SEQ ID NO: 20 is the VH CDR3 of mAbs B405 and B409 | ASDGILRPFA (SEQ ID NO: 20) |

TABLE IA-continued

Exemplary variable and constant regions

| SEQUENCE INFORMATION | SEQUENCE (where applicable, CDRs are bolded and underlined) |
|---|---|
| SEQ ID NO: 21 is the VH CDR3 of mAbs B407 and B411 | ASDGIIRPFA (SEQ ID NO: 21) |
| SEQ ID NO: 22 is the mouse mAb VL domain | DIVMTQSHKFMSTSVGDRVSITCKASQDVSIDVAWYQQKPGQ SPKLLIYSASHRYTGVPDRFTGSGSGTDFTFTISGVQAEDLAVY FCQQHYSTPLTFGAGTKLELK (SEQ ID NO: 22) |
| SEQ ID NO: 23 is the mouse mAb CL domain | RADAAPTVSIFPPSSEQLTSGGASVVCFLNNFYPKDINVKWKID GSERQNGVLNSWTDQ DSKDSTYSMSSTLTLTKDEYERHNSYTCEATHKTSTSPIVKSFN RNEC (SEQ ID NO: 23) |
| SEQ ID NO: 24 is the mouse mAb VH domain | EVKLVESGGGLVQPGGSLKLSCAASGFTFSSYTMSWVRQTPE KRLEWVAYISNGGGSTYYPDTVKGRFTISRDNAKNTLYLQMS SLKSEDTAMYYCASDGLLRPFAYWGQGTLVTVSA (SEQ ID NO: 24) |
| SEQ ID NO: 25 is CH1 for the mouse mAb | AKTTPPSVYPLAPGSAAQTNSMVTLGCLVKGYFPEPVTVTWNS GSLSSGVHTFPAVLQSDLYTLSSSVTVPSSTWPSETVTCNVAHP ASSTKVDKKIVPRDCGCKPCICTVPEVSSVFIFPPK (SEQ ID NO: 25) |
| SEQ ID NO: 26 is CH2 for the mouse mAb | PKDVLTITLTPKVTCVVVDISKDDPEVQFSWFVDDVEVHTAQT QPREEQFNSTFRSVSELPIMHQDWLNGKEFK (SEQ ID NO: 26) |
| SEQ ID NO: 27 is CH3 for the mouse mAb | CRVNSAAFPAPIEKTISKTKGRPKAPQVYTIPPPKEQMAKDKVS LTCMITDFFPEDITVEWQWNGQPAENYKNTQPIMDTDGSYFVY SKLNVQKSNWEAGNTFTCSVLHEGLHNHEITEKSLSHSPGK (SEQ ID NO: 27) |
| SEQ ID NO: 28 is the mouse mAb constant domain | AKTTPPSVYPLAPGSAAQTNSMVTLGCLVKGYFPEPVTVTWNS GSLSSGVHTFPAVLQSDLYTLSSSVTVPSSTWPSETVTCNVAHP ASSTKVDKKIVPRDCGCKPCICTVPEVSSVFIFPPKPKDVLTITLT PKVTCVVVDISKDDPEVQFSWFVDDVEVHTAQTQPREEQFNST FRSVSELPIMHQDWLNGKEFKCRVNSAAFPAPIEKTISKTKGRP KAPQVYTIPPPKEQMAKDKVSLTCMITDFFPEDITVEWQWNGQ PAENYKNTQPIMDTDGSYFVYSKLNVQKSNWEAGNTFTCSVL HEGLHNHEITEKSLSHSPGK (SEQ ID NO: 28) |

SEQ ID NO:1, the light chain variable amino acid sequence for the human chimeric mAb, comprises an isoleucine at residue 31 which may, in one embodiment, instead comprise a leucine. For Example, in some embodiments, the light chain variable amino acid sequence comprises SEQ ID NO: 1. In some embodiments, the CDR regions of SEQ ID NOs: 1 and 2 comprise amino acid residues 27-32 (CDR1), 50-53 (CDR2), and 88-96 (CDR3).

SEQ ID NO:4, the heavy chain variable amino acid sequence for the human chimeric mAb, comprises two leucines at residues 101 and 102 which may, in one embodiment, instead comprise two isoleucines, or may in another embodiment, comprise a leucine at one position and isoleucine at the other. For example, in some embodiments, the heavy chain variable amino acid sequence comprises SEQ ID NO: 5, 6, or 7. In some embodiments, the CDR regions of SEQ ID NOs: 4-7 comprise amino acid residues 26-33 (CDR1), 51-58 (CDR2), and 97-106 (CDR3).

Antibodies and Antibody Fragments

Antibody AHO1402 is a monoclonal antibody obtained from Life Technologies, which is a commercially available murine IgG1k antibody to filamin-A produced using a protein fraction from the breast carcinoma cell line MDA.MB.231 (Alper et al., "Novel anti-filamin-A antibody detects a secreted filamin-A antigen in plasma from patients with breast carcinoma and high-grade astrocytoma," Cancer Sci., Vol. 100 (9), pgs. 1748-1756, 2009, which is incorporated herein by reference in its entirety).

The present disclosure includes antibodies and antibody fragments for filamin-A antigens, including an antibody or antibody fragment capable of binding to a soluble form or cell-associated form of filamin-A with a specific affinity of between $10^{-5}$ M and $10^{-11}$ M; an antibody or antibody fragment capable of binding to a soluble form of filamin-A; an antibody or antibody fragment capable of selectively reducing the activity of a soluble filamin-A; and an antibody or antibody fragment capable of binding to a filamin-A.

An antibody or antibody fragment can be any antibody or antibody fragment and, without limitation, can be a monoclonal antibody, a chimeric antibody, a humanized antibody, and scFv (including Chimeric Antigen Receptor, or CAR), or an antibody or antibody fragment conjugate. In an aspect, an antibody is a mouse monoclonal antibody that identifies a human filamin-A antigen of the present disclosure.

In an aspect, an antibody or antibody fragment can be any gamma globulin protein found in blood or other bodily fluids of vertebrates, and used by the host immune system to identify and neutralize foreign objects, such as bacteria and viruses. In one aspect, the antibody or antibody fragment can be selected from an antibody, a monoclonal antibody, a chimeric antibody, a humanized antibody, and scFv, CAR, or an antibody conjugate. In some embodiments, the scFv or other antibody fragment comprises a light chain variable region provided herein, a heavy chain variable region provided herein, and a linker. Exemplary amino acid sequences of an scFv provided herein are provided in Table 1B. In an aspect, an antibody or antibody fragment can be any type of immunoglobulin protein, such as IgA, IgD, IgE, IgG or IgM. In an aspect, an antibody can be an IgG.

In one aspect, an antibody or antibody fragment is capable of reducing the activity of filamin-A in at least one form. In one aspect, an antibody or antibody fragment is capable of reducing the activity of filamin-A in a soluble form. In another aspect, an antibody or antibody fragment is capable of reducing the activity of filamin-A in a secreted form. In another aspect, the disclosed antibody or antibody fragment is capable of reducing the activity of filamin-A antigen associated with a cell surface, for example a cell membrane associated filamin-A antigen, or an intracellular vesicle associated filamin-A antigen. Thus, it is possible that the antibodies taught herein are taken up by a cell. In some embodiments, a soluble filamin-A protein can have a molecular weight of about 250-280 kDa, as measured by gradient polyacrylamide gel electrophoresis. In one aspect, a soluble filamin-A antigen of the present disclosure is phosphorylated. In some embodiments, the antibodies provided herein bind a filamin-A fragment. For example, in some embodiments, the antibodies provided herein bind a filamin-A protein that is a p180 fragment or a p100 fragment. In particular embodiments, the antibodies provided herein bind the p180 fragment.

In another aspect of the present disclosure, antibodies or antibody fragments can be used to detect a secreted form of filamin-A. In another aspect of the present disclosure, antibodies or antibody fragments can be used to detect a soluble and secreted form or forms of filamin-A. In another aspect of the present disclosure, antibodies or antibody fragments can be used to detect the filamin-A epitopes or fragments thereof.

In one aspect of the present disclosure, an antibody or antibody fragment is capable of preferentially binding to a soluble form of filamin-A protein. In this aspect, such preferential binding to filamin-A can be relative to any other protein. In a particular aspect, such preferential binding to filamin-A is relative to filamin-A that is membrane bound or associated. However, in other aspects, an antibody or antibody fragment taught herein is capable of preferentially binding to a cell membrane bound form of filamin-A protein, relative to an unbound form of the antigen. Thus, provided in the present disclosure, are antibodies and fragments thereof that can preferentially bind: membrane bound forms of filamin-A antigen, non-membrane bound forms of filamin-A antigen, or both.

In one aspect of the present disclosure, an antibody or antibody fragment is capable of preferentially binding to a secreted form of filamin-A protein. In another aspect of the present disclosure, an antibody or antibody fragment is capable of binding to a secreted and soluble form or forms of filamin-A protein. In another aspect of the present disclosure, an antibody or antibody fragment is capable of binding to filamin-A epitopes of the present disclosure or fragments thereof.

As used herein, a membrane associated protein or membrane bound protein, is a protein that can be found localized with a membrane upon examination of cell. A membrane bound protein is one that interfaces at least in part with the lipid bilayer. In one aspect, it is bound to the membrane via ionic interactions. In another aspect, a membrane bound protein is bound to the membrane via covalent interactions. In one aspect, a membrane bound protein is bound to the membrane via hydrophobic interactions. The antibodies taught herein may bind to the aforementioned membrane bound, or membrane associated, protein.

In one aspect of the present disclosure, preferential binding is relative to background. In another aspect, the preferential binding is at least 2-fold, 3-fold, 4-fold, 5-fold, 10-fold, 100-fold, 1,000-fold, 10,000-fold or 1,000,000-fold. In another aspect, an antibody of the present disclosure preferentially binds a soluble form of filamin-A compared to a membrane form of filamin-A. In a particular aspect, an antibody of the present disclosure preferentially binds a soluble form of filamin-A compared to a nuclear membrane form of filamin-A, or the reverse, in another aspect. That is, in some aspects, the above preferential binding relates to the ability of the taught antibodies to preferentially bind to filamin-A antigen associated with a cell membrane.

In an aspect, an antibody or antibody fragment taught herein binds filamin-A or a particular form of filamin-A, such as a secreted or soluble form (e.g. from human breast cancer), or a membrane bound form, with a specific affinity of greater than about $10^{-5}$ M, about $10^{-6}$ M, about $10^{-7}$ M, about $10^{-8}$ M, about $10^{-9}$ M, about $10^{-10}$ M, about $10^{-11}$ M, or about $10^{-12}$ M, or between about $10^{-8}$ M to about $10^{-11}$ M, or about $10^{-9}$ M to about $10^{-10}$ M, or about $10^{-10}$ M to about $10^{-11}$ M. In one aspect, specific activity is measured using a competitive binding assay.

In some embodiments, the present disclosure provides an anti-filamin-A antibody comprising a light chain CDR1 sequence selected from SEQ ID NOs: 12 and 13. In some embodiments, the present disclosure provides an anti-filamin-A antibody comprising a light chain CDR2 sequence according to SEQ ID NO: 14. In some embodiments, the present disclosure provides an anti-filamin-A antibody comprising a light chain CDR3 sequence according to SEQ ID NO: 15. In some embodiments, the present disclosure provides an anti-filamin-A antibody comprising a heavy chain CDR1 sequence according to SEQ ID NO: 16. In some embodiments, the present disclosure provides an anti-filamin-A antibody comprising a heavy chain CDR2 sequence according to SEQ ID NO: 17. In some embodiments, the present disclosure provides an anti-filamin-A antibody comprising a heavy chain CDR3 sequence selected from SEQ ID NOs: 18, 19, 20, and 21. In some embodiments, the present disclosure provides an antibody comprising any of the light and heavy chain CDR1, CDR2, and CDR3 sequences provided herein.

In some embodiments, the present disclosure provides an anti-filamin-A antibody comprising a light chain variable region selected from SEQ ID NOs: 1 and 2. In some embodiments, the present disclosure provides and anti-filamin-A antibody comprising a heavy chain variable regions selected from SEQ ID NOs: 4, 5, 6, and 7. In some embodiments, the present disclosure provides an antibody comprising any of the light and heavy chain variable region sequences provided herein. In further embodiments, the present disclosure provides an antibody comprising a constant light chain region comprising SEQ NO: 3 or SEQ ID NO: 23. IN some embodiments, the present disclosure provides an antibody comprising a constant heavy chain region comprising SEQ ID NO: 11 or SEQ ID NO: 28.

In some embodiments, the present disclosure provides an anti-filamin-A antibody B185, comprising a light chain variable region according to SEQ ID NO:1 and a heavy chain variable region according to SEQ ID NO:4. In some embodiments, the present disclosure provides an anti-filamin-A antibody B405, comprising a light chain variable region according to SEQ ID NO:1 and a heavy chain variable region according to SEQ ID NO:6. In some embodiments, the present disclosure provides an anti-filamin-A antibody B406, comprising a light chain variable region according to SEQ ID NO:1 and a heavy chain variable region according to SEQ ID NO:5. In some embodiments, the present disclosure provides an anti-filamin-A antibody B407, comprising a light chain variable region according to SEQ ID NO:1 and a heavy chain variable region according to SEQ ID NO:7. In some embodiments, the present disclosure provides an anti-filamin-A antibody B408, comprising a light chain variable region according to SEQ ID NO:2 and a heavy chain variable region according to SEQ ID NO: 4. In some embodiments, the present disclosure provides an anti-filamin-A antibody B409, comprising a light chain In some embodiments, the present disclosure provides an intrabody comprising the light and variable chain regions provided herein. In some embodiments, the intrabody comprises an scFv sequence provided herein. Amino acid and DNA sequences of exemplary intrabodies provided herein are provided below in Table 1B. In some embodiments, the scFv or intrabody comprises an amino acid sequence selected from SEQ ID NOs: 67 and 69. In some embodiments, the scFv or intrabody comprises a DNA sequence selected from SEQ ID NOs: 68 and 70.

TABLE 1B

Exemplary scFv or intrabody sequences

| SEQ ID NO | Description | SEQUENCE |
| --- | --- | --- |
| 67 | Amino acid sequence of VH-VL intrabody | EVKLVESGGGLVQPGGSLKLSCAASGFTFSSYTMSWVRQTPEKRLEWVAYIS NGGGSTYYPDTVKGRFTISRDNAKNTLYLQMSSLKSEDTAMYYCASDGLLRP FAYWGQGTLVTVSAGGGGSGGGGSGGGGSDIVMTQSHKFMSTSVGDRVSITC KASQDVSIDVAWYQQKPGQSPKLLIYSASHRYTGVPDRFTGSGSGTDFTFTI SGVQAEDLAVYFCQQHYSTPLTFGAGTKLELK |
| 68 | DNA sequence of VH-VL intrabody | GAGGTTAAATTGGTTGAGTCCGGGGGTGGCCTGGTACAACCAGGCGGAAGTC TTAAGCTCTCTTGTGCAGCGTCAGGGTTCACATTTTCCTCATATACCATGTC TTGGGTGCGCCAGACACCAGAAAAGCGCTTGGAGTGGGTGGCTTACATAAGC AACGGGGGAGGCAGCACGTACTATCCTGACACGGTTAAGGGACGATTTACCA TTTCCAGGGACAATGCGAAAAATACGCTGTACCTGCAAATGTCTTCTTTGAA ATCCGAAGACACAGCCATGTACTACTGCGCATCAGATGGACTCCTGAGACCG TTTGCATATTGGGGTCAAGGGACATTGGTAACGGTCAGCGCAGGCGGCGGAG GCTCTGGTGGTGGAGGGAGTGGGGGAGGGGGATCTGACATAGTCATGACGCA GAGTCATAAGTTTATGAGCACTTCTGTAGGCGATCGAGTTTCAATCACCTGT AAAGCAAGTCAGGACGTAAGTATCGATGTTGCTTGGTATCAACAAAAACCAG GGCAGAGCCCTAAGTTGCTGATCTATAGTGCTTCACACCGATACACCGGAGT CCCCGACCGCTTCACCGGATCAGGGTCCGGCACCGACTTCACGTTTACGATC AGCGGCGTGCAAGCGGAAGACCTCGCGGTTTACTTCTGTCAGCAGCACTATT CAACGCCCCTGACCTTTGGGGCGGGAACGAAATTGGAATTGAAA |
| 69 | Amino acid sequence of VL-VH intrabody | DIVMTQSHKFMSTSVGDRVSITCKASQDVSIDVAWYQQKPGQSPKLLIYSAS HRYTGVPDRFTGSGSGTDFTFTISGVQAEDLAVYFCQQHYSTPLTFGAGTKL ELKGGGGSGGGGSGGGGSEVKLVESGGGLVQPGGSLKLSCAASGFTFSSYTM SWVRQTPEKRLEWVAYISNGGGSTYYPDTVKGRFTISRDNAKNTLYLQMSSL KSEDTAMYYCASDGLLRPFAYWGQGTLVTVSA |
| 70 | DNA sequence of VL-VH intrabody | GACATTGTAATGACACAAAGTCATAAGTTCATGTCAACAAGCGTCGGCGACC GGGTGTCTATAACTTGCAAGGCGTCTCAAGATGTGTCCATCGATGTAGCGTG GTATCAACAGAAACCCGGGCAAAGCCCGAAGCTGCTGATATACTCAGCCTCC CACCGATATACTGGAGTTCCAGATCGATTCACTGGTAGTGGGTCAGGAACTG ATTTCACATTTACCATCAGCGGGGTGCAAGCGGAGGATCTGGCAGTCTATTT CTGCCAGCAACACTATTCCACGCCCCTGACCTTCGGCGCAGGAACGAAGTTG GAGTTGAAAGGCGGCGGAGGCTCTGGTGGTGGAGGGAGTGGGGGAGGGGGAT CTGAAGTGAAACTGGTTGAATCTGGTGGCGGTCTTGTACAACCGGGAGGATC TTTGAAACTCTCATGCGCTGCCAGTGGTTTTACCTTCAGCAGCTACACCATG AGCTGGGTTCGCCAAACCCCAGAAAAAAGACTTGAGTGGGTCGCTTACATCT CTAATGGTGGTGGGAGTACTTACTATCCAGACACTGTAAAAGGTCGATTCAC GATCAGTCGAGATAATGCAAAAAATACCCTGTACTTGCAAATGAGTAGCTTG AAATCCGAAGACACAGCCATGTATTACTGCGCCTCAGATGGCTTGCTCCGGC CTTTTGCCTATTGGGGACAGGGTACTCTCGTAACCGTATCTGCA | variable region according to SEQ ID NO:2 and a heavy chain variable region according to SEQ ID NO:6. In some embodiments, the present disclosure provides an anti-filamin-A antibody B410, comprising a light chain variable region according to SEQ ID NO:2 and a heavy chain variable region according to SEQ ID NO:5. In some embodiments, the present disclosure provides an anti-filamin-A antibody B411, comprising a light chain variable region according to SEQ ID NO:2 and a heavy chain variable region according to SEQ ID NO: 7. In some embodiments, antibody B411 comprises a light chain CDR1, CDR2, and CDR3 according to SEQ ID NOs: 13, 14, and 15, respectively; and a heavy chain CDR1, CDR2, and CDR3 according to SEQ ID NOs: 16, 17, and 21, respectively.

In another aspect, an antibody or antibody fragment of the present disclosure can be used to detect breast cancer in tissue of a subject. In some embodiments, an antibody or antibody fragment of the present disclosure can be used to detect cancer in any sample from a patient, such as, for example, a biopsy sample, plasma or serum.

A further aspect of the present disclosure provides a composition comprising: a tissue specimen, an antibody-antigen complex between an antibody capable of preferentially binding to a soluble form of filamin-A antigen and a soluble form of filamin-A antigen within the said specimen. In one aspect of the disclosure, the tissue specimen is from a patient suffering from a disease characterized by the expression of gene products of filamin-A and homologues thereof. In a further aspect of the disclosure, the patient is suffering from breast cancer, ovarian cancer, lung cancer, prostate cancer, head/neck cancer, or brain cancer. In another aspect of the disclosure, the soluble form of filamin-A antigen is overexpressed in said tissue specimen. In one aspect, the present disclosure provides a use of said composition for detecting a disease in a patient characterized by the expression of gene products of filamin-A and homologs thereof. In one aspect of the disclosure, immunohistochemical staining of said composition indicates the presence of a disease in the patient. In one aspect of the disclosure, said disease is breast cancer, ovarian cancer, lung cancer, prostate cancer, or head/neck cancer. In another aspect, the disease is breast cancer, stomach cancer, colon cancer. In an aspect, the disease is breast cancer.

In one aspect, a filamin-A antibody of the present disclosure can identify a subset of filamin-A-antibody-positive cancer cells (metastatic or nonmetastatic) that are likely to benefit from treatment. Such a filamin-A antibody of the present disclosure can be used in a method of identifying a subject in need thereof, such as a patient having cancer, that will benefit from treatment. Methods of the present disclosure can include a method of detecting lower levels of filamin-A in blood, plasma, or sera using a filamin-A antibody of the present disclosure. In one aspect, the method detects filamin-A earlier in the course of disease in plasma than currently available tests.

Antibodies and antibody fragments can optionally be immobilized on a solid phase, detectably labeled, or conjugated to a cytotoxic radionuclide, a cytotoxic drug, or a cytotoxic protein and the like.

Antibodies and antibody fragments of the present disclosure can target expression of filamin-A antigen by cells, mammalian cells, mammalian cancer cells, human cells, and human cancer cells. Exemplary cancers include solid tumors of human breast, ovary, cervix, prostate, colon, stomach, kidney, liver, head, neck, lung, blood, pancreas, skin, testicle, thyroid and brain cancer cells. In one aspect, the antibodies or antibody fragments target human breast, stomach, and colon cells. Exemplary cancers also include non-solid cancers. For example, cancers include, but are not limited to: leukemias including acute leukemias and chronic leukemias such as acute lymphocytic leukemia (ALL), acute myeloid leukemia (AML), chronic lymphocytic leukemia (CLL), chronic myelogenous leukemia (CML) and hairy cell leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas; and multiple myeloma. Expressed filamin-A antigens can include any form of the gene product, although particular aspects relate to the detection of the soluble or secreted form of filamin-A. Such antigens can also include gene produced homologues of the filamin-A gene and modified filamin-A antigens expressed by cancer cells.

In one aspect, the present disclosure includes an antibody or an antibody fragment with preferential binding for a filamin-A antigen, including the heavy chain CDR antigen binding site amino acid sequences and the light chain CDR antigen binding site amino acid sequences. The present disclosure also includes an antibody with preferential binding for a filamin-A antigen, comprising one or more of the heavy chain CDR antigen binding site amino acid sequences and one or more of the light chain CDR antigen binding site amino acid sequences.

The present disclosure includes filamin-A antibodies or antibody fragments having antigen binding sites with one or more of the CDRs from both heavy and light chains. The disclosure also includes antibodies and antibody fragments specific to filamin-A expression products that contain antigen binding sites that are substantially homologous to these, or that result in substantially similar binding properties. Such antibodies or fragments thereof can be at least 99%, 98%, 97%, 96%, 95%, 94%, 93%, 92%, 91%, 90%, 89%, 88%, 87%, 86%, 85%, 84%, 83%, 82%, 81%, or 80% identical to one or more of the CDR heavy or light chains from filamin-A antibodies of the present disclosure.

The present disclosure also includes novel protein expression cell lines, and the monoclonal antibody molecules that they secrete, which are specific to filamin-A antigen expressed by normal or cancer cells. As aforementioned, the antibodies produced herein are capable of binding, in one embodiment, a soluble or secreted form of filamin-A that is produced by cancer cells, e.g. breast cancer cells. However, in other embodiments, the antibodies produced herein are capable of binding a membrane-bound or membrane-associated form of filamin-A that is produced by, or associated with, cancer cells, e.g. breast cancer cells. In some embodiments, the antibodies produced herein are capable of binding a soluble or membrane associated fragment of FLNa.

The present disclosure includes chimeric antibodies, humanized antibodies, and fully human antibodies. The disclosure also includes antibody fragments and other modified antibodies and antibody fragments.

The present disclosure also encompasses antibodies and antibody fragments that have preferential binding to filamin-A antigens, but which have FWR and/or CDR antigen binding site amino acid sequences that are not identical to those contained in Table 1A. Such antibodies can be preferentially selective for the filamin-A antigen at least 2-fold, at least 5-fold, at least 10-fold, or at least 50-fold higher affinity for a filamin-A antigen of the present disclosure or antibody fragment thereof. In one aspect, a variant of an antibody or antibody fragment of the present disclosure can be as specific for the filamin-A antigen as a non-variant antibody or antibody fragment of the present disclosure, or can be more specific.

Antibodies and antibody fragments that are specific to filamin-A, but which have FWR and/or CDR antigen binding site amino acid sequences that are not identical to those contained in Table 1A, can possess the same or different specificity determining regions (SDRs) as the FWRs and/or CDRs contained in Table 1A are included.

Modifications to the amino acid sequences set forth in Table 1A can occur in either or both of the FWR and CDR sequences. In one aspect, modifications can be made to another filamin-A antibody to match one or more amino acid sequence of the antigen binding sites set forth in Table 1A. According to certain aspects of the disclosure, variations in antibodies or antibody fragments can occur where they have substantially homologous amino acid sequences, antibodies having substantially similar binding properties, or both. In one aspect of the disclosure, there can be a single amino acid change in the CDR antigen binding sites. Amino acid sequence variants of the filamin-A antibody are prepared by introducing appropriate nucleotide changes into the filamin-A antibody nucleic acid, or by peptide synthesis. Such modifications include, for example, deletions from, and/or insertions into and/or substitutions of, residues within the amino acid sequences of the filamin-A antibody. Any combination of deletion, insertion, and substitution is made to arrive at the final construct, provided that the final construct possesses the desired characteristics. The amino acid changes also may alter post-translational processes of the filamin-A antibody, such as changing the number or position of glycosylation sites.

Amino acid substitution variants have at least one amino acid residue in the filamin-A antibody molecule replaced by a different residue. The sites of greatest interest for substitutional mutagenesis include the hypervariable regions or CDRs, but alterations in FWR regions are also contemplated.

Conservative substitutions involve replacing amino acids with those that have similar charge or hydrophobicity, for example: (1) non-polar: Ala (A), Val (V), Leu (L), Ile (I), Pro (P), Phe (F), Trp (W), Met (M); (2) uncharged polar: Gly (G), Ser(S), Thr (T), Cys (C), Tyr (Y), Asn (N), Gln (Q); (3) acidic: Asp (D), Glu (E); and (4) basic: Lys (K), Arg (R), His (H).

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

A particularly embodied type of substitutional variant involves substituting one or more hypervariable region residues of a parent antibody (e.g. a humanized or human antibody). Generally, the resulting variant(s) selected for further development will have improved biological properties relative to the parent antibody from which they are generated.

Humanized variants of the antibodies or antibody fragments of the disclosure can contain a reduced murine content, and potentially, reduced immunogenicity, when compared to murine antibodies, such as AHO1402, or antibody fragments thereof. Humanized variants include those that retain a binding affinity that is substantially similar to that of the original antibody or antibody fragment. An aspect of the disclosure provides CDR variants of humanized filamin-A antibodies or antibody fragments in which 1, 2, 3, 4, 5, or 6 (three heavy chain and three light chain) CDRs are humanized. In another aspect, the disclosure contemplates SDR variants of humanized filamin-A antibodies and antibody fragments in which only Specificity Determining Residues (SDRs) of at least one CDR from the filamin-A antibodies and antibody fragments are present in the humanized antibodies.

CDR variants can be formed by replacing at least one CDR of a humanized filamin-A antibody and antibody fragments with a corresponding CDR from a human antibody. CDR variants in which one, two, three, four, five, or six CDRs are replaced by a corresponding CDR from a human antibody and retain biological activity that is substantially similar to the binding affinity of the parental filamin-A mAb. CDR variants of the disclosure can have a binding affinity that is 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% more than the binding affinity of the parental filamin-A antibody or antibody fragment.

CDR variants can have altered immunogenicity when compared to filamin-A antibodies and antibody fragments can be formed by grafting all six (three heavy chain and three light chain) CDRs from the filamin-A antibodies and antibody fragments of the present disclosure onto the variable light ($V_L$) and variable heavy ($V_H$) frameworks of human antibodies and antibody fragments. However, less than all six of the CDRs of the filamin-A antibodies and antibody fragments of the present disclosure can be present, while still permitting an antibody of the present disclosure to retain activity. Residues that are directly involved in antigen contact, such as Specificity Determining Residues (SDRs), can be refined. SDR variants are formed by replacing at least one SDR of the filamin-A antibody or antibody fragment with a residue at a corresponding position from a human antibody. It should be noted that not all CDRs must include SDRs.

In one aspect, the variants of the present antibodies and antibody fragments include a combination of CDR and/or SDR substitutions to generate variants having reduced immunogenicity in humans and a binding affinity that is substantially similar to that of the parental antibody or antibody fragment to filamin-A.

In addition to variants specifically described herein, other "substantially homologous" modified immunoglobulins can be readily designed and manufactured using various recombinant DNA techniques. For example, the framework regions (FWRs) can be varied at the primary structure level. Moreover, a variety of different human framework regions can be used singly or in combination as a basis for the variant. In general, modifications of the genes can be readily accomplished by a variety of techniques, such as site-directed mutagenesis and random mutagenesis.

Alternatively, polypeptide fragments comprising only a portion of the primary antibody structure can be produced where the fragment substantially retains the immunoreactivity properties of the variant. Such polypeptide fragments include fragments produced by proteolytic cleavage of intact antibodies or fragments produced by inserting stop codons at the desired locations nucleotide sequence using site-directed mutagenesis. Single chain antibodies and fusion proteins, which include at least an immunoreactivity fragment of the variant, are also included within the scope of the disclosure.

The antibodies and their variants in accordance with the present disclosure can be directly or indirectly attached to effector moieties having therapeutic activity. Suitable effector moieties include cytokines, cytotoxins, radionuclides, drugs, immunomodulators, therapeutic enzymes, anti-proliferative agents, etc. Methods for attaching antibodies to such effectors are known in the art. These conjugated antibodies can be incorporated into any composition, including pharmaceutical compositions for use in treating diseases characterized by the expression of filamin-A, including cancer, such as cancer of the breast, ovary, cervix, prostate, colon, stomach, kidney, liver, head, neck, lung, blood, pancreas, skin, testicle, thyroid and brain. In one aspect, the cells are from human breast, ovary, head, neck, or brain. The pharmaceutical compositions are administered to a mammal, which can include a human patient in need of such treatment, in order to treat the disease.

Antibodies and antibody fragments can either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available.

Sequences and CDR Regions of a Second Embodiment

Additional sequences of the disclosure can be found in the below Tables 2-5.

These sequences correspond, inter alia, to alternative CDR binding domain regions from the sequences aforementioned in Table 1A. Further, these binding domain sequences and their positions within the overall antibody sequence are mapped in FIGS. 28-31.

Figure 31:
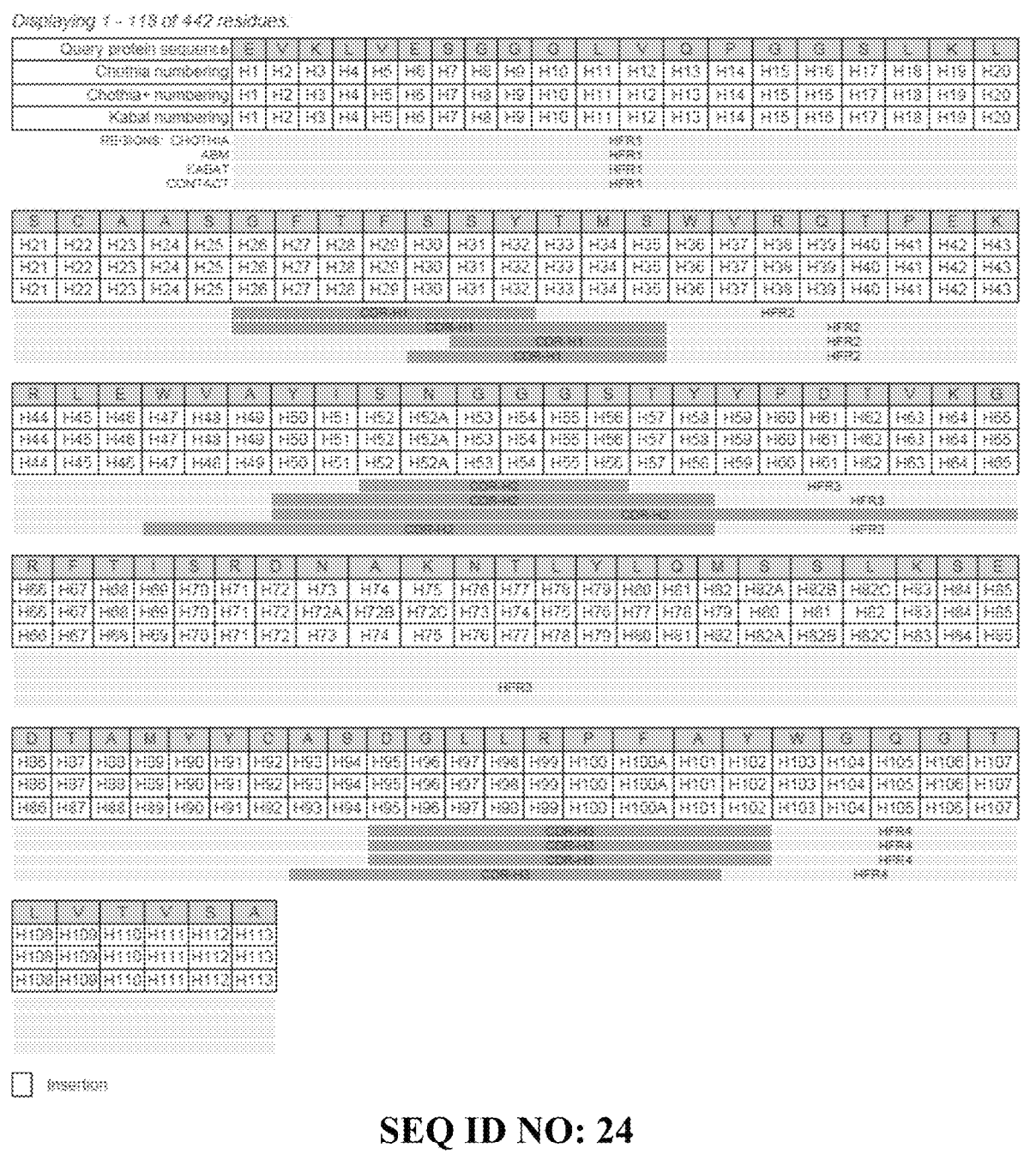

The FIGS. 28-31 depict the alignment consensus among CDR regions predicted by Chothia, ABM, Kabat, and Contact for the human chimeric light chain variable CDR binding domain regions (FIG. 28), human chimeric heavy chain variable CDR binding domain regions (FIG. 29), murine light chain variable CDR binding domain regions (FIG. 30), and murine heavy chain variable CDR binding domain regions (FIG. 31).

TABLE 2

Human chimeric light chain variable CDR binding domain regions

| Region | Definition | Sequence Fragment | SEQ ID NO. |
|---|---|---|---|
| LFR1 | Chothia | DIVMTQSHKFMSTSVGDRVSITC------ | 29 |
|  | AbM | DIVMTQSHKFMSTSVGDRVSITC------ | 29 |
|  | Kabat | DIVMTQSHKFMSTSVGDRVSITC------ | 29 |
|  | Contact | DIVMTQSHKFMSTSVGDRVSITCKASQDV | 30 |
| CDR-L1 | Chothia | KASQDVSIDVA-- | 31 |
|  | AbM | KASQDVSIDVA-- | 31 |
|  | Kabat | KASQDVSIDVA-- | 31 |
|  | Contact | ------SIDVAWY | 32 |

TABLE 2-continued

Human chimeric light chain variable CDR binding domain regions

| Region | Definition | Sequence Fragment | SEQ ID NO. |
|---|---|---|---|
| LFR2 | Chothia | WYQQKPGQSPKLLIY | 33 |
|  | AbM | WYQQKPGQSPKLLIY | 33 |
|  | Kabat | WYQQKPGQSPKLLIY | 33 |
|  | Contact | --QQKPGQSPK---- | 34 |
| CDR-L2 | Chothia | ----SASHRYT | 35 |
|  | AbM | ----SASHRYT | 35 |
|  | Kabat | ----SASHRYT | 35 |
|  | Contact | LLIYSASHRY- | 36 |
| LFR3 | Chothia | -GVPDRFTGSGSGTDFTFTISGVQAEDLAVYFC | 37 |
|  | AbM | -GVPDRFTGSGSGTDFTFTISGVQAEDLAVYFC | 37 |
|  | Kabat | -GVPDRFTGSGSGTDFTFTISGVQAEDLAVYFC | 37 |
|  | Contact | TGVPDRFTGSGSGTDFTFTISGVQAEDLAVYFC | 38 |
| CDR-L3 | Chothia | QQHYSTPLT | 39 |
|  | AbM | QQHYSTPLT | 39 |
|  | Kabat | QQHYSTPLT | 39 |
|  | Contact | QQHYSTPL- | 40 |
| LFR4 | Chothia | -FGAGTKLELKRTV | 41 |
|  | AbM | -FGAGTKLELKRTV | 41 |
|  | Kabat | -FGAGTKLELKRTV | 41 |
|  | Contact | TFGAGTKLELKRTV | 42 |

TABLE 3

Human chimeric heavy chain variable CDR binding domain regions

| Region | Definition | Sequence Fragment | SEQ ID NO. |
|---|---|---|---|
| HFR1 | Chothia | EVKLVESGGGLVQPGGSLKLSCAAS----- | 43 |
|  | AbM | EVKLVESGGGLVQPGGSLKLSCAAS----- | 43 |
|  | Kabat | EVKLVESGGGLVQPGGSLKLSCAASGFTFS | 44 |
|  | Contact | EVKLVESGGGLVQPGGSLKLSCAASGFTF- | 45 |
| CDR-H1 | Chothia | GFTFSSY--- | 46 |
|  | AbM | GFTFSSYTMS | 47 |
|  | Kabat | -----SYTMS | 48 |
|  | Contact | ----SSYTMS | 49 |
| HFR2 | Chothia | TMSWVRQTPEKRLEWVAYI | 50 |
|  | AbM | ---WVRQTPEKRLEWVA-- | 51 |
|  | Kabat | ---WVRQTPEKRLEWVA-- | 51 |
|  | Contact | ---WVRQTPEKRLE----- | 52 |
| CDR-H2 | Chothia | -----SNGGGS--------- | 53 |
|  | AbM | ---YISNGGGSTY------- | 54 |
|  | Kabat | ---YISNGGGSTYYPDTVKG | 55 |
|  | Contact | WVAYISNGGGSTY------- | 56 |
| HFR3 | Chothia | TYYPDTVKGRFTISRDNAKNTLYLQMSSLKSEDTAMYYCAS | 57 |
|  | AbM | --YPDTVKGRFTISRDNAKNTLYLQMSSLKSEDTAMYYCAS | 58 |
|  | Kabat | ---------RFTISRDNAKNTLYLQMSSLKSEDTAMYYCAS | 59 |
|  | Contact | --YPDTVKGRFTISRDNAKNTLYLQMSSLKSEDTAMYYC-- | 60 |
| CDR-H3 | Chothia | --DGLLRPFAY | 61 |
|  | AbM | --DGLLRPFAY | 61 |
|  | Kabat | --DGLLRPFAY | 61 |
|  | Contact | ASDGLLRPFA- | 62 |

TABLE 3-continued

Human chimeric heavy chain variable CDR binding domain regions

| Region | Definition | Sequence Fragment | SEQ ID NO. |
|---|---|---|---|
| HFR4 | Chothia | -WGQGTLVTVSA | 63 |
|  | AbM | -WGQGTLVTVSA | 63 |
|  | Kabat | -WGQGTLVTVSA | 63 |
|  | Contact | YWGQGTLVTVSA | 64 |

TABLE 4

Murine light chain variable CDR binding domain regions

| Region | Definition | Sequence Fragment | SEQ ID NO. |
|---|---|---|---|
| LFR1 | Chothia | DIVMTQSHKFMSTSVGDRVSITC------ | 29 |
|  | AbM | DIVMTQSHKFMSTSVGDRVSITC------ | 29 |
|  | Kabat | DIVMTQSHKFMSTSVGDRVSITC------ | 29 |
|  | Contact | DIVMTQSHKFMSTSVGDRVSITCKASQDV | 30 |
| CDR-L1 | Chothia | KASQDVSIDVA-- | 31 |
|  | AbM | KASQDVSIDVA-- | 31 |
|  | Kabat | KASQDVSIDVA-- | 31 |
|  | Contact | ------SIDVAWY | 32 |
| LFR2 | Chothia | WYQQKPGQSPKLLIY | 33 |
|  | AbM | WYQQKPGQSPKLLIY | 33 |
|  | Kabat | WYQQKPGQSPKLLIY | 33 |
|  | Contact | --QQKPGQSPK---- | 34 |
| CDR-L2 | Chothia | ----SASHRYT | 35 |
|  | AbM | ----SASHRYT | 35 |
|  | Kabat | ----SASHRYT | 35 |
|  | Contact | LLIYSASHRY- | 36 |
| LFR3 | Chothia | -GVPDRFTGSGSGTDFTFTISGVQAEDLAVYFC | 37 |
|  | AbM | -GVPDRFTGSGSGTDFTFTISGVQAEDLAVYFC | 37 |
|  | Kabat | -GVPDRFTGSGSGTDFTFTISGVQAEDLAVYFC | 37 |
|  | Contact | TGVPDRFTGSGSGTDFTFTISGVQAEDLAVYFC | 38 |
| CDR-L3 | Chothia | QQHYSTPLT | 39 |
|  | AbM | QQHYSTPLT | 39 |
|  | Kabat | QQHYSTPLT | 39 |
|  | Contact | QQHYSTPL- | 40 |
| LFR4 | Chothia | -FGAGTKLELKRA | 65 |
|  | AbM | -FGAGTKLELKRA | 65 |
|  | Kabat | -FGAGTKLELKRA | 65 |
|  | Contact | TFGAGTKLELKRA | 66 |

TABLE 5

Murine heavy chain variable CDR binding domain regions

| Region | Definition | Sequence Fragment | SEQ ID NO. |
|---|---|---|---|
| HFR1 | Chothia | EVKLVESGGGLVQPGGSLKLSCAAS----- | 43 |
|  | AbM | EVKLVESGGGLVQPGGSLKLSCAAS----- | 43 |
|  | Kabat | EVKLVESGGGLVQPGGSLKLSCAASGFTFS | 44 |
|  | Contact | EVKLVESGGGLVQPGGSLKLSCAASGFTF- | 45 |
| CDR-H1 | Chothia | GFTFSSY--- | 46 |
|  | AbM | GFTFSSYTMS | 47 |
|  | Kabat | -----SYTMS | 48 |
|  | Contact | ----SSYTMS | 49 |
| HFR2 | Chothia | TMSWVRQTPEKRLEWVAYI | 50 |
|  | AbM | ---WVRQTPEKRLEWVA-- | 51 |
|  | Kabat | ---WVRQTPEKRLEWVA-- | 51 |
|  | Contact | ---WVRQTPEKRLE----- | 52 |
| CDR-H2 | Chothia | -----SNGGGS--------- | 53 |
|  | AbM | ---YISNGGGSTY------- | 54 |
|  | Kabat | ---YISNGGGSTYYPDTVKG | 55 |
|  | Contact | WVAYISNGGGSTY------- | 56 |
| HFR3 | Chothia | TYYPDTVKGRFTISRDNAKNTLYLQMSSLKSEDTAMYYCAS | 57 |
|  | AbM | --YPDTVKGRFTISRDNAKNTLYLQMSSLKSEDTAMYYCAS | 58 |
|  | Kabat | ---------RFTISRDNAKNTLYLQMSSLKSEDTAMYYCAS | 59 |
|  | Contact | --YPDTVKGRFTISRDNAKNTLYLQMSSLKSEDTAMYYC-- | 60 |

TABLE 5-continued

Murine heavy chain variable CDR binding domain regions

| Region | Definition | Sequence Fragment | SEQ ID NO. |
|---|---|---|---|
| CDR-H3 | Chothia | --DGLLRPFAY | 61 |
|  | AbM | --DGLLRPFAY | 61 |
|  | Kabat | --DGLLRPFAY | 61 |
|  | Contact | ASDGLLRPFA- | 62 |
| HFR4 | Chothia | -WGQGTLVTVSA | 63 |
|  | AbM | -WGQGTLVTVSA | 63 |
|  | Kabat | -WGQGTLVTVSA | 63 |
|  | Contact | YWGQGTLVTVSA | 64 |

The identification of CDR boundaries is often used to pinpoint sequences that many believe are critical for antibody binding of antigen. The definition of CDRs thus tends to focus on regions of hypervariability, but also includes key amino acids and positions in the antibody sequence. As a result, the boundaries of these regions can vary depending on the criteria one sets for the analysis of the sequence databases. The composition of the database itself may also influence the results. In this regard, the boundaries defining CDRs can vary from one system to another. In addition, there are known instances where an amino acid falling outside the CDR/hypervariable regions may also contribute to direct binding of antigen although this is not always the case for all antibodies containing that particular amino acid. Because of this, there are several methods for identifying the CDRs and antibody positions that may interact directly with antigen.

In one aspect, the sequence database utilized within the scope of the present disclosure is the Abysis database (bioinf.org.uk), which integrates sequence data from several databases, including the Kabat, IMGT, PDB databases, in addition to structural data from the PDB. In using the Abysis system a practitioner can simultaneously obtain CDR boundaries as defined by Kabat, Chothia, Martin (enhanced Chothia), and contact information. The antibody sequence numbering system for Kabat and others may differ. Rather than being focused on the numbering systems, the focus is trained on the actual amino acid sequences defining the CDRs under the different systems. General information regarding the Abysis database can be found at bioinf.org.uk/abs/, which is incorporated herein by reference in its entirety for all purposes.

The CDR definitions in the Abysis analysis includes the following: (1) Kabat, based on sequence variability, which is the most commonly used system; (2) Chothia, based on the location of the structural loop regions; (3) Abysis-Martin (AbM), a compromise between the Kabat and Chothia definitions based on Oxford Molecular's antibody modeling software; and (4) Contact, based on analysis of available complex antibody-antigen crystal structures, and likely to be useful for grafting and mutagenesis.

While the results are not always in 100% agreement amongst the aforementioned systems, by using these different systems a better understanding of the regions of the antibody that may be important for antigen binding can be gained. With regard to antibodies of the present disclosure, the results of the Abysis analysis are detailed in Tables 2-5 and FIGS. 28-31.

Antigens and Binding Regions of the Antibodies of the Disclosure

Antibodies and fragments thereof, of the present disclosure, are capable of binding to filamin-A antigen.

As aforementioned, some embodiments of the disclosure bind a soluble or secreted filamin-A antigen. In particular aspects, the soluble or secreted filamin-A antigen is derived from human breast cancer cells.

In some aspects, the antigen bound by the antibodies of the present disclosure is the antigen discussed in Alper et al., "Novel anti-filamin-A antibody detects a secreted variant of filamin-A in plasma from patients with breast carcinoma and high-grade astrocytoma," Cancer Sci., Vol. 100 (9), pgs. 1748-1756, 2009, which is incorporated herein by reference in its entirety for all purposes. Thus, in some aspects, the disclosure proposes a filamin-A antigen model in which the taught antibodies bind upstream (N-terminal) to the calpain cleavage site in FLNa that results in creation of two fragments with sizes of ~180 kDa (p180, N-terminal to calpain site) and ~100 kDa (p100, C-terminal to cleavage site). In this model, the taught antibodies appear to not bind the p100 C-terminal cleavage product, but do bind the p280 (full-length) and p180 fragments. See FIG. 1c of Alper et al., 2009.

In some aspects, the antigen bound by the antibodies of the present disclosure is a membrane bound or membrane associated filamin-A antigen, as discussed in Bachman, et al. "Actin-binding protein filamin A is displayed on the surface of human neuroblastoma cells," Cancer Sci., Vol. 97 (12), pgs. 1359-1365, 2006, which is incorporated herein by reference in its entirety for all purposes. Thus, in some aspects, the disclosure proposes a filamin-A antigen model in which the C-terminus of FLNa is exposed to the extracellular matrix and the N-terminus of FLNa is located in the cytoplasm. In this model, the actin-binding domain of the N-terminus continues to associate with the actin cytoskeleton, while the surface-displayed portion allows for the interaction with various extracellular ligands, including the antibodies taught herein.

Nucleic Acid Molecules and Host Cells

Any of the antibodies or antibody fragments of the present disclosure can be encoded by nucleic acids. The present disclosure includes such molecules, fragments of such molecules and such molecules included in vectors and the like. Nucleic acid molecules also include the complement of such nucleic acid molecules. Both DNA and RNA molecules are examples of nucleic acid molecules.

In another aspect, the present disclosure provides an isolated DNA sequence, which encodes the heavy chain of an antibody molecule, where the antibody molecule has preferential binding for filamin-A antigens, including at least filamin-A, and where the variable domain of the heavy chain comprises a CDR having the antigen binding site amino acid sequences of at least one, two, or three CDRs.

In yet another aspect, the present disclosure provides an isolated DNA sequence which encodes the light chain of an antibody molecule, where the antibody molecule has preferential binding for filamin-A antigens, including at least filamin-A, and further where the variable domain of the light chain comprises a CDR having the antigen binding site amino acid sequences of at least one, two, or three CDRs.

In another aspect, the present disclosure includes a nucleic acid molecule in a host cell. Such a nucleic acid molecule can be integrated into the genome of the host cell or can be present on a vector such as a plasmid or viral vector. A nucleic acid molecule of the present disclosure may be transiently present in such a host cell. In one aspect, a host cell is selected from the group consisting of: *E. coli*; Bacilli, including *Bacillus subtilis*; enterobacteriacae, including *Salmonella, Serratia* and *Pseudomonas*, yeast, including *Saccharomyces; Pichia pastoris*; Sf9 insect cells; Sp2/0, VERO, and HeLa cells, human embryonic kidney (HEK) cell lines, Chinese hamster ovary (CHO) cell lines; W138, BHK, COS-7 and MDCK cell lines. In one aspect, a host cell is selected from a breast cancer cell line such as SKBR3, MCF-7, MDA-MB-231, MDA-MB-435, and ZR75B cells. In another aspect, a host cell is selected from a prostate cancer cell line such as PC3, DU145 and LNCap cells. In another aspect, a host cell is selected from a colon cancer cell line such as HT-29 cells. In another aspect, a host cell is selected from a skin cancer cell line such as A431 cells. In another aspect, a host cell is selected from a kidney cancer cell line such as BHK-21 or COS-7 cells. In another aspect, a host cell is selected from an ovarian cancer cell line such as A2780, A2780ADR, or A2780cis cells. In another aspect, it is a CHO cell. In another aspect, it is a lung cancer cell (e.g., A549 cell line).

Methods of Making Filamin-A Antibodies, Intrabodies, or Antibody Fragments

Filamin-A antibodies or antibody fragments of the present disclosure can be developed, for example, by immunizing animals with a protein preparation from the MDA-MB-231 breast carcinoma cell line.

The present disclosure includes processes for producing monoclonal, chimeric, including humanized antibodies using recombinant DNA technology. See, for example, Antibodies, A Laboratory Manual (Harlow & Lane Eds., Cold Spring Harbor Press, 1988), which is herein incorporated by reference in its entirety.

Filamin-A antibodies or antibody fragments of the present disclosure can be produced by any known method including, without limitation, generating murine hybridomas which produce antibodies or antibody fragments specific for filamin-A. Hybridomas can be formed, for example, by the fusion of a mouse fusion partner cell and spleen cells from mice immunized against filamin-A. To immunize the mice, a variety of different conventional protocols can be followed. For example, mice can receive primary and boosting immunizations of antigenic preparations.

The present disclosure provides methods for making intrabodies. Filamin-A specific intrabodies may be produced by any known method including, for example, expressing a Filamin-A specific scFv in a cell, wherein the scFv is modified for intracellular localization. For example, the scFv may be fused at the N- and/or C-terminus with a protein to aid in expression, increase stability, increase resistance to intracellular environments, and/or target the scFv to a particular subcellular structure or region. In some embodiments, the intrabody comprises, from amino to carboxy terminus, a variable light chain, a linker, and a variable heavy chain. In some embodiments, the intrabody comprises, from amino to carboxy terminus, a variable heavy chain, a linker and a variable light chain. The linker may be any fusion protein linker known in the art. For example, in some embodiments, the linker is a flexible linker. In some embodiments, the linker is a glycine-serine linker, such as, for example (GGGS)$_3$ (SEQ ID NO: 71) or (GGGGS)$_3$ (SEQ ID NO: 72). Exemplary amino acid sequences of an intrabody provided herein are provided in Table 1B. In some embodiments, the variable heavy and/or light chain of the scFv comprises or is linked to a tag such as a poly-histidine tag, FLAG tag, or other tags known in the art. Thus, in some embodiments, the present disclosure provides a histidine tagged anti-Filamin A intrabody. In some embodiments, the intrabody comprises a fusion protein to aid in expression of the intrabody. For example, in some embodiments, the fusion protein comprises a fusion at the N- and/or C-terminus of the scFv such as GST, Ig-Fc, or protein sequences that target the intrabody to a subcellular structure or region such as the nucleus, ER, golgi apparatus, mitochondria, lysosomes, or other subcellular structures or regions.

In some embodiments, intrabody constructs are genetically linked to reporter genes, such as green fluorescent protein (GFP), red fluorescent protein (RFP), luciferase, or others. In some embodiments, the linked reporter gene is driven by its own promoter. In some embodiments, the linked reporter gene is driven via an IRES sequence for driving expression from the intrabody promoter. Thus, in some embodiments, the intrabody comprises a Filamin-A specific scFv comprising a variable heavy and light chain, a tag, and a reporter gene (e.g., Vh-Vl-His-IRES-GFP or Vl-Vh-His-IRES-GFP). In some embodiments, the intrabody comprises a filamin-A specific scFv comprising a variable heavy and light chain driven by an EF promoter, a tag (e.g., a His tag), and a reporter gene (e.g., GFP) driven by an IRES sequence (e.g., EF-Vh-Vl-His-IRES-GFP or EF-Vl-Vh-His-IRES-GFP). In some embodiments, the intrabody is delivered via a viral vector, e.g., a retroviral, lentiviral, or adenoviral vector. In some embodiments, the intrabody is delivered via a bicistronic lentiviral vector, for example, as in Reiser et al., "Development of Multigene and Regulated Lentivirus Vectors," Journal of Virology, vol. 74 (22) pp. 10589-99 (2000), which is incorporated herein by reference in its entirety.

In some embodiments, the intrabody is a protein delivered or translocated into the cell via cell penetrating peptides, other chemical moiety or a nanocarrier delivery system to translocate the intrabody across the cell membrane. Exemplary cell penetrating peptides, other chemical moieties and the like are known in the art and include, without limitation, Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (BisGuanidinium-Tren-Cholesterol). Thus, in some embodiments, the present disclosure provides a fusion protein comprising a protein transduction domain fused to an antibody provided herein, e.g., an scFv. Nanocarrier delivery systems include lipid-based nanocarriers (e.g., liposomes and other lipid-based nanoparticles), polymer based nanocarriers (e.g., polymer-based liposomes or polymerosomes), inorganic nanoparticles (e.g., silica nanoparticles), microparticles, and modified viral or viral-like particles. The intrabodies provided herein may be delivered to the cell as a protein via any of the translocating systems known in the art.

Cell fusions can be accomplished by procedures known to those skilled in the field of immunology. Fusion partner cell lines and methods for fusing and selecting hybridomas and screening for antibodies or antibody fragments are known.

Antibodies or antibody fragments of the present disclosure can be produced in large quantities, for example, by injecting hybridoma cells secreting the antibody into the peritoneal cavity of mice and, after appropriate time, harvesting the ascites fluid which contains a high titer of the antibody or antibody fragment, and isolating the antibody or antibody fragment therefrom. Alternatively, the antibodies and antibody fragments can be produced by culturing hybridoma cells in vitro and isolating the secreted antibody or antibody fragment from the cell culture medium.

Filamin-A antibodies or antibody fragments of the present disclosure can also be produced by expressing the appropriate DNA sequence in a host cell after the sequence has been operably linked to an expression control sequence. Such expression vectors are often replicable in a host organism either as episomes or as an integral part of the host chromosomal DNA. Expression vectors often contain expression control sequences compatible with the host cell, such as an origin of replication. In addition, an expression vector can include a promoter to control expression of the gene, optionally, with operator sequences, and have ribosome binding site sequences and the like for initiating and completing transcription and translation. Suitable promoters include, without limitation, the polyhedrin promoter, lactose promoter system, a tryptophan promoter system, a beta-lactamase promoter system, or a promoter system from phage lambda. Expression vectors can also contain selection markers. DNA sequences encoding the light chain and heavy chain of a filamin-A antibody or antibody fragments can be inserted into separate expression vectors, or into the same expression vector.

Suitable hosts include, without limitation, prokaryotic strains such as *E. coli*; Bacilli, including *Bacillus subtilis*; enterobacteriacae, including *Salmonella, Serratia* and *Pseudomonas*. Suitable hosts also include eukaryotic hosts such as yeast, including *Saccharomyces; Pichia pastoris*; Sf9 insect cells; Sp2/0, VERO and HeLa cells, Human embryonic kidney (HEK) cell lines; Chinese hamster ovary (CHO) cell lines; W138, BHK, COS-7 and MDCK cell lines. Other suitable hosts can also be used in accordance with known expression techniques.

The vectors containing the DNA segments of interest can be transferred into the host cell by any method, which varies depending on the type of cellular host. For example, calcium chloride transfection, calcium phosphate treatment, electroporation or cationic liposome mediated transfection (such as DOTAP). Successfully transformed cells can be identified by a variety of techniques for detecting the binding of a receptor to a ligand.

Expressed gene products can be purified according to any method, including, without limitation, ammonium sulfate precipitation, affinity columns, column chromatography, and gel electrophoresis. Substantially pure immunoglobulins of at least 85%, 86%, 87%, 88%, 89%, 90%, 91%, 92%, 93%, 94%, 95%, 96%, 97%, 98%, or 99% homogeneity are envisioned.

Isolated or purified DNA sequences can be incorporated into a cloning or expression vector, which can in turn be used to transform a host cell. The transformed host cells can be used in a process for the production of an antibody molecule having specificity for filamin-A antigens, including culturing the host cells and isolating the antibody molecules they produce.

Filamin-A Antibodies in Chimeric Antigen Receptor Form

For use as an extracellular immune therapy, filamin-A antibodies may require access from the extracellular side of the membrane. In some embodiments, the antibodies provided herein bind filamin-A on the extracellular side of the membrane and are useful in a cellular immune therapy such as a CAR-T therapy. Accordingly, in some embodiments, the present disclosure provides filamin-A-specific antibodies in a Chimeric Antigen Receptor (CAR) format. For example, the present disclosure provides antibodies, CARs, and cells expressing CARs, wherein the antibody, CAR, or cell expressing CAR specifically binds to filamin-A expressed on a cell surface. For example, in some embodiments, the present disclosure provides a filamin-A-specific CAR polypeptide comprising a filamin-A antibody or fragment thereof (e.g., an scFv). In further embodiments, the CAR polypeptide comprises an intracellular signaling domain, a transmembrane domain, and one or more extracellular domain(s), wherein at least one extracellular domain is a filamin-A antibody or fragment thereof. In some embodiments, the intracellular signaling domain comprises a costimulatory domain (e.g. CD27, CD28, 4-1BB, OX-40, CD30, CD40, PD-1, ICOS, LFA-1, CD2, CD7, LIGHT, NKG2C, NKG2D, B7-H3, and any combination thereof) and/or a T cell receptor (TCR) zeta chain signaling domain. In some embodiments, the filamin-A antibody or fragment thereof of the CAR polypeptide comprises the CDR regions of the heavy and light chain variable regions provided herein. In some embodiments, the filamin-A antibody or fragment thereof of the CAR polypeptide comprises the amino acid sequences of the heavy and light chain variable regions provided herein. In some embodiments, the present disclosure provides a nucleotide sequence encoding the CAR polypeptide described herein. In some embodiments, the CAR polypeptide comprising the filamin-A antibody or fragment thereof is expressed on an immune cell (e.g., a T cell, NK cell, NK-T cell, B cell, macrophage, or stem cell). In further embodiments, the immune cell is a T cell. Thus, in some embodiments, the present disclosure provides engineered cells such as CAR-T cells that target the T cells to cells expressing filamin-A on the cell surface. In other embodiments, the present disclosure provides engineered NK cells or NK-T cells that target the NK cell or NK-T cell to cells expressing filamin-A on the cell surface, via a filamin-A CAR. In other embodiments, the present disclosure provides engineered macrophages expressing the filamin-A antibody or fragment thereof in CAR format, wherein the engineered macrophage targets macrophages to engulf cells expressing filamin-A on the cell surface. In some embodiments, the filamin-A specific antibody or fragment thereof (e.g., expressed on the CAR-expressing immune cell) preferentially binds to cancer cells expressing extracellular filamin-A.

Diagnostic Methods, Assays, and Kits

In a further aspect, the present disclosure includes an immunoassay for detecting a filamin-A antigen comprising an antibody or antibody fragment of the present disclosure.

The present disclosure also includes an immunoassay for preferentially detecting one or more filamin-A antigens, including a filamin-A antigen, which bind to a monoclonal antibody having one or more of the heavy chain or light chain CDR antigen binding site amino acid sequences set forth in Table 1A.

Such immunoassays can be used in any suitable manner, including, without limitation, by comprising: (a) contacting the sample with an effective binding amount of one of the antibodies or antibody fragments of the disclosure; and (b) detecting the antigen by detecting the binding of the antibody to a filamin-A antigen. Immunoassays of the present disclosure can be used to detect cancer cells expressing a filamin-A antigen, particularly cancer, tumor, carcinoma cells or neoplastic disease cells selected from the group consisting of breast, ovarian, cervical, prostate, colon, stomach, kidney, liver, head, neck, lung, blood, pancreatic, skin, testicular, thyroid and brain cancers.

In a further aspect, the present disclosure provides a kit for the immunohistochemical detection of cancer comprising: (a) an antibody or antibody fragment of the present disclosure; and (b) a secondary antibody conjugated to a detectable label.

In a further aspect, the present disclosure provides a kit for the immunohistochemical detection of cancer comprising: (a) a monoclonal antibody having one or more of the heavy chain or light chain CDR antigen binding site amino acid sequences set forth in Table 1A; and (b) a secondary antibody conjugated to a detectable label.

Kits can include reagents for assaying a sample for a filamin-A antigen, where such kits may include: filamin-A antigen specific affinity reagents, such as an antibody, or fragment or mimetic thereof, and/or immunoassay devices comprising the same members of a signal producing system, such as antibodies, enzyme substrates, and the like; various buffers for use in carrying out the subject detection assays; a reference for determining the amount of one or more filamin-A antigens in a sample; and the like. Other examples of kits or kit formats are found in U.S. Patent Application Publication No. 2008/0293162 A1, corresponding to U.S. patent application Ser. No. 12/189,051, filed on Aug. 8, 2008, which is herein incorporated by reference in its entirety for all purposes.

In a further aspect, the present disclosure provides a method for diagnosing cancer in humans comprising: (a) removing a specimen from a patient suspected of having a cancer; (b) contacting the specimen with an antibody or antibody fragment of the present disclosure; and (c) detecting the presence of the antigen-antibody complex. In some aspects, a label is used and detected. Such a method of diagnosing cancer can be performed in vivo or in vitro.

In a still further aspect, the present disclosure provides a method for diagnosing cancer in humans comprising: (a) removing a specimen from a patient suspected of having a cancer; (b) contacting the specimen with a monoclonal antibody having one or more of the heavy chain or light chain CDR antigen binding site amino acid sequences set forth in Table 1A; and (c) detecting the presence of the antigen-antibody complex. In some aspects, a label is used and detected. The method of diagnosing cancer can be performed in vivo or in vitro.

The cancers being diagnosed include those that are selected from the group consisting of solid tumors of the breast, ovary, cervix, prostate, colon, stomach, kidney, liver, head, neck, lung, pancreas, skin, testicle, thyroid and brain. The cells can further include human breast, ovary, head, neck, and brain cells.

In one aspect, filamin-A levels are higher in early-stage breast cancer patients relative to age-matched healthy controls. In another aspect, filamin-A levels are higher in middle-stage breast cancer patients relative to age-matched healthy controls. In another aspect, filamin-A levels are higher in late-stage breast cancer patients relative to age-matched healthy controls. In one aspect, the levels of filamin-A are higher in early-stage breast cancer patients relative to age-matched healthy controls, and similar to healthy control levels during the late stage of breast cancer. An increase in filamin-A levels means, in some aspects, that they are statistically significant relative to age-matched healthy controls. Levels similar to healthy control levels can mean that the levels are not statistically significant. In an aspect, the statistically significant differences in levels of filamin-A have a p-value of $p<0.05$ as measured by the Mann-Whitney test or Student's t-test or any other statistical test known in the art. In another aspect, the statistically significant differences in levels of filamin-A have a p-value of $p<0.01$ as measured by the Mann-Whitney test or Student's t-test or any other statistical test known in the art. In a further aspect, the statistically significant differences in levels of filamin-A have a p-value of $p<0.005$ as measured by the Mann-Whitney test or Student's t-test or any other statistical test known in the art. In a further aspect, the statistically significant differences in levels of filamin-A have a p-value of $p<0.001$ as measured by the Mann-Whitney test or Student's t-test or any other statistical test known in the art. In some embodiments, the levels between patients are not statistically significant; however, the results are still quantifiable and can indicate a difference between a patient with cancer and a normal non-cancerous individual.

In a further aspect, the present disclosure provides a method for diagnosing breast cancer in a subject in need thereof comprising: (a) contacting a specimen from said subject with an antibody or antibody fragment of the present disclosure; and (b) detecting an increase of filamin-A in a patient with breast cancer, where such breast cancer can be in early-stage, mid-stage, or late-stage. Such a method of diagnosing breast cancer can be performed in vivo or in vitro.

The breast cancer being diagnosed can be any of early-, mid- or late-stage breast cancer or a combination thereof.

In an additional aspect, the present disclosure includes a method for developing drugs useful in treating, diagnosing, or both treating and diagnosing, diseases characterized by the expression of gene products of filamin-A and homologues thereof. These methods include identifying gene products expressed by filamin-A and homologues thereof, and utilizing the gene products as biomarkers in the development and identification of drugs selected from the group consisting of: filamin-A antibodies and antibody fragments, inhibiting peptides, siRNA, antisense oligonucleotides, vaccines, and chemical compounds, which specifically target the gene products.

Antibodies and antibody fragments can be used in immunoassays to screen body fluids, such as serum, sputum, effusions, urine, cerebrospinal fluid, and the like, for the presence of filamin-A. Antibodies and antibody fragments can be used for scanning or radioimaging, when labeled with an appropriate radiolabel, to detect primary or metastatic foci of tumor cells. Furthermore, the antibodies are useful in lymphoscintigraphy to detect lymph node involvement in the disease.

A filamin-A antibody or antibody fragment, which can include any or all of the antibodies or antibody fragments specific for filamin-A-related gene products, and/or chimeric, such as humanized, or other variants thereof, can be used therapeutically, or in developing and performing assays, in vivo or in vitro diagnostic procedures, and imaging. The antibodies can be used alone or in combination with a pharmaceutically-acceptable or diagnostic carrier formulation. Filamin-A antibodies or antibody fragments can be incorporated into a pharmaceutically or diagnostically acceptable, non-toxic, sterile carrier as a suspension or solution. They can be used as separately administered compositions or given in conjunction with chemotherapeutic or immunosuppressive agents.

The present disclosure includes therapeutic and diagnostic compositions comprising an antibody or antibody fragment of the present disclosure in combination with a pharmaceutically acceptable excipient, diluent, or carrier. The present disclosure also includes a process for preparation of a therapeutic or diagnostic composition comprising admixing an antibody molecule of the present disclosure together with a pharmaceutically acceptable excipient, diluent, or carrier. An antibody molecule can be the sole active ingredient in the therapeutic or diagnostic composition, or can be accompanied by other active ingredients including other antibody ingredients, for example anti-T cell, anti-IFNγ or anti-LPS antibodies, or non-antibody ingredients such as xanthines. Compositions can be incorporated into kits for diagnosing or treating diseases characterized by the expression of filamin-A, including, without limitation, solid tumors, and particularly solid tumors of the breast, ovary, cervix, prostate, colon, stomach, kidney, liver, head, neck, lung, pancreas, skin, testicle, thyroid and brain. The cells can also be human breast, ovary, head, neck, or brain cells.

Antibodies or antibody fragments of the present disclosure are useful for immunoassays which detect or quantitate filamin-A or cells bearing filamin-A in a sample. Such an immunoassay typically comprises incubating a biological sample from a subject with a need therefor in the presence of a detectably labeled antibody of the present disclosure capable of identifying the tumor antigen, and detecting the labeled antibody which is bound in a sample.

In one aspect of the present disclosure, the observation of filamin-A distribution can be used to detect the stages associated with a particular disease, for example, breast cancer. The tissue specimens can be incubated with filamin-A antibody, and the resultant filamin-A-antigen-filamin-A antibody complex can be detected using standard immunohistochemical staining.

One of the ways in which the antibody of the present disclosure can be detectably labeled is by linking the same to an enzyme and use in an enzyme immunoassay (EIA) or enzyme-linked immunosorbent assay (ELISA). This enzyme, when subsequently exposed to its substrate, will react with the substrate generating a chemical moiety which can be detected, for example, by spectrophotometric, fluorometric or by visual means. In an alternate embodiment, the enzyme is used to label a binding partner for the antibody of the disclosure. Such a binding partner can be an antibody against the constant or variable region of the antibody of the disclosure, such as a heterologous anti-mouse immunoglobulin antibody. Alternatively, the binding partner can be a non-antibody protein capable of binding to the antibody of the present disclosure.

By radioactively labeling the antibodies of the present disclosure, it is possible to detect filamin-A through the use of a radioimmunoassay (RIA). The radioactive isotope can be detected by such means as the use of a gamma counter or a scintillation counter or by autoradiography. Isotopes which are particularly useful for the purpose of the present disclosure are known in the art.

It is also possible to label the antibodies of the present disclosure with a fluorescent compound. When the fluorescently labeled antibody is exposed to light of the proper wave length, its presence can then be detected due to fluorescence. The antibodies of the present disclosure also can be detectably labeled by coupling to a chemiluminescent compound. The presence of the chemiluminescently labeled antibody is then determined by detecting the presence of luminescence that arises during the course of a chemical reaction. A bioluminescent compound can also be used to label the antibodies of the present disclosure. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and sequorin.

Detection of the antibody, fragment or derivative can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection can also be accomplished by visual comparison of the extent of enzymatic reaction of a substrate in comparison with similarly prepared standards.

In situ detection can be accomplished by removing a specimen from a patient, and providing the labeled antibody, or the unlabeled antibody plus a labeled binding partner to such a specimen. Through the use of such a procedure, it is possible to determine not only the presence of the antigen but also its distribution in the examined tissue. Using the present disclosure, those of ordinary skill will readily perceive that any of a wide variety of histological methods (such as staining procedures) can be modified in order to achieve such in situ detection. Such methods include, for example, immunohistochemical staining procedures. In an aspect, an avidin-biotin immunoperoxidase staining system can be used, and a kit utilizing this system is also contemplated, although the methods of the present disclosure can utilize any suitable staining procedures known in the art.

Kits according to the present disclosure can include frozen or lyophilized antibodies to be reconstituted by thawing or by suspension in a liquid vehicle. The kits can also include a carrier or buffer. In another embodiment, the kit also comprises instructions for reconstituting and using the antibody. The kit employing antibodies, including chimeric and humanized antibodies of the present disclosure, can be used for immunohistochemical evaluation of cancers, including cancer of the breast, ovary, cervix, prostate, colon, stomach, kidney, liver, head, neck, lung, blood, pancreas, skin, testicle, thyroid and brain. The cells can also be human breast, ovary, head, neck, and brain cells.

The kits including the reagents necessary for immunohistochemical analysis can be provided as follows: (a) filamin-A antibody or antibody fragment of the present disclosure, or chimeric or humanized variants thereof; (b) blocking reagent (in the form of, for example, goat serum) and secondary antibody (such as, for example, goat anti-mouse antibody); (c) detectable marker (such as, for example, immunoperoxidase or alkaline phosphatase); and (d) developing reagents. The primary antibody (filamin-A antibody or antibody fragment or variants thereof) serves as an antigen which can bind more than one secondary antibody. The secondary antibodies form a "bridge" between the primary antibody and the complex formed by the detectable marker and developing reagent (for example, a horseradish peroxidase-antiperoxidase complex).

Any suitable detection system can be used in accordance with the methods and kits of the present disclosure. Such detection systems are widely used in immunofluorescence applications, and can be imaged using techniques including, but not limited to, flow cytometry, microscopy, Western blotting, and ELISAs. Suitable detection systems can employ conjugates of secondary antibodies, conjugates of colloidal gold, or conjugates of secondary proteins, in order to amplify the signal from a primary protein (in the context of the present disclosure, the primary protein signal being amplified is bound a filamin-A antibody, which can or cannot be labeled, for example with a protein such as biotin), which is in turn being used to detect a specific target (in the context of the present disclosure, the target is a filamin-A expression product).

Suitable secondary conjugates for use in the methods and kits of the present disclosure can include, but are not limited to, enzyme conjugates of a secondary antibody and an enzyme such as horseradish peroxidase or alkaline phosphatase; enzyme conjugates of avidin or streptavidin and an enzyme such as horseradish peroxidase or alkaline phosphatase; enzyme conjugates of protein A or protein G and an enzyme such as horseradish peroxidase or alkaline phosphatase; conjugates of colloidal gold and a secondary antibody; conjugates of colloidal gold and avidin or streptavidin; conjugates of magnetic particles and a secondary antibody; and conjugates of secondary antibodies and labels such as fluorescent dyes and biotin. The present disclosure is not limited to any particular detection systems, and it is considered within the ability of the person of ordinary skill in the art to utilize these or other detection systems in accordance with the present disclosure. These secondary conjugates (also referred to as labels in the context of the present disclosure) are useful for visualizing antigen-antibody complexes.

The antibody or antibody fragment of the present disclosure can also be adapted for utilization in an immunometric assay, also known as a "two-site" or "sandwich" assay. In a typical immunometric assay, a quantity of unlabeled antibody (or fragment of antibody), is bound to a solid support that is insoluble in the fluid being tested and a quantity of detectably labeled soluble antibody is added to permit detection and/or quantitation of the ternary complex formed between solid-phase antibody, antigen, and labeled antibody.

For purposes of in vivo imaging of breast, ovary, cervix, prostate, colon, stomach, kidney, liver, head, neck, lung, blood, pancreas, skin, testicle, thyroid and brain; including human breast, ovary, head, neck, and brain cancer and other cancers using the antibodies or antibody fragments of the present disclosure, there are many different labels and methods of labeling known to those of ordinary skill in the art. Examples of the types of labels which can be used in the present disclosure include radioactive isotopes, paramagnetic isotopes, and compounds which can be imaged by positron emission tomography (PET).

Devices

Also provided are devices that find use in practicing the subject methods, as described above. Devices for practicing the subject methods at least include reagents for assaying a sample derived from a subject for a filamin-Analyte, where such devices may include: filamin-Analyte specific affinity reagents, such as an antibody, or fragment or mimetic thereof, immobilized on the surface of a solid support. In some embodiments, the filamin-Analyte is a filamin-A analyte.

Additional items that are required or desired in the methods to be practiced with the devices may be present, which additional items include, but are not limited to: means for obtaining the patient sample, e.g. a syringe; one or more reagents necessary for preparation of the patient derived sample, such as heparin, Ficoll-Hypaque, lysing buffer, protease inhibitor, and the like; instructions for carrying out the subject methods using the subject devices; one or more reagents from an additional biochemical assay which is used to detect the presence of and/or characterize the neoplastic disease involving abnormal levels a filamin-Analyte.

A number of such devices are known in the art. In one non-limiting example, the apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it the first affinity reagent, and second labeled affinity reagent combined with the assayed sample and the sandwich assay performed as above.

In another non-limiting example the device is a dipstick, to the surface of which is bound an affinity reagent, such an antibody, or fragment or mimetic thereof, which specifically binds a filamin-Analyte. In such an exemplary device, the dipstick is inserted directly into a test sample (e.g., blood, serum, or urine) derived from a subject for a period of time sufficient to permit binding of a filamin-Analyte to the affinity reagent bound to the dipstick. The dipstick may be then withdrawn and, if necessary, washed to remove non-specifically bound material. The dipstick is then inserted into a container containing a detectably labeled second affinity reagent, such an antibody, or fragment or mimetic thereof, which specifically binds a filamin-Analyte. After incubation for a time sufficient for binding of the second antibody to the filamin-Analyte-affinity reagent complexes, the dipstick may be washed and binding of the second affinity reagent detected by standard means. Where necessary for detection of the second antibody, the dipstick may be inserted into a second container containing a reagent which activates the detectable label on the second antibody.

Pharmaceutical Compositions and Methods of Treatment

Another aspect of the disclosure provides a composition comprising any of the disclosed antibodies, optionally in combination with a pharmaceutically acceptable carrier. In another aspect, an antibody of the present disclosure is optionally in combination with one or more active agents, drugs, other antibodies, or hormones.

The present disclosure also provides a method of treating human or animal subjects suffering from or at risk of a cancer that expresses filamin-A, such as solid tumors of the breast, ovary, cervix, prostate, colon, stomach, kidney, liver, head, neck, lung, blood, pancreas, skin, testicle, thyroid and brain; and human breast, ovary, head, neck, and brain, in particular human breast cells, the method comprising: administering to the subject a therapeutically effective amount of an antibody of the present disclosure, or a pharmaceutical composition comprising a therapeutically effective amount of an antibody of the present disclosure. The present disclosure also provides uses of the antibodies provided herein in a method of treating human or animal subjects suffering from or at risk of a cancer that expresses filamin-A; and uses of the antibodies provided herein in the manufacture of a medicament for treating human or animal subjects suffering from or at risk of a cancer that expresses filamin-A. Further, the disclosure provides the antibodies disclosed herein for use in a method of treating a human or animal subject suffering from or at risk of a cancer that expresses filamin-A, and/or antibodies disclosed herein.

The term "subject" as used herein refers to any subject in need of treatment, including a human patient or subject.

The term "therapeutically effective amount" as used herein refers to an amount of a therapeutic agent needed to treat, ameliorate, or prevent a targeted disease or condition, or to exhibit a detectable therapeutic or preventative effect.

For any antibody, the therapeutically effective dose can be estimated initially either in cell culture assays or in animal models, usually in rodents, rabbits, dogs, pigs, or primates. The animal model can also be used to determine the appropriate concentration range and route of administration. Such information can then be used to determine useful doses and routes for administration in humans.

An effective amount for a human subject can depend upon the severity of the disease state, the general health of the subject, the age, weight and gender of the subject, diet, time and frequency of administration, drug combination(s), reaction sensitivities and tolerance/response to therapy and can be determined by routine experimentation and is within the judgment of the clinician. Generally, an effective dose may be from about 0.001 mg/kg to about 100 mg/kg, or about 0.01 mg/kg to about 50 mg/kg, or about 0.1 mg/kg to about 20 mg/kg, or about 1 mg/kg to about 15 mg/kg.

Compositions can be administered individually to a patient or can be administered in combination with other agents, drugs, antibodies, or hormones. According to some aspects, antibodies can be conjugated with these agents. A summary of the ways in which the antibodies of the present disclosure can be used therapeutically includes direct cytotoxicity by the antibody, either mediated by complement or by effector cells, or conjugated to anti-tumor drugs, toxins, and radionuclides. Accordingly, the present disclosure provides methods for treating cancer comprising administering antibodies of the present disclosure, wherein the antibodies target cancer cells and induce ADCC and/or CDC. Further, the present disclosure provides methods for treating cancer comprising administering antibodies of the present disclosure linked or conjugated to targeted therapeutics. In some embodiments, the antibodies provided herein are endocytosed by cells and thus are capable of delivery of targeted therapeutics to filamin-A expressing cells. Thus, the present disclosure provides pharmaceutical compositions comprising antibodies provided herein in a pharmaceutically acceptable carrier, as well as antibodies provided herein that are linked or conjugated to a therapeutic agent and in a pharmaceutically acceptable carrier. Antibodies can also be used for ex vivo removal of tumor cells from the circulation or from bone marrow.

Cytotoxic proteins can include, but are not limited to, Ricin-A, *Pseudomonas* toxin, Diphtheria toxin, and tumor necrosis factor. Diagnostic radionuclides and cytotoxic agents such as cytotoxic radionuclides, drug and proteins can also be conjugated to the antibodies of the present disclosure. Examples of radionuclides which can be coupled to antibodies and selectively delivered in vivo to sites of antigen include $^{212}$Bi, $^{131}$I, $^{186}$Re, and $^{90}$Y, among others. Radionuclides can exert their cytotoxic effect by locally irradiating the cells, leading to various intracellular lesions, as is known in the art of radiotherapy. Examples of cytotoxic drugs which can be conjugated to antibodies and subsequently used for in vivo therapy include, but are not limited to, daunorubicin, doxorubicin, methotrexate, and Mitomycin C. Cytotoxic drugs can interface with critical cellular processes including DNA, RNA, and protein synthesis.

A dose at which the antibody molecule of the present disclosure is administered depends on the nature of the condition to be treated, and on whether the antibody molecule is being used prophylactically or to treat an existing condition. If administered prophylactically, i.e., as a vaccine, the antibody is administered in an amount effective to elicit an immune response in the subject.

If the antibody molecule has a short half-life (e.g. 2 to 10 hours) it can be necessary to give one or more doses per day. Alternatively, if the antibody molecule has a long half-life (e.g. 2 to 15 days) it can only be necessary to give a dosage once per day, per week, or even once every 1 or 2 months.

A pharmaceutical composition can also contain a pharmaceutically acceptable carrier for administration of the antibody. The carrier should not itself induce the production of antibodies harmful to the individual receiving the composition and should not be toxic. Suitable carriers include those known in the art, and can be selected from large, slowly metabolized macromolecules such as proteins, polypeptides, liposomes, polysaccharides, polylactic acids, polyglycolic acids, polymeric amino acids, amino acid copolymers and inactive virus particles, although suitable carriers are not limited to these examples.

In one embodiment, forms for administration include forms suitable for parenteral administration, e.g. by injection or infusion, for example by bolus injection or continuous infusion. Where the product is for injection or infusion, it can take the form of a suspension, solution, or emulsion in an oily or aqueous vehicle and it can contain formulatory agents, such as suspending, preservative, stabilizing and/or dispersing agents. Alternatively, the antibody molecule can be in dry form, for reconstitution before use with an appropriate sterile liquid.

Once formulated, the compositions of the disclosure can be administered directly to the subject. The subjects to be treated can be animals or humans.

A pharmaceutical composition of this disclosure can be administered by any number of routes including, but not limited to: oral, intravenous, intramuscular, intra-arterial, intramedullary, intrathecal, intraventricular, transdermal, transcutaneous, subcutaneous, intraperitoneal, intranasal, enteral, topical, sublingual, intravaginal or rectal routes. Hyposprays can also be used to administer the pharmaceutical compositions of the disclosure. Therapeutic compositions can be prepared as injectables, either as liquid solutions or suspensions. Solid forms suitable for solution in, or suspension in, liquid vehicles prior to injection can also be prepared.

Direct delivery of the compositions can generally be accomplished by injection, subcutaneously, intraperitoneally, intravenously or intramuscularly, or delivered to the interstitial space of a tissue. Dosage treatment can be a single dose schedule or a multiple dose schedule.

When an antibody or antibody fragment composition is to be administered by a route using the gastrointestinal tract, the composition can contain additional agents which protect the antibody from degradation, but which release the antibody once it has been absorbed from the gastrointestinal tract. Such additional agents are well-known to those skilled in the art.

Antibodies of the present disclosure can also be administered in methods of conducting gene therapy. In order to achieve this, nucleic acid sequences encoding the heavy and light chains of the antibody molecule under the control of appropriate expression components are introduced into a patient such that the antibody chains are expressed from the nucleic acid sequences and assembled in situ. For example, intrabody constructs may be delivered intracellularly as plasmid constructs (e.g., plasmids with eukaryotic promoters to drive intrabody expression), virus-based constructions (e.g., lentiviral or retroviral vectors), or non-virus based delivery vehicles (e.g., lipid-based or polymer based delivery vehicles). Intrabody constructs may be delivered as DNA or RNA. Alternatively, recombinant intrabody protein constructs may be delivered to cells via proteins with cell membrane-penetrating peptides, or via chemical or mechanical delivery systems.

Antibodies of the present disclosure can also be administered in CAR format via an immune cell. In some embodiments, the disclosure provides a pharmaceutical composition comprising a cell expressing a chimeric antigen receptor (CAR), wherein the CAR comprises a filamin-A binding domain provided herein. In some embodiments, the pharmaceutical composition comprises an immune cell (e.g., a T cell, NK cell, B cell, or stem cell). In further embodiments, the immune cell is a T cell. Thus, in some embodiments, the present disclosure provides pharmaceutical compositions comprising CAR-T cells that target the T cells to cells expressing filamin-A on the cell surface.

EXAMPLES

Example 1: Preparation of the Human Chimeric Filamin-A Antibody

AHO1402, a monoclonal murine filamin-A IgG1k antibody, was obtained in a solution of 95% BSA and 5% antibody from Life Technologies. In order to remove the BSA and purify the antibody, the antibodies were isolated and purified with gel electrophoresis and separated by size, and excised from the gel.

Gel slices comprising the antibodies were subjected to de novo sequencing utilizing Database Assisted Shotgun Sequencing (DASS) technology, which utilizes high resolution MS/MS peptide determinations to obtain sequence information that is then compiled by overlapping peptide sequence analysis to reconstruct the sequence. The DASS methods are generally described on the Creative Biolabs web site (creative-biolabs.com/next-generation-antibody-sequencing.html).

The constructed amino acid sequences for the light and heavy chain variable domains were then added onto murine and human constant region sequences selected by the inventors. Certain amino acid selections were made at position 31 in the light chain CDR1 and at positions 101 and 102 in the heavy chain CDR3. The amino acid sequences showing the various mutations are provided above in Table 1A.

These amino acid sequences were then back translated with codon optimization for mammalian cell expression. Nucleic acid sequences of the reconstructed genes were confirmed for fidelity prior to further use and then cloned into expression vectors. The cloned genes in the expression vectors were then transfected into HEK293 cells and the recombinant mAb proteins purified.

Example 2: scFv Preparation and Characterization

The heavy and light chain variable regions were subcloned into a scFv vector system to generate scFvs in two possible orientations, light-heavy (VL-VH or vl-vh) and heavy-light (VH-VL or vh-vl).

The resulting single chain antibodies will be tested in assays that include immunofluorescence staining of cells, cell motility, proliferation, apoptosis, and other assays that evaluate functional biological activity.

The scFvs will further be evaluated for use in diagnostic tests and methods of treating disease, e.g. breast cancer.

Example 3: Cell Motility Assays

Cell motility assays were utilized in exploring functional activity of the created mAbs of the present disclosure (mouse antibody B186, human chimeric antibody B185, and human chimeric antibody B411).

Evidence of activity was obtained with both murine and human chimeric antibodies. However, surprisingly, the human chimeric mAbs exhibited stronger biological activity than the murine mAbs. The effect was also more pronounced on fibronectin-coated tissue culture surfaces than on collagen-coated surfaces.

Cell motility assays utilized the Platypus Technologies ORIS™ cell migration assay platform, which is generally described at platypustech.com/discoverAssay.html.

Such motility assays, including the 3D iteration, are recognized as correlating with cancer cell invasiveness and malignancy, and are thus surrogates for cancer metastasis and other activity.

Specifically, the filamin-A antibodies of the present disclosure were evaluated in the ORIS™ cell migration assay, which used tri-coated 96 well plates (Platypus #CMATR1.101). Cells were seeded at approximately 50,000 cells/well. Cells were incubated overnight at 37° C. without $CO_2$ in DMEM, in the case of HEK-293 cells, or L-15 containing 10% FBS, in the case of MDA-MB-231 cells. Stoppers covering cell growth chambers were removed with the ORIS™ stopper tool, growth media was removed, and wells were gently washed with 100 microliters of sterile PBS. Stoppers were left in place in reference wells until the staining step to serve as pre-migration controls. After washing, a 100 microliter volume of fresh culture media containing the specific treatment was added to each well. The cells were then allowed to incubate overnight. At the end of the incubation period, cells were fluorescently stained with Calcein AM for 30 minutes. Fluorescence was then measured using a microplate reader with a Detection Mask in place.

Figure 2:
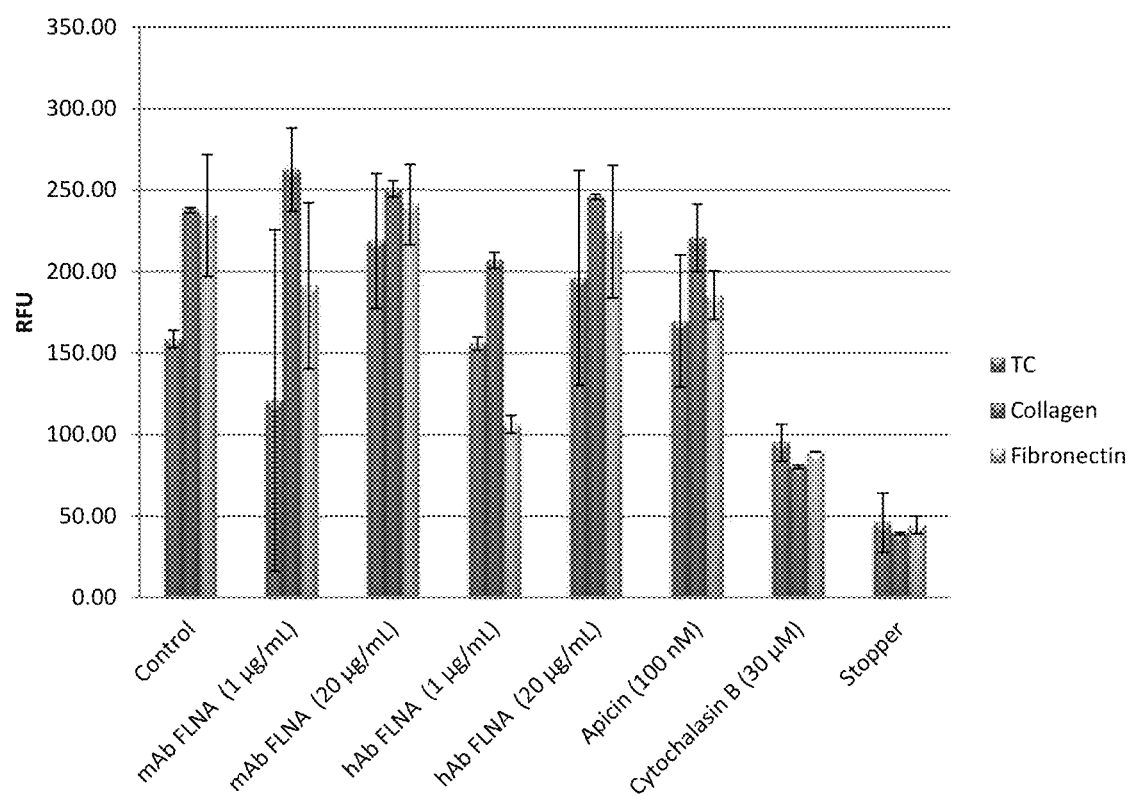
FIG. 2: A graphical representation of the motility assays of MDA-MB-231 cells. The error bars represent standard deviation and the peaks of the colored bars represent the average RFU of the pooled data. Data appear in three peaks, each of which represent the tissue culture plate surface coating utilized. Specifically, for each treatment, the left bar is TC (no coating); the middle bar is collagen coated wells, and the right bar is fibronectin coated wells. The data illustrate that the human chimeric mAb led to a greater reduction in cell motility than the murine mAbs at the 1 μg/mL treatment.

FIGS. 1 and 2 depict the relative fluorescence units (RFUs) present in the detection zones for each condition (mean+/−S.D., n=2 wells/condition).

Wells containing the cells existed in three formats: coated with collagen, coated with fibronectin, or a tissue culture (TC) treatment.

Well treatments were as follows: no antibody control, mouse antibody (mAb FLNA 1 mcg/ml), mouse antibody (mAb FLNA 20 mcg/ml), human chimeric antibody (hAb FLNA 1 mcg/ml), human chimeric antibody (hAb FLNA 20 mcg/ml), apicdin (100 nM), cytochalasin B (30 micromolar); see FIG. 1. An increase in the number of RFUs correlates with an increase in cellular motility.

Cell Motility Assay Results

Cell migration was greatest in wells coated with collagen or fibronectin. With regard to the tissue culture treatment wells, there appears to be little effect across treatments with the exception of cytochalasin B, which is known to interrupt cytoskeletal fiber interactions and is thus expected to inhibit motility.

The apparent lack of response to antibody treatments on the TC surface is perhaps due to the lack of extracellular proteins, such as collagen or fibronectin, known to aid cellular adhesion and impact cellular signaling and processes, and migration. The antibodies are not expected to be toxic, thus there is no toxicity component. Thus, the cells migrate and are not affected by the filamin-A antibody. See FIG. 2.

Within the fibronectin and collagen coated wells, cell migration is weakest with the lower concentration of antibody (i.e. 1 µg/mL vs. 20 µg/mL).

The mouse antibody in the collagen coated wells resulted in no considerable differences at the reading timepoint.

However, the human chimeric antibody exhibited an inhibitory effect on cell motility in the collagen coated wells. See FIG. 1 and FIG. 2.

For fibronectin, there are decreases in cell motility with both the murine and human chimeric antibodies, at the lower concentration (1 µg/mL). However, the human chimeric antibody can be seen to lead to a substantially lower level of cell motility than the murine antibody. In fact, the human chimeric antibody exhibited almost a 100% difference in inhibiting cell motility, as compared to the murine antibody, i.e. 191.34 RFU for murine antibody vs. 106.26 RFU for human chimeric antibody. See FIG. 1 and FIG. 2.

With only two points per test, a trend can be seen that shows an effect of the monoclonal antibodies on cell spreading and motility enhanced by collagen or fibronectin.

The global trend that can be seen in FIG. 2 is that the human chimeric anti filamin-A antibody provides superior results relative to the murine filamin-A antibody.

At the 1 µg/mL concentration, the human chimeric mAbs led to a reduction in cell migration in both the collagen and fibronectin treated wells. This is in contrast to the murine mAbs, which did not lead to a reduction in cell migration in the collagen treated wells and led to less of a reduction in the fibronectin treated wells, compared to the human chimeric mAbs, at the specific endpoint reading.

The cause of the lack of effect at the higher antibody concentration is unknown; however, it may be explained by valency interactions. At the lower antibody concentration, there is a higher probability that a single antibody molecule can cross-link and bind two filamin-A molecules on the cell surface, or plate surface. At the higher antibody concentration, all the binding sites may be taken by separate antibodies, with only one filamin-A bound per antibody, so no cross-linking occurs. Thus, crosslinking may interfere with filamin-A motility functions. This suggests an optimum for dosing.

Example 4: Immunofluorescence (IF) Assays

Characterization of the filamin-A mAbs was performed using immunofluorescence assays with the MDA-MB-231 breast cancer cell line. This is the cell line utilized in generating the antigen preparation with which to immunize mice that resulted in selection of the Life Technologies AHO1402 mAb. For comparison, the AHO1402 mAb and another commercially available mAb, TI10 (Millipore MAB1680-C), were assayed at the same time. It was previously shown that the TI10 and AHO1402 mAbs results in different staining patterns on cells, indicating that they recognize different forms of the filamin-A protein (Alper et al., 2009).

Both the murine and human chimeric antibodies of the present disclosure resulted in a punctate staining pattern similar to that observed with the commercial AHO1402, also known as p280 or clone 209 #13. The staining pattern of TI10 was different, revealing a general staining of the cytoplasm. Based upon this result, it was concluded that the binding of the murine mAbs and human chimeric mAbs was similar to that of the AHO1402 mAb.

The primary antibodies utilized in the immunofluorescence assays were as follows:
Anti-Filamin-A, clone TI10 (Millipore, p/n MAB1680-C)
Anti-Filamin-A, clone 209 #13 (Life Technologies, p/n AHO1402)
Anti-Filamin-A, mouse mAb
Anti-Filamin-A, human chimeric mAb
Anti-beta Actin, rabbit polyclonal (Rockland, p/n 600-401-886S)

Two primary methods of Immunofluorescence staining were utilized. The first method comprises single staining or double staining with methanol as a fixative and 0.2% Triton as a permeabilization agent, which is described in Alper et al. 2009. The second method utilizes a double staining technique with 2% paraformaldehyde as a fixative and 0.2% triton as a permeabilization agent.

Figure 11:
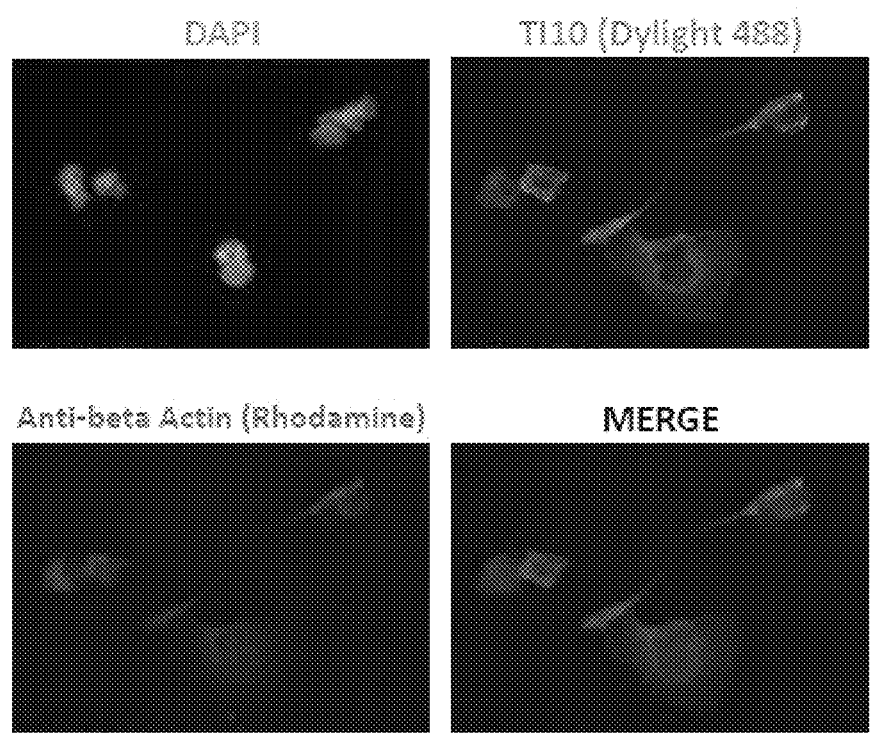
FIG. 11: Immunofluorescence micrograph of MDA-MB-231 cancer cells stained with DAPI DNA stain, TI10 filamin-A antibody with DYLIGHT 488 stain, and beta actin rabbit antibody with rhodamine stain.
Figure 12:
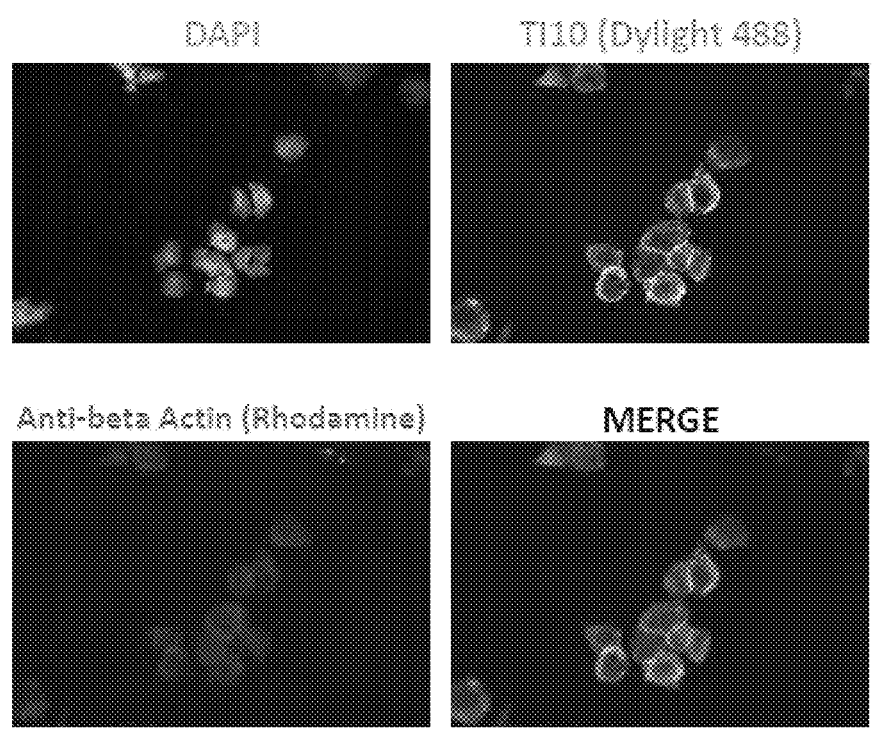
FIG. 12: Immunofluorescence micrograph of MDA-MB-231 cancer cells stained with DAPI DNA stain, TI10 filamin-A antibody with DYLIGHT 488 stain, and beta actin rabbit antibody with rhodamine stain.
Figure 13:
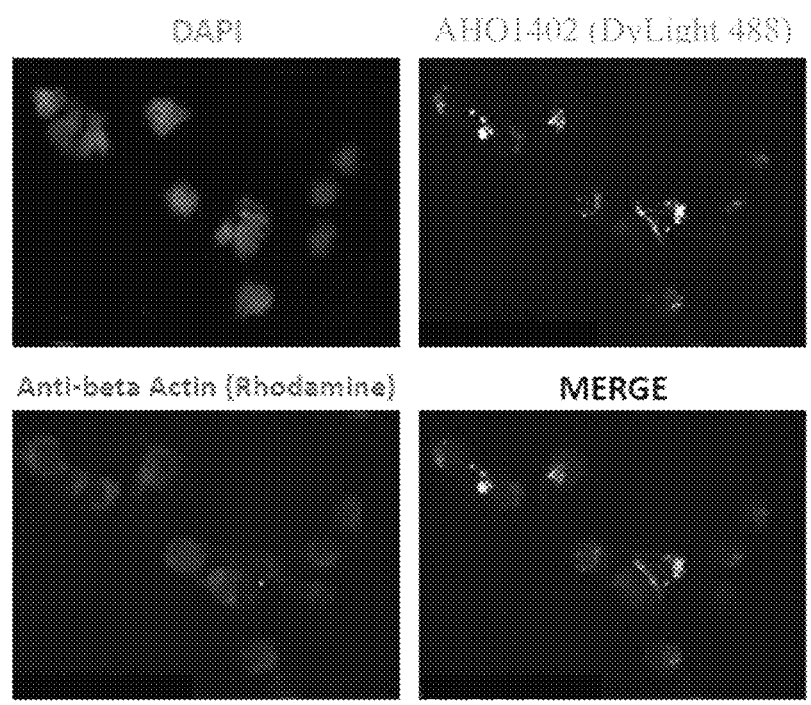
FIG. 13: Immunofluorescence micrograph of MDA-MB-231 cancer cells stained with DAPI DNA stain, AHO1402 filamin-A antibody with DYLIGHT 488 stain, and beta actin rabbit antibody with rhodamine stain.
Figure 14:
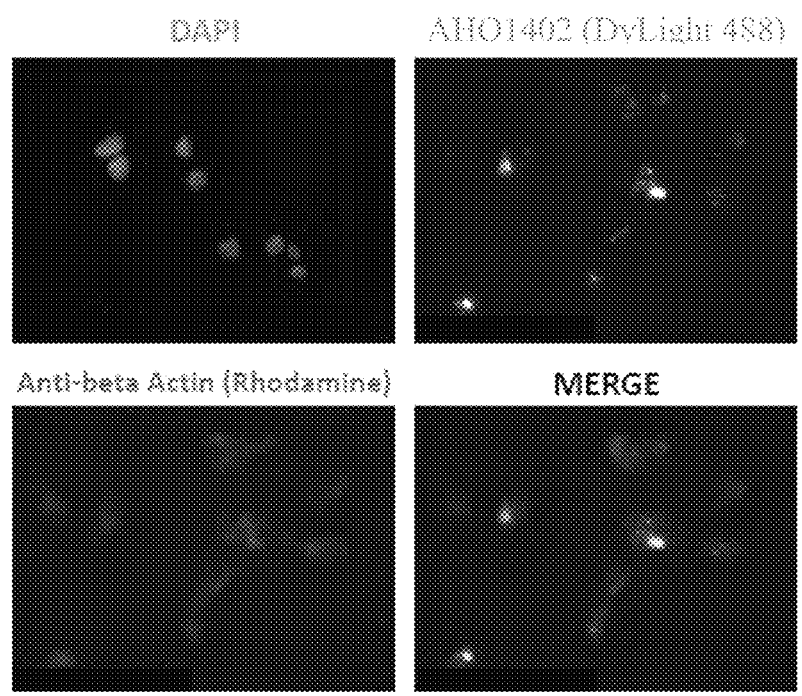
FIG. 14: Immunofluorescence micrograph of MDA-MB-231 cancer cells stained with DAPI DNA stain, AHO1402 filamin-A antibody with DYLIGHT 488 stain, and beta actin rabbit antibody with rhodamine stain.
Figure 16:
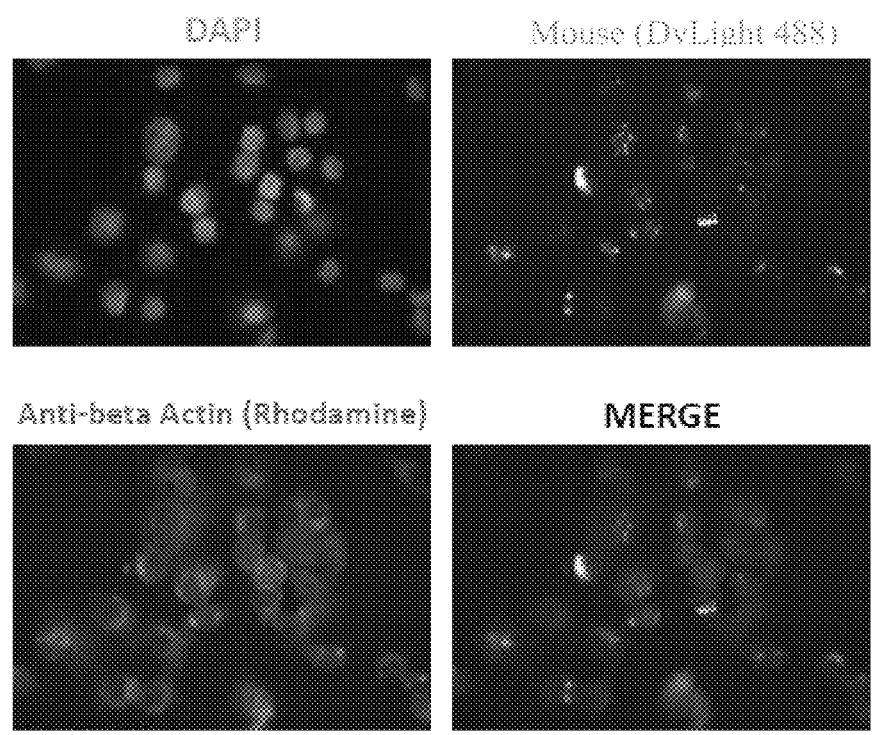
FIG. 16: Immunofluorescence micrograph of MDA-MB-231 cancer cells stained with DAPI DNA stain, mouse filamin-A antibody with DYLIGHT 488 stain, and beta actin rabbit antibody with rhodamine stain.
Figure 17:
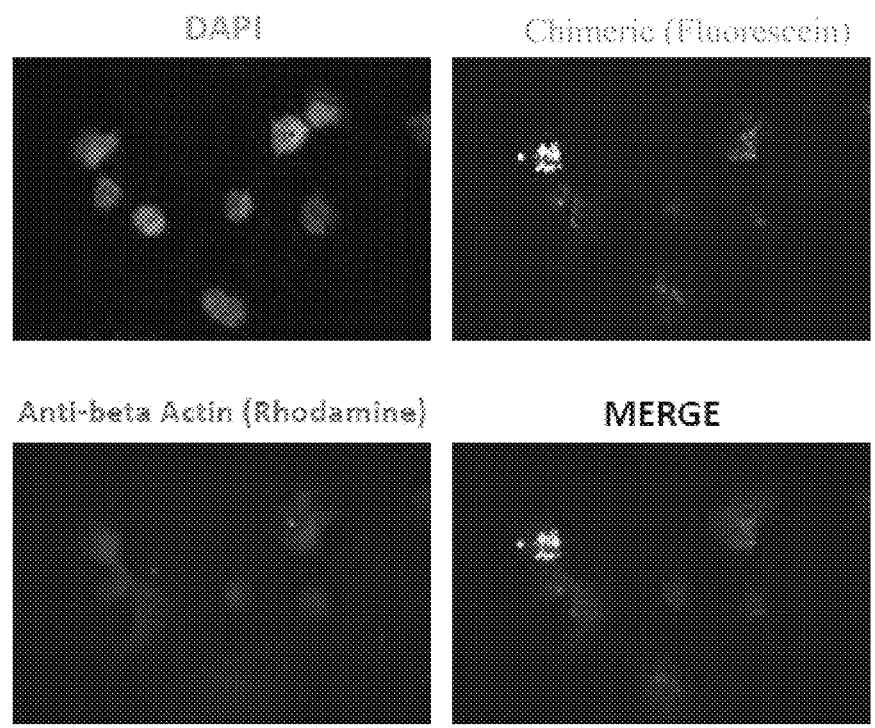
FIG. 17: Immunofluorescence micrograph of MDA-MB-231 cancer cells stained with DAPI DNA stain, chimeric filamin-A antibody with fluorescein stain, and beta actin rabbit antibody with rhodamine stain.
Figure 18:
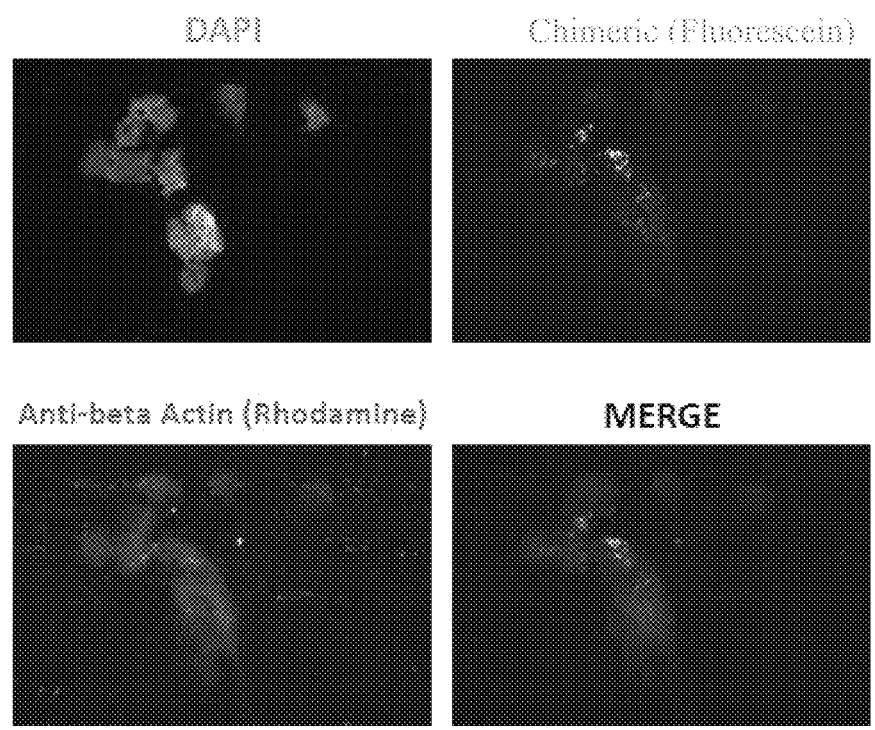
FIG. 18: Immunofluorescence micrograph of MDA-MB-231 cancer cells stained with DAPI DNA stain, chimeric filamin-A antibody with fluorescein stain, and beta actin rabbit antibody with rhodamine stain.
Figure 19:
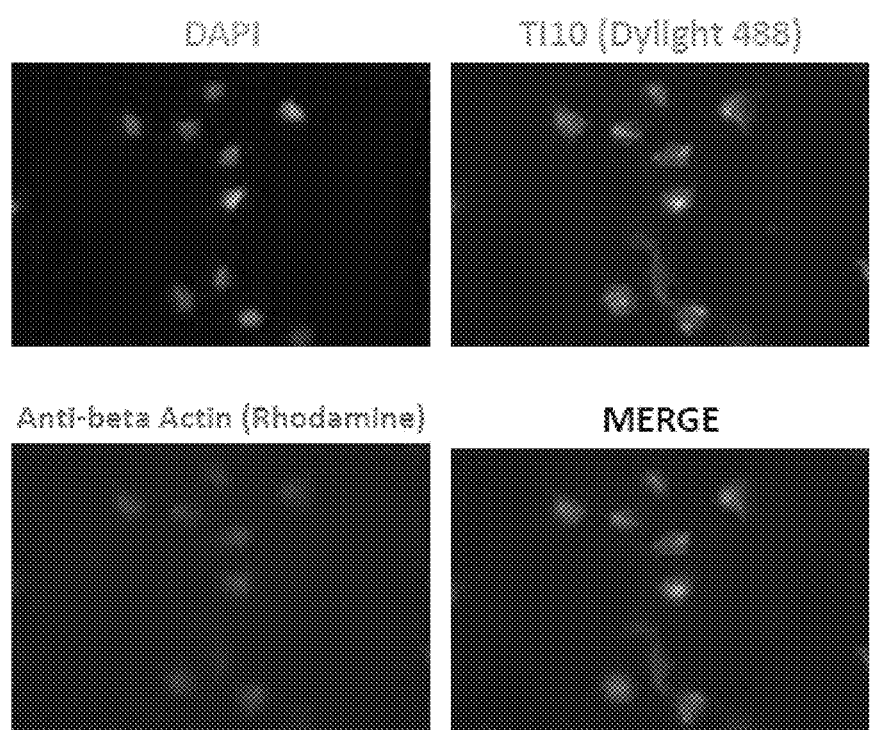
FIG. 19: Immunofluorescence micrograph of MDA-MB-231 cancer cells stained with DAPI DNA stain, TI10 filamin-A antibody with DYLIGHT 488 stain, and beta actin rabbit antibody with rhodamine stain.
Figure 20:
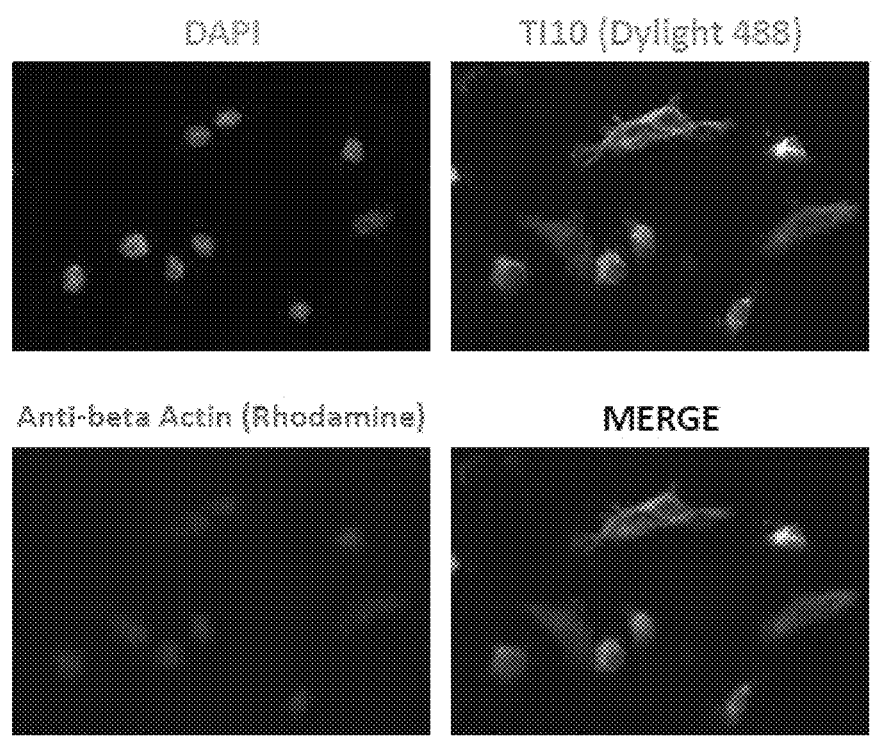
FIG. 20: Immunofluorescence micrograph of MDA-MB-231 cancer cells stained with DAPI DNA stain, TI10 filamin-A antibody with DYLIGHT 488 stain, and beta actin rabbit antibody with rhodamine stain.
Figure 21:
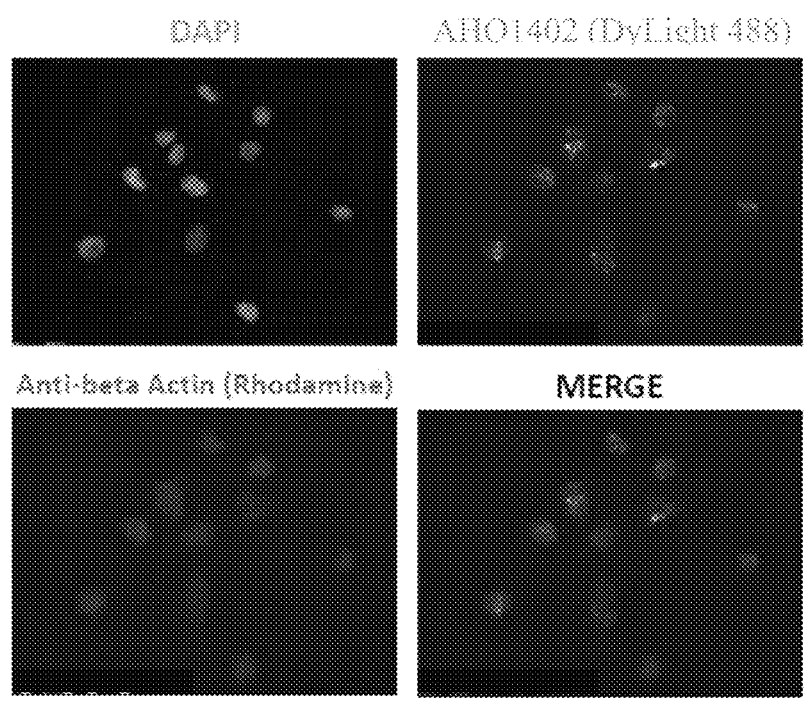
FIG. 21: Immunofluorescence micrograph of MDA-MB-231 cancer cells stained with DAPI DNA stain, AHO1402 filamin-A antibody with DYLIGHT 488 stain, and beta actin rabbit antibody with rhodamine stain.
Figure 22:
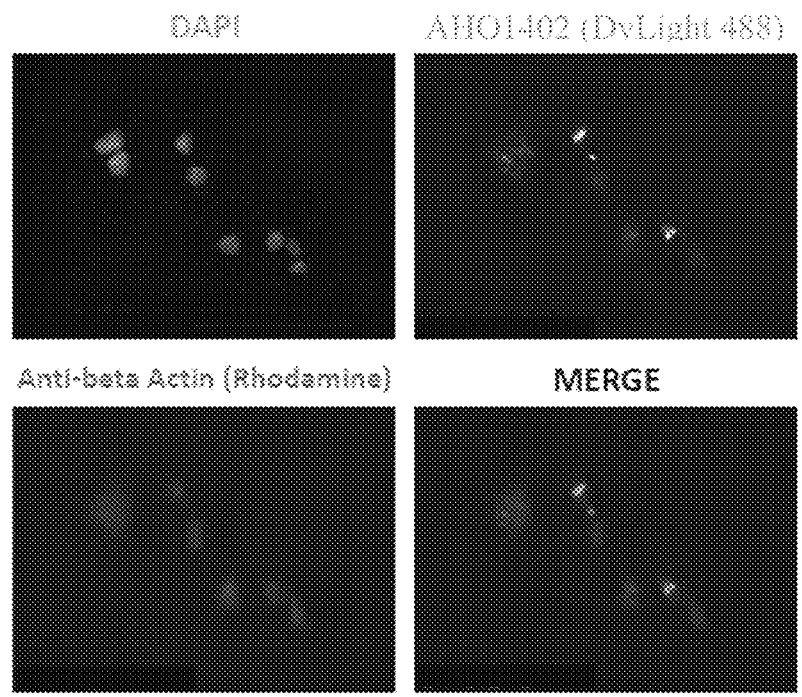
FIG. 22: Immunofluorescence micrograph of MDA-MB-231 cancer cells stained with DAPI DNA stain, AHO1402 filamin-A antibody with DYLIGHT 488 stain, and beta actin rabbit antibody with rhodamine stain.
Figure 23:
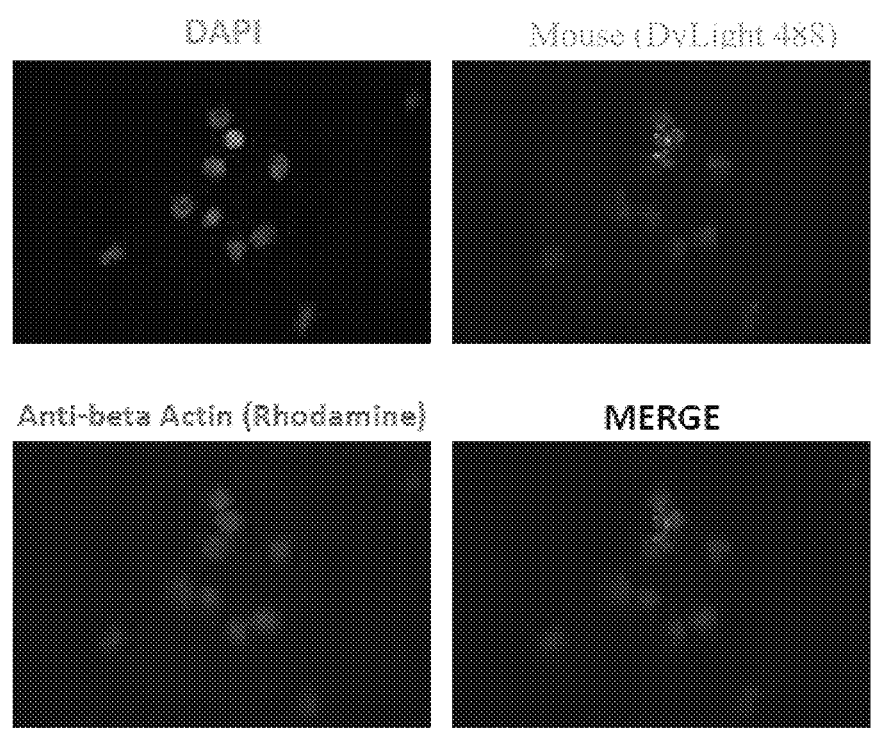
FIG. 23: Immunofluorescence micrograph of MDA-MB-231 cancer cells stained with DAPI DNA stain, mouse filamin-A antibody with DYLIGHT 488 stain, and beta actin rabbit antibody with rhodamine stain.
Figure 24:
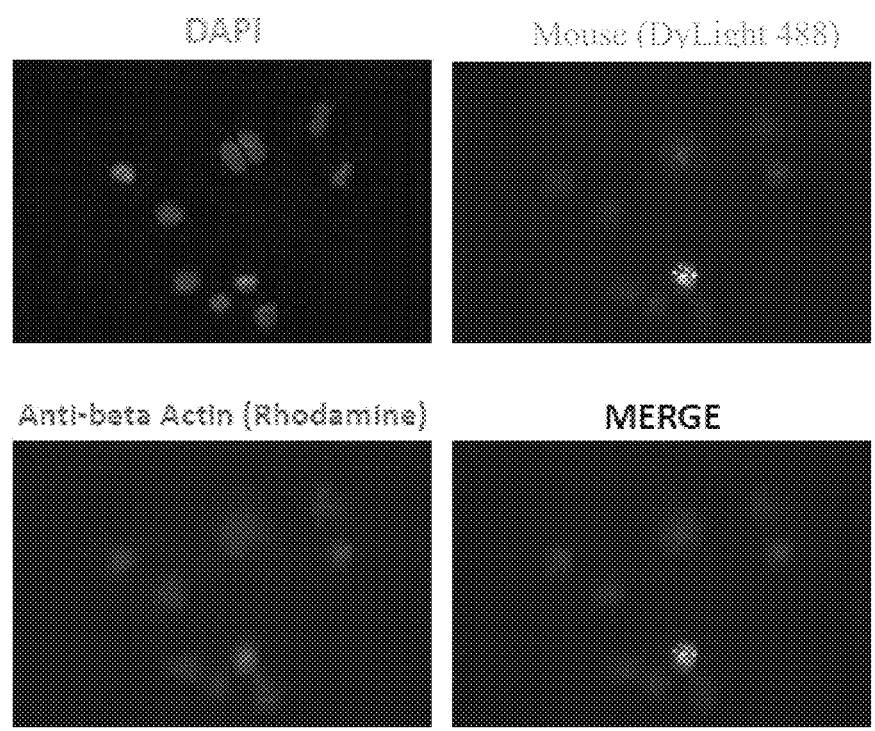
FIG. 24: Immunofluorescence micrograph of MDA-MB-231 cancer cells stained with DAPI DNA stain, mouse filamin-A antibody with DYLIGHT 488 stain, and beta actin rabbit antibody with rhodamine stain.
Figure 25:
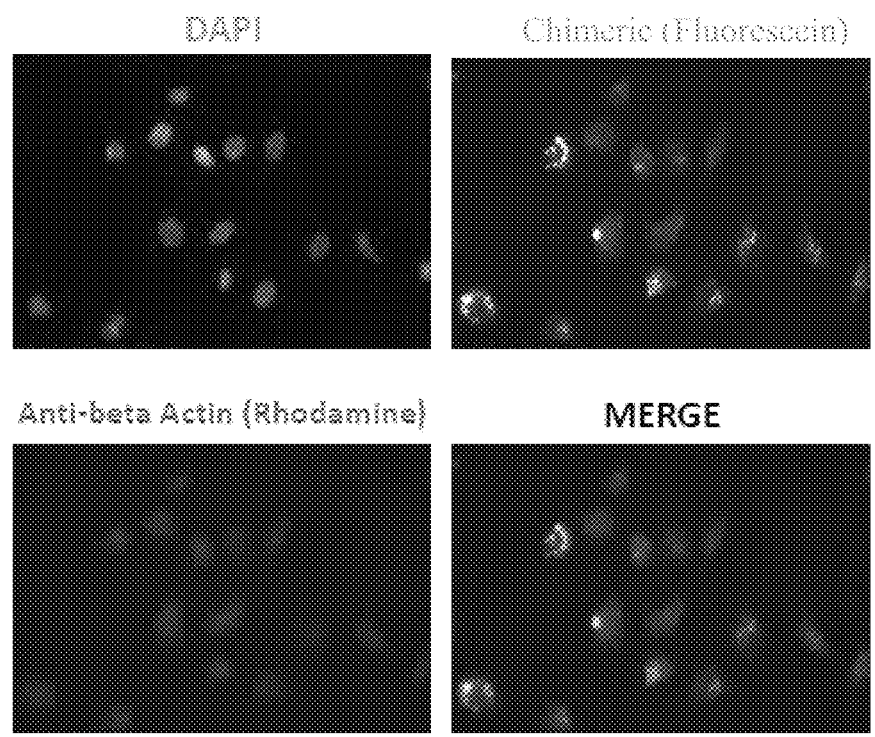
FIG. 25: Immunofluorescence micrograph of MDA-MB-231 cancer cells stained with DAPI DNA stain, chimeric filamin-A antibody with fluorescein stain, and beta actin rabbit antibody with rhodamine stain.
Figure 26:
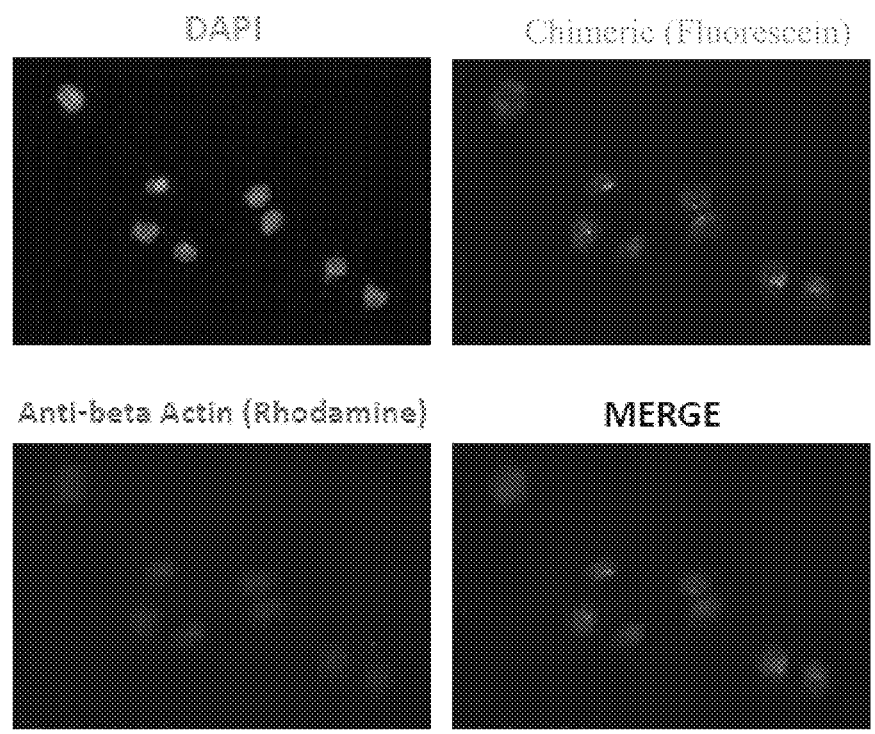
FIG. 26: Immunofluorescence micrograph of MDA-MB-231 cancer cells stained with DAPI DNA stain, chimeric filamin-A antibody with fluorescein stain, and beta actin rabbit antibody with rhodamine stain.
Figure 27:
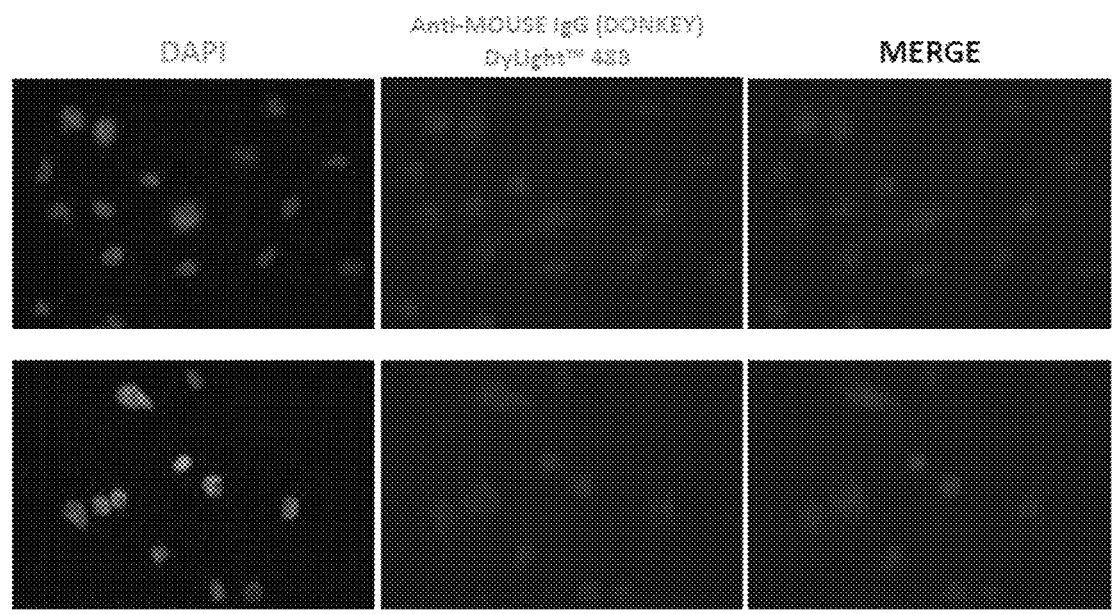
FIG. 27: Immunofluorescence micrograph of MDA-MB-231 cancer cells stained with DAPI DNA stain, mouse IgG antibody from donkey with DYLIGHT 488 stain.
Figure 29:
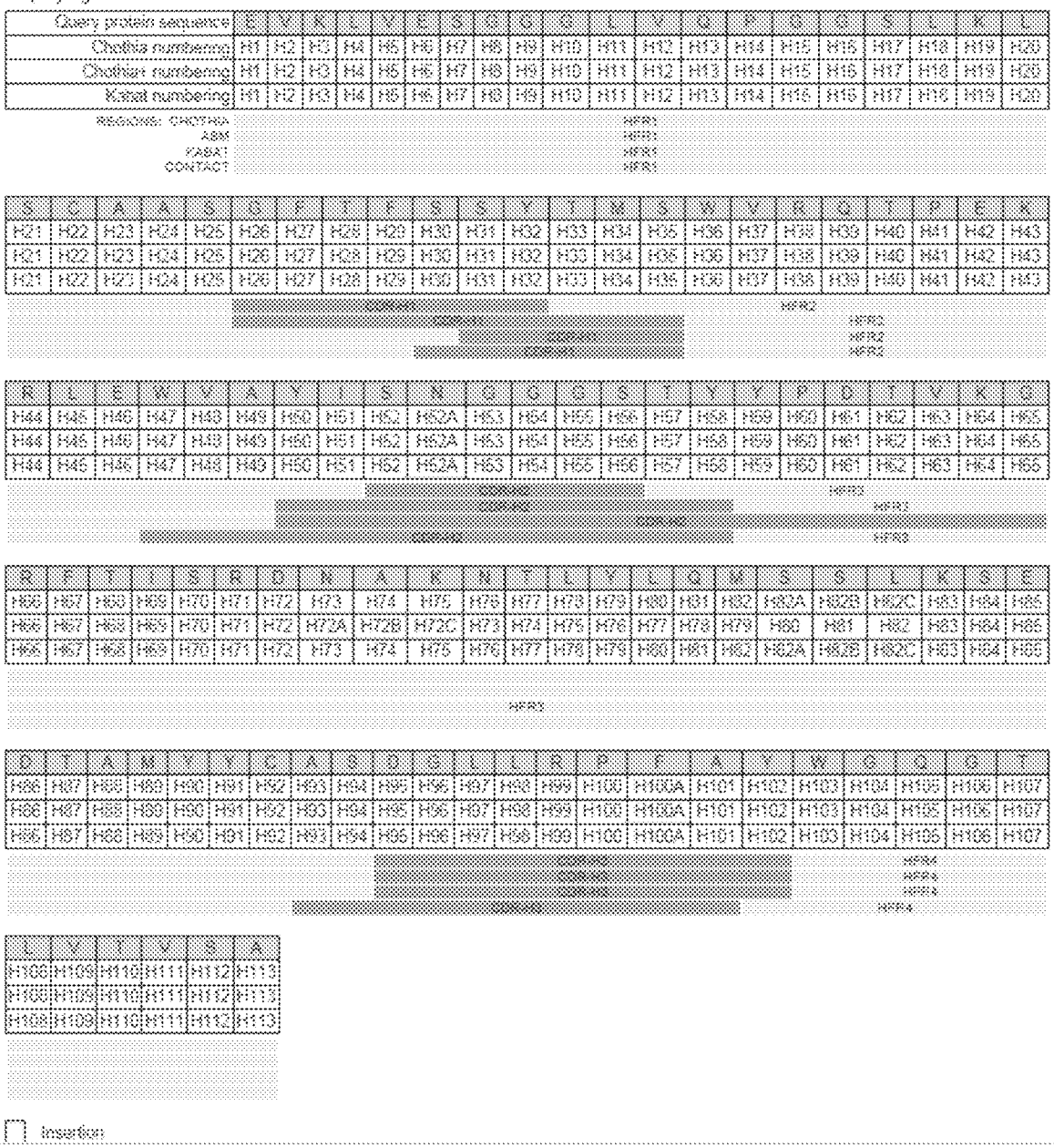
FIG. 29: SEQ ID NO: 4 with depiction of residue alignments amongst CDR regions as predicted by Chothia, ABM, Kabat, and Contact systems utilizing the Abysis database; predicted CDR regions for human chimeric heavy chain variable CDR binding domain regions.
Figure 30:
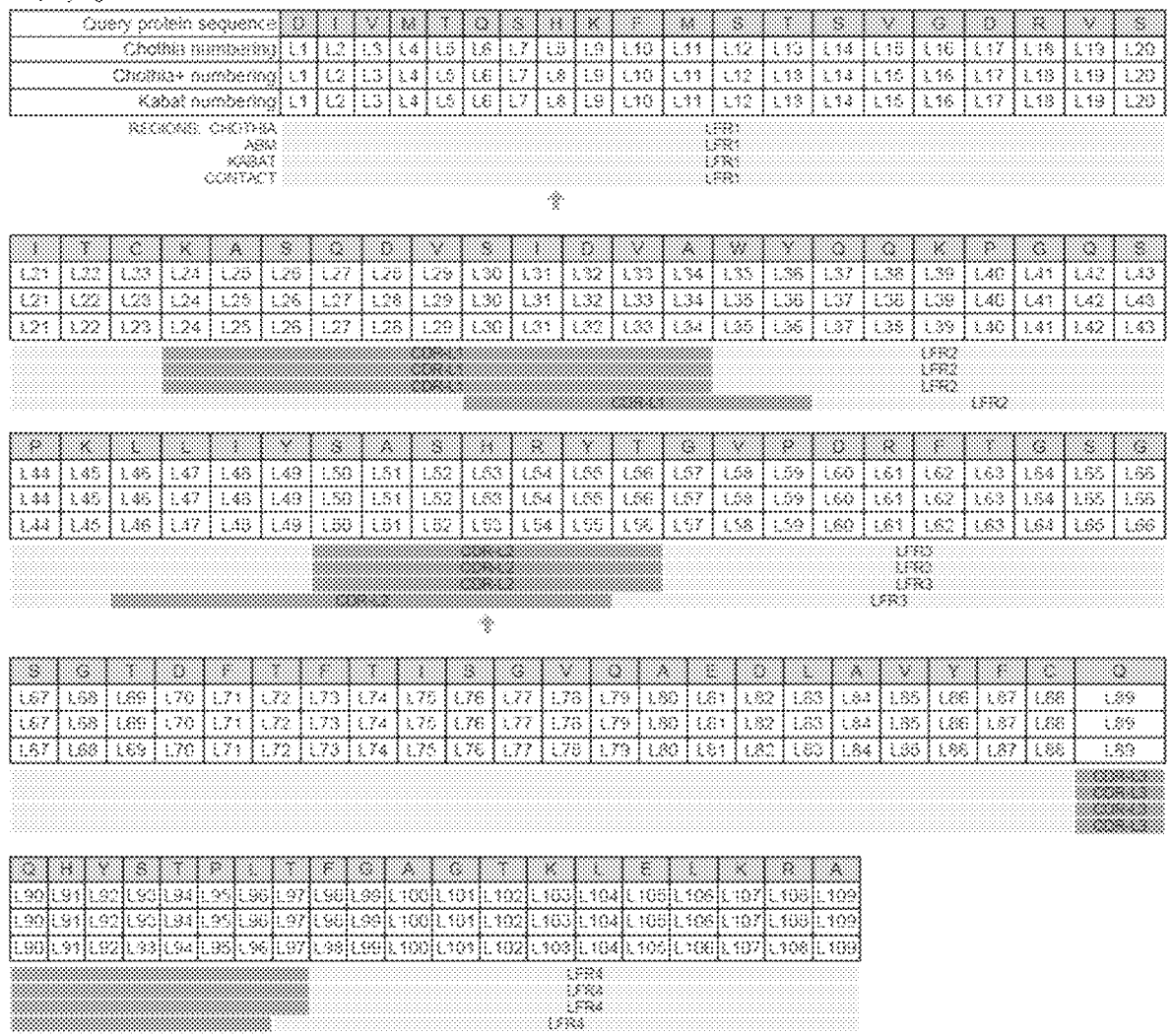
FIG. 30: SEQ ID NO: 74 with depiction of residue alignments amongst CDR regions as predicted by Chothia, ABM, Kabat, and Contact systems utilizing the Abysis database; predicted CDR regions for murine light chain variable CDR binding domain regions.

Primary antibodies were incubated with the fixed and permeabilized cells for 1 hour at room temperature at a concentration of 1.25 mcg/ml. After one or more wash steps, secondary antibodies were incubated with the cells for 1 hour at room temperature. The secondary antibodies utilized in the assays with corresponding concentrations used are as follows:
1.25 µg/ml ANTI-MOUSE IgG (H&L) (DONKEY) DYLIGHT™ 488
5.0 µg/ml ANTI-HUMAN IgG (H&L) (DONKEY) Fluorescein
1.25 µg/ml F(ab')$_2$ Anti-RABBIT IgG [H&L] (DONKEY) Rhodamine Utilizing the first method with the methanol and triton fixation/permeabilization technique significantly compromises cellular integrity and causes DAPI stain to leak out of the nucleus, see FIGS. 3-18. Utilizing the first method reveals punctate staining patterns in clones TI10 (FIGS. 3, 11, and 12) and AHO1402 (FIGS. 4, 13, and 14), which is consistent with the staining pattern described by Alper et al., 2009.

While using the same method, mouse (FIGS. 5, 15, and 16) and human chimeric (FIGS. 6, 17, and 18) monoclonal antibodies reproduced the punctuate staining pattern seen in the aforementioned antibodies.

Figure 8:
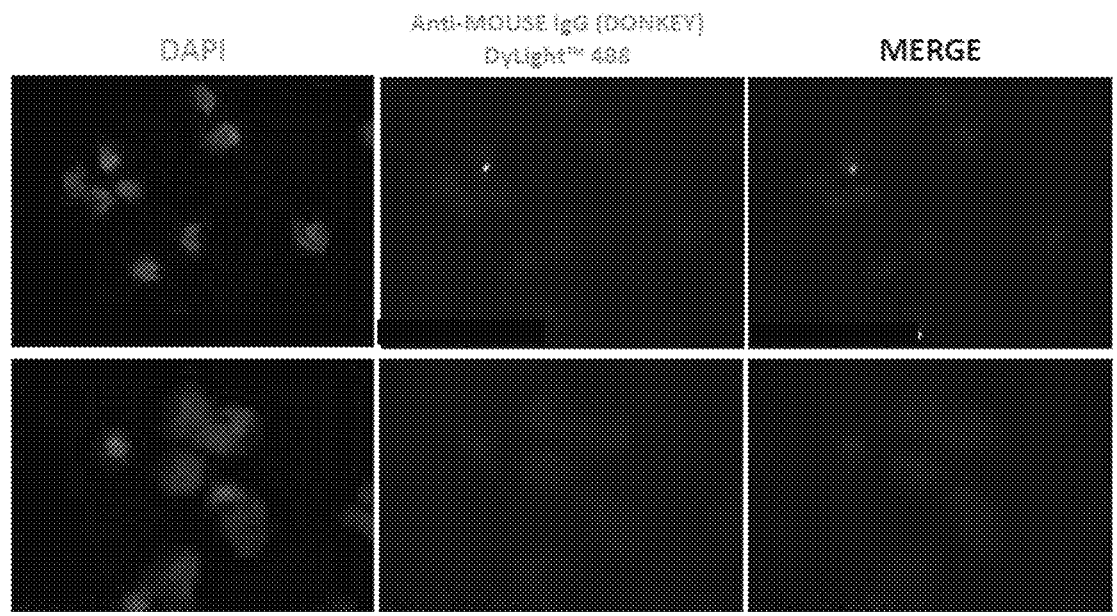
FIG. 8: Immunofluorescence micrograph of MDA-MB-231 cancer cells stained with DAPI DNA stain, anti-mouse IgG donkey antibody with DYLIGHT 488 stain.
Figure 9:
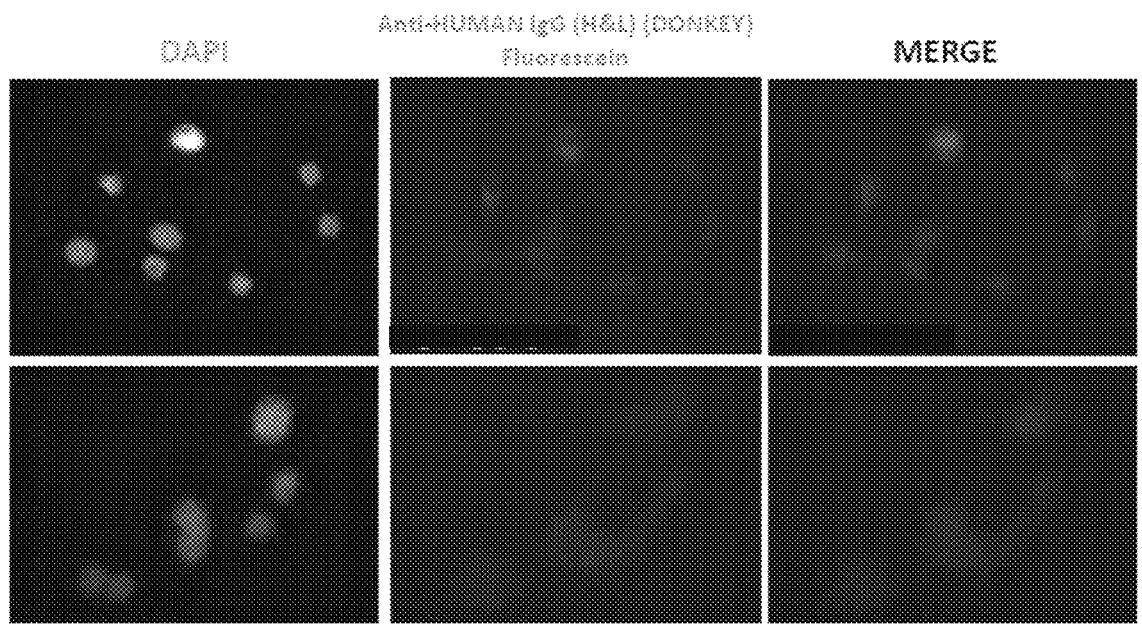
FIG. 9: Immunofluorescence micrograph of MDA-MB-231 cancer cells stained with DAPI DNA stain, anti-human IgG donkey antibody with fluorescein stain.
Figure 10:
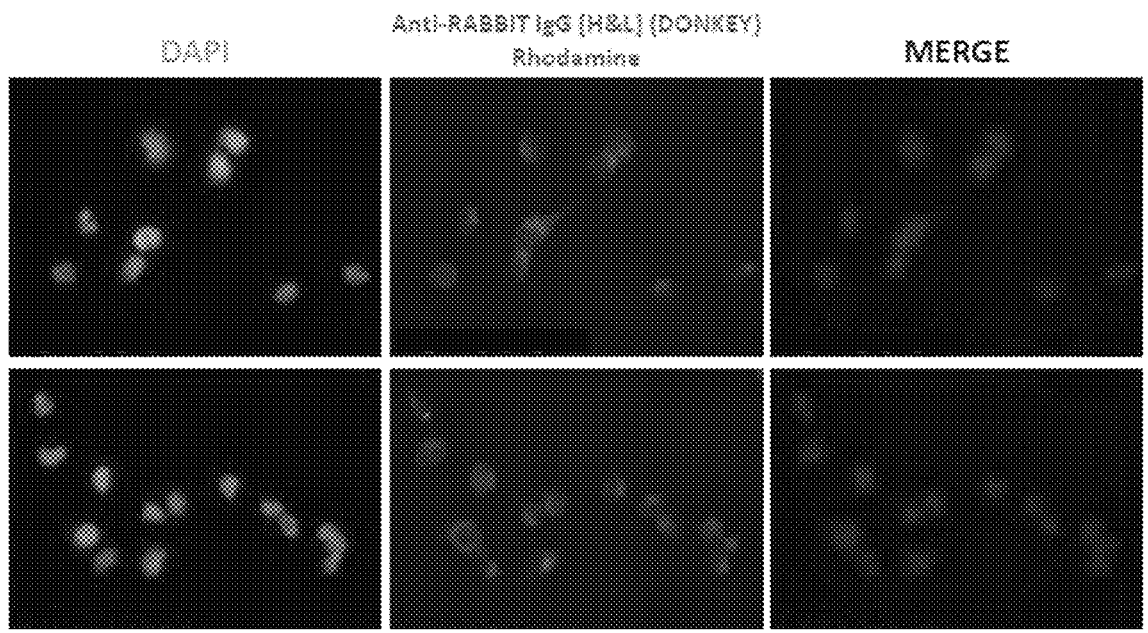
FIG. 10: Immunofluorescence micrograph of MDA-MB-231 cancer cells stained with DAPI DNA stain, F(ab')$_2$ anti-rabbit IgG donkey antibody with rhodamine stain.

Thus, the mouse mAb and developed human chimeric mAb appear to bind a similar form of filamin-A, as the aforementioned AHO1402 antibody The beta-actin staining (FIG. 7) does not appear different from background fluorescence generated by secondary antibody alone, see FIGS. 8-10.

Utilizing the second method with the paraformaldehyde and triton fixation/permeabilization technique did not result in DAPI leaking and otherwise reproduced staining patterns observed by the first method, see FIGS. 19-27.

Example 5: Further Characterization of Antibodies of the Disclosure

The antibodies of the present disclosure are evaluated for their ability to be utilized in the diagnosis of disease in diagnostic methods that include immunohistochemistry, ELISA, and other diagnostic methods that utilize antibodies on biopsied tissue samples (e.g., tumor samples, blood, or blood derived fractions, urine, etc.).

The antibodies of the present disclosure are subjected to further assays in characterizing the antibodies with ELISA, immunoblotting techniques, cell staining (e.g., immunofluorescence, flow cytometry), immunohistochemistry. Cell-based assays will include evaluation for effect on cell motility, cell proliferation, apoptosis, and various cell signaling assays.

The present disclosure provides numerous cell types that are further utilized for motility assays. Characterization of the antibodies of the present disclosure includes analysis of motility in a 3D MATRIGEL assay with and without various protein additives that may be found in the extracellular matrix. In addition to collagen and fibronectin, these may include, but are not limited to, molecules such as filamin-A, plasmin, laminin, keratins, elastins, proteoglycans, chondroitins, integrins, among others. Additional molecules may include proteases and other factors such as urokinase plasminogen activator, tissue-type plasminogen activator, chymotrypsin, matrix metalloproteinases, among others.

Additionally, further assays are performed in the context of cell motility assays with additional cell lines and tissues, antibody titrations, antibody derivatives (e.g., antibody-drug conjugates, scFvs, and other antibody formats).

Example 6: Further Studies Performed with B411 v. Shelf Reagent

Additional cell assays were carried out using the B411 antibody and the breast cancer cell lines MDA-MB-231 and SKBR3. Specifically, the filamin-A antibody B411 was evaluated in the ORIS™ cell migration assay, which used tri-coated 96 well plates (Platypus #CMATR1.101). Cells were seeded at approximately 25,000 or 50,000 cells/well. Cells were incubated overnight at 37° C., $CO_2$, McCoy's in the case of SKBR3 cells, or L-15 containing 10% FBS, without $CO_2$ in the case of MDA-MB-231 cells. Stoppers covering cell growth and migration zones were removed with the ORIS™ stopper tool, growth media was removed, and wells gently washed with 100 microliters of sterile PBS. Stoppers were left in place in reference wells until the staining step to serve as no-migration controls. After washing, a 100 microliter volume of fresh culture media containing the specific treatment was added to each well. The cells were then allowed to incubate overnight. At the end of the incubation period, cells were fluorescently stained as follows:

Carefully remove remaining culture medium from wells and wash with 100 μL of PBS. Remove PBS.
Add 100 μL of 1× Calcein AM (eBioscience, 65-0853-78) solution to each well.
Incubate plate at 37° C. for 30 minutes. Fluorescence was then measured using a microplate reader with a Detection Mask in place.
Carefully remove Calcein AM and wash with 100 μL of PBS. Remove PBS.
Add 100 μL of PBS containing propidium iodide (for detection of dead cells) and Hoechst 33342 (for detection of apoptotic cells) (1:3,000 and 1:4,000 dilution, respectively) to each well. Incubate 5-10 min at room temperature.
Take a fluorescence image (blue, green and red channels) of a representative well(s) using 5× magnification.

Figure 32:
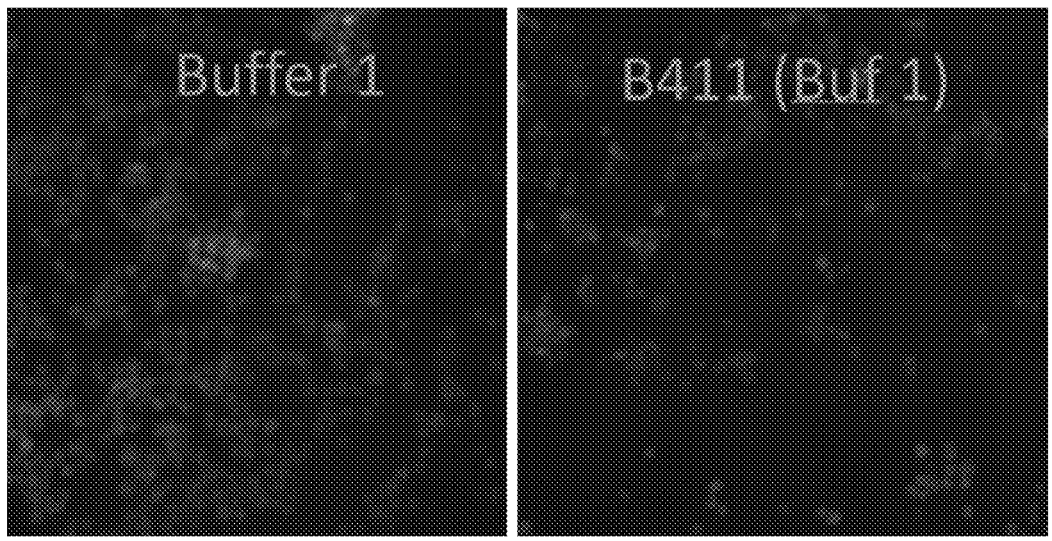
FIG. 32: Images of fluorescent staining of MDA-MB-321 cells following overnight incubation with buffer control (left panel) or filamin A antibody B411 (right panel), in a cell migration assay.

As may be seen in FIG. 32, there is an increase in Hoechst 33342 staining (blue) on MDA-MB-231 breast cancer cells treated with the anti-filamin-A B411 antibody, suggesting an increase in cells with an apoptosis-like phenotype (Hoechst 33342 stains condensed chromatin in apoptotic cells more brightly than the chromatin in normal cells). Furthermore, there is more variability in Calcein AM staining (green) with some cells staining with high intensely and some not at all, suggesting significant alterations in metabolic activity upon anti-filamin-A antibody treatment. Dead cells are identified by staining of nuclei with propidium iodide (red).

Example 7: Filamin-A-Specific Intrabodies

Intrabodies specific for filamin-A antigen are generated and experiments are conducted to test the expression and functionality of the intrabodies. Intrabody constructs are transiently expressed in a cell line (e.g., MDA-MB-231, HEK392, HeLa, or other cell lines). Transfected cells are assessed to confirm antibody (e.g., scFv) expression via Western blotting. For example, for tagged intrabodies, scFv expression may be confirmed via the tag (e.g., using anti-His or anti-GST tag antibodies) or via an anti-scFv antibody or other anti-intrabody construct antibody. Alternatively or additionally, immunofluorescence assay is used to confirm scFv expression (e.g., by staining with and detection of anti-His tag, anti-GST, anti-scFv, or other anti-intrabody construct antibody).

Cell phenotypic and metabolic differences are monitored in transfected cells and compared to non-transfected cells, or compared to cells transfected with an irrelevant construct such as a vector without the anti-filamin A antibody fragment (e.g., a GST fusion partner with no antibody component). Cell phenotypic and metabolic assessments include, for example and without limitation, cell morphology, proliferation rate, adhesion, migration, live/dead cell numbers and ratios, metabolic rate, Western blot and/or immunohistochemistry, and flow cytometry to monitor or direct expression of the intrabody, fusion partner, and/or cell marker.

Intrabody expression, functionality, and efficacy is also tested in vivo. For example, a xenograft model of cancer may be utilized in which immunodeficient mice are inoculated (e.g., intraperitoneally, subcutaneously, or orthotopically) with cancer cells. Tumor growth is monitored and a potentially therapeutic or diagnostic intrabody is administered prior to or following the development of tumors. For example, in an orthotopic model of breast cancer, cancer cells are implanted into the inguinal mammary fat pad of immunodeficient mice prior to, or concurrently with, administration or intracellular expression of an anti-filamin A antigen intrabody. For example, an anti-filamin A intrabody construct may be delivered to breast cancer cells for intracellular expression via a plasmid, virus-based or non-virus based delivery vehicle. In some embodiments, an anti-filamin A intrabody construct may be delivered as a protein to a breast cancer cell via a cell membrane-penetrating peptide. The effect on tumor growth of the presence of the anti-filamin A intrabody is measured compared to control animals that received vector control, or irrelevant intrabody. The results of the study show that the administration and intracellular expression of an anti-filamin A intrabody reduces tumor volume, or slows the growth of tumors, or prevents the generation of tumors, in a xenograft model of cancer.

Example 8: Cell Viability Assays

A study was conducted to assess cell survival following incubation with antibody B411. DU145 (human prostate cancer cell line) and HEK293A (human embryonic kidney cell line) cells were seeded on 96-well plates ($10^4$ cells/well) and incubated for 4 hours at 37° C. 1 μg or 10 μg B411 (endotoxin removed, 1.2 EU/mL) was added to the wells and incubated for 24 or 48 hours. An untreated group for both cell types was also included. Cell survival was detected using CellCountzEZ™ Cell Survival Assay kit and results were determined by reading $OD_{412}$ with a reference to $OD_{650}$.

Figure 33:
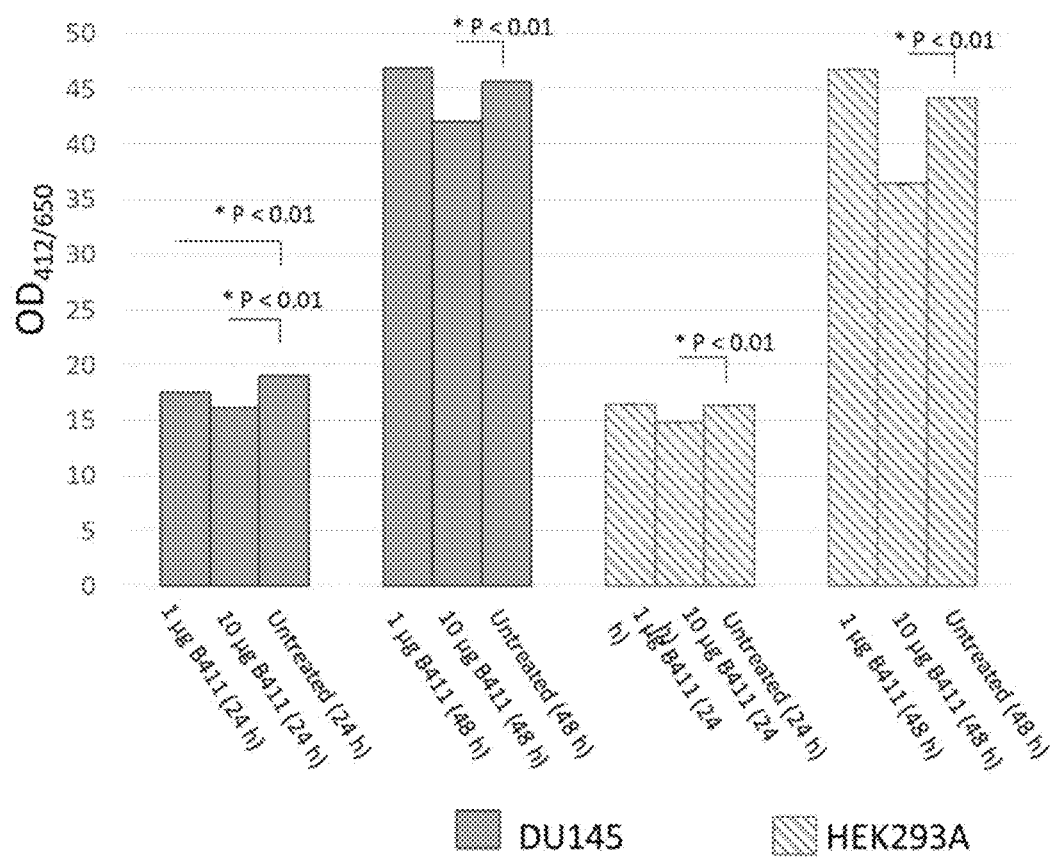
FIG. 33: Bar graph showing that B411 inhibits DU145 (cancer) cell proliferation. DU145 or HEK293A (non-cancer) cells were untreated or treated for 24 or 48 hours with 1 μg or 10 μg B4111 and cell proliferation was measured by $OD_{412}$ with reference to $OD_{650}$.
Figure 34E:
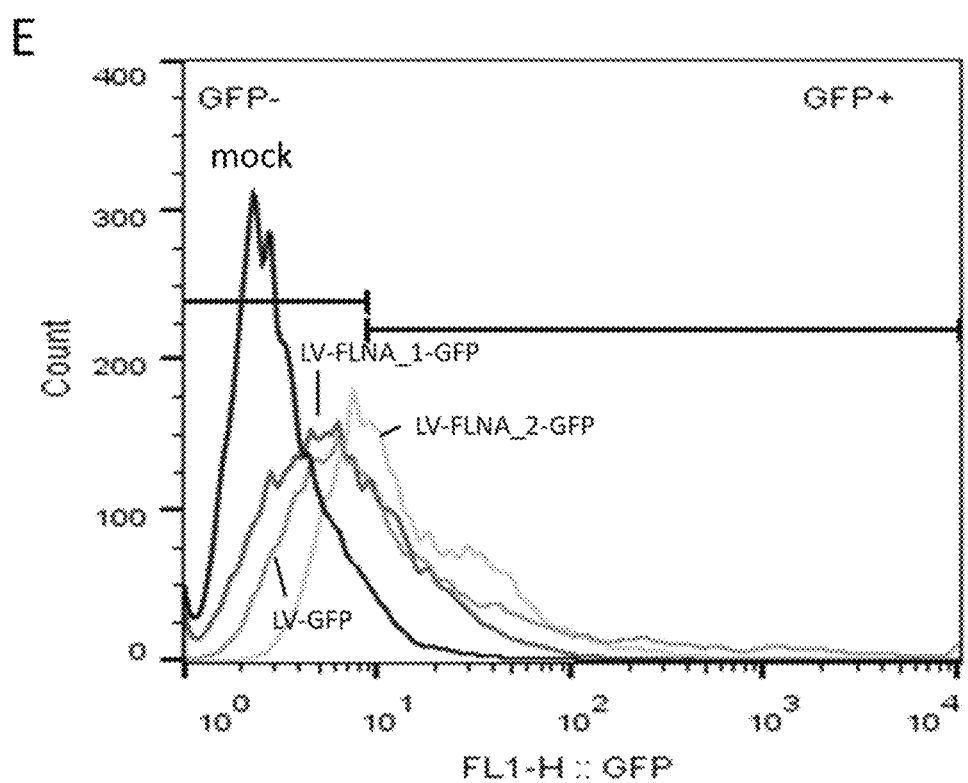
FIG. 34E is a merge of FIG. 34A-D. Total ungated acquisition events (cell #) for each group: 10,000.

The results of the study are provided in FIG. 33, and showed that B411 inhibited DU145 (cancer) cell proliferation. At 1 μg dosing, B411 exhibited significant inhibition effect on proliferation of the DU145 cell growth at 24 h (*p<0.01) when compared with the untreated group of DU145; but no statistically significant effect at 48 h. A 1 μg dose of B411 did not have an effect on the HEK293A cell line at either time point (24 h or 48 h). At 10 μg dosing, B411 showed significant inhibition effects on proliferation of the DU145 cells at both time points of 24 h and 48 h when compared with the untreated group of DU145. Inhibition of HEK293 cell proliferation was also observed at 10 μg.

The ratios of inhibition by B411 on the DU145 at 24 h and 48 h were 7.8% and 14.6%, respectively and both were significant (*p<0.01). Ratios of inhibition of HEK293 at 24 h and 48 h were 9.3% and 17.7% and were also significant (*p<0.01).

Example 9: Filamin A Intrabodies Reduce FLNA Protein Levels in Cancer Cells and Reduce Cancer Cell Proliferation Intrabodies were generated using a bicistronic lentiviral vector to co-express two genes in a single vector. The vector was designated LV-EF-intrabodyFLNA/Histag-IRES-GFP. When the vector is delivered into a cell, the first gene product, intrabodyFLNA, is driven by an EF promoter, and IRES initiates translation of the second gene product, GFP. Studies were conducted to assess the effects of exemplary filamin A intrabodies on various cancer cell types. Two lentiviral vectored FLNA intrabody constructs comprising a GFP reporter gene were tested: LV-FLNA 1-GFP comprises the heavy and light chain variable regions of B411 in the VH-VL orientation, and LV-FLNA_2-GFP comprises the light and heavy chain variable regions of B411 in the opposite orientation, VL-VH. A GFP expressing lentiviral control vector (LV-GFP) was also used in the studies.

Lung Cancer

A549 (lung cancer cell line) cells were transfected with 1 μg DNA (LV-GFP, LV-FLNA 1-GFP, or LV-FLNA_2-GFP) using lipofectamine 3000, or mock transfected. Cells were harvested at 72 hours post-transfection and stained with Calcein-Deep-Red or EthD-1 for live and dead cell analysis, respectively. Cell viability was assessed by flow cytometry.

The results of the cell viability assays are provided in FIGS. 34-38. FIGS. 34A-E show the GFP expression in the transfected cells 72 hours post-transfection. FIG. 34A shows no GFP expression in the mock-transfected cells. FIGS. 34B, C, and D show GFP expression in LV-GFP, LV-FLNA_1-GFP, and LV-FLNA_2-GFP transfected cells. FIG. 34E is an overlay of the histograms in FIG. 34A-D.

Figure 35F:
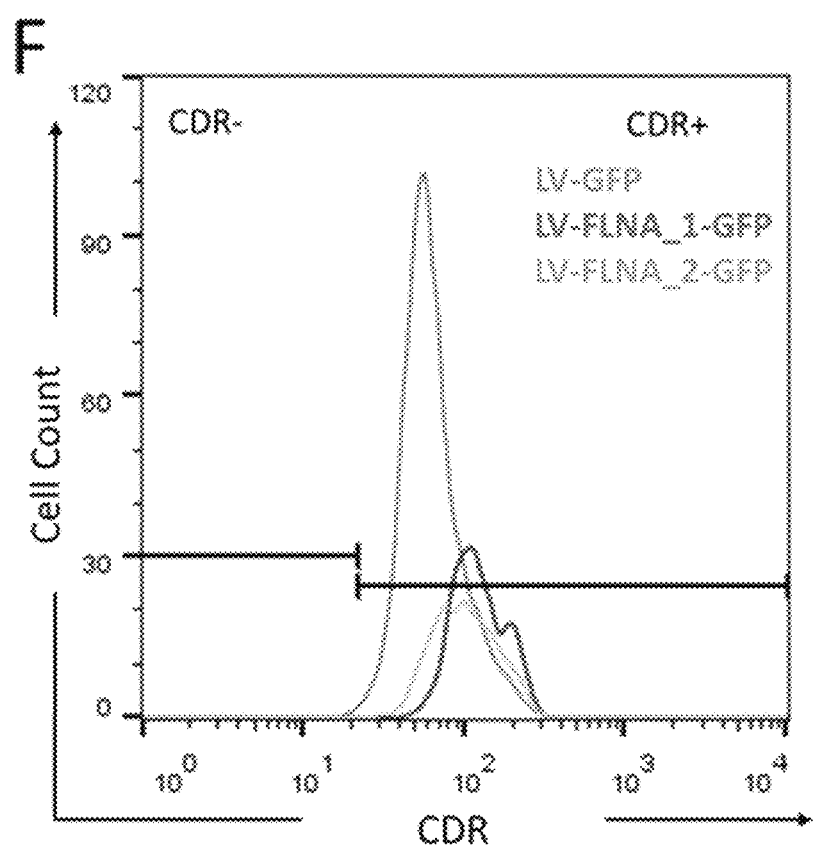
FIG. 35F is a merge of FIGS. 35C-E. Total ungated acquisition events (cell #) for each group: 10,000.
Figure 36:
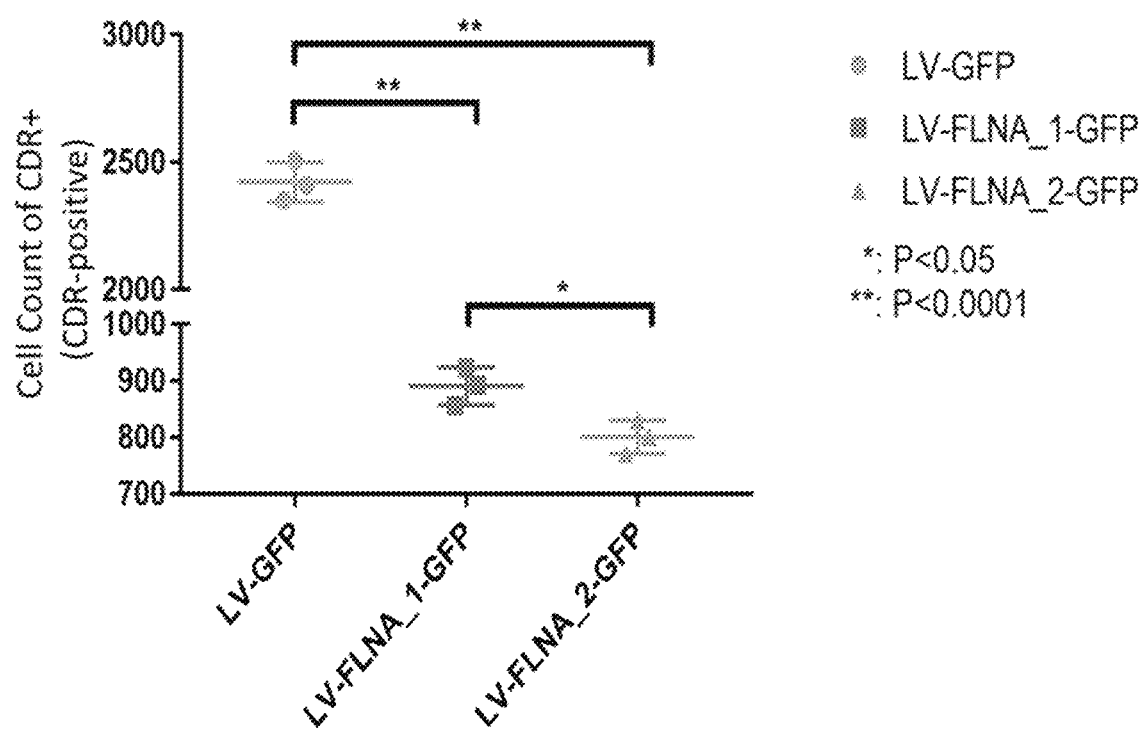
FIG. 36: Statistical analysis of FIG. 35A-F, showing that expression of FLNA intrabody in A549 cells results in decreased cell viability. N=3; student's t-test, two-tail unpaired.

FIGS. 35A-F show the live cell analysis of GFP-gated cells 72 hours after transfection. FIGS. 35A and B show the unstained control (FIG. 35A) and the positive control cells (Calcein Deep Red (CDR) live cell stain) (FIG. 35B). FIGS. 35C, D, and E show the CDR positive staining in the GFP positive cells 72 hours after transfection with LV-GFP, LV-FLNA 1-GFP, or LV-FLNA_2-GFP. FIG. 35F is a histogram overlay of the live cell analysis from FIGS. 35C, D, and E. FIG. 36 show the total count of CDR-positive (live) cells in the GFP positive cells population. Both LV-FLNA 1-GFP and LV-FLNA_2-GFP significantly reduced the number of live cells (p<0.0001).

Figure 37F:
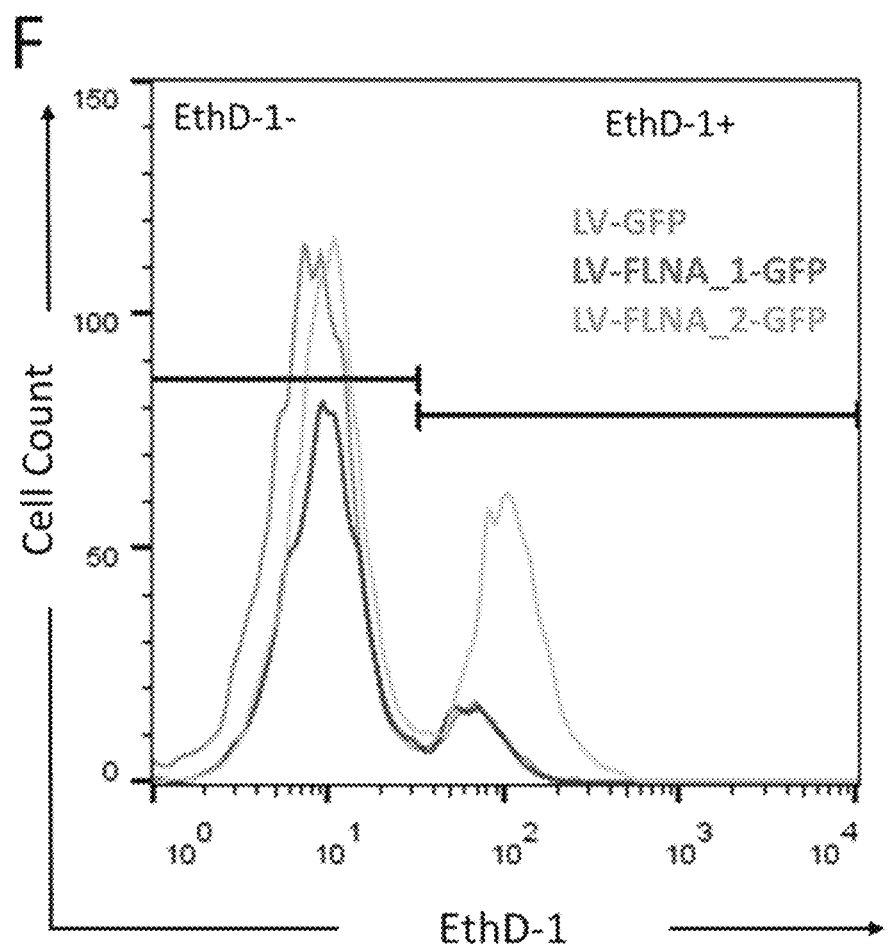
FIG. 37F is a merge of FIGS. 37C-E. Total ungated acquisition events (cell #) for each group: 10,000.
Figure 38:
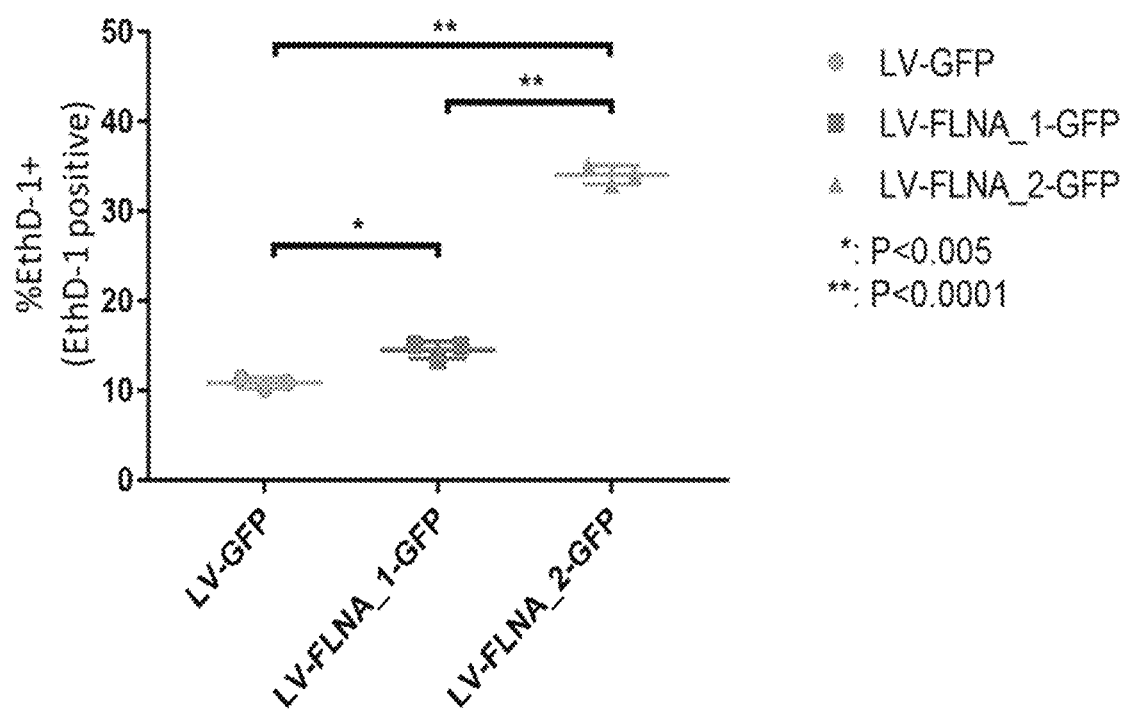
FIG. 38: Statistical analysis of FIG. 37A-F, showing that expression of FLNA intrabody in A549 cells results in increased cell death. N=3; student's t-test, two-tail unpaired.

FIGS. 37A-E show the dead cell analysis of GFP-gated cells 72 hours after transfection. FIGS. 37A and B show the unstained control (FIG. 37A) and the positive control cells (EthD-1 dead cell stain) (FIG. 37B). FIGS. 37C, D, and E show the EthD-1 staining in the GFP positive cells 72 hours after transfection with LV-GFP, LV-FLNA_1-GFP, or LV-FLNA_2-GFP. FIG. 38A is a histogram overlay of the dead cell analysis from FIGS. 37C, D, and E. FIG. 38B shows the total count of EthD-1 positive (dead) cells in the GFP positive cell population. Both LV-FLNA 1-GFP and LV-FLNA_2-GFP significantly increased the number of dead cells relative to the LV control (p<0.005 and p<0.0001, respectively). LV-FLNA_2-GFP significantly increased the number of dead cells relative to both LV control and LV-FLNA_1-GFP (p<0.0001).

For cell proliferation assays, 2.5 μg of DNA was transfected into A549 cells in each well of a 6 well plate using lipofectamine 3000. Cells were harvested at 72 hours post-transfection and incubated with EdU reagent for two hours. Cells not contacted with EdU reagent served as negative controls. Proliferation was assessed by flow cytometry.

Figure 39:
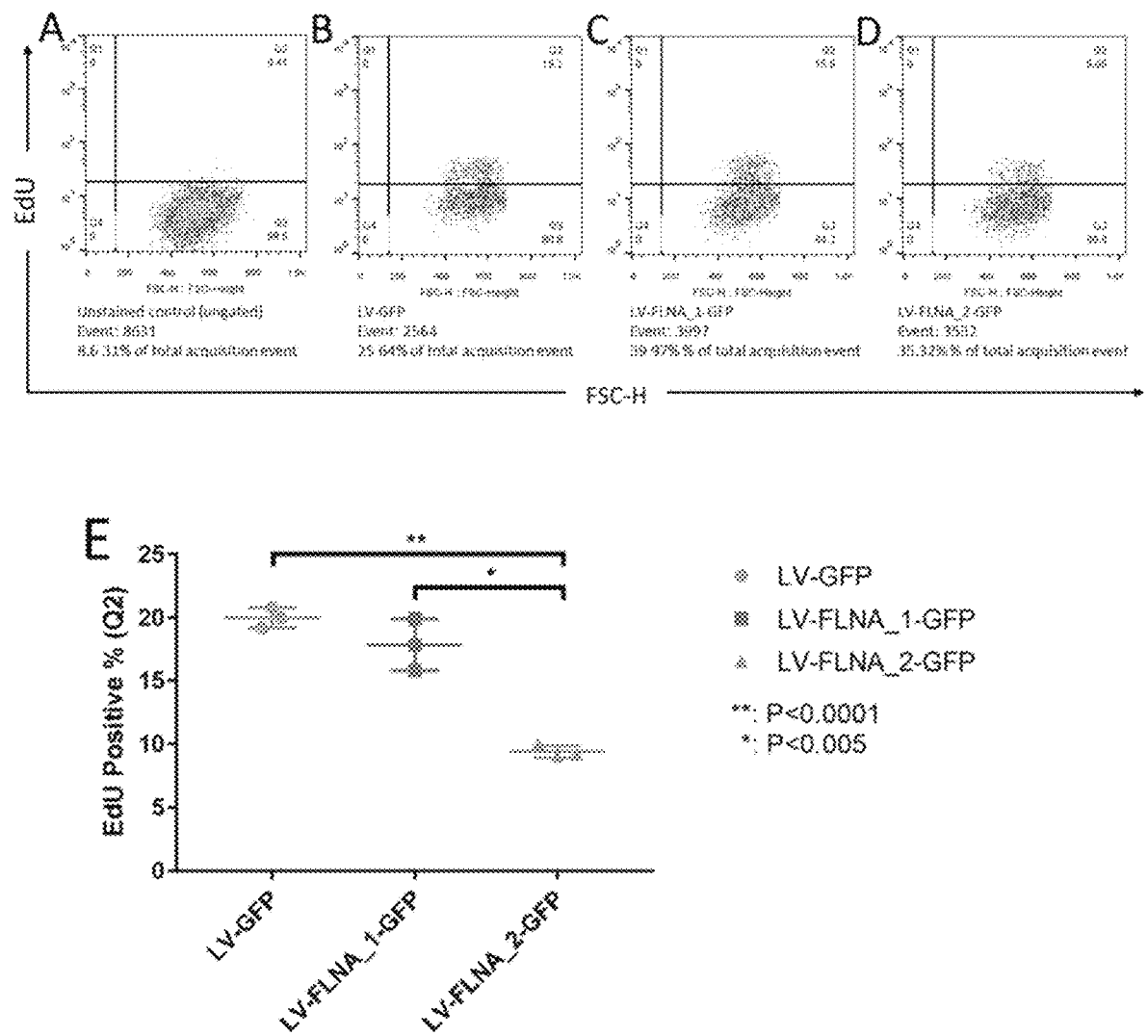
FIG. 39: A549 cells expressing FLNA intrabody show reduced cell proliferation (GFP gated and stained by EdU).

The results of the proliferation assays are provided in FIG. 39. FIG. 39A is unstained control. FIG. 39B shows proliferation of vector control transfected cells. FIGS. 39C and 39D show proliferation of LV-FLNA_1-GFP and LV-FLNA 2-GFP transfected cells, respectively. FIG. 39E is a graph showing the percent EdU positive (proliferated) cells in each group. LV-FLNA_2-GFP significantly reduced proliferation of A549 cells relative to LV-GFP (p<0.0001).

Figure 3:
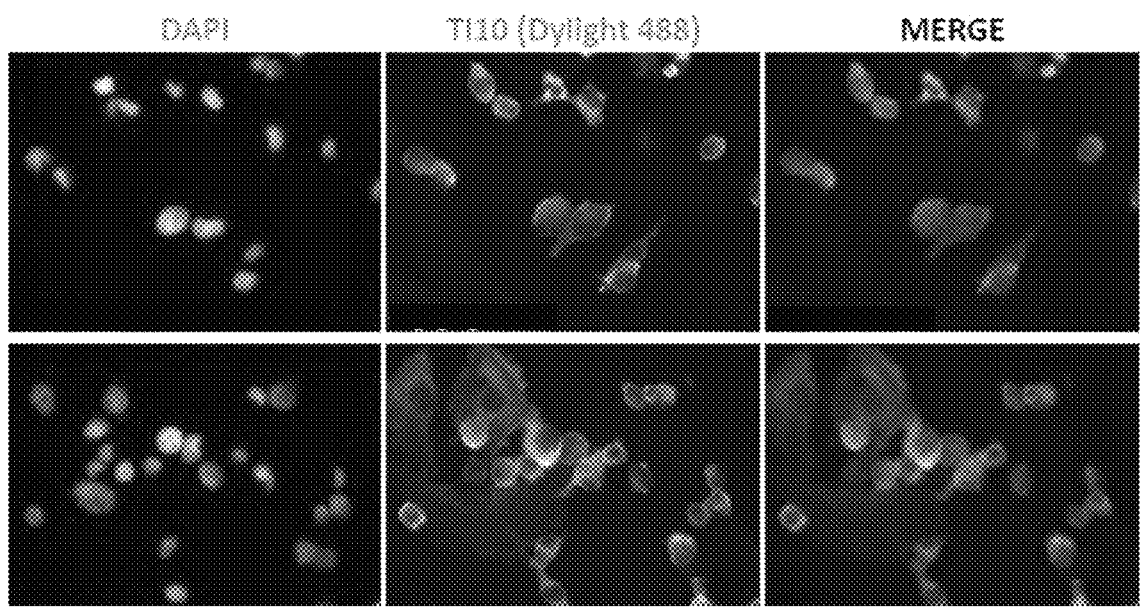
FIG. 3: Immunofluorescence micrograph of MDA-MB-231 cancer cells stained with DAPI DNA stain, TI10 filamin-A antibody with DYLIGHT 488 stain.
Figure 4:
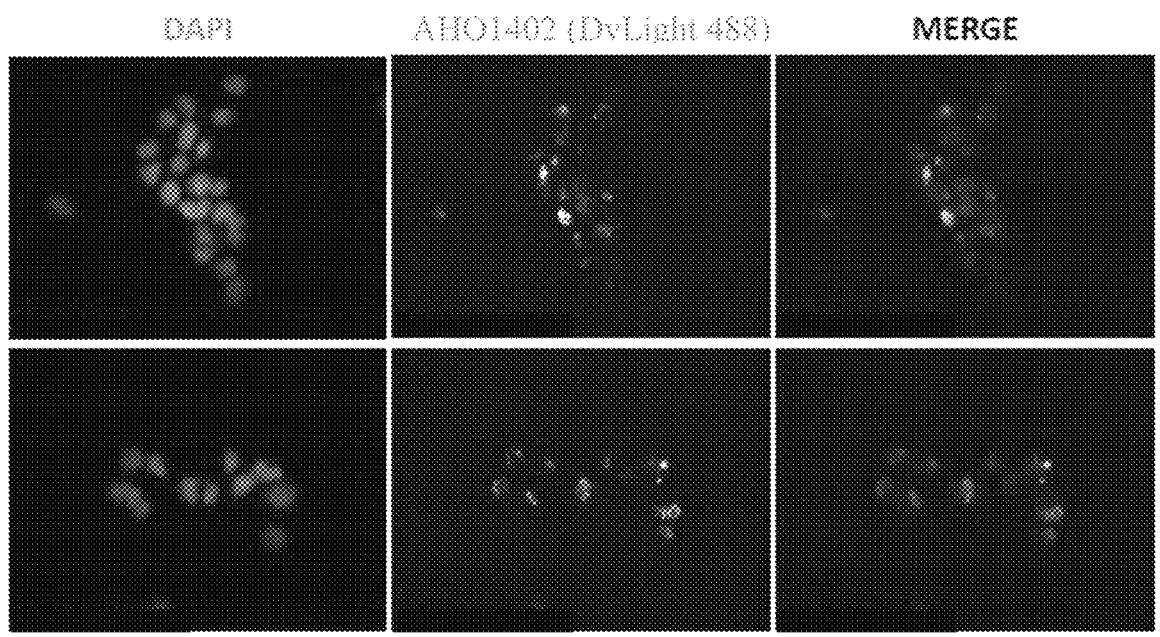
FIG. 4: Immunofluorescence micrograph of MDA-MB-231 cancer cells stained with DAPI DNA stain, AHO1402 filamin-A antibody with DYLIGHT 488 stain.
Figure 5:
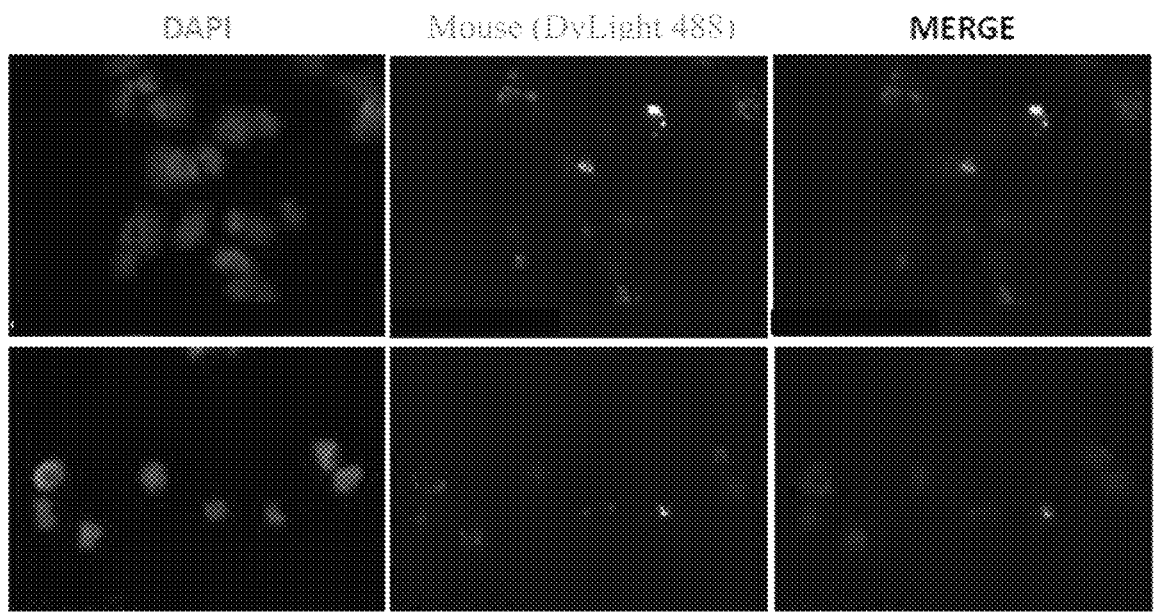
FIG. 5: Immunofluorescence micrograph of MDA-MB-231 cancer cells stained with DAPI DNA stain, mouse filamin-A antibody with DYLIGHT 488 stain.
Figure 6:
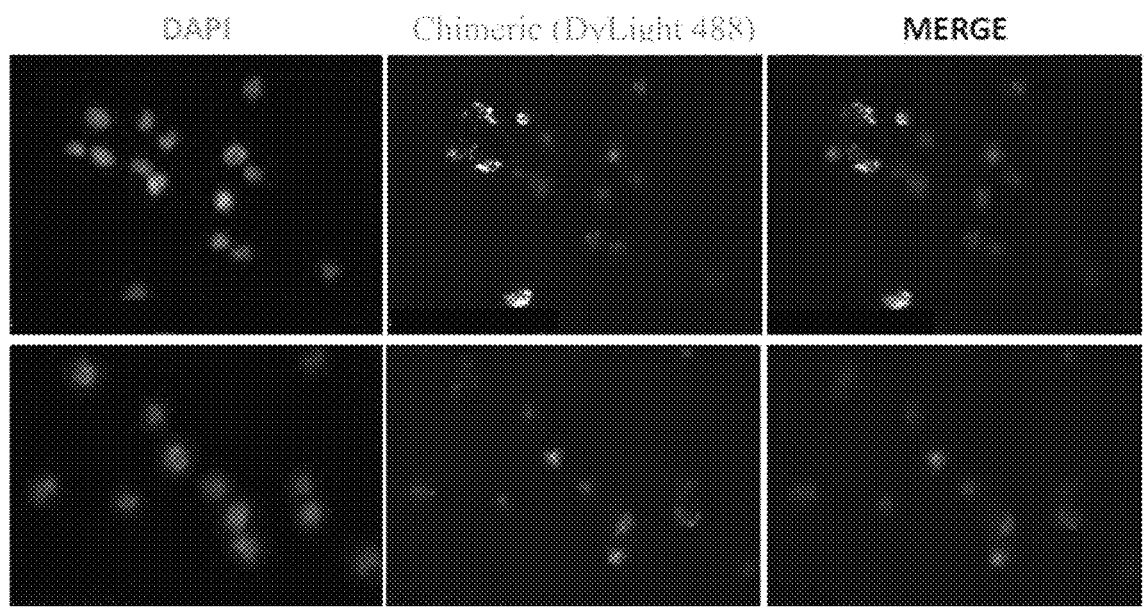
FIG. 6: Immunofluorescence micrograph of MDA-MB-231 cancer cells stained with DAPI DNA stain, chimeric filamin-A antibody with DYLIGHT 488 stain.
Figure 7:
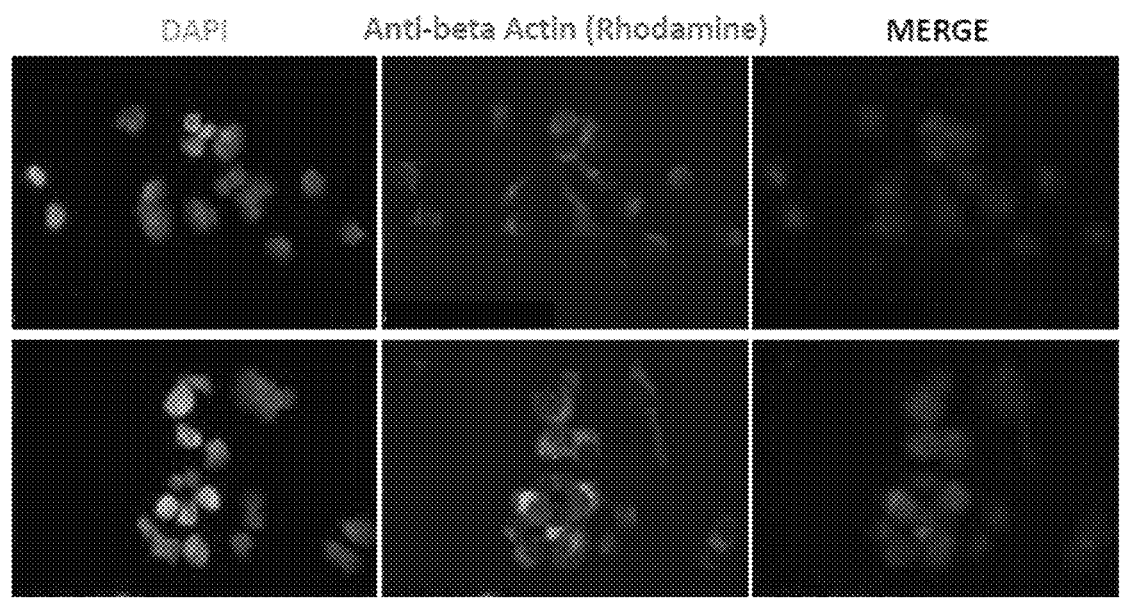
FIG. 7: Immunofluorescence micrograph of MDA-MB-231 cancer cells stained with DAPI DNA stain, beta actin rabbit polyclonal antibody with rhodamine stain.
Figure 40:
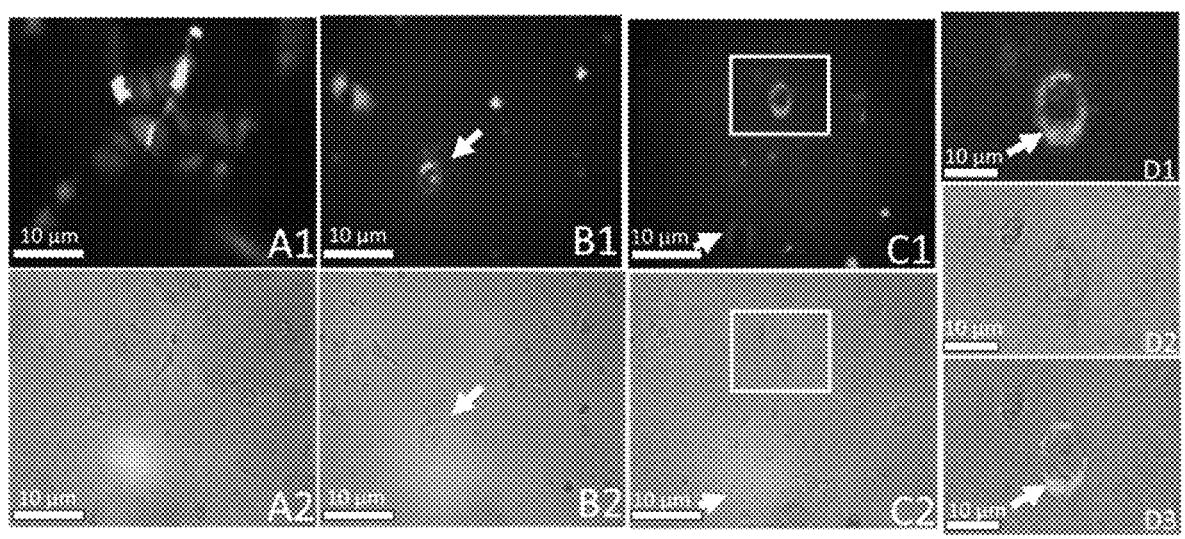
FIG. 40: Expression in A549 cells transfected with LV-GFP and LV-FLNA-GFP intrabody.

For microscopy studies, 2.5 μg of DNA was transfected into A549 cells in each well of a 6 well plate using lipofectamine 3000, and cells were imaged 24 hours post-transfection using a confocal microscope. FIG. 40 provides the results. FIGS. 40A1, B1, and C1 show the fluorescent images of LV-GFP transfected, LV-FLNA_2-GFP transfected, and LV-FLNA_1-GFP transfected cells, respectively. FIGS. 40A2, B2, and C2 show the bright field images of LV-GFP transfected, LV-FLNA 2-GFP transfected, and LV-FLNA 1-GFP transfected cells, respectively. FIGS. 40D1 and 40D2 show the zoomed-in view of the selected views (white triangles) in FIGS. 40C1 and 40C2, respectively. FIG. 40D3 is a merged view of FIGS. 40D1 and 40D2. The white arrows suggest co-expression of FLNA with GFP in the A549 cells.

Figure 41:
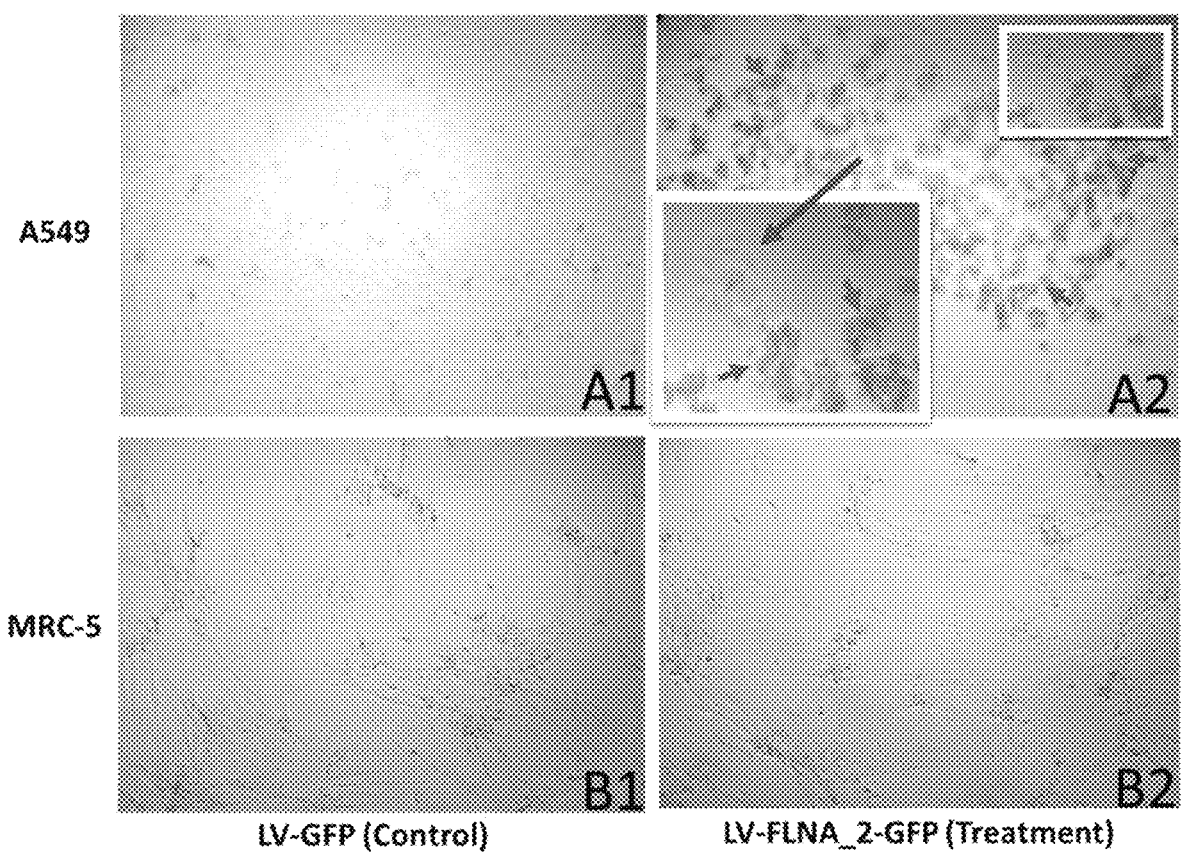
FIG. 41: Comparison of FLNA intrabody treatment between A549 cells and non-cancer MRC-5 cells (normal cells). FLNA intrabody treatment results in visible cell death in A549 cells but not MRC-5 lung normal fibroblasts Bright field images of A549 cells (FIG. 40A left panel, A1) and MRC-5 lung normal fibroblast cells (FIG. 40B left panel, B1) transfected with LV-GFP (2.5 μg). A549 (FIG. 40A right panel, A2) and MRC-5 cells (FIG. 40B right panel, B2) transfected with LV-FLNA_2-GFP intrabody (2.5 μg). Short arrows show detached dead cells (10× magnification). Inset: high magnification view to show the differences between dead cell clusters (short arrows) and live cells (long arrow).

A study was further conducted to compare the effects of FLNA intrabody treatment in A549 cells to non-cancer MRC-5 cells. 2.5 μg of DNA was transfected into A549 cells in each well of a 6 well plate using lipofectamine 3000, and cells were imaged at 72 hours post transfection using a confocal microscope. FIG. 41 provides the results. There was visible cell death in the LV-FLNA_2-GFP treated A549 cells (FIG. 41A2), but not in the control LV-GFP treated A549 cells (FIG. 41A1). In contrast, there was no visible cell death in the LV-FLNA 2-GFP treated MRC-5 cells (FIG. 41B2). The results of the study indicate that the cell death elicited by the FLNA intrabody treatment is specific to cancer cells.

Glioblastoma

U87MG (glioblastoma cell line) cells were transfected with 1 μg DNA (LV-GFP, LV-FLNA_1-GFP, or LV-FLNA_2-GFP) in 12-well plates using lipofectamine 3000, or mock transfected. Cells were harvested at 72 hours post-transfection and stained with Calcein-Deep-Red or EthD-1 for live and dead cell analysis, respectively. Cell viability was assessed by flow cytometry.

The results of the cell viability assays are provided in FIGS. 42-44. In FIG. 42, the left column shows the live cell count in LV-GFP (top), LV-FLNA_1-GFP (middle), and LV-FLNA 2-GFP (bottom) transfected cells. The middle column shows the dead cell count in LV-GFP (top), LV-FLNA_1-GFP (middle), and LV-FLNA_2-GFP (bottom) transfected cells. The right column shows the live/dead cell count (merge of columns 1 and 2) in LV-GFP (top), LV-FLNA_1-GFP (middle), and LV-FLNA_2-GFP (bottom) transfected cells. The study shows the shift from live to dead cells upon transfection of U87MG cells with FLNA intrabody.

FIGS. 43A and 43B show the live cell analysis 72 hours after transfection. FIG. 43A is a histogram overlay of the live cell analysis staining of LV-GFP, LV-FLNA_1-GFP, and LV-FLNA 2-GFP transfected cells. FIG. 43B shows the total count of CDR-positive (live) cells. Both LV-FLNA_1-GFP and LV-FLNA_2-GFP significantly reduced the number of live cells ($p<0.0001$).

FIGS. 44A and 44B show the dead cell analysis of GFP-gated cells 72 hours after transfection. FIG. 44A is a histogram overlay of the dead cell analysis staining of LV-GFP, LV-FLNA 1-GFP, and LV-FLNA_2-GFP transfected cells. FIG. 44B shows the total count of EthD-1 positive (dead) cells. Both LV-FLNA 1-GFP and LV-FLNA_2-GFP significantly increased the number of dead cells relative to the LV control ($p<0.005$ and $p<0.0001$, respectively) . . .

A study was conducted to compare the effects of FLNA intrabody treatment between the glioblastoma cell line and non-cancer HBEC-5i cells. The results are provided in FIG. 45. 72 hours post-transfection, FLNA intrabody treatment resulted in cell death in LN229 cells (glioblastoma cell line; FIG. 45A), but not in HBEC-5i cells (non-cancer cell line; FIG. 45B). The results of the study indicated that the cell death elicited by FLNA intrabody treatment is specific to cancer cells.

For microscopy studies, 2.5 μg of DNA was transfected into U87MG cells in each well of a 6 well plate using lipofectamine 3000, and cells were imaged 24 and 72 hours post-transfection using a confocal microscope. FIGS. 46 and 47 provide the results. FIGS. 46A1, B1, and C1 show the fluorescent images of LV-GFP transfected, LV-FLNA_1-GFP transfected, and LV-FLNA 2-GFP transfected U87MG cells, respectively, 24 hours after transfection. FIGS. 46A2, B2, and C2 show the bright field images of LV-GFP transfected, LV-FLNA_1-GFP transfected, and LV-FLNA_2-GFP transfected U87MG cells, respectively, 24 hours after transfection. FIGS. 47A and 47B show the fluorescent and bright field images of LV-GFP transfected U87MG cells 72 hours after transfection. FIGS. 47C and 47D show the fluorescent and bright field images of LV-FLNA 1-GFP transfected U87MG cells 72 hours after transfection, and FIGS. 47E and 47F show the fluorescent and bright field images of LV-FLNA 2-GFP transfected U87MG cells 72 hours after transfection. Similarly, FIGS. 48A-F show bright field images of LV-GFP (FIGS. 48A, 48B), LV-FLNA_1-GFP transfected (FIGS. 48C, 48D), and LV-FLNA 2-GFP transfected (FIGS. 48E, 48F) cells at 72 hours. The images show that at 72 hours, LV-FLNA 1-GFP and LV-FLNA 2-GFP treatment resulted in loss of cellular adherence and death of U87MG glioblastoma cells.

FLNA in U87MG cells treated with FLNA intrabodies was analyzed by immunocytochemistry (ICC). Cells were seeded on chamber slides and fixed in 4% formaldehyde 72 hours post-transfection. Cells were then permeabalized using 0.5% Triton X-100 in PBS. Blocking was performed using 5% BSA in PBS for 1 hour at room temperature. Anti-filamin A primary antibody incubation was conducted at 4° C., overnight; secondary antibody incubation was performed for 1 hour at room temperature. Cells were also stained with the nuclear DAPI stain. The results are provided in FIG. 49. U87MG cells treated with FLNA intrabody showed disruption in FLNA protein at 72 hours after transfection.

FIG. 50 shows the analysis of FLNA scFv in U87MG cells transfected with LV-FLNA_2 intrabody and GFP by immunocytochemistry (ICC) staining for the His tag on the intrabody and for GFP. The top row of FIG. 50 shows anti-His (first panel), anti-GFP (second panel), DAPI staining (third panel) and a merged image showing co-expression of FLNA intrabody and GFP. The bottom row of FIG. 50 shows the LV-GFP control. The data show that FLNA intrabody is co-expressed with GFP (see white arrows).

Prostate Cancer

Cell viability assays were also carried out on DU145 (prostate cancer cell line) cells treated with FLNA intrabodies. DU145 cells were transfected with 0.5 μg DNA (LV-GFP, LV-FLNA 1-GFP, or LV-FLNA_2-GFP) using lipofectamine 3000, or mock transfected. Cells were harvested at 72 hours post-transfection and stained with Calcein-Deep-Red or EthD-1 for live and dead cell analysis, respectively. Cell viability was assessed by flow cytometry.

The results of the cell viability assays are provided in FIGS. 51-55. FIGS. 51A-E show the GFP expression in the transfected cells 72 hours post-transfection. FIG. 51A shows no GFP expression in the mock-transfected cells. FIGS. 51B, C, and D show GFP expression in LV-GFP, LV-FLNA_1-GFP, and LV-FLNA_2-GFP transfected cells. FIG. 51E is an overlay of the histograms in FIG. 51A-D.

FIGS. 52A-C shows the live cell analysis of GFP-gated DU145 cells 72 hours after transfection. The CDR positive staining in the GFP positive cells 72 hours after transfection with LV-GFP, LV-FLNA_1-GFP, or LV-FLNA_2-GFP is shown in FIGS. 52A, 52B, and 52C, respectively. FIG. 53A is a histogram overlay of the live cell analysis from FIGS. 52A-C. FIG. 53B show the total count of CDR-positive (live) cells in the GFP positive cells population. Both LV-FLNA_1-GFP and LV-FLNA_2-GFP significantly reduced the number of live DU145 cells ($p<0.0005$ and $p<0.0001$, respectively) relative to LV-GFP transfection.

FIGS. 54A-C show the dead cell analysis of GFP-gated DU145 cells 72 hours after transfection. EthD-1 positive staining 72 hours after transfection with LV-GFP, LV-FLNA 1-GFP, or LV-FLNA_2-GFP is shown in FIGS. 54A, 54B, and 54C, respectively. FIG. 55A is a histogram overlay of the dead cell analysis from FIGS. 54A-C. FIG. 55B shows the total count of EthD-1 positive (dead) cells in the GFP positive cell population. Both LV-FLNA 1-GFP and LV-FLNA_2-GFP significantly increased the number of dead cells relative to the LV control ($p<0.05$ and $p<0.0001$, respectively).

Breast Cancer

MDA-MB-231 (breast cancer cell line) cells were transfected with 2.5 μg DNA (LV-GFP, LV-FLNA_1-GFP, or LV-FLNA_2-GFP) using lipofectamine 3000, or mock transfected. Cells were harvested at 72 hours post-transfection for cell proliferation and microscopy studies. For cell proliferation assays, at 72 hours post transfection, cells were harvested and incubated with EdU reagent for two hours. Cells not contacted with EdU reagent served as negative controls. Proliferation was assessed by flow cytometry.

GFP expression 72 hours post-transfection of MDA-MB-231 cells is provided in FIG. 56. FIG. 56A is mock transfected. FIG. 56B shows proliferation of LV-GFP control transfected MDA-MB-231 cells. FIGS. 56C and 56D show proliferation of LV-FLNA_1-GFP and LV-FLNA 2-GFP transfected MDA-MB-231 cells, respectively. FIG. 56E is a histogram overlay of the data in FIGS. 56A-D. FIG. 57 shows proliferation as measured by EdU staining in GFP gated cells 72 hours post transfection. FIG. 57A is unstained control. FIGS. 57B, 57C, and 57D show EdU staining in GFP+ cells 72 hours after transfection with LV-GFP, LV-FLNA_1-GFP, or LV-FLNA_2-GFP, respectively. FIG. 57E is a graphical representation of the proliferation study. Both LV-FLNA_1 and LV-FLNA_2-GFP significantly reduced proliferation of MDA-MB-231 cells relative to LV-GFP (p<0.001 and p<0.0001, respectively).

For microscopy studies, cells were imaged 24 hours post-transfection using a confocal microscope. FIG. 58 provides the results. GFP was expressed in MDA-MB-231 cells at 24 hours for all three groups.

FLNA protein levels post-intrabody treatment of MDA-MB-231 cells was assessed by western blot. Cells were lysed at 48 hours post-transfection, and 35 µg of protein per sample was subjected to SDS-PAGE. Primary anti-filamin A antibody was diluted 1:500 and anti-GAPDH antibody was diluted 1:3000. Secondary antibody for filamin-A detection was HRP-conjugated donkey anti-mouse, diluted 1:1000. Secondary antibody for GAPDH was HRP-conjugated goat anti-rat, diluted 1:1000. The results of the study are provided in FIG. 59. Treatment with FLNA intrabody resulted in decreased FLNA protein levels in MDA-MB-231 cells.

Example 10: Toxicity Studies

Normal human astrocyte cells (N7805100) were seeded in 24 well plates and transfected with LV-GFP, LV-FLNA_1-GFP, or LV-FLNA_2-GFP, or mock transfected. A lysis control group and a negative control group were also included. 24 hours post-transfection, cells were harvested for flow cytometry to analyze transfection efficiency. 72 hours post transfection, cells from different wells were used to perform the LDH cytotoxicity assay.

The results of the study are provided in FIGS. 60-62. FIGS. 60A-E confirm GFP expression in normal human astrocyte cells at 24 hours post-transfection. FIGS. 61A-C provide microscopic analysis of normal human astrocyte cells at 24 hours post-transfection. GFP expression was observed in all three groups: LV-GFP, LV-FLNA_1-GFP, and LV-FLNA_2-GFP. FIG. 62 provides the results of the LDH cytotoxicity assay. The percent cytotoxicity was calculated using the commercial kit protocol (ThermoFisher, 88954). In normal cells, the % cytotoxicity was low, and there was no difference in % cytotoxicity among the groups.

Example 11: B411 Surface Staining on Cancer Cells

B411 surface staining on several different cell types was conducted. Cells were plated at a concentration of 0.5-1.0 million cells per well, and incubated overnight. Cells were then lifted from the wells, washed, and resuspended in flow cytometry media with 2 µg of primary antibody for 1 hour on ice. Cells were washed and incubated with the secondary antibody (5 µg/ml) for 30 minutes on ice. Cells were washed again and analyzed by flow cytometry.

FIG. 63 provides the results for the SKNAS (human neuroblastoma) cell line. The left panel is a histogram showing positive staining for B411, and negative staining for the isotype control, no primary antibody control, and unstained cells. The right two panels show the % of positive cells in each group (top) and the total cell count of positive cells in each group (bottom).

FIG. 64 provides the results for the SKBR3 (breast adenocarcinoma) cell line. The left panel is histogram showing some positive staining for B411, and negative staining for the no primary antibody control and unstained cells. The right two panels show the % of positive cells in each group (top)_and the total cell count of positive cells in each group (bottom).

Figure 65:
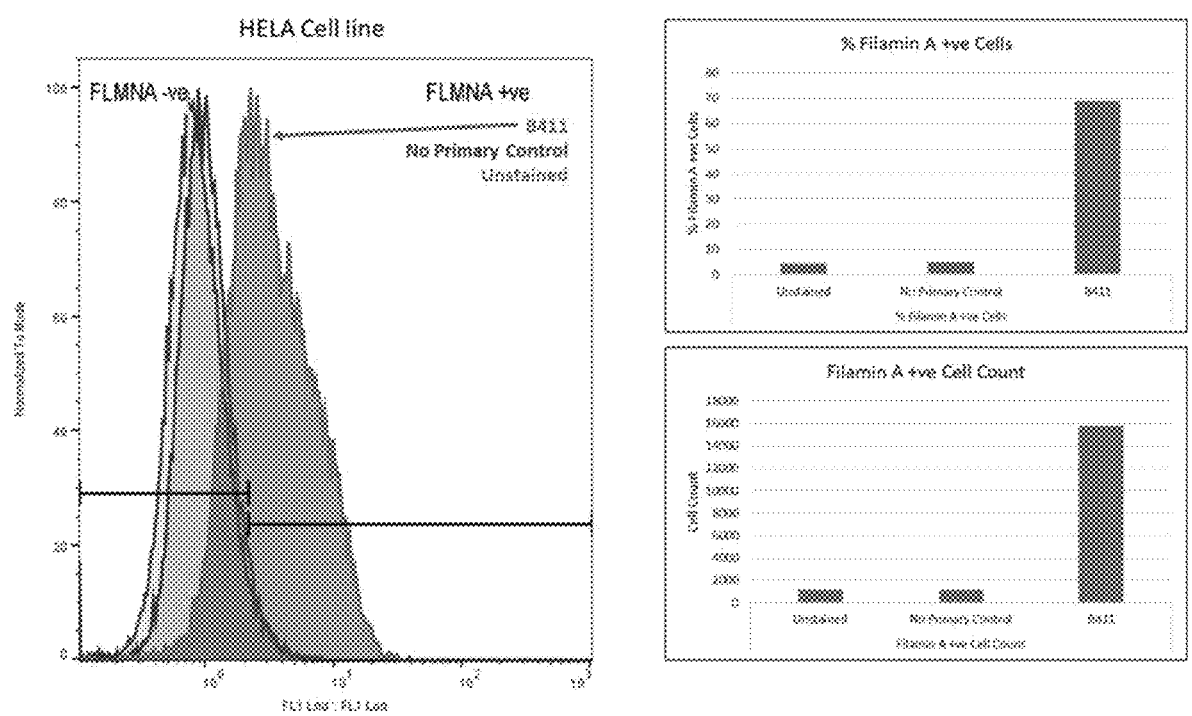

FIG. 65 provides the results for the HeLa cells (ovarian cancer). The left panel is a histogram showing positive staining for B411, and negative staining for the no primary antibody control and unstained cells. The right two panels show the % of positive cells in each group (top)_and the total cell count of positive cells in each group (bottom).

FIG. 66 provides the results for the SKOV3 cell line (ovarian cancer). The left panel is a histogram showing positive staining for B411, and negative staining for the no primary antibody control and unstained cells. The right two panels show the % of positive cells in each group (top)_and the total cell count of positive cells in each group (bottom).

The results of the study indicated that B411 can detect surface filamin A in various cancer cell lines. For SKBR3 cell lines, there was positive staining for B411, but it was weaker compared to the other cell lines tested. Highly Positive staining for B411 was observed in SKNAS, SKOV3, and HeLa cell lines.

Example 12: Endocytosis

Experiments were conducted to determine if antibody B411 is endocytosed by cells. 250,000 cells/well were plated and incubated overnight at 37° C., 5% $CO_2$. 12 µg/mL of antibodies were labelled with Zenon pHrodo kit (human green) according to the manufacturer's protocol for 5 minutes at room temperature, in the dark. The plated cells were then incubated with the labeled antibodies for 24 hours, at 37° C., 5% $CO_2$. Cells were then lifted by manual scraping, and washed prior to analysis by flow cytometry.

FIGS. 67-68 provide the results. The percent endocytosis positive SKBR3 cells (breast adenocarcinoma) and HEK cells (non-cancer) are shown in FIG. 67. FIG. 68 shows the total number of cells positive for endocytosis. Endocytosis of B411 was detected in SKBR3 cells (breast adenocarcinoma) incubated with the antibody (FIG. 67, left panel). More SKBR3 cells were positive for B411 than HEK cells (FIG. 68), suggesting that SKBR3 cells have a higher degree of endocytosis of B411 bound filamin A, compared to HEK (non-cancer) cells. The results of the study indicated that endocytosis of filamin A antibodies provided herein can be used to deliver targeted therapeutics for treatment.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. An antibody, comprising:
   a. a light chain variable domain comprising three complementarity determining regions (CDRs) comprising CDR1, CDR2, and CDR3, wherein the light chain CDR1 comprises an amino acid sequence selected from SEQ ID NOs: 12 and 13; the light chain CDR2 comprises an amino acid sequence of SEQ ID NO: 14, and the light chain CDR3 comprises an amino acid sequence of SEQ ID NO: 15; and
   b. a heavy chain variable domain comprising three CDRs comprising CDR1, CDR2, and CDR3, wherein the heavy chain CDR1 comprises an amino acid sequence of SEQ ID NO: 16, the heavy chain CDR2 comprises an amino acid sequence of SEQ ID NO: 17, and the heavy chain CDR3 comprises an amino acid sequence selected from SEQ ID NOs: 18, 19, 20, and 21.

2. The antibody according to claim 1, wherein the light chain CDR1 comprises SEQ ID NO: 13 and the heavy chain CDR3 comprises SEQ ID NO: 21.

3. The antibody according to claim 1, wherein the light chain variable domain comprises SEQ ID NO:2 and the heavy chain variable domain comprises SEQ ID NO:7.

4. The antibody according to claim 1, wherein the light and heavy chain variable regions are in a light-heavy orientation.

5. The antibody according to any one of claim 1, wherein the light and heavy chain variable regions are in a heavy-light orientation.

6. The antibody according to claim 1, further comprising:
   c. a light chain constant domain comprising SEQ ID NO:3; and
   d. a heavy chain constant domain comprising SEQ ID NO:11.

7. The antibody according to claim 1, wherein the antibody is a human chimeric antibody, or a scFv.

8. The antibody according to claim 1, wherein the antibody binds filamin-A antigen, and wherein:
   (a) said filamin-A antigen is a gene product encoded by the FLNA gene, or a homologue thereof;
   (b) said filamin-A antigen is an approximately 280-kDa breast cancer cell secreted soluble filamin-A antigen;

(c) the antibody is capable of preferentially binding a breast cancer cell secreted soluble filamin-A antigen, wherein said preferential binding is relative to a non-breast cancer cell secreted soluble filamin-A antigen;
(d) the antibody is capable of binding to a breast cancer cell secreted soluble filamin-A antigen with a specific affinity of between $10^{-7}$ M and $10^{-11}$ M;
(e) said filamin-A antigen is an approximately 280-kDa breast cancer cell membrane associated filamin-A antigen;
(f) the antibody is capable of preferentially binding a breast cancer cell membrane associated filamin-A antigen, wherein said preferential binding is relative to a non-breast cancer cell membrane associated filamin-A antigen; and
(g) the antibody is capable of binding to a breast cancer cell membrane associated filamin-A antigen with a specific affinity of between $10^{-7}$ M and $10^{-11}$ M.

9. An isolated polynucleotide DNA sequence that comprises a sequence encoding the antibody of claim 1.

10. An isolated vector comprising the polynucleotide of claim 9.

11. An isolated host cell comprising the vector of claim 10.

12. The antibody according to claim 1, wherein:
(a) the antibody is immobilized on a solid phase;
(b) the antibody is detectably labeled;
(c) the antibody is conjugated to a radionuclide;
(d) the antibody is conjugated to a chemotherapeutic agent; and/or
(e) the antibody is conjugated to a protein.

13. A pharmaceutical composition, comprising:
a. the antibody according to claim 1; and
b. a pharmaceutically acceptable carrier.

14. A kit for diagnosing cancer, comprising:
a. the antibody according to claim 1 as a primary antibody; and
b. a secondary antibody that binds to the primary antibody, wherein the secondary antibody is conjugated to a detectable label.

15. A method for detecting cancer in a patient, comprising:
a. obtaining a biological sample from a patient;
b. contacting the biological sample with the antibody according to claim 1; and
c. detecting whether the antibody binds antigen in the sample, wherein a positive binding interaction between said antibody and antigen is indicative of cancer.

16. The method of claim 15, wherein the cancer is breast cancer.

17. A method for treating cancer in a patient, comprising: administering an effective amount of the antibody according to claim 1 to a patient in need thereof.

18. The method of claim 17, wherein the cancer is breast cancer.

19. The method of claim 17, wherein
(i) the antibody induces antibody-dependent cellular cytotoxicity (ADCC) and/or complement-dependent cytotoxicity (CDC) of a cancer cell;
(ii) the antibody is endocytosed by a cancer cell; and/or
(iii) the antibody is linked or conjugated to at therapeutic agent.

20. A method for reducing the growth of tumor cells, comprising:
a. administering to a human patient in need thereof, an effective amount of an antibody, said antibody comprising:
i. a light chain variable domain comprising SEQ ID NO:1 or SEQ ID NO: 2;
ii. a light chain constant domain comprising SEQ ID NO:3;
iii. a heavy chain variable domain comprising SEQ ID NO:4, 5, 6, or 7; and
iv. a heavy chain constant domain comprising SEQ ID NO:11.

21. The method of claim 20, wherein the cancer is breast cancer.

22. The method of claim 20, wherein the antibody is a monoclonal antibody, a human chimeric antibody, or a humanized antibody.

23. An intrabody, comprising:
(a) a light chain variable domain comprising three complementarity determining regions (CDRs) comprising CDR1, CDR2, and CDR3, wherein the light chain CDR1 comprises an amino acid sequence selected from SEQ ID NOs: 12 and 13; the light chain CDR2 comprises an amino acid sequence of SEQ ID NO: 14, and the light chain CDR3 comprises an amino acid sequence of SEQ ID NO: 15; and
(b) a heavy chain variable domain comprising three CDRs comprising CDR1, CDR2, and CDR3, wherein the heavy chain CDR1 comprises an amino acid sequence of SEQ ID NO: 16, the heavy chain CDR2 comprises an amino acid sequence of SEQ ID NO: 17, and the heavy chain CDR3 comprises an amino acid sequence selected from SEQ ID NOs: 18, 19, 20, and 21.

24. The intrabody according to claim 23, wherein the light chain CDR1 comprises SEQ ID NO: 13 and the heavy chain CDR3 comprises SEQ ID NO: 21.

25. The intrabody according to claim 23, wherein the light chain variable domain comprises SEQ ID NO:2 and the heavy chain variable domain comprises SEQ ID NO:7.

26. The intrabody according to claim 23, wherein the intrabody is capable of binding to filamin-A with a specific affinity of between $10^{-7}$ M and $10^{-11}$ M.

27. The intrabody of claim 23, wherein the intrabody is an scFv.

28. An isolated RNA encoding the intrabody of claim 23.

29. An isolated polynucleotide DNA sequence that comprises a sequence encoding the intrabody of claim 23.

30. A fusion protein comprising the intrabody of claim 23 and (i) a protein for translocating the intrabody across a cell membrane and/or (ii) a protein for targeting the intrabody to a subcellular structure.

31. The isolated intrabody of claim 23, wherein
(i) the intrabody is detectably labeled;
(ii) the intrabody is conjugated to a radionuclide;
(iii) the intrabody is conjugated to a chemotherapeutic agent;
(iv) the intrabody is conjugated to a protein; and/or
(v) the intrabody is linked or conjugated to a cell membrane-penetrating peptide or cell membrane-penetrating protein.

32. A pharmaceutical composition, comprising:
a. the isolated intrabody according to claim 23; and
b. a pharmaceutically acceptable carrier.

33. A pharmaceutical composition, comprising:
a. a delivery system comprising a DNA or RNA encoding the intrabody of claim 23; and
b. a pharmaceutically acceptable carrier.

34. A method for treating cancer in a patient, comprising administering an effective amount of the isolated intrabody of claim 23 to a patient in need thereof.

35. The method of claim 34, wherein the cancer is breast cancer.

36. A bispecific or multispecific antibody comprising a first antibody according to claim 1 and a second antibody that binds to an antigen expressed on an immune cell.

37. The bispecific or multispecific antibody of claim 36, wherein the immune cell is T cell, NK cell, or macrophage.

38. A bispecific antibody comprising a first antibody according to claim 1 and a second antibody that binds to CD3.

39. A chimeric antigen receptor (CAR) polypeptide comprising:
(a) a light chain variable domain comprising three complementarity determining regions (CDRs) comprising CDR1, CDR2, and CDR3, wherein the light chain CDR1 comprises an amino acid sequence selected from SEQ ID NOs: 12 and 13; the light chain CDR2 comprises an amino acid sequence of SEQ ID NO: 14, and the light chain CDR3 comprises an amino acid sequence of SEQ ID NO: 15; and
(b) heavy chain variable domain comprising three CDRs comprising CDR1, CDR2, and CDR3, wherein the heavy chain CDR1 comprises an amino acid sequence of SEQ ID NO: 16, the heavy chain CDR2 comprises an amino acid sequence of SEQ ID NO: 17, and the heavy chain CDR3 comprises an amino acid sequence selected from SEQ ID NOs: 18, 19, 20, and 21.

40. The CAR polypeptide of claim 39, wherein the CAR polypeptide comprises an intracellular signaling domain comprising a costimulatory domain selected from the group consisting of CD27, CD28, 4-1BB, OX-40, CD30, CD40, PD-1, ICOS, LFA-1, CD2, CD7, LIGHT, NKG2C, NKG2D, B7-H3, and any combination thereof.

41. The CAR polypeptide of claim 39, wherein the CAR polypeptide comprises a T cell receptor (TCR) zeta chain signaling domain.

42. A cell expressing the CAR of claim 39.

43. The cell of claim 42, wherein the cell is selected from the group consisting of a T cell, an NK cell, an NK-T cell, a B cell, a macrophage, or a stem cell.

44. A method for treating cancer in a subject in need thereof, comprising administering to the subject the cell of claim 42.

* * * * *

SEQUENCE LISTING

<160> NUMBER OF SEQ ID NOS: 74

<210> SEQ ID NO 1

```
<211> LENGTH: 107
<212> TYPE: PRT
<213> ORGANISM: Artificial Sequence
<220> FEATURE:
<223> OTHER INFORMATION: VL domain of mAbs B185, B405, B406, and B407

<400> SEQUENCE: 1

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ile Asp
            20                  25                  30

Val Ala Trp Tyr Gln Gln Lys Pro Gly Gln Ser Pro Lys Leu Leu Ile
        35                  40                  45

Tyr Ser Ala Ser His Arg Tyr Thr Gly Val Pro Asp Arg Phe Thr Gly
50                  55                  60

Ser Gly Ser Gly Thr Asp Phe Thr Phe Thr Ile Ser Gly Val Gln Ala
65                  70                  75                  80

Glu Asp Leu Ala Val Tyr Phe Cys Gln Gln His Tyr Ser Thr Pro Leu
                85                  90                  95

Thr Phe Gly Ala Gly Thr Lys Leu Glu Leu Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: human chimeric mAb VL domain of mAbs B408,
      B409, B410, and B411

<400> SEQUENCE: 2

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Leu Asp
            20                  25                  30

Val Ala Trp Tyr Gln Gln Lys Pro Gly Gln Ser Pro Lys Leu Leu Ile
        35                  40                  45

Tyr Ser Ala Ser His Arg Tyr Thr Gly Val Pro Asp Arg Phe Thr Gly
50                  55                  60

Ser Gly Ser Gly Thr Asp Phe Thr Phe Thr Ile Ser Gly Val Gln Ala
65                  70                  75                  80

Glu Asp Leu Ala Val Tyr Phe Cys Gln Gln His Tyr Ser Thr Pro Leu
                85                  90                  95

Thr Phe Gly Ala Gly Thr Lys Leu Glu Leu Lys
            100                 105

<210> SEQ ID NO 3
<211> LENGTH: 107
<212> TYPE: PRT
<213> ORGANISM: Homo sapiens

<400> SEQUENCE: 3

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
```

```
                50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

```
<210> SEQ ID NO 4
<211> LENGTH: 118
<212> TYPE: PRT
<213> ORGANISM: Artificial Sequence
<220> FEATURE:
<223> OTHER INFORMATION: VH domain of mAbs B185 and B408

<400> SEQUENCE: 4

Glu Val Lys Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
             20                  25                  30

Thr Met Ser Trp Val Arg Gln Thr Pro Glu Lys Arg Leu Glu Trp Val
         35                  40                  45

Ala Tyr Ile Ser Asn Gly Gly Gly Ser Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Ser Asp Gly Leu Leu Arg Pro Phe Ala Tyr Trp Gly Gln Gly Thr
            100                 105                 110

Leu Val Thr Val Ser Ala
        115
```

```
<210> SEQ ID NO 5
<211> LENGTH: 118
<212> TYPE: PRT
<213> ORGANISM: Artificial Sequence
<220> FEATURE:
<223> OTHER INFORMATION: VH domain of mAbs B406 and B410

<400> SEQUENCE: 5

Glu Val Lys Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
             20                  25                  30

Thr Met Ser Trp Val Arg Gln Thr Pro Glu Lys Arg Leu Glu Trp Val
         35                  40                  45

Ala Tyr Ile Ser Asn Gly Gly Gly Ser Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Ser Asp Gly Leu Ile Arg Pro Phe Ala Tyr Trp Gly Gln Gly Thr
            100                 105                 110

Leu Val Thr Val Ser Ala
        115
```

```
<210> SEQ ID NO 6
<211> LENGTH: 118
<212> TYPE: PRT
<213> ORGANISM: Artificial Sequence
<220> FEATURE:
<223> OTHER INFORMATION: VH domain of mAbs B405 and B409

<400> SEQUENCE: 6

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Trp Val
            35                  40                  45

Ala Tyr Ile Ser Asn Gly Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Asp Gly Ile Leu Arg Pro Phe Ala Tyr Trp Gly Gln Gly Thr
            100                 105                 110

Leu Val Thr Val Ser Ala
        115

<210> SEQ ID NO 7
<211> LENGTH: 118
<212> TYPE: PRT
<213> ORGANISM: Artificial Sequence
<220> FEATURE:
<223> OTHER INFORMATION: VH domain of mAbs B407 and B411

<400> SEQUENCE: 7

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Trp Val
            35                  40                  45

Ala Tyr Ile Ser Asn Gly Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Asp Gly Ile Ile Arg Pro Phe Ala Tyr Trp Gly Gln Gly Thr
            100                 105                 110

Leu Val Thr Val Ser Ala
        115

<210> SEQ ID NO 8
<211> LENGTH: 113
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys
1               5                   10                  15
```

-continued

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro

<210> SEQ ID NO 9
<211> LENGTH: 110
<212> TYPE: PRT
<213> ORGANISM: Homo sapiens

<400> SEQUENCE: 9

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 10
<211> LENGTH: 107
<212> TYPE: PRT
<213> ORGANISM: Homo sapiens

<400> SEQUENCE: 10

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

```
<210> SEQ ID NO 11
<211> LENGTH: 330
<212> TYPE: PRT
<213> ORGANISM: Homo sapiens

<400> SEQUENCE: 11
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| 130 | | | | | 135 | | | | | 140 | | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | 195 | | | | | 200 | | | | | 205 | | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Asp | Glu |
| 225 | | | | | 230 | | | | | 235 | | | | | 240 |
| Leu | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

```
<210> SEQ ID NO 12
<211> LENGTH: 6
<212> TYPE: PRT
<213> ORGANISM: Mus sp.

<400> SEQUENCE: 12

Gln Asp Val Ser Ile Asp
```

```
<210> SEQ ID NO 13
<211> LENGTH: 6
<212> TYPE: PRT
<213> ORGANISM: Mus sp.

<400> SEQUENCE: 13

Gln Asp Val Ser Leu Asp
1               5

<210> SEQ ID NO 14
<211> LENGTH: 4
<212> TYPE: PRT
<213> ORGANISM: Mus sp.

<400> SEQUENCE: 14

Ser Ala Ser His
1

<210> SEQ ID NO 15
<211> LENGTH: 9
<212> TYPE: PRT
<213> ORGANISM: Mus sp.

<400> SEQUENCE: 15

Cys Gln Gln His Tyr Ser Thr Pro Leu
1               5

<210> SEQ ID NO 16
<211> LENGTH: 8
<212> TYPE: PRT
<213> ORGANISM: Mus sp.

<400> SEQUENCE: 16

Gly Phe Thr Phe Ser Ser Tyr Thr
1               5

<210> SEQ ID NO 17
<211> LENGTH: 8
<212> TYPE: PRT
<213> ORGANISM: Mus sp.

<400> SEQUENCE: 17

Ile Ser Asn Gly Gly Gly Ser Thr
1               5

<210> SEQ ID NO 18
<211> LENGTH: 10
<212> TYPE: PRT
<213> ORGANISM: Mus sp.

<400> SEQUENCE: 18

Ala Ser Asp Gly Leu Leu Arg Pro Phe Ala
1               5                   10

<210> SEQ ID NO 19
<211> LENGTH: 10
<212> TYPE: PRT
<213> ORGANISM: Mus sp.

<400> SEQUENCE: 19

Ala Ser Asp Gly Leu Ile Arg Pro Phe Ala
1               5                   10
```

<210> SEQ ID NO 20
<211> LENGTH: 10
<212> TYPE: PRT
<213> ORGANISM: Mus sp.

<400> SEQUENCE: 20

Ala Ser Asp Gly Ile Leu Arg Pro Phe Ala
1               5                   10

<210> SEQ ID NO 21
<211> LENGTH: 10
<212> TYPE: PRT
<213> ORGANISM: Mus sp.

<400> SEQUENCE: 21

Ala Ser Asp Gly Ile Ile Arg Pro Phe Ala
1               5                   10

<210> SEQ ID NO 22
<211> LENGTH: 107
<212> TYPE: PRT
<213> ORGANISM: Mus sp.

<400> SEQUENCE: 22

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ile Asp
            20                  25                  30

Val Ala Trp Tyr Gln Gln Lys Pro Gly Gln Ser Pro Lys Leu Leu Ile
        35                  40                  45

Tyr Ser Ala Ser His Arg Tyr Thr Gly Val Pro Asp Arg Phe Thr Gly
    50                  55                  60

Ser Gly Ser Gly Thr Asp Phe Thr Phe Thr Ile Ser Gly Val Gln Ala
65                  70                  75                  80

Glu Asp Leu Ala Val Tyr Phe Cys Gln Gln His Tyr Ser Thr Pro Leu
                85                  90                  95

Thr Phe Gly Ala Gly Thr Lys Leu Glu Leu Lys
            100                 105

<210> SEQ ID NO 23
<211> LENGTH: 107
<212> TYPE: PRT
<213> ORGANISM: Mus sp.

<400> SEQUENCE: 23

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 24
<211> LENGTH: 118
<212> TYPE: PRT
<213> ORGANISM: Mus sp.

<400> SEQUENCE: 24

Glu Val Lys Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
             20                  25                  30

Thr Met Ser Trp Val Arg Gln Thr Pro Glu Lys Arg Leu Glu Trp Val
         35                  40                  45

Ala Tyr Ile Ser Asn Gly Gly Ser Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Ser Asp Gly Leu Leu Arg Pro Phe Ala Tyr Trp Gly Gln Gly Thr
            100                 105                 110

Leu Val Thr Val Ser Ala
        115

<210> SEQ ID NO 25
<211> LENGTH: 123
<212> TYPE: PRT
<213> ORGANISM: Mus sp.

<400> SEQUENCE: 25

Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
             20                  25                  30

Phe Pro Glu Pro Val Thr Val Thr Trp Asn Ser Gly Ser Leu Ser Ser
         35                  40                  45

Gly Val His Thr Phe Pro Ala Val Leu Gln Ser Asp Leu Tyr Thr Leu
     50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys
        115                 120

<210> SEQ ID NO 26
<211> LENGTH: 74
<212> TYPE: PRT
<213> ORGANISM: Mus sp.

<400> SEQUENCE: 26

Pro Lys Asp Val Leu Thr Ile Thr Leu Thr Pro Lys Val Thr Cys Val
 1               5                  10                  15

Val Val Asp Ile Ser Lys Asp Asp Pro Glu Val Gln Phe Ser Trp Phe
             20                  25                  30

```
Val Asp Asp Val Glu Val His Thr Ala Gln Thr Gln Pro Arg Glu Glu
            35                  40                  45

Gln Phe Asn Ser Thr Phe Arg Ser Val Ser Glu Leu Pro Ile Met His
 50                  55                  60

Gln Asp Trp Leu Asn Gly Lys Glu Phe Lys
 65                  70

<210> SEQ ID NO 27
<211> LENGTH: 127
<212> TYPE: PRT
<213> ORGANISM: Mus sp.

<400> SEQUENCE: 27

Cys Arg Val Asn Ser Ala Ala Phe Pro Ala Pro Ile Glu Lys Thr Ile
 1               5                  10                  15

Ser Lys Thr Lys Gly Arg Pro Lys Ala Pro Gln Val Tyr Thr Ile Pro
            20                  25                  30

Pro Pro Lys Glu Gln Met Ala Lys Asp Lys Val Ser Leu Thr Cys Met
            35                  40                  45

Ile Thr Asp Phe Phe Pro Glu Asp Ile Thr Val Glu Trp Gln Trp Asn
 50                  55                  60

Gly Gln Pro Ala Glu Asn Tyr Lys Asn Thr Gln Pro Ile Met Asp Thr
 65                  70                  75                  80

Asp Gly Ser Tyr Phe Val Tyr Ser Lys Leu Asn Val Gln Lys Ser Asn
                 85                  90                  95

Trp Glu Ala Gly Asn Thr Phe Thr Cys Ser Val Leu His Glu Gly Leu
            100                 105                 110

His Asn His His Thr Glu Lys Ser Leu Ser His Ser Pro Gly Lys
            115                 120                 125

<210> SEQ ID NO 28
<211> LENGTH: 324
<212> TYPE: PRT
<213> ORGANISM: Mus sp.

<400> SEQUENCE: 28

Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
 50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
            130                 135                 140

Lys Asp Asp Pro Glu Val Gln Phe Ser Trp Phe Val Asp Asp Val Glu
145                 150                 155                 160
```

Val His Thr Ala Gln Thr Gln Pro Arg Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 29
<211> LENGTH: 23
<212> TYPE: PRT
<213> ORGANISM: Homo sapiens

<400> SEQUENCE: 29

Asp Ile Val Met Thr Gln Ser His Lys Phe Met Ser Thr Ser Val Gly
1               5                   10                  15

Asp Arg Val Ser Ile Thr Cys
            20

<210> SEQ ID NO 30
<211> LENGTH: 29
<212> TYPE: PRT
<213> ORGANISM: Homo sapiens

<400> SEQUENCE: 30

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val
            20                  25

<210> SEQ ID NO 31
<211> LENGTH: 11
<212> TYPE: PRT
<213> ORGANISM: Mus sp.

<400> SEQUENCE: 31

Lys Ala Ser Gln Asp Val Ser Ile Asp Val Ala
1               5                   10

<210> SEQ ID NO 32
<211> LENGTH: 7
<212> TYPE: PRT
<213> ORGANISM: Mus sp.

<400> SEQUENCE: 32

Ser Ile Asp Val Ala Trp Tyr
1               5

<210> SEQ ID NO 33
<211> LENGTH: 15
<212> TYPE: PRT
<213> ORGANISM: Homo sapiens

<400> SEQUENCE: 33

Trp Tyr Gln Gln Lys Pro Gly Gln Ser Pro Lys Leu Leu Ile Tyr
1               5                   10                  15

<210> SEQ ID NO 34
<211> LENGTH: 9
<212> TYPE: PRT
<213> ORGANISM: Homo sapiens

<400> SEQUENCE: 34

Gln Gln Lys Pro Gly Gln Ser Pro Lys
1               5

<210> SEQ ID NO 35
<211> LENGTH: 7
<212> TYPE: PRT
<213> ORGANISM: Mus sp.

<400> SEQUENCE: 35

Ser Ala Ser His Arg Tyr Thr
1               5

<210> SEQ ID NO 36
<211> LENGTH: 10
<212> TYPE: PRT
<213> ORGANISM: Mus sp.

<400> SEQUENCE: 36

Leu Leu Ile Tyr Ser Ala Ser His Arg Tyr
1               5                   10

<210> SEQ ID NO 37
<211> LENGTH: 32
<212> TYPE: PRT
<213> ORGANISM: Homo sapiens

<400> SEQUENCE: 37

Gly Val Pro Asp Arg Phe Thr Gly Ser Gly Ser Gly Thr Asp Phe Thr
1               5                   10                  15

Phe Thr Ile Ser Gly Val Gln Ala Glu Asp Leu Ala Val Tyr Phe Cys
                20                  25                  30

<210> SEQ ID NO 38
<211> LENGTH: 33
<212> TYPE: PRT
<213> ORGANISM: Homo sapiens

<400> SEQUENCE: 38

Thr Gly Val Pro Asp Arg Phe Thr Gly Ser Gly Ser Gly Thr Asp Phe
1               5                   10                  15

Thr Phe Thr Ile Ser Gly Val Gln Ala Glu Asp Leu Ala Val Tyr Phe
                20                  25                  30

Cys

<210> SEQ ID NO 39

```
<211> LENGTH: 9
<212> TYPE: PRT
<213> ORGANISM: Mus sp.

<400> SEQUENCE: 39

Gln Gln His Tyr Ser Thr Pro Leu Thr
1               5

<210> SEQ ID NO 40
<211> LENGTH: 8
<212> TYPE: PRT
<213> ORGANISM: Mus sp.

<400> SEQUENCE: 40

Gln Gln His Tyr Ser Thr Pro Leu
1               5

<210> SEQ ID NO 41
<211> LENGTH: 13
<212> TYPE: PRT
<213> ORGANISM: Homo sapiens

<400> SEQUENCE: 41

Phe Gly Ala Gly Thr Lys Leu Glu Leu Lys Arg Thr Val
1               5                   10

<210> SEQ ID NO 42
<211> LENGTH: 14
<212> TYPE: PRT
<213> ORGANISM: Homo sapiens

<400> SEQUENCE: 42

Thr Phe Gly Ala Gly Thr Lys Leu Glu Leu Lys Arg Thr Val
1               5                   10

<210> SEQ ID NO 43
<211> LENGTH: 25
<212> TYPE: PRT
<213> ORGANISM: Homo sapiens

<400> SEQUENCE: 43

Glu Val Lys Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 44
<211> LENGTH: 30
<212> TYPE: PRT
<213> ORGANISM: Homo sapiens

<400> SEQUENCE: 44

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser
            20                  25                  30

<210> SEQ ID NO 45
<211> LENGTH: 29
<212> TYPE: PRT
<213> ORGANISM: Homo sapiens

<400> SEQUENCE: 45

Glu Val Lys Leu Val Glu Ser Gly Gly Gly Leu Val Gln Pro Gly Gly
```

```
                1               5                   10                  15
Ser Leu Lys Leu Ser Cys Ala Ala Ser Gly Phe Thr Phe
            20                  25
```

<210> SEQ ID NO 46
<211> LENGTH: 7
<212> TYPE: PRT
<213> ORGANISM: Mus sp.

<400> SEQUENCE: 46

```
Gly Phe Thr Phe Ser Ser Tyr
1               5
```

<210> SEQ ID NO 47
<211> LENGTH: 10
<212> TYPE: PRT
<213> ORGANISM: Mus sp.

<400> SEQUENCE: 47

```
Gly Phe Thr Phe Ser Ser Tyr Thr Met Ser
1               5                   10
```

<210> SEQ ID NO 48
<211> LENGTH: 5
<212> TYPE: PRT
<213> ORGANISM: Mus sp.

<400> SEQUENCE: 48

```
Ser Tyr Thr Met Ser
1               5
```

<210> SEQ ID NO 49
<211> LENGTH: 6
<212> TYPE: PRT
<213> ORGANISM: Mus sp.

<400> SEQUENCE: 49

```
Ser Ser Tyr Thr Met Ser
1               5
```

<210> SEQ ID NO 50
<211> LENGTH: 19
<212> TYPE: PRT
<213> ORGANISM: Homo sapiens

<400> SEQUENCE: 50

```
Thr Met Ser Trp Val Arg Gln Thr Pro Glu Lys Arg Leu Glu Trp Val
1               5                   10                  15
Ala Tyr Ile
```

<210> SEQ ID NO 51
<211> LENGTH: 14
<212> TYPE: PRT
<213> ORGANISM: Homo sapiens

<400> SEQUENCE: 51

```
Trp Val Arg Gln Thr Pro Glu Lys Arg Leu Glu Trp Val Ala
1               5                   10
```

<210> SEQ ID NO 52
<211> LENGTH: 11
<212> TYPE: PRT
<213> ORGANISM: Homo sapiens

```
<400> SEQUENCE: 52

Trp Val Arg Gln Thr Pro Glu Lys Arg Leu Glu
1               5                   10

<210> SEQ ID NO 53
<211> LENGTH: 6
<212> TYPE: PRT
<213> ORGANISM: Mus sp.

<400> SEQUENCE: 53

Ser Asn Gly Gly Gly Ser
1               5

<210> SEQ ID NO 54
<211> LENGTH: 10
<212> TYPE: PRT
<213> ORGANISM: Mus sp.

<400> SEQUENCE: 54

Tyr Ile Ser Asn Gly Gly Gly Ser Thr Tyr
1               5                   10

<210> SEQ ID NO 55
<211> LENGTH: 17
<212> TYPE: PRT
<213> ORGANISM: Mus sp.

<400> SEQUENCE: 55

Tyr Ile Ser Asn Gly Gly Gly Ser Thr Tyr Tyr Pro Asp Thr Val Lys
1               5                   10                  15

Gly

<210> SEQ ID NO 56
<211> LENGTH: 13
<212> TYPE: PRT
<213> ORGANISM: Mus sp.

<400> SEQUENCE: 56

Trp Val Ala Tyr Ile Ser Asn Gly Gly Gly Ser Thr Tyr
1               5                   10

<210> SEQ ID NO 57
<211> LENGTH: 41
<212> TYPE: PRT
<213> ORGANISM: Homo sapiens

<400> SEQUENCE: 57

Thr Tyr Tyr Pro Asp Thr Val Lys Gly Arg Phe Thr Ile Ser Arg Asp
1               5                   10                  15

Asn Ala Lys Asn Thr Leu Tyr Leu Gln Met Ser Ser Leu Lys Ser Glu
                20                  25                  30

Asp Thr Ala Met Tyr Tyr Cys Ala Ser
            35                  40

<210> SEQ ID NO 58
<211> LENGTH: 39
<212> TYPE: PRT
<213> ORGANISM: Homo sapiens

<400> SEQUENCE: 58

Tyr Pro Asp Thr Val Lys Gly Arg Phe Thr Ile Ser Arg Asp Asn Ala
1               5                   10                  15
```

```
Lys Asn Thr Leu Tyr Leu Gln Met Ser Ser Leu Lys Ser Glu Asp Thr
                20                  25                  30

Ala Met Tyr Tyr Cys Ala Ser
            35
```

<210> SEQ ID NO 59
<211> LENGTH: 32
<212> TYPE: PRT
<213> ORGANISM: Homo sapiens

<400> SEQUENCE: 59

```
Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr Tyr Cys Ala Ser
                20                  25                  30
```

<210> SEQ ID NO 60
<211> LENGTH: 37
<212> TYPE: PRT
<213> ORGANISM: Homo sapiens

<400> SEQUENCE: 60

```
Tyr Pro Asp Thr Val Lys Gly Arg Phe Thr Ile Ser Arg Asp Asn Ala
1               5                   10                  15

Lys Asn Thr Leu Tyr Leu Gln Met Ser Ser Leu Lys Ser Glu Asp Thr
                20                  25                  30

Ala Met Tyr Tyr Cys
            35
```

<210> SEQ ID NO 61
<211> LENGTH: 9
<212> TYPE: PRT
<213> ORGANISM: Mus sp.

<400> SEQUENCE: 61

```
Asp Gly Leu Leu Arg Pro Phe Ala Tyr
1               5
```

<210> SEQ ID NO 62
<211> LENGTH: 10
<212> TYPE: PRT
<213> ORGANISM: Mus sp.

<400> SEQUENCE: 62

```
Ala Ser Asp Gly Leu Leu Arg Pro Phe Ala
1               5                   10
```

<210> SEQ ID NO 63
<211> LENGTH: 11
<212> TYPE: PRT
<213> ORGANISM: Homo sapiens

<400> SEQUENCE: 63

```
Trp Gly Gln Gly Thr Leu Val Thr Val Ser Ala
1               5                   10
```

<210> SEQ ID NO 64
<211> LENGTH: 12
<212> TYPE: PRT
<213> ORGANISM: Homo sapiens

<400> SEQUENCE: 64

```
Tyr Trp Gly Gln Gly Thr Leu Val Thr Val Ser Ala
1               5                   10
```

-continued

<210> SEQ ID NO 65
<211> LENGTH: 12
<212> TYPE: PRT
<213> ORGANISM: Mus sp.

<400> SEQUENCE: 65

Phe Gly Ala Gly Thr Lys Leu Glu Leu Lys Arg Ala
1               5                   10

<210> SEQ ID NO 66
<211> LENGTH: 13
<212> TYPE: PRT
<213> ORGANISM: Mus sp.

<400> SEQUENCE: 66

Thr Phe Gly Ala Gly Thr Lys Leu Glu Leu Lys Arg Ala
1               5                   10

<210> SEQ ID NO 67
<211> LENGTH: 240
<212> TYPE: PRT
<213> ORGANISM: Artificial Sequence
<220> FEATURE:
<223> OTHER INFORMATION: Amino acid sequence of VH-VL intrabody

<400> SEQUENCE: 67

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Tyr Ile Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Asp Gly Leu Leu Arg Pro Phe Ala Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Asp Ile Val Met Thr Gln Ser His Lys Phe Met
    130                 135                 140

Ser Thr Ser Val Gly Asp Arg Val Ser Ile Thr Cys Lys Ala Ser Gln
145                 150                 155                 160

Asp Val Ser Ile Asp Val Ala Trp Tyr Gln Gln Lys Pro Gly Gln Ser
                165                 170                 175

Pro Lys Leu Leu Ile Tyr Ser Ala Ser His Arg Tyr Thr Gly Val Pro
            180                 185                 190

Asp Arg Phe Thr Gly Ser Gly Ser Gly Thr Asp Phe Thr Phe Thr Ile
        195                 200                 205

Ser Gly Val Gln Ala Glu Asp Leu Ala Val Tyr Phe Cys Gln Gln His
    210                 215                 220

Tyr Ser Thr Pro Leu Thr Phe Gly Ala Gly Thr Lys Leu Glu Leu Lys
225                 230                 235                 240

<210> SEQ ID NO 68
<211> LENGTH: 720
<212> TYPE: DNA
<213> ORGANISM: Artificial Sequence
<220> FEATURE:
<223> OTHER INFORMATION: DNA sequence of VH-VL intrabody

<400> SEQUENCE: 68

```
gaggttaaat tggttgagtc cgggggtggc ctggtacaac caggcggaag tcttaagctc      60
tcttgtgcag cgtcagggtt cacatttttcc tcatatacca tgtcttgggt gcgccagaca    120
ccagaaaagc gcttggagtg ggtggcttac ataagcaacg ggggaggcag cacgtactat    180
cctgacacgg ttaagggacg atttaccatt tccaggaca atgcgaaaaa tacgctgtac     240
ctgcaaatgt cttctttgaa atccgaagac acagccatgt actactgcgc atcagatgga    300
ctcctgagac cgtttgcata ttggggtcaa gggacattgg taacggtcag cgcaggcggc    360
ggaggctctg gtggtggagg gagtggggga ggggatctg acatagtcat gacgcagagt     420
cataagttta tgagcacttc tgtaggcgat cgagtttcaa tcacctgtaa agcaagtcag    480
gacgtaagta tcgatgttgc ttggtatcaa caaaaaccag ggcagagccc taagttgctg    540
atctatagtg cttcacaccg atacaccgga gtccccgacc gcttcaccgg atcagggtcc    600
ggcaccgact tcacgtttac gatcagcggc gtgcaagcgg aagacctcgc ggtttacttc    660
tgtcagcagc actattcaac gccccctgacc tttggggcgg gaacgaaatt ggaattgaaa  720
```

<210> SEQ ID NO 69
<211> LENGTH: 240
<212> TYPE: PRT
<213> ORGANISM: Artificial Sequence
<220> FEATURE:
<223> OTHER INFORMATION: Amino acid sequence of VL-VH intrabody

<400> SEQUENCE: 69

```
Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Ser Ile Asp
                 20                  25                  30

Val Ala Trp Tyr Gln Gln Lys Pro Gly Gln Ser Pro Lys Leu Leu Ile
             35                  40                  45

Tyr Ser Ala Ser His Arg Tyr Thr Gly Val Pro Asp Arg Phe Thr Gly
 50                  55                  60

Ser Gly Ser Gly Thr Asp Phe Thr Phe Thr Ile Ser Gly Val Gln Ala
 65                  70                  75                  80

Glu Asp Leu Ala Val Tyr Phe Cys Gln Gln His Tyr Ser Thr Pro Leu
                 85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Ser Glu Val Lys Leu Val Glu
            115                 120                 125

Ser Gly Gly Gly Leu Val Gln Pro Gly Gly Ser Leu Lys Leu Ser Cys
130                 135                 140

Ala Ala Ser Gly Phe Thr Phe Ser Ser Tyr Thr Met Ser Trp Val Arg
145                 150                 155                 160

Gln Thr Pro Glu Lys Arg Leu Glu Trp Val Ala Tyr Ile Ser Asn Gly
                165                 170                 175

Gly Gly Ser Thr Tyr Tyr Pro Asp Thr Val Lys Gly Arg Phe Thr Ile
            180                 185                 190
```

```
Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Ser Asp Gly Leu Leu
    210                 215                 220

Arg Pro Phe Ala Tyr Trp Gly Gln Gly Thr Leu Val Thr Val Ser Ala
225                 230                 235                 240
```

```
<210> SEQ ID NO 70
<211> LENGTH: 720
<212> TYPE: DNA
<213> ORGANISM: Artificial Sequence
<220> FEATURE:
<223> OTHER INFORMATION: DNA sequence of VL-VH intrabody

<400> SEQUENCE: 70
gacattgtaa tgacacaaag tcataagttc atgtcaacaa gcgtcggcga ccgggtgtct      60
ataacttgca aggcgtctca agatgtgtcc atcgatgtag cgtggtatca acagaaaccc     120
gggcaaagcc cgaagctgct gatatactca gcctcccacc gatatactgg agttccagat     180
cgattcactg gtagtgggtc aggaactgat ttcacattta ccatcagcgg ggtgcaagcg     240
gaggatctgg cagtctattt ctgccagcaa cactattcca cgcccctgac cttcggcgca     300
ggaacgaagt tggagttgaa aggcggcgga ggctctggtg gtggaggag tggggagg      360
ggatctgaag tgaaactggt tgaatctggt ggcggtcttg tacaaccggg aggatctttg     420
aaactctcat gcgctgccag tggttttacc ttcagcagct acaccatgag ctgggttcgc     480
caaaccccag aaaaaagact tgagtgggtc gcttacatct ctaatggtgg tgggagtact     540
tactatccag acactgtaaa aggtcgattc acgatcagtc gagataatgc aaaaaatacc     600
ctgtacttgc aaatgagtag cttgaaatcc gaagacacag ccatgtatta ctgcgcctca     660
gatggcttgc tccggccttt tgcctattgg ggacaggta ctctcgtaac cgtatctgca     720
```

```
<210> SEQ ID NO 71
<211> LENGTH: 12
<212> TYPE: PRT
<213> ORGANISM: Artificial Sequence
<220> FEATURE:
<223> OTHER INFORMATION: Linker

<400> SEQUENCE: 71

Gly Gly Gly Ser Gly Gly Gly Ser Gly Gly Gly Ser
1               5                   10
```

```
<210> SEQ ID NO 72
<211> LENGTH: 15
<212> TYPE: PRT
<213> ORGANISM: Artificial Sequence
<220> FEATURE:
<223> OTHER INFORMATION: Linker

<400> SEQUENCE: 72

Gly Gly Gly Gly Ser Gly Gly Gly Gly Ser Gly Gly Gly Gly Ser
1               5                   10                  15
```

```
<210> SEQ ID NO 73
<211> LENGTH: 110
<212> TYPE: PRT
<213> ORGANISM: Artificial Sequence
<220> FEATURE:
<223> OTHER INFORMATION: variable light chain of murine antibody

<400> SEQUENCE: 73
```

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ile Asp
                20                  25                  30

Val Ala Trp Tyr Gln Gln Lys Pro Gly Gln Ser Pro Lys Leu Leu Ile
            35                  40                  45

Tyr Ser Ala Ser His Arg Tyr Thr Gly Val Pro Asp Arg Phe Thr Gly
        50                  55                  60

Ser Gly Ser Gly Thr Asp Phe Thr Phe Thr Ile Ser Gly Val Gln Ala
65                  70                      75                  80

Glu Asp Leu Ala Val Tyr Phe Cys Gln Gln His Tyr Ser Thr Pro Leu
                85                  90                  95

Thr Phe Gly Ala Gly Thr Lys Leu Glu Leu Lys Arg Thr Val
                100                 105                 110

<210> SEQ ID NO 74
<211> LENGTH: 109
<212> TYPE: PRT
<213> ORGANISM: Artificial Sequence
<220> FEATURE:
<223> OTHER INFORMATION: variable light chain of murine antibody

<400> SEQUENCE: 74

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ile Asp
                20                  25                  30

Val Ala Trp Tyr Gln Gln Lys Pro Gly Gln Ser Pro Lys Leu Leu Ile
            35                  40                  45

Tyr Ser Ala Ser His Arg Tyr Thr Gly Val Pro Asp Arg Phe Thr Gly
        50                  55                  60

Ser Gly Ser Gly Thr Asp Phe Thr Phe Thr Ile Ser Gly Val Gln Ala
65                  70                      75                  80

Glu Asp Leu Ala Val Tyr Phe Cys Gln Gln His Tyr Ser Thr Pro Leu
                85                  90                  95

Thr Phe Gly Ala Gly Thr Lys Leu Glu Leu Lys Arg Ala
                100                 105
```